(12) United States Patent
Kato et al.

(10) Patent No.: US 9,966,539 B2
(45) Date of Patent: May 8, 2018

(54) ORGANIC ELECTROLUMINESCENCE DEVICE

(71) Applicant: IDEMITSU KOSAN CO., LTD., Chiyoda-ku (JP)

(72) Inventors: Tomoki Kato, Chiba (JP); Takayasu Sado, Chiba (JP); Takahiro Fujiyama, Osaka (JP)

(73) Assignee: IDEMITSU KOSAN CO., LTD., Chiyoda-ku (JP)

(*) Notice: Subject to any disclaimer, the term of this patent is extended or adjusted under 35 U.S.C. 154(b) by 632 days.

(21) Appl. No.: 13/767,417

(22) Filed: Feb. 14, 2013

(65) Prior Publication Data

US 2014/0061602 A1    Mar. 6, 2014

Related U.S. Application Data

(60) Provisional application No. 61/695,498, filed on Aug. 31, 2012.

(51) Int. Cl.
| | | |
|---|---|---|
| H01L 51/00 | (2006.01) | |
| C07C 211/61 | (2006.01) | |
| H01L 51/50 | (2006.01) | |

(52) U.S. Cl.
CPC ........ *H01L 51/0072* (2013.01); *C07C 211/61* (2013.01); *H01L 51/006* (2013.01); *B32B 2457/202* (2013.01); *C07C 2603/18* (2017.05); *H01L 51/0059* (2013.01); *H01L 51/0073* (2013.01); *H01L 51/0085* (2013.01); *H01L 51/5056* (2013.01); *H01L 51/5064* (2013.01)

(58) Field of Classification Search
None
See application file for complete search history.

(56) References Cited

U.S. PATENT DOCUMENTS

| | | | | |
|---|---|---|---|---|
| 2004/0241491 A1* | 12/2004 | Hatwar | ............... | H01L 51/0079 428/690 |
| 2006/0232198 A1 | 10/2006 | Kawamura et al. | | |
| 2007/0082226 A1 | 4/2007 | Yu | | |
| 2008/0265216 A1 | 10/2008 | Hartmann et al. | | |
| 2009/0115320 A1 | 5/2009 | Kawamura et al. | | |
| 2009/0315022 A1* | 12/2009 | Morishita et al. | ............... | 257/40 |
| 2010/0102709 A1 | 4/2010 | Zeika et al. | | |
| 2010/0187518 A1* | 7/2010 | Yamauchi | ........... | H01L 51/0003 257/40 |
| 2010/0219400 A1 | 9/2010 | Arakane et al. | | |
| 2010/0219404 A1* | 9/2010 | Endo | ..................... | H01L 51/006 257/40 |
| 2011/0297924 A1* | 12/2011 | Yabunouchi et al. | .......... | 257/40 |
| 2011/0309309 A1 | 12/2011 | Hartmann et al. | | |
| 2011/0315967 A1* | 12/2011 | Schmidhalter et al. | ........ | 257/40 |
| 2012/0025183 A1 | 2/2012 | Kamatani et al. | | |
| 2012/0074395 A1 | 3/2012 | Yabunouchi et al. | | |

FOREIGN PATENT DOCUMENTS

| | | |
|---|---|---|
| JP | 11-162649 | 6/1999 |
| JP | 11-224779 | 8/1999 |
| JP | 2003-519432 | 6/2003 |
| JP | 3792029 B2 | 6/2006 |
| JP | 3801330 B2 | 7/2006 |
| JP | 3835917 B2 | 10/2006 |
| JP | 2008071993 A * | 3/2008 |
| JP | 3813003 B2 | 8/2008 |
| JP | 2009-10338 | 1/2009 |
| JP | 2010-270103 | 12/2010 |
| WO | WO 01/49806 A1 | 7/2001 |
| WO | WO 2005/079118 A1 | 8/2005 |
| WO | WO 2008/114921 A1 | 11/2006 |
| WO | WO 2009/041635 A1 | 4/2009 |
| WO | WO 2010/098458 A1 | 9/2010 |
| WO | WO 2010/114017 A1 | 10/2010 |
| WO | WO 2010/134350 A1 | 11/2010 |
| WO | WO 2010/134352 A1 | 11/2010 |
| WO | WO 2011/024451 A1 | 3/2011 |
| WO | WO 2011/090149 A1 | 7/2011 |
| WO | WO 2012011756 * | 1/2012 |

OTHER PUBLICATIONS

International Search Report and Written Opinion dated Apr. 9, 2013 in PCT/JP2013/052842.
C.W. Tang, et al., "Organic Electroluminescent Diodes", Appl. Phys. Lett. 51, (12), Sep. 21, 1987, American Institute of Physics, 3 pages.

* cited by examiner

*Primary Examiner* — Anthony J Frost
(74) *Attorney, Agent, or Firm* — Oblon, McClelland, Maier & Neustadt, L.L.P.

(57) ABSTRACT

An organic electroluminescence device contains an anode and a cathode facing each other, and intervening therebetween at least two hole transporting layers and a light emitting layer sequentially, and one of the hole transporting layers contains a compound having a particular structure having a fluorene structure at the center thereof, and is not adjacent to the light emitting layer. The organic electroluminescence device has a hole transporting layer having an increased thickness, is capable of being controlled in the thickness of the optical film, and has an enhanced device capability.

34 Claims, No Drawings

ORGANIC ELECTROLUMINESCENCE DEVICE

FIELD

The present invention relates to an organic electroluminescence device, and particularly relates to an organic electroluminescence device that has a hole transporting layer having an increased thickness, is capable of being controlled in the thickness of the optical film, and has an enhanced device capability.

BACKGROUND ART

An organic electroluminescence (EL) device is a self-luminous device utilizing such a principle that a fluorescent substance emits light with recombination energy of holes injected from an anode and electrons injected from a cathode on application of an electric field. An organic EL device containing an organic material as a constitutional material has been actively investigated since C. W. Tang, et al., Eastman Kodak Corporation, reported a low voltage driving organic EL device with a stacked device (C. W. Tang and S. A. Vanslyke, Applied Physics Letters, vol. 51, p. 913 (1987), etc.).

For example, Patent Documents 1 to 4 disclose a diamine compound having a fluorene skeleton between two nitrogen atoms, and disclose the use of the diamine compound as a material of a hole transporting layer that is adjacent to a light emitting layer, by which crystallization of the hole transporting material due to heat generation or the like on light emission in the light emitting layer is suppressed, and thus an organic EL device is provided that is improved in stability and durability as compared to a diamine compound having a biphenylene group between two nitrogen atoms or a monoamine compound having a fluorene skeleton.

Patent Document 5 discloses the use of a diamine compound having two nitrogen atoms bonded through a biphenylene group as a material of a first hole transporting layer, and the use of an aromatic amine derivative having a dibenzofuran structure and a carbazole structure as a material of a second hole transporting layer that is adjacent to a light emitting layer, and thus an organic EL device is provided that has a low driving voltage and a long service life. Patent Document 6 discloses the use of a diamine compound having two nitrogen atoms bonded through a biphenylene group in a first hole transporting layer, and the use of an amine compound having a particular hetero aryl structure in a second hole transporting layer, in a phosphorescent organic EL device, by which the second hole transporting layer has electron blocking property, electroresistance, and hole injecting and transporting property, and thus an organic EL device is provided that has a high efficiency and a long service life. Patent Document 7 discloses the use of a compound having a carbazole ring structure in a hole transporting layer that is adjacent to a light emitting layer, and thus an organic EL device is provided that has a high light emitting efficiency and a low driving voltage.

In summary, an organic EL device, particularly a phosphorescent device, has been enhanced in the capability of the device in such a manner that the hole transporting layer has a two-layer structure including the first hole transporting layer and the second hole transporting layer, and a highly functional material is used in the second hole transporting layer that is adjacent to the light emitting layer.

The capabilities that are required for the second hole transporting layer are as follows: (i) the second hole transporting layer has higher triplet energy (preferably 2.6 eV or more) for preventing the excitation energy of the phosphorescent light emitting layer from being diffused; (ii) the second hole transporting layer has electroresistance since the layer is adjacent to the light emitting layer; (iii) the second hole transporting layer is an organic layer that has a small affinity (preferably 2.4 eV or less) for preventing electrons from leaking from the light emitting layer; and (iv) the second hole transporting layer is an organic layer that has a large ionization potential (preferably 5.5 eV or more) for accelerating injection of holes to the light emitting layer. As a material satisfying these requirements, a molecular skeleton with high electroresistance having a triphenylamine skeleton and bonded thereto a hetero aryl ring, such as carbazole and dibenzofuran has been preferably used.

The first hole transporting layer is generally demanded to be excellent in the hole injection property to the second hole transporting layer.

It has been considered that a compound having a nature of a p type semiconductor (which may also be referred to herein as an acceptor material) is contained in the hole injecting layer for enhancing the hole injection property (see Patent Documents 8 and 9).

In view of the progress of research and development of the organic EL devices mentioned above, it is necessary in a commercial device that light that is internally emitted is taken out to the outside of the device with high efficiency for each of the light emission colors of the organic EL device. Accordingly, it is necessary to control the optical path length of the total device by controlling the thickness of the hole transporting layer having a higher carrier transporting property than the other organic layers. Under the present situation, therefore, a hole transporting material is demanded that has a high mobility to such an extent that the driving voltage may not be increased even when the thickness of the hole transporting layer is increased, and it is also demanded that a hole transporting material having a large carrier formation amount through interaction with an acceptor material, and the hole transporting material is used in the first hole transporting layer.

RELATED ART DOCUMENTS

Patent Documents

Patent Document 1
  Japanese Patent No. 3,813,003
Patent Document 2
  Japanese Patent No. 3,801,330
Patent Document 3
  Japanese Patent No. 3,792,029
Patent Document 4
  Japanese Patent No. 3,835,917
Patent Document 5
  WO 2010/114017
Patent Document 6
  WO 2009/041635
Patent Document 7
  WO 2011/024451
Patent Document 8
  WO 01/49806 (JP-A-2003-519432)
Patent Document 9
  WO 2011/090149

SUMMARY OF THE INVENTION

Problems to be Solved by the Invention

The present invention has been made for solving the aforementioned problems, and an object thereof is to provide an organic EL device that has an increased efficiency and a prolonged service life.

Means for Solving the Problems

As a result of earnest investigations made by the present inventors for attaining the object, it has been found that an organic EL device may have an increased efficiency and a prolonged service life to solve the problems in such a manner that two or more hole transporting layers are provided between an anode and a cathode of the organic EL device, and a compound represented by the following formula (1) is contained in the hole transporting layer that is not adjacent to the light emitting layer, thereby enhancing interaction with an acceptor material and preventing the driving voltage from being increased even when the thickness of the hole transporting layer is increased, and thus holes are injected to the light emitting layer with high efficiency. In addition, it has also been found that the use of a heteroaryl-substituted amine derivative in the hole transporting layer that is adjacent to the light emitting layer achieves excellent advantages not only as a phosphorescent organic EL device but also as a fluorescent organic EL device. The present invention has been completed based on the knowledge.

The present invention provides an organic EL device containing an anode and a cathode facing each other, and intervening therebetween at least two hole transporting layers and a light emitting layer sequentially, one of the hole transporting layers containing a compound represented by the following formula (1) and being not adjacent to the light emitting layer:

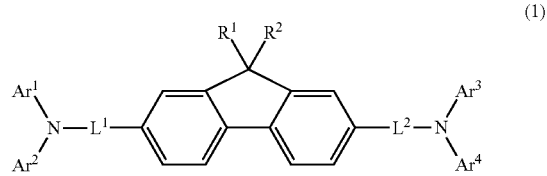

(1)

wherein in the formula (1),
$R^1$ and $R^2$ each independently represent a hydrogen atom or an alkyl group having from 1 to 10 carbon atoms;
$L^1$ and $L^2$ each independently represent a single bond or a substituted or unsubstituted arylene group having from 6 to 30 ring carbon atoms; and
$Ar^1$ to $Ar^4$ each independently represent a substituted or unsubstituted aryl group having from 6 to 30 ring carbon atoms.

Advantages of the Invention

The organic EL device of the present invention may have a hole transporting layer having an increased thickness, may enable control of the optical film thickness of the organic EL device, and may be enhanced in the light emitting efficiency and the service life of the device.

EMBODIMENTS FOR CARRYING OUT THE INVENTION

The organic EL device of the present invention contains an anode and a cathode facing each other, and intervening therebetween at least two hole transporting layers and a light emitting layer sequentially, and one of the hole transporting layers contains a compound represented by the following formula (1) and is not adjacent to the light emitting layer:

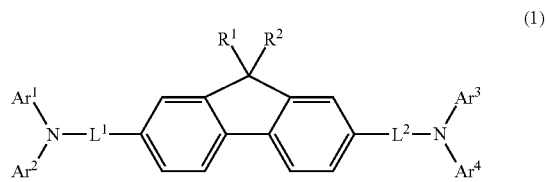

(1)

wherein in the formula (1),
$R^1$ and $R^2$ each independently represent a hydrogen atom or an alkyl group having from 1 to 10 carbon atoms;
$L^1$ and $L^2$ each independently represent a single bond or a substituted or unsubstituted arylene group having from 6 to 30 ring carbon atoms; and
$Ar^1$ to $Ar^4$ each independently represent a substituted or unsubstituted aryl group having from 6 to 30 ring carbon atoms.

The compound represented by the formula (1) is preferably a compound represented by the following formula (2) or (3). $R^1$, $R^2$, $L^2$ and $Ar^1$ to $Ar^4$ have the same meanings as in the formula (1).

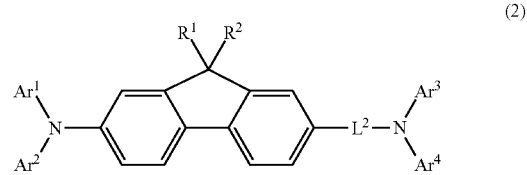

(2)

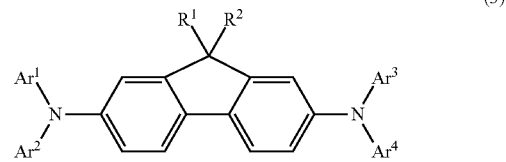

(3)

Examples of the alkyl group having from 1 to 10 carbon atoms represented by $R^1$ and $R^2$ include a methyl group, an ethyl group, a n-propyl group, an isopropyl group, a n-butyl group, a s-butyl group, an isobutyl group, a t-butyl group, a n-pentyl group, a n-hexyl group, a n-heptyl group, a n-octyl group, a n-nonyl group, a n-decyl group and a neopentyl group, and a methyl group, an ethyl group, a n-propyl group, an isopropyl group, a n-butyl group, a s-butyl group, an isobutyl group and a t-butyl group are preferred.

Examples of the aryl group having from 6 to 30 ring carbon atoms represented by $Ar^1$ to $Ar^4$ include a phenyl group, a naphthyl group, an anthryl group, a phenanthryl group, a naphthacenyl group, a chrysenyl group, a pyrenyl group, a biphenyl group, a terphenyl group, a tolyl group, a fluorantenyl group and a fluorenyl group, and a phenyl group, a naphthyl group, a biphenyl group and a terphenyl group are preferred.

Examples of the arylene group having from 6 to 30 ring carbon atoms represented by $L^1$ and $L^2$ include divalent groups derived from the aryl groups represented by $Ar^1$ to $Ar^4$, and a phenylene group is preferred.

Examples of an arbitrary substituent, which is referred for the language "substituted or unsubstituted" described above and later, include a halogen atom (such as fluorine, chlorine, bromine and iodine), a cyano group, an alkyl group having from 1 to 20 (preferably from 1 to 6) carbon atoms, a cycloalkyl group having from 3 to 20 (preferably from 5 to 12) carbon atoms, an alkoxy group having from 1 to 20 (preferably from 1 to 5) carbon atoms, a haloalkyl group having from 1 to 20 (preferably from 1 to 5) carbon atoms, a haloalkoxy group having from 1 to 20 (preferably from 1 to 5) carbon atoms, an alkylsilyl group having from 1 to 10 (preferably from 1 to 5) carbon atoms, an aryl group having from 6 to 30 (preferably from 6 to 18) ring carbon atoms, an aryloxy group having from 6 to 30 (preferably from 6 to 18) ring carbon atoms, an arylsilyl group having from 6 to 30 (preferably from 6 to 18) carbon atoms, an aralkyl group having from 7 to 30 (preferably 7 to 20) carbon atoms and a heteroaryl group having from 5 to 30 (preferably from 5 to 18) ring carbon atoms.

In the present specification, the language "from a to b carbon atoms" in the expression "a substituted or unsubstituted X group having from a to b carbon atoms" means the number of carbon atoms in the case where the X group is unsubstituted, and does not include the number of carbon atoms of the substituent when the X group is substituted. In the compound represented by the formula (1) used in the present invention, a part or the whole of the hydrogen atoms thereof may be deuterium atoms.

Specific examples of the compound represented by the formula (1) used in the present invention are shown below, but the present invention is not limited thereto.

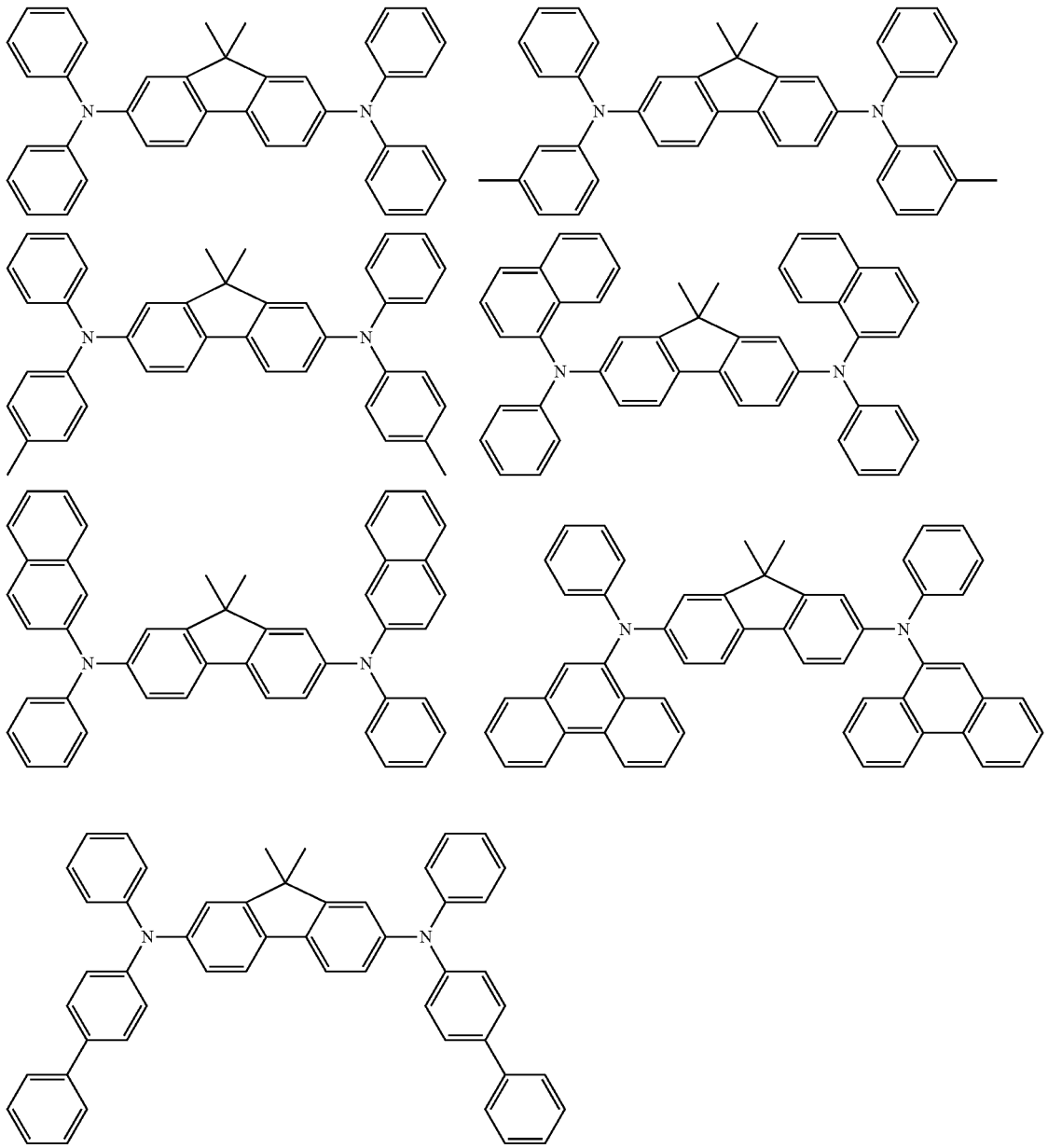

-continued
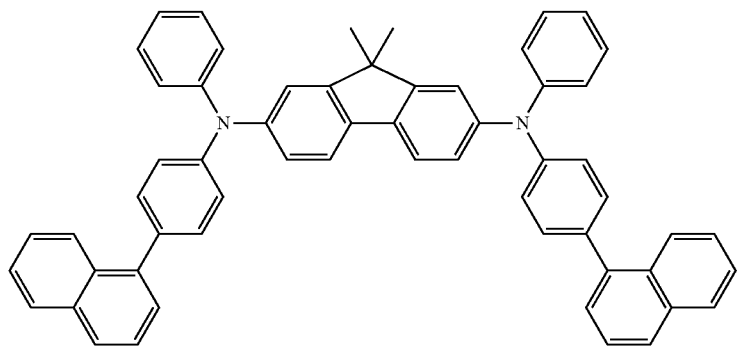
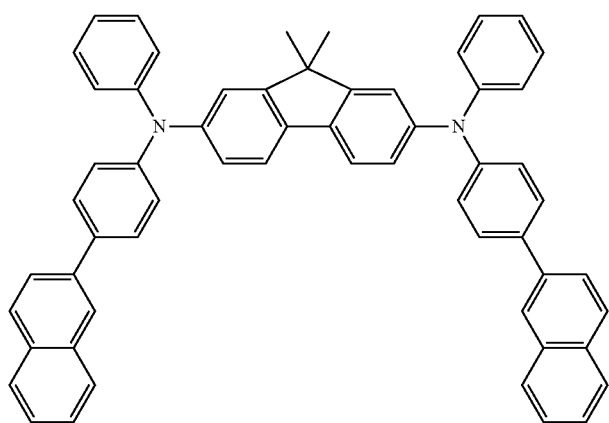
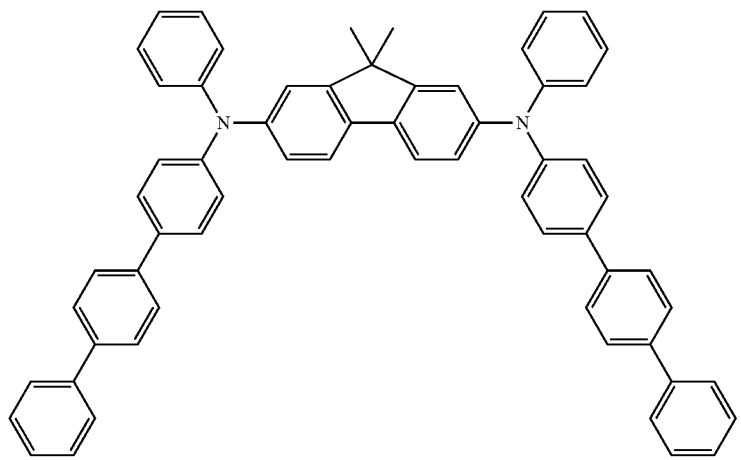
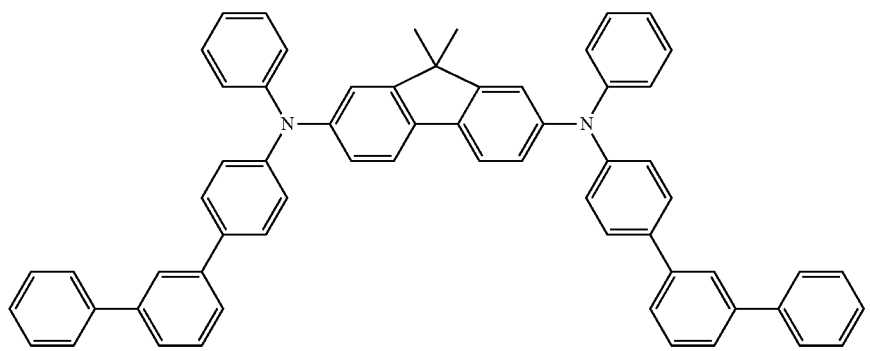

-continued
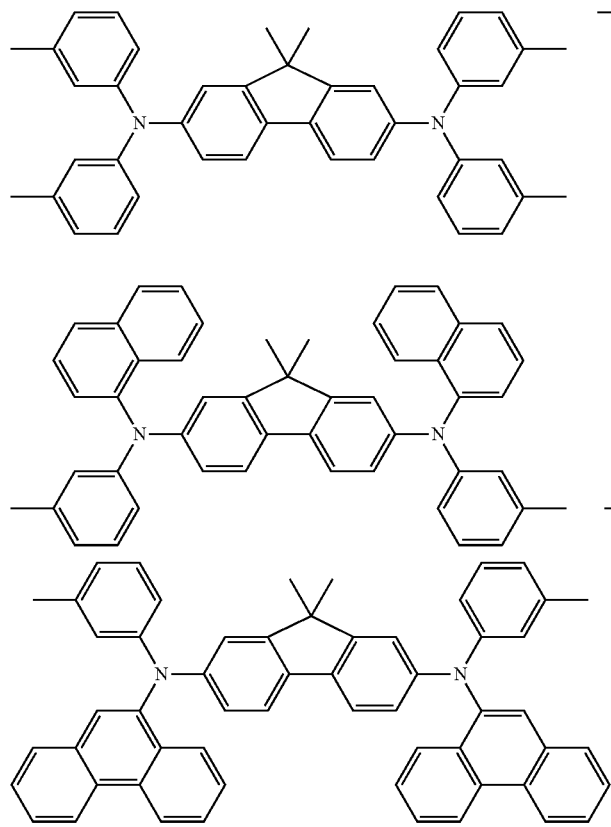
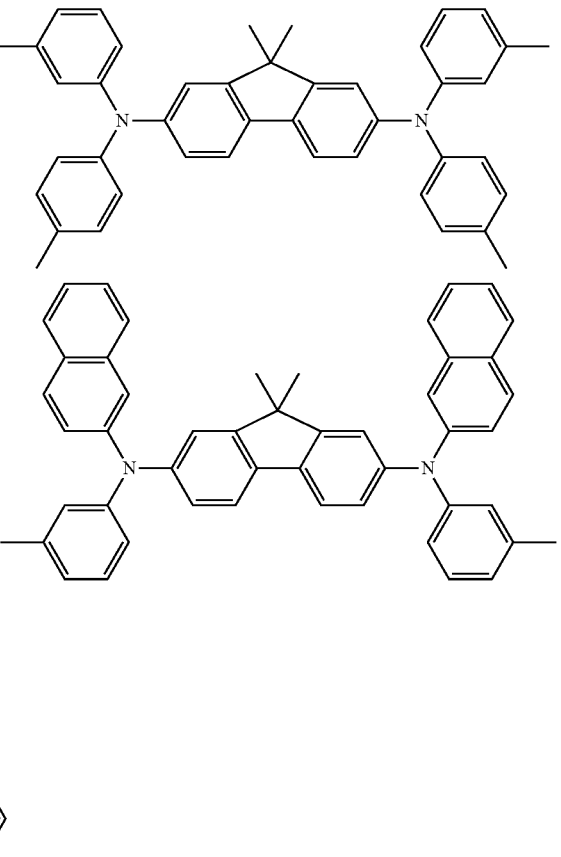
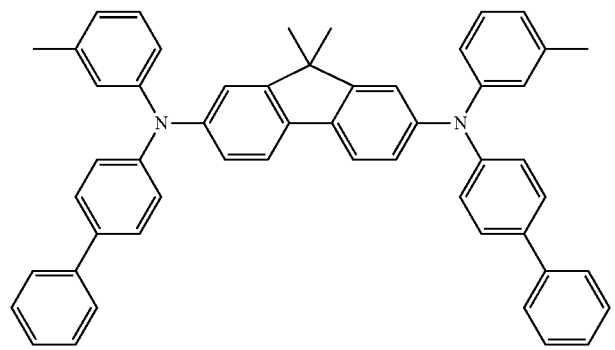
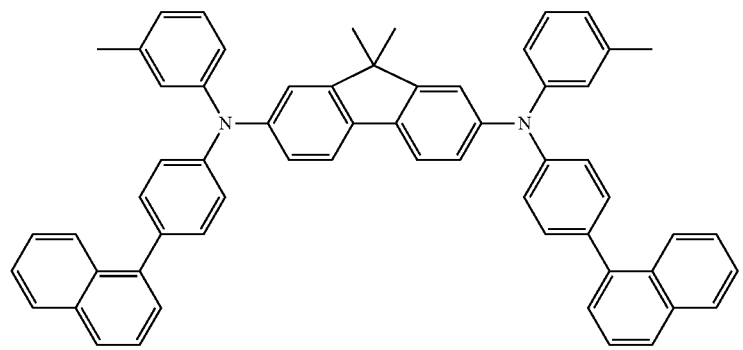

-continued
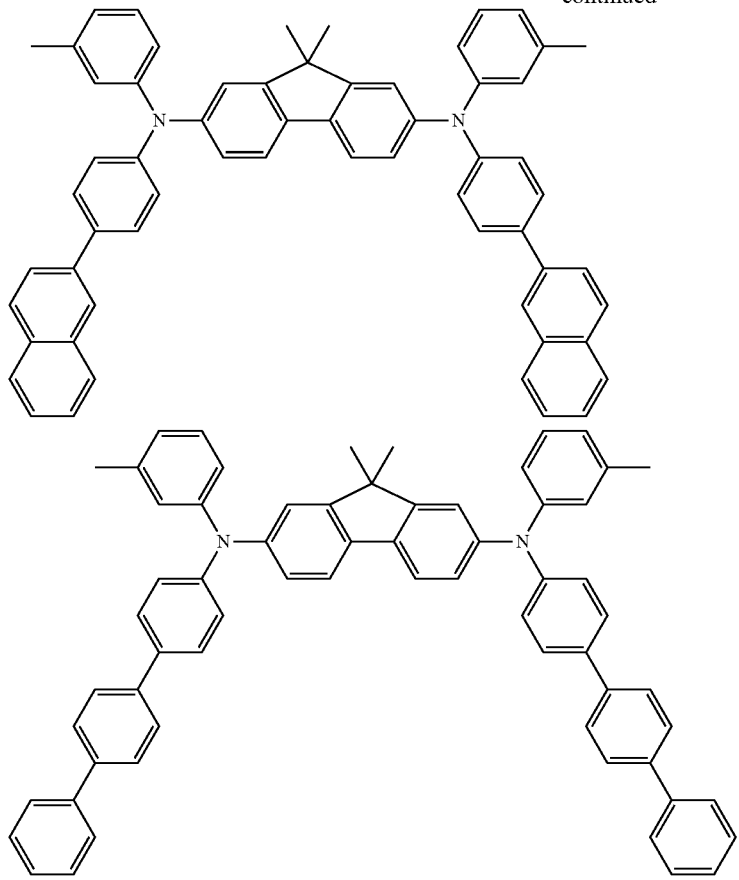
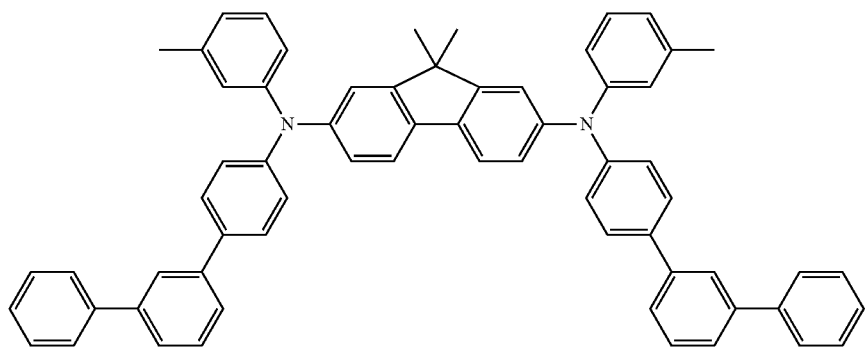
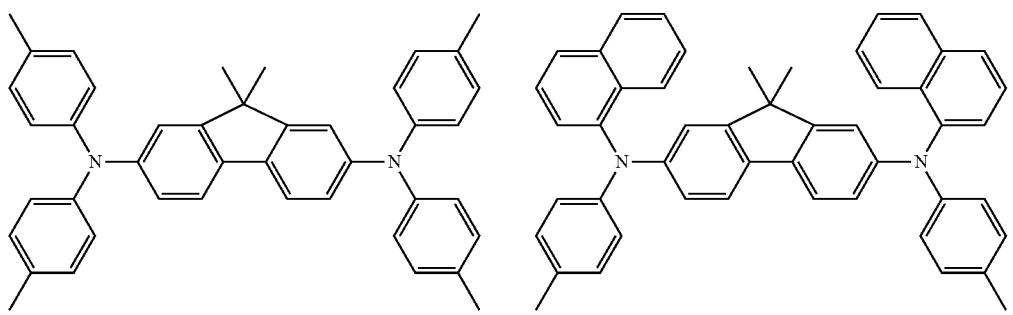

-continued
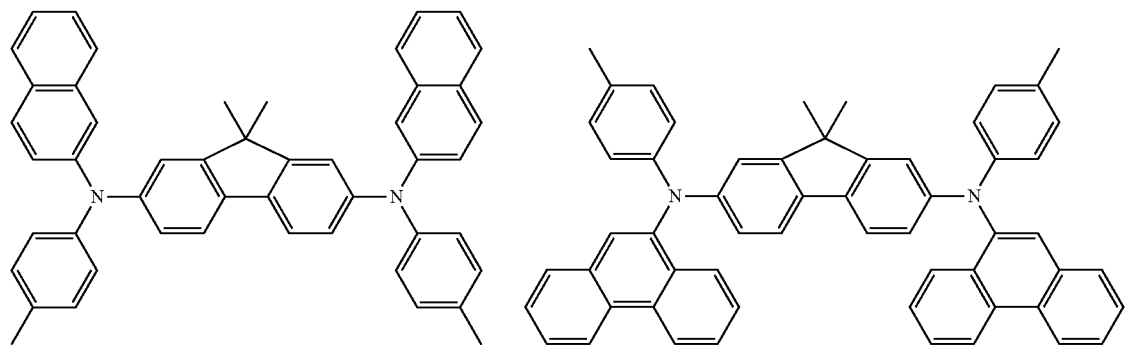
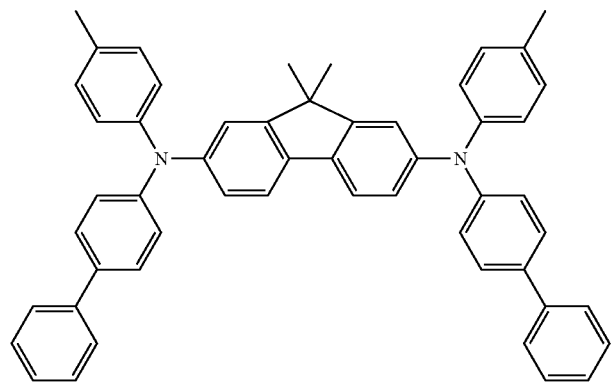
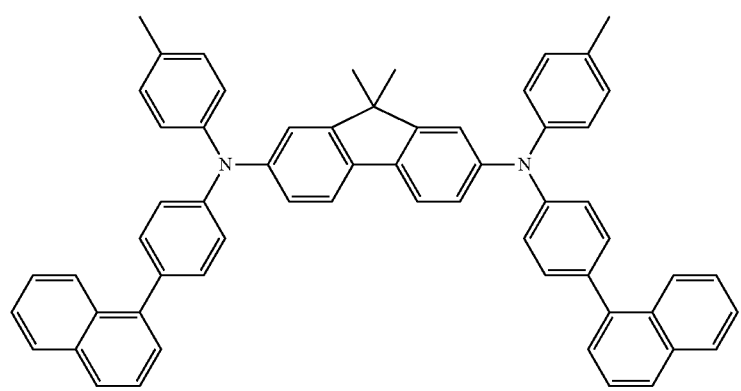
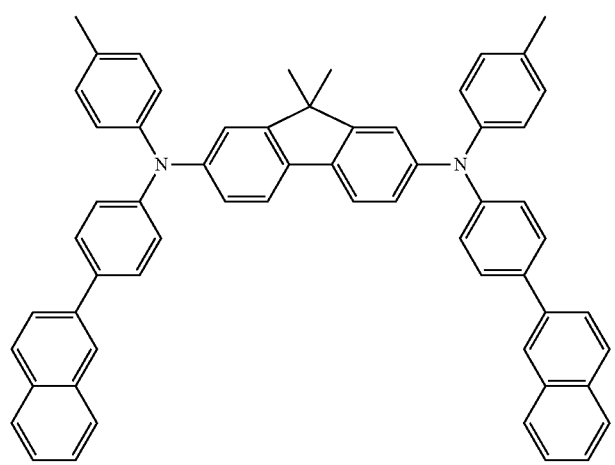

-continued
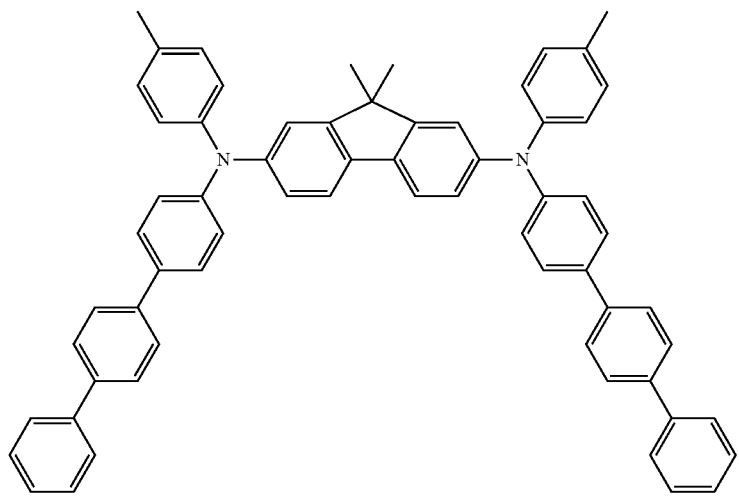
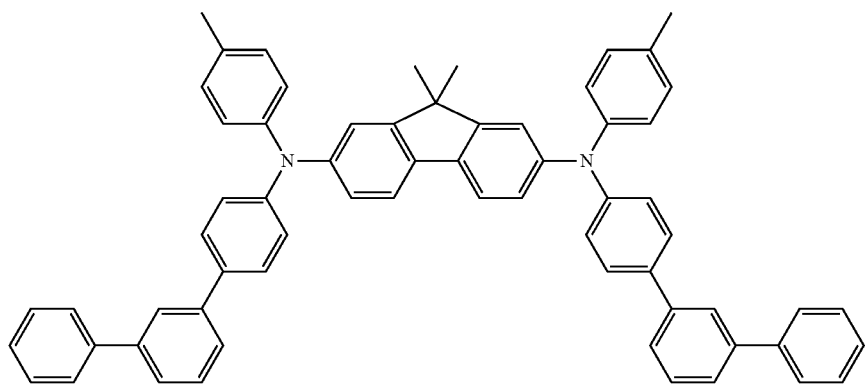
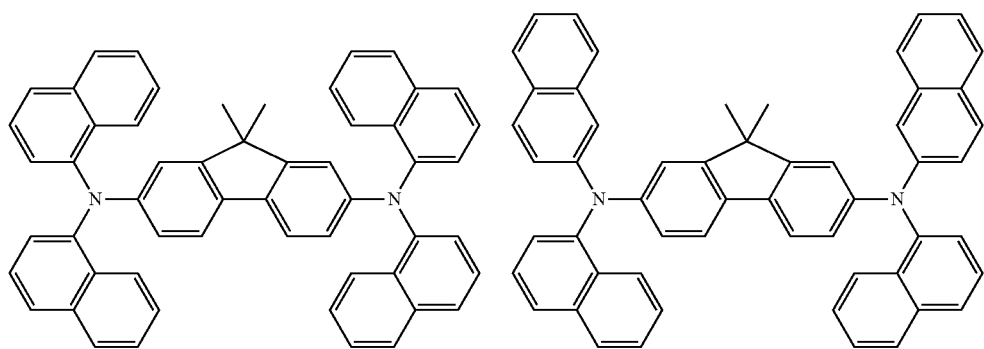
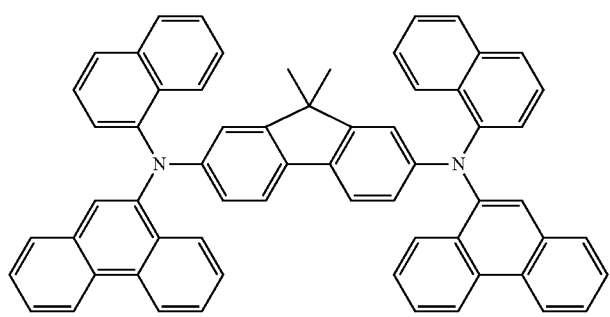

-continued
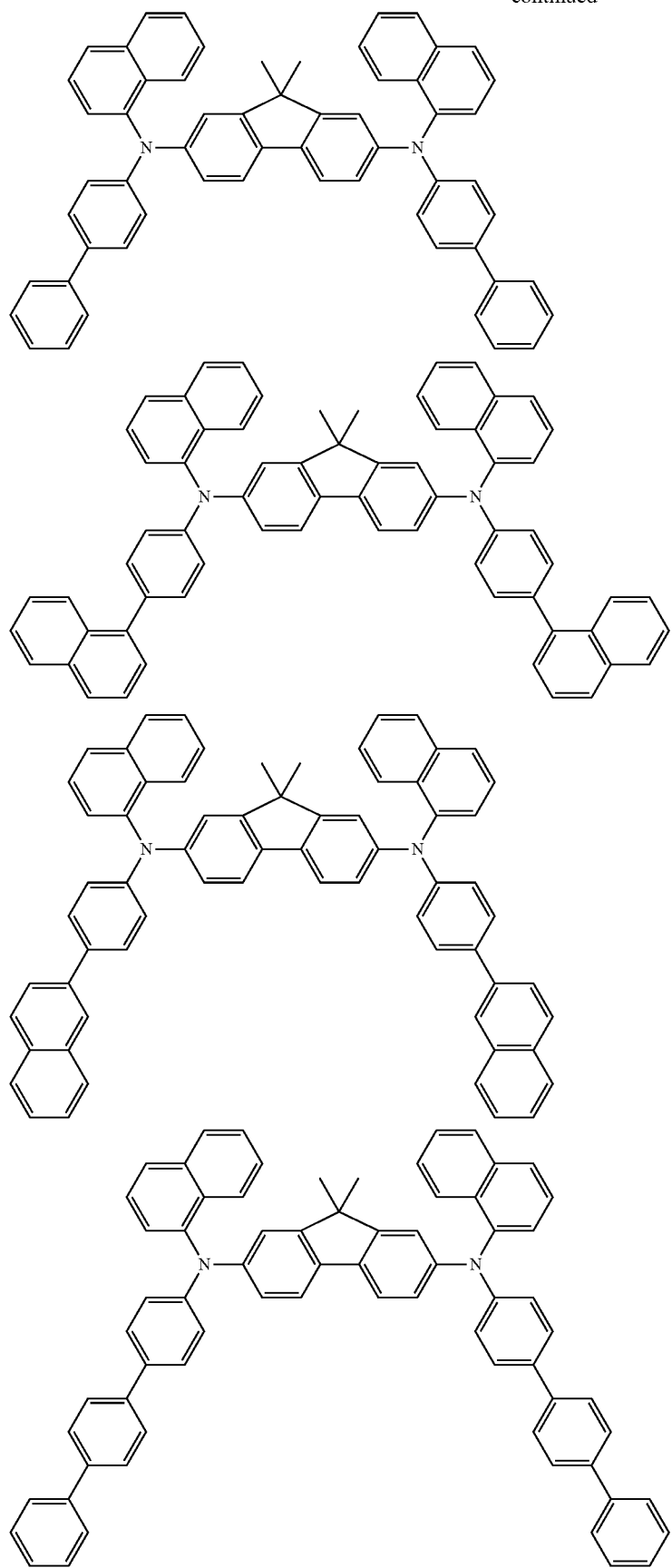

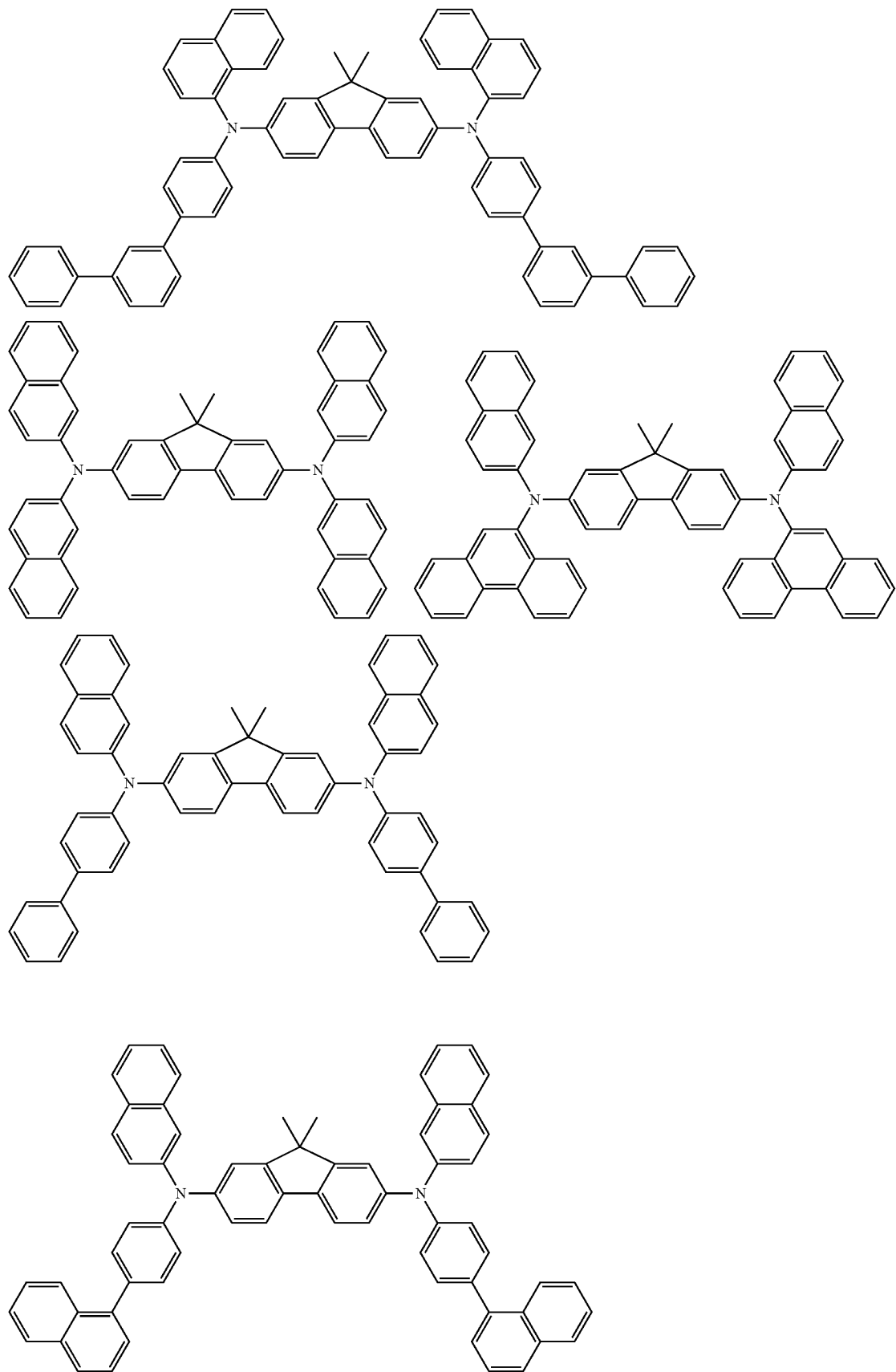

-continued
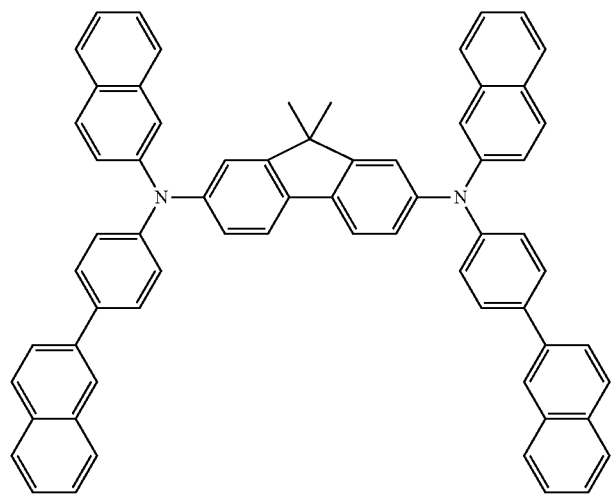
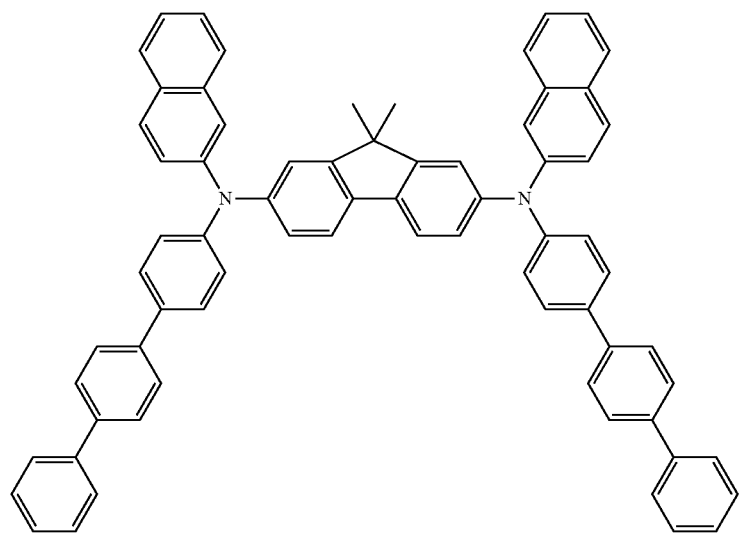
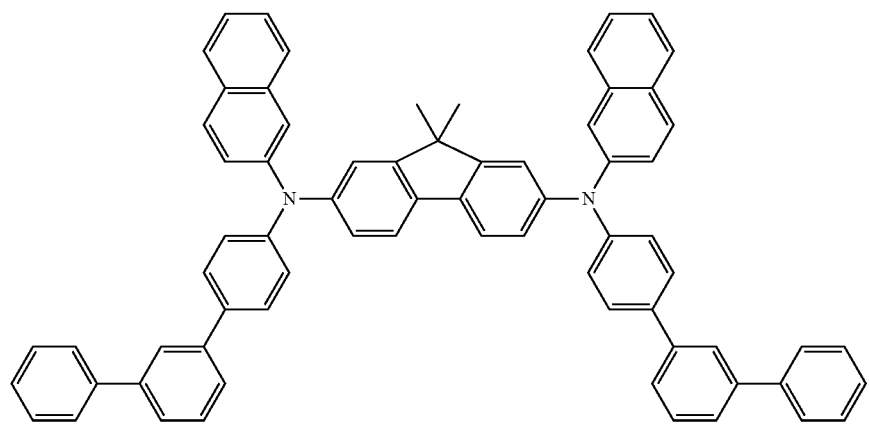

-continued
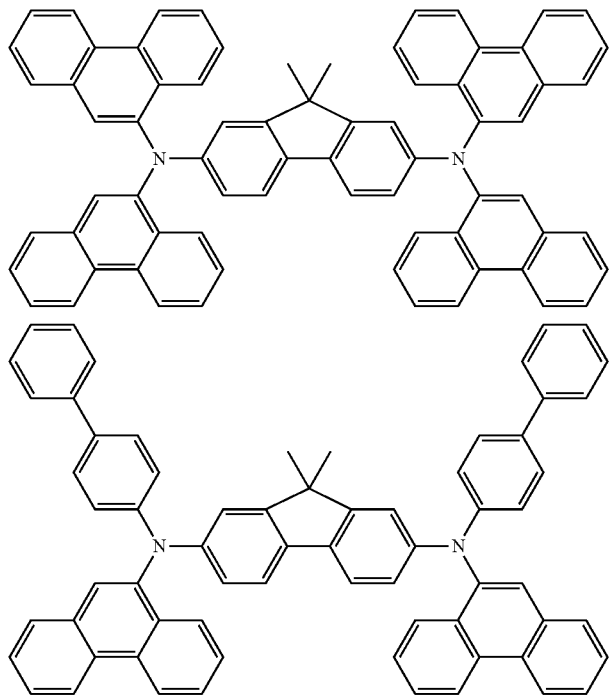
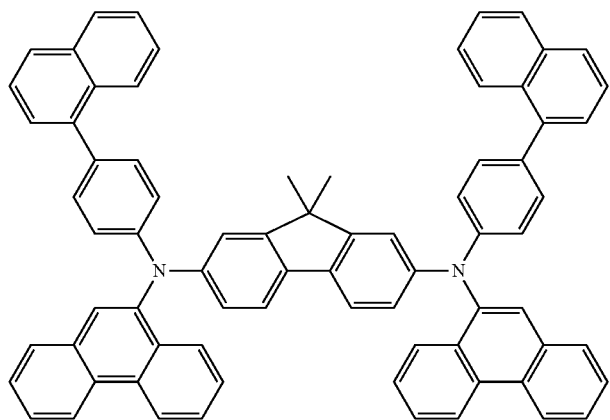
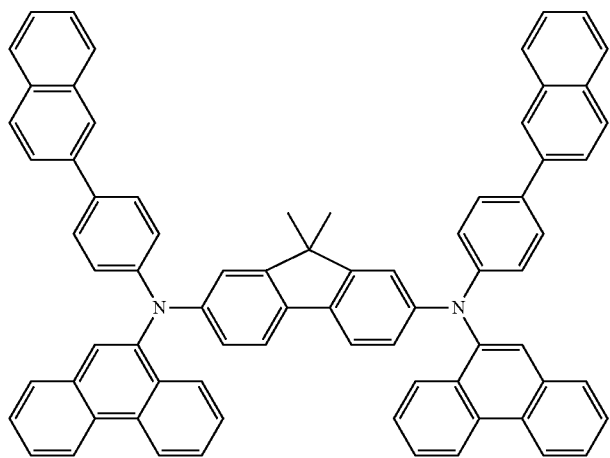

-continued
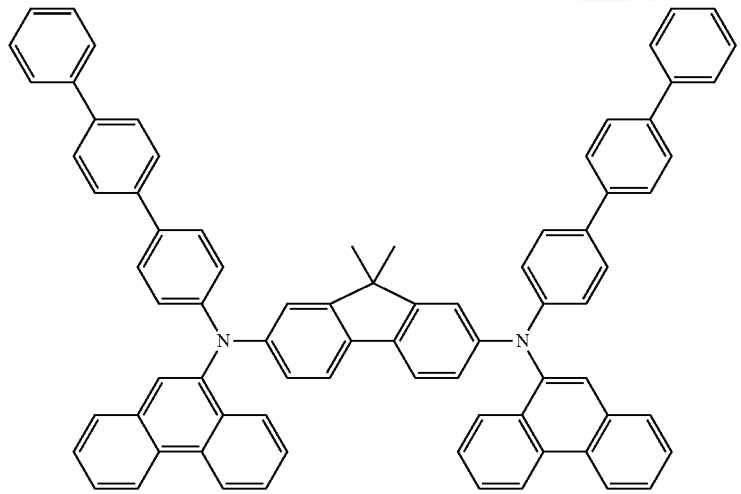
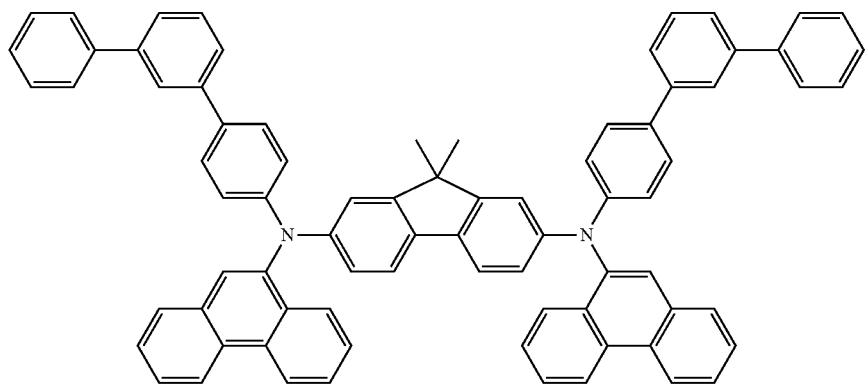
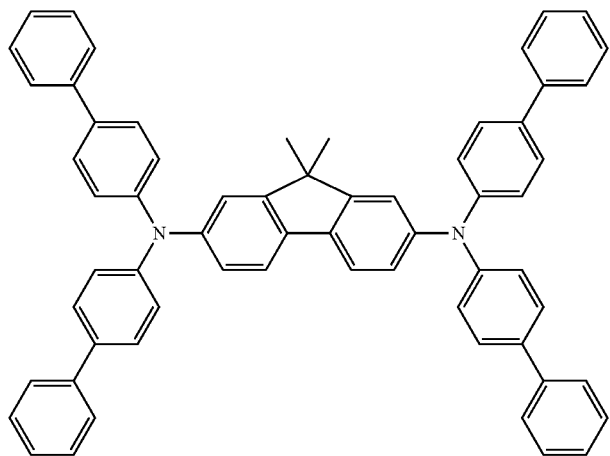

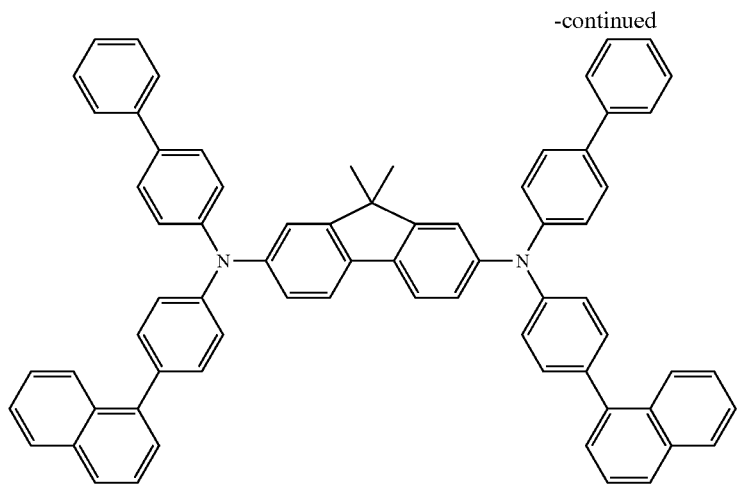
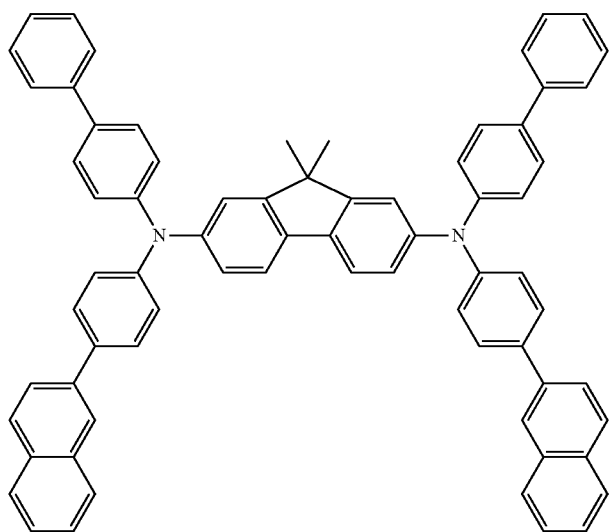
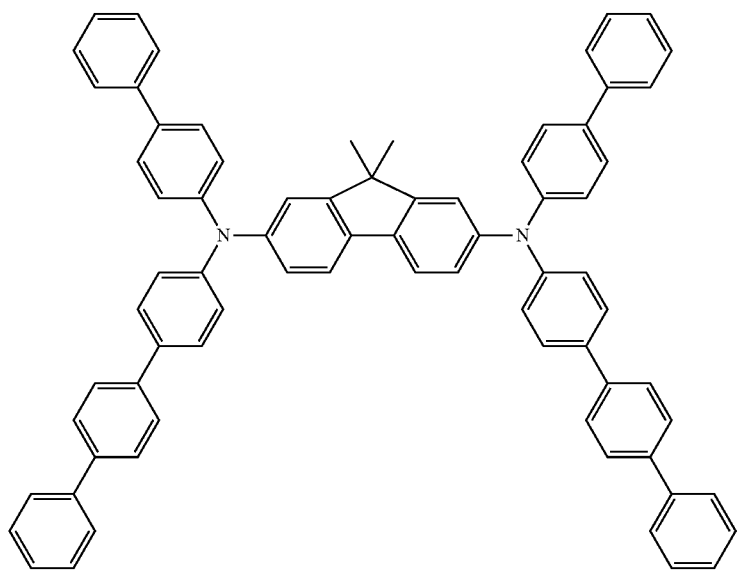

-continued
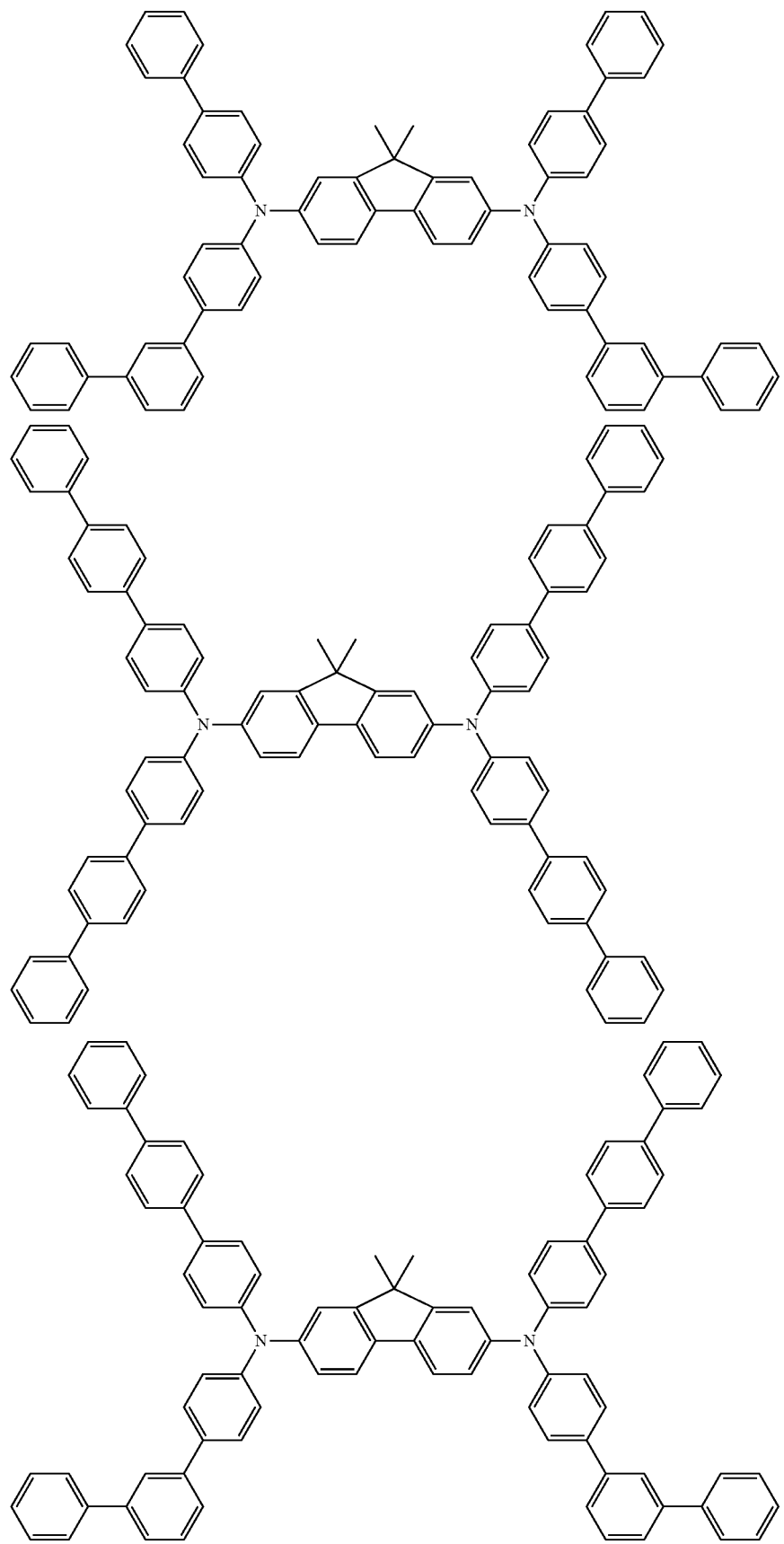

-continued
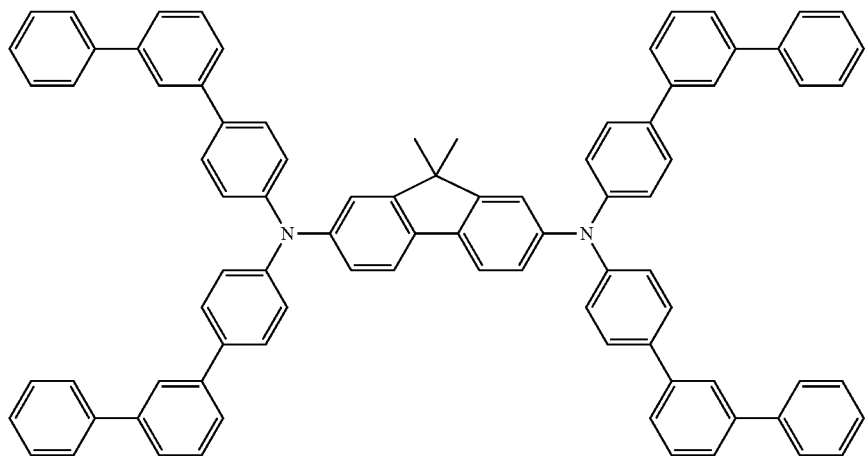
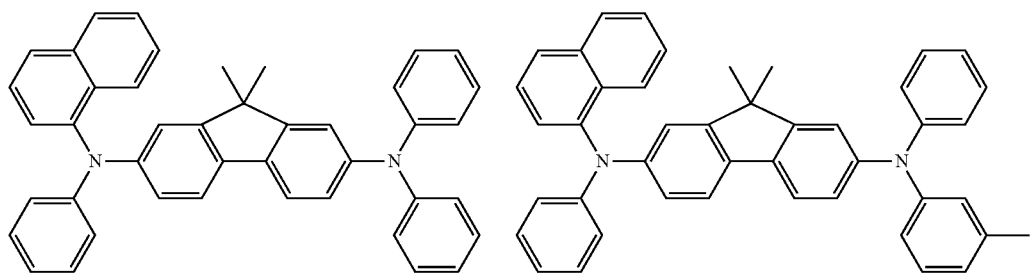
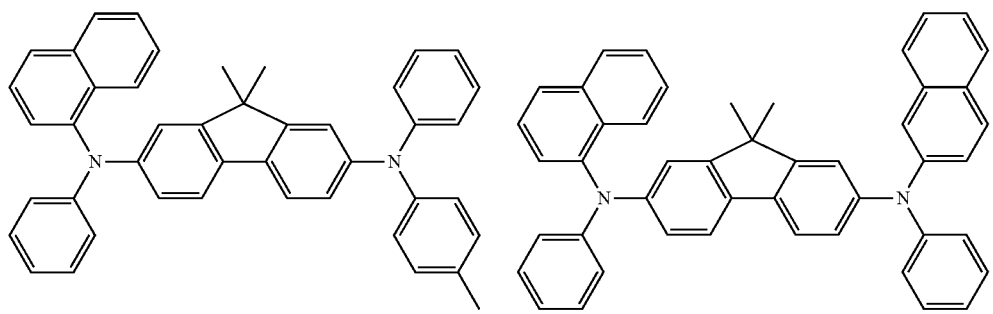
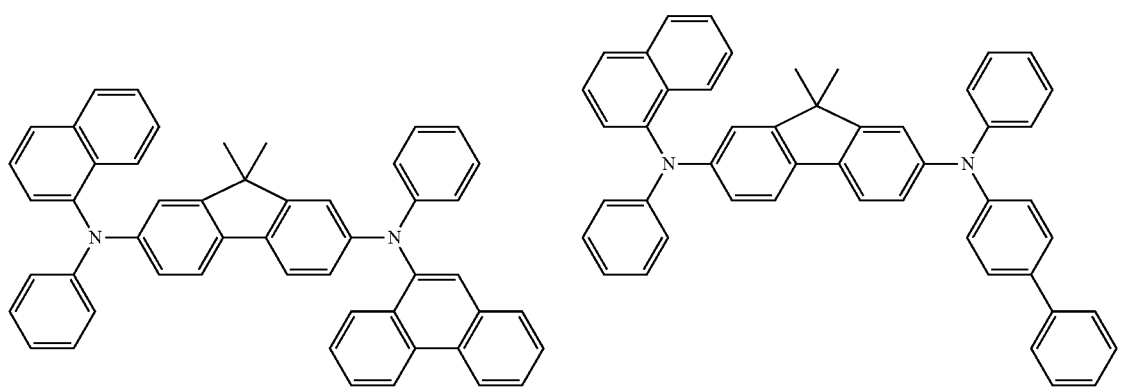

-continued
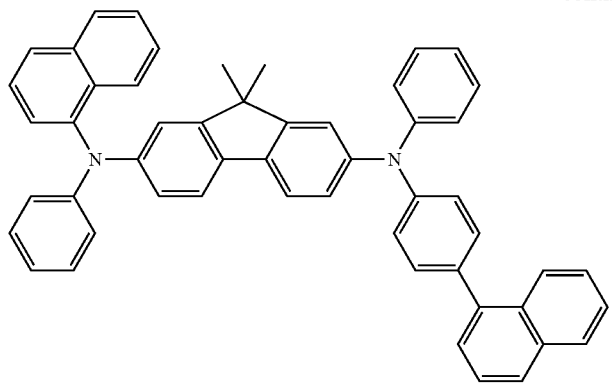
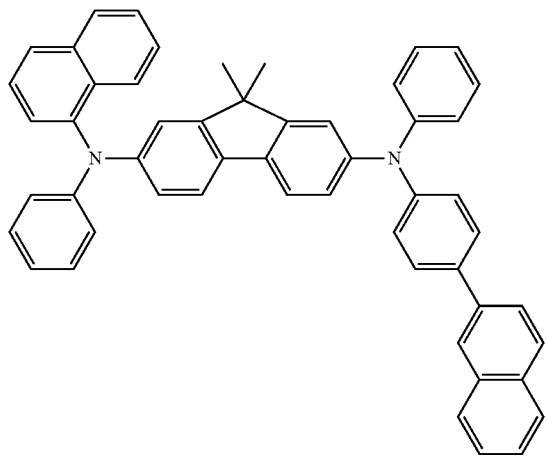
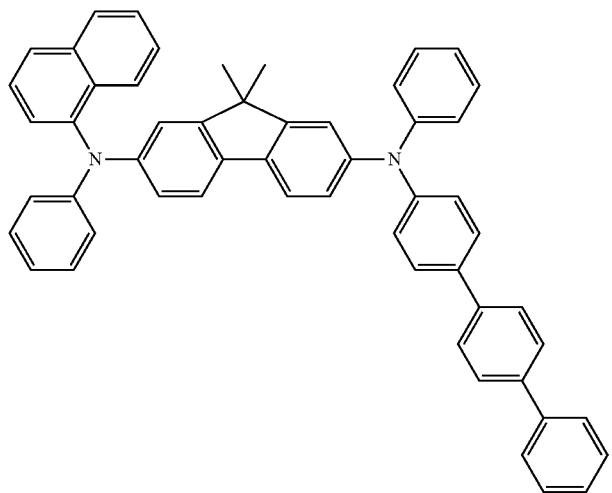
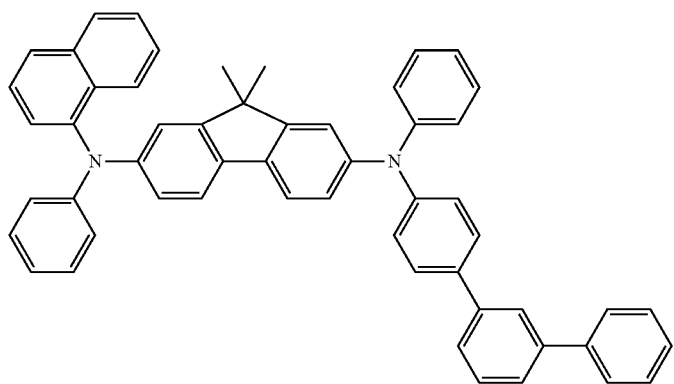

-continued
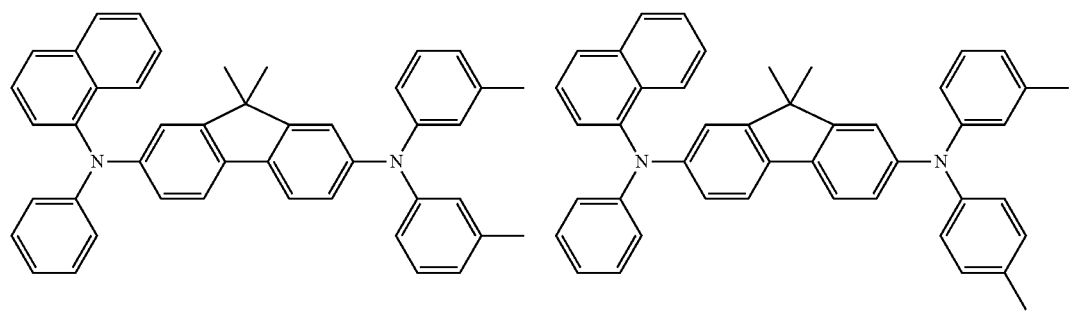
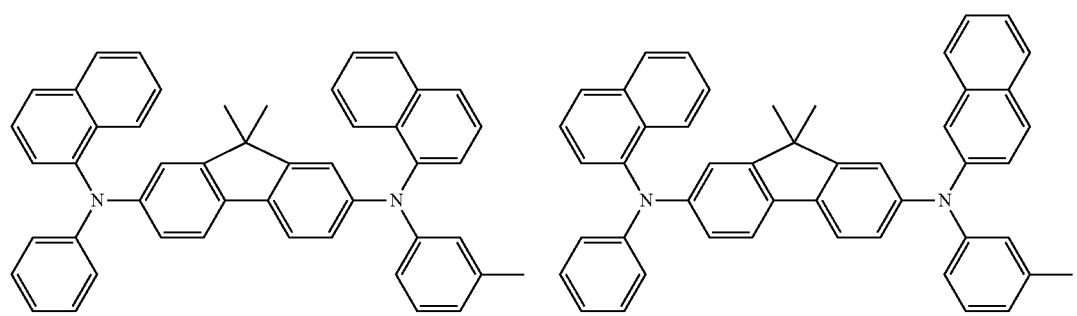
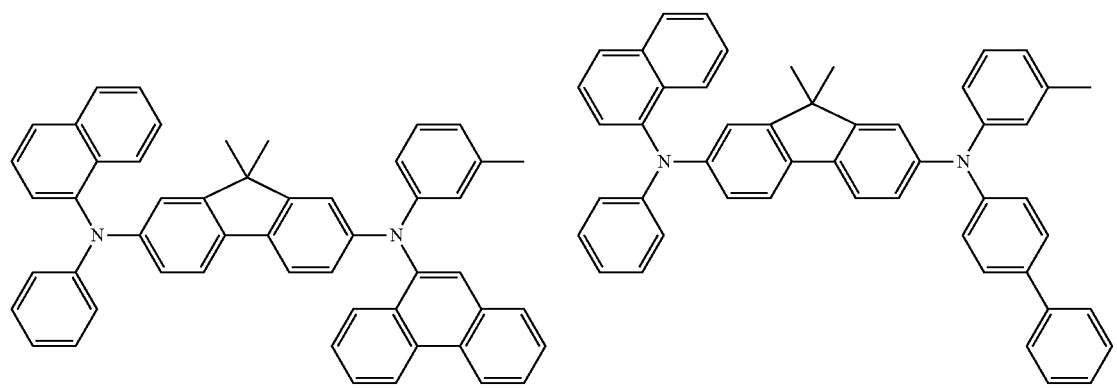
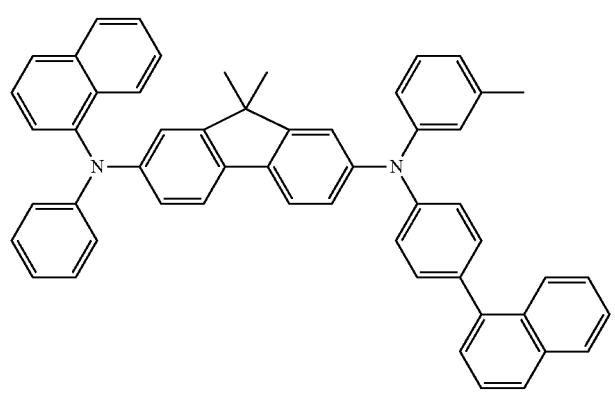

-continued
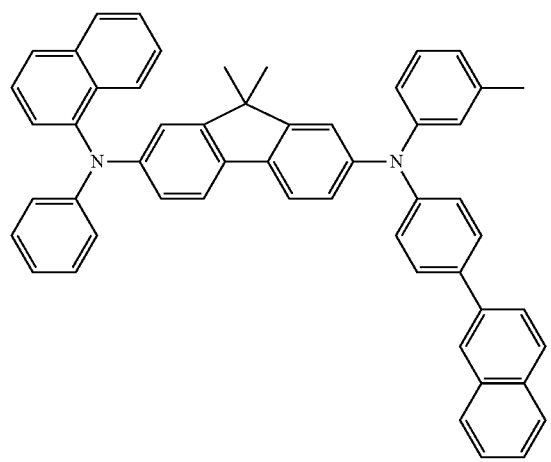
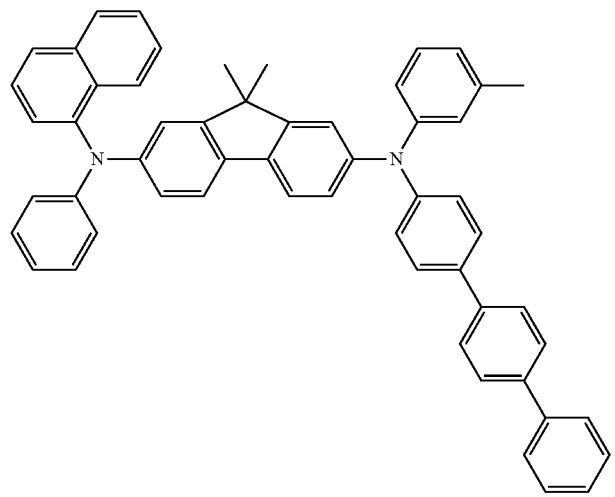
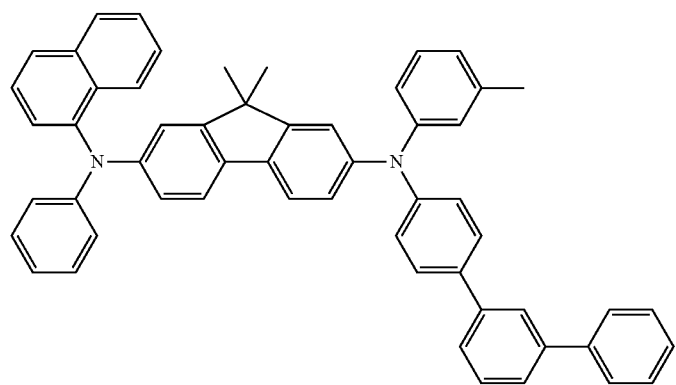
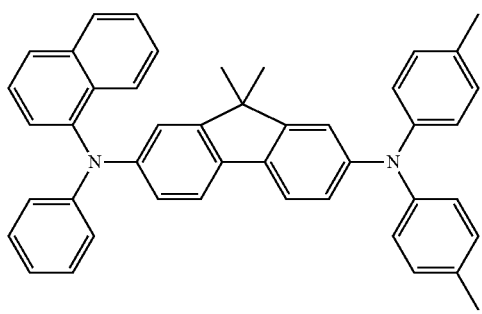
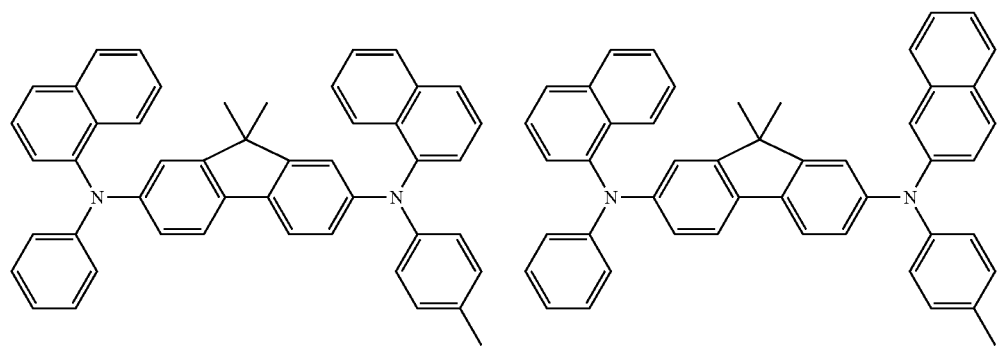

-continued
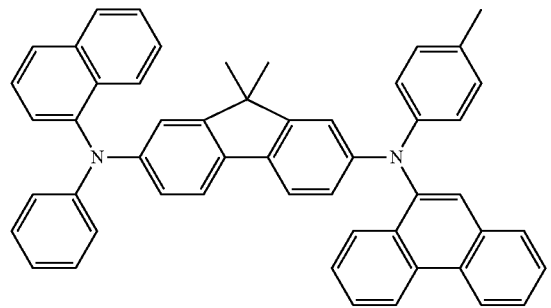
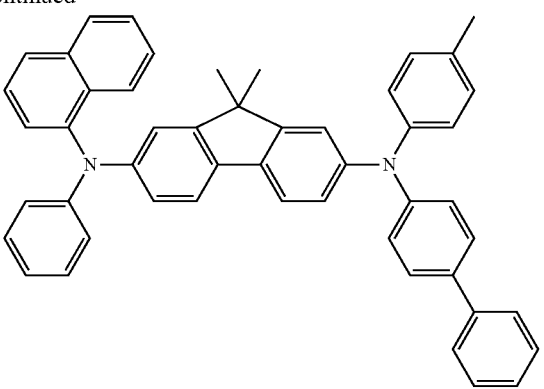
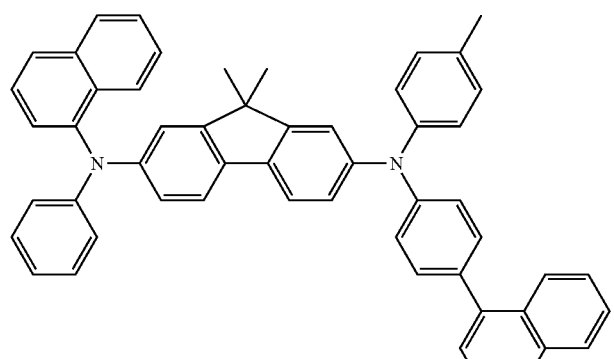
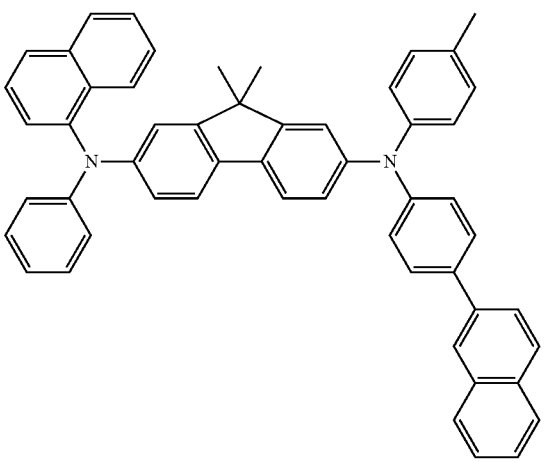
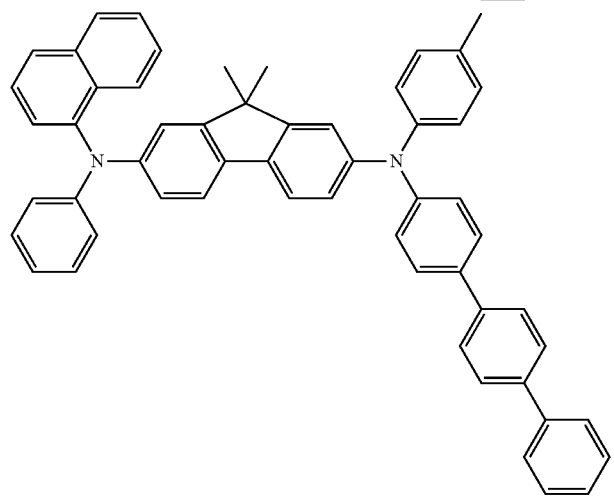
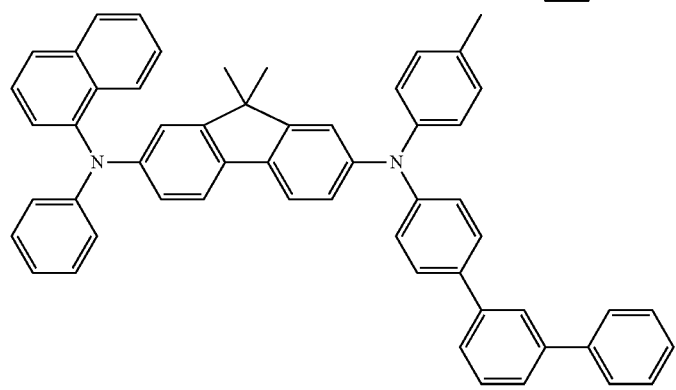

-continued
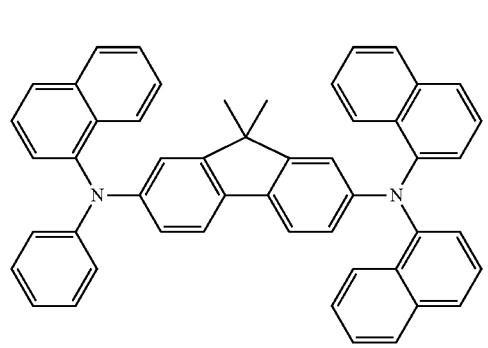
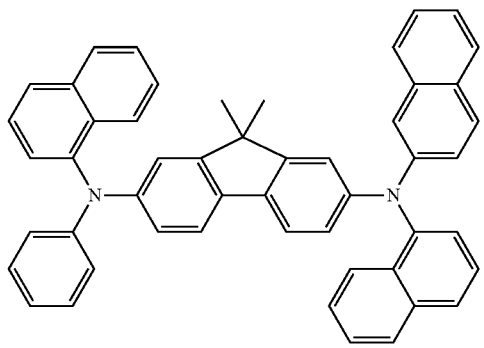
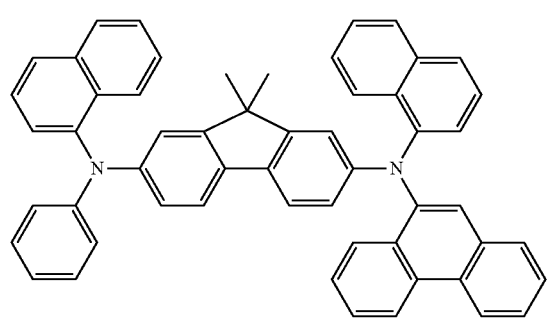
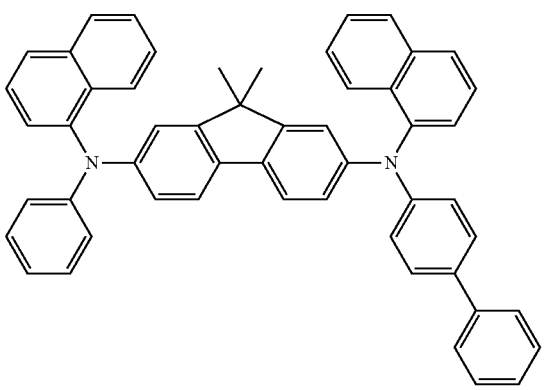
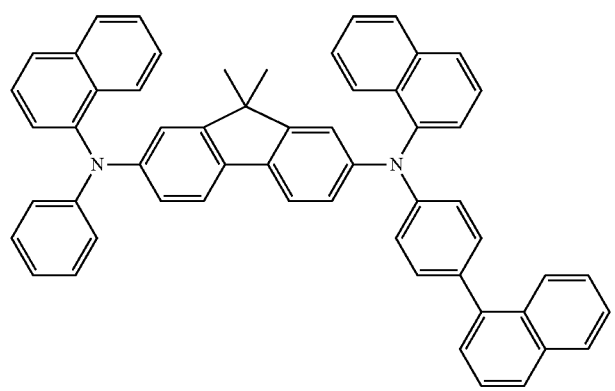
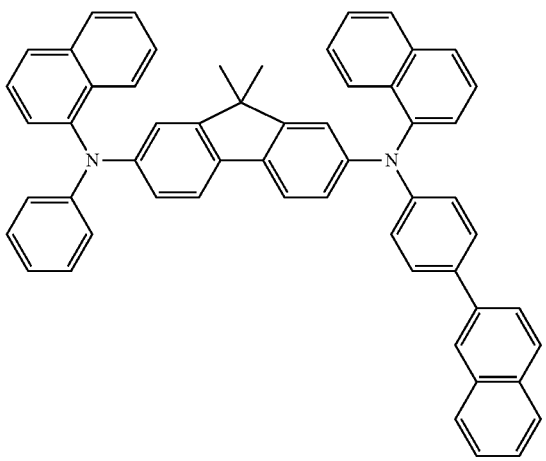
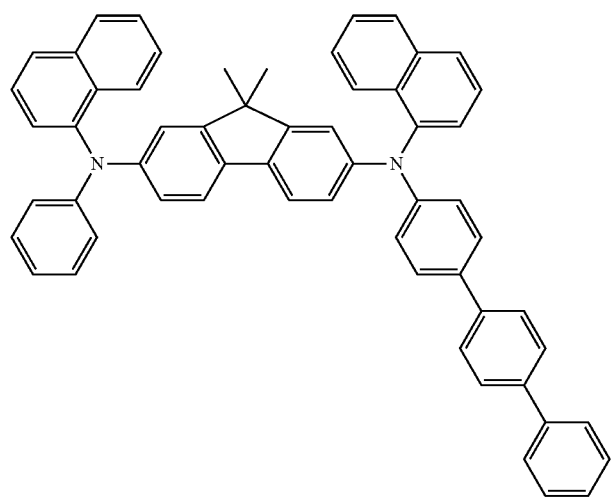

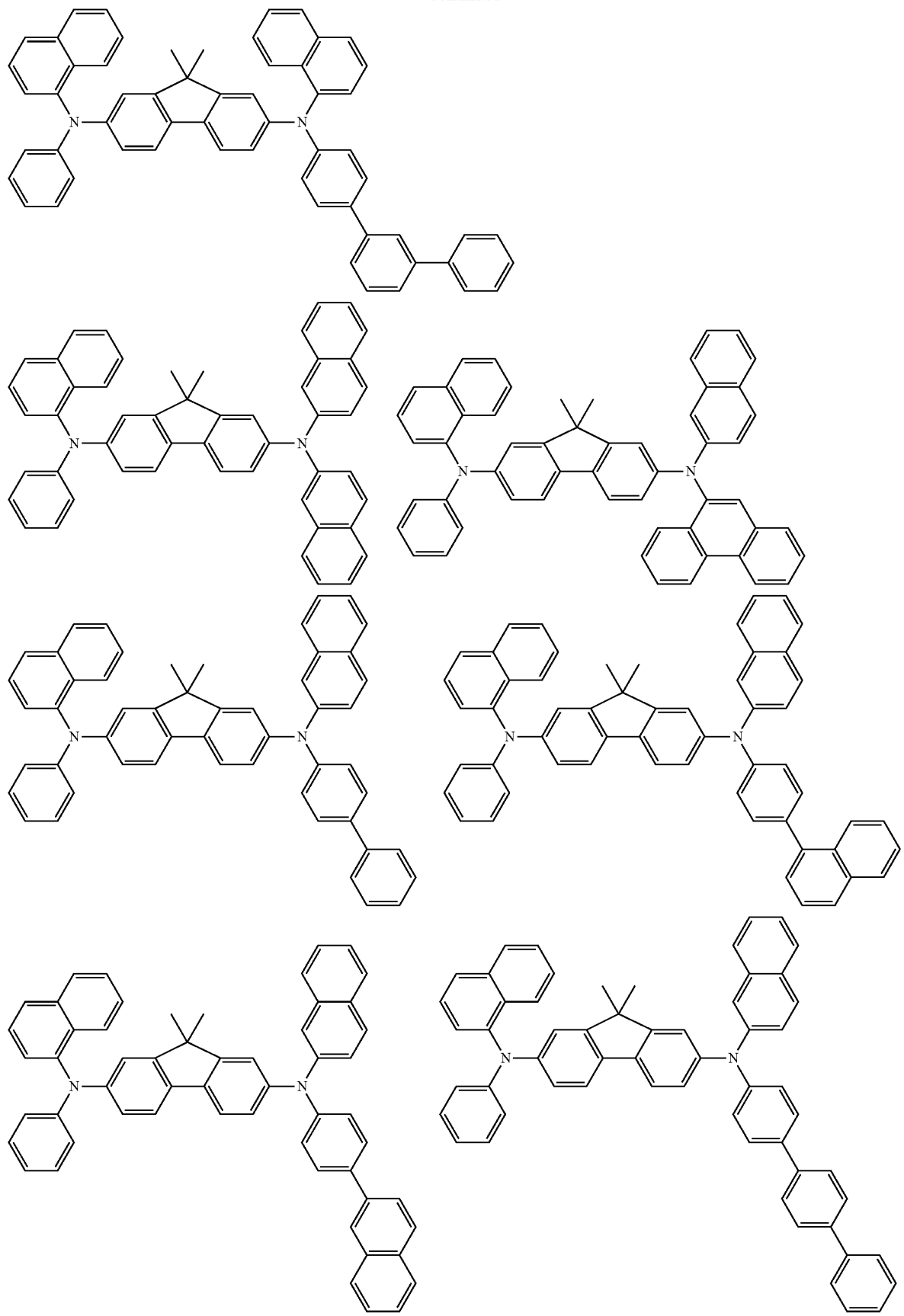

-continued
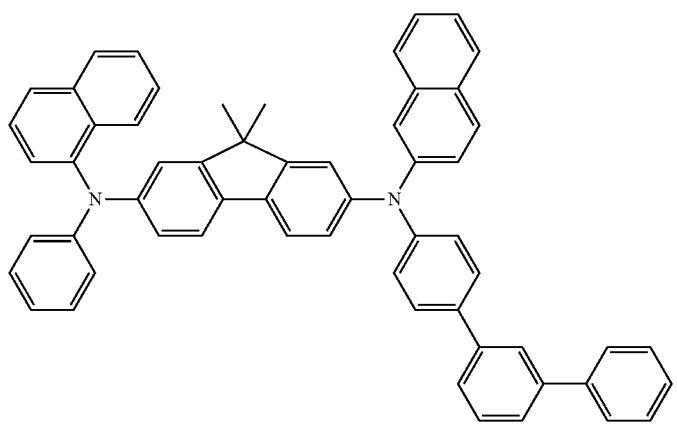
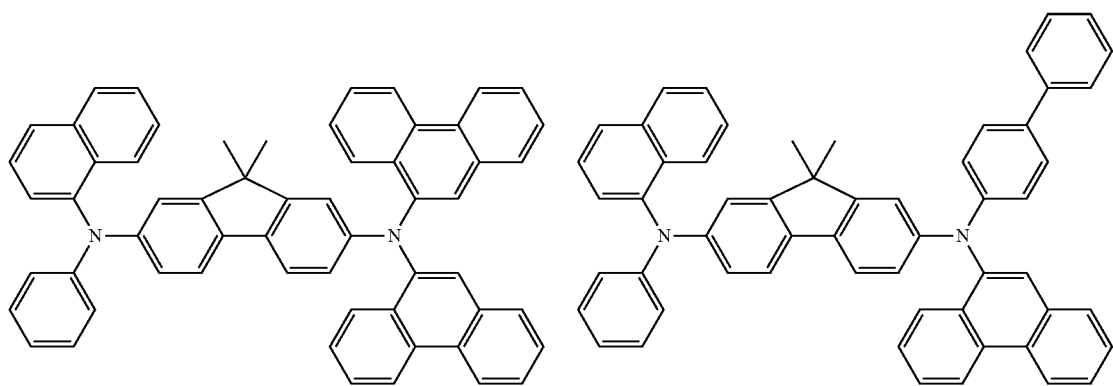
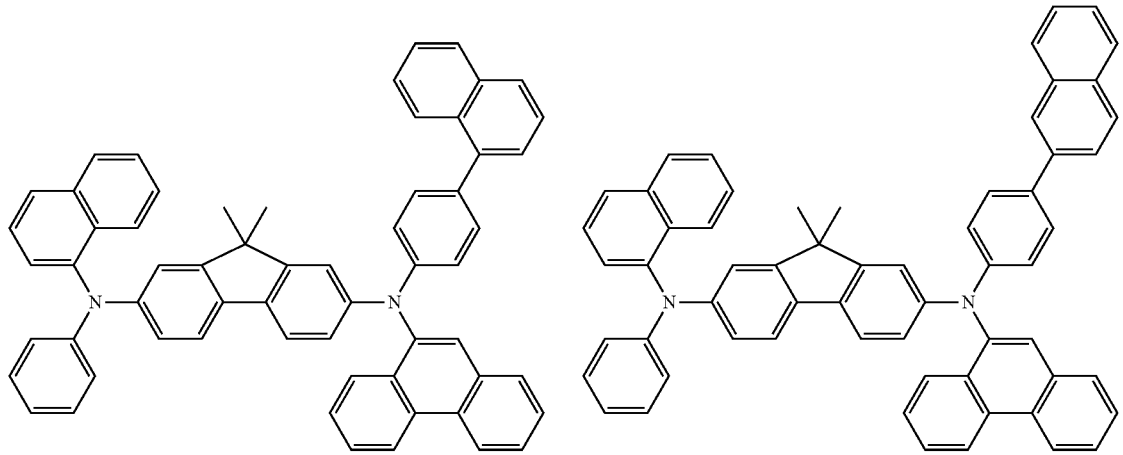

-continued
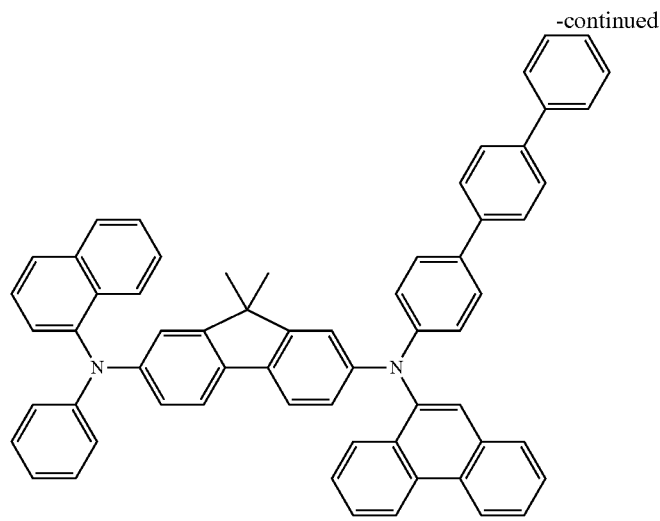
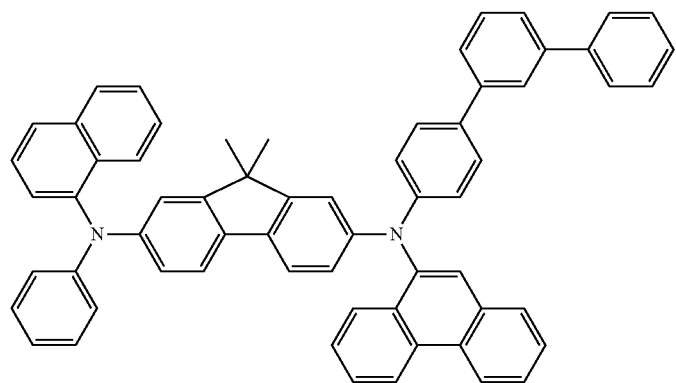
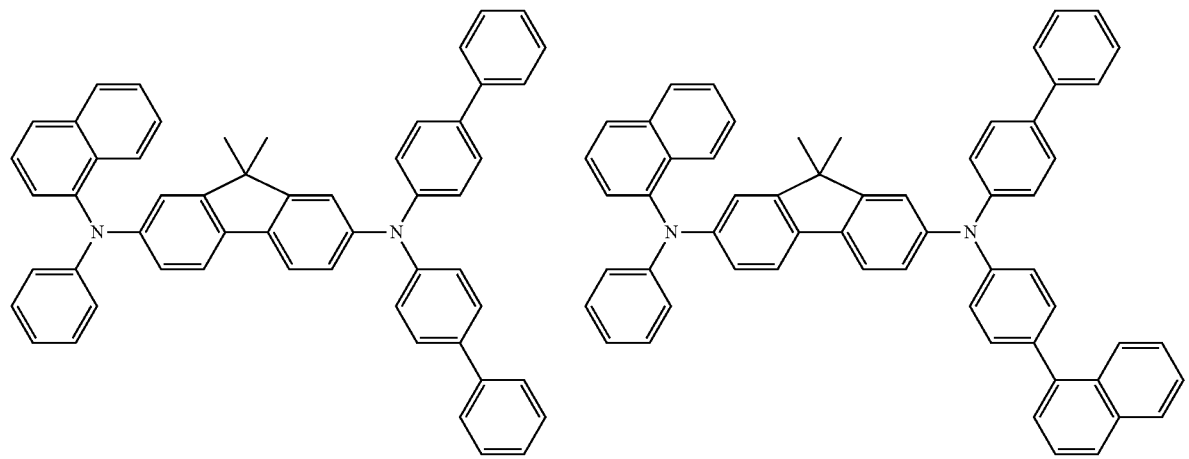

-continued
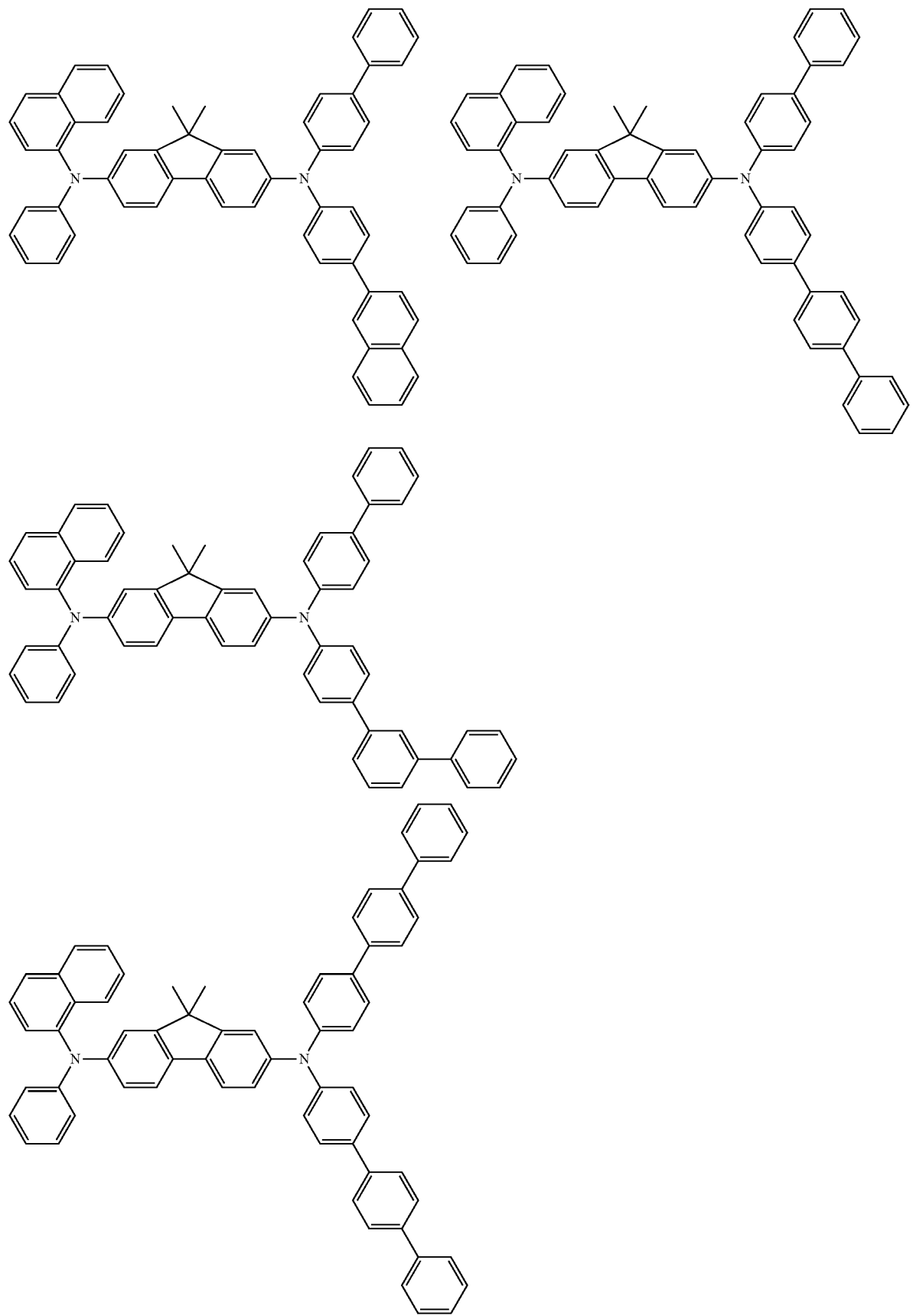

-continued
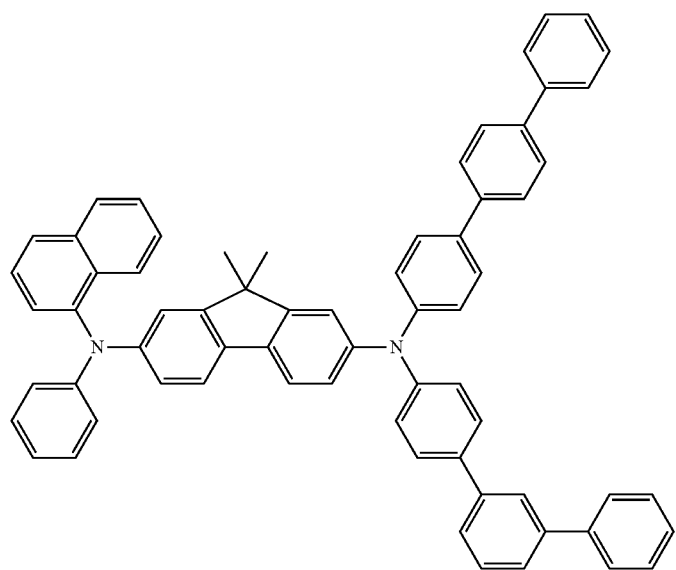
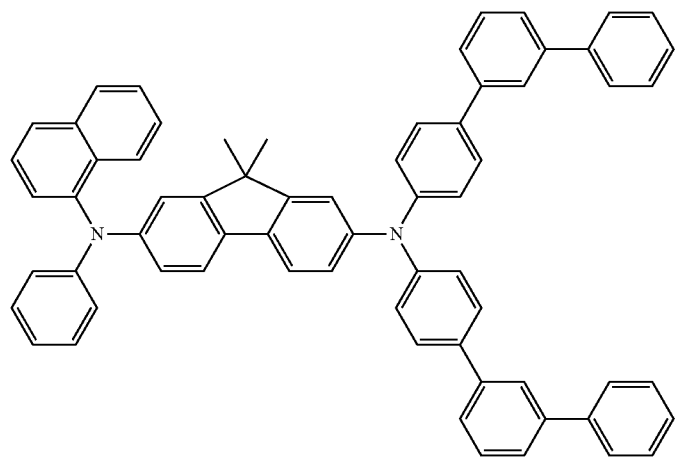
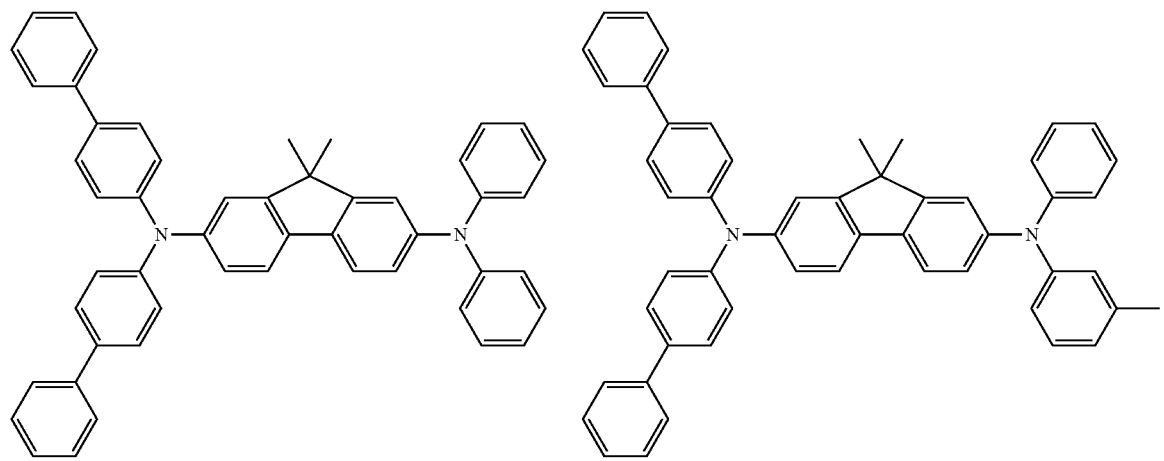

-continued
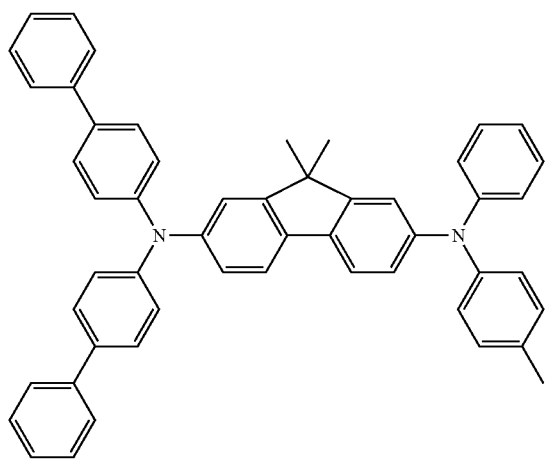
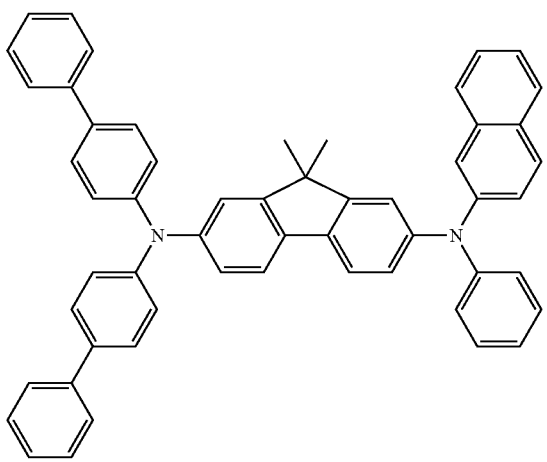
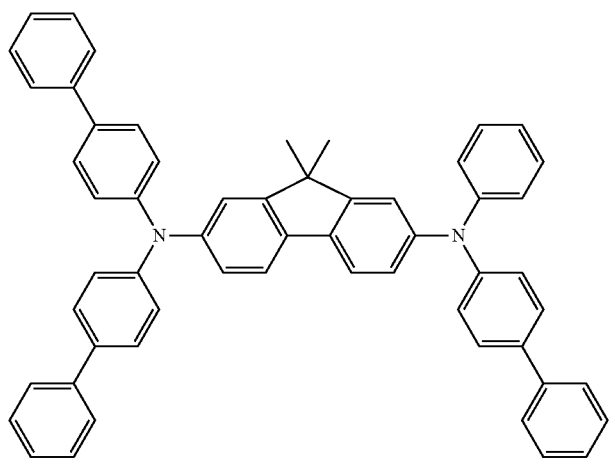

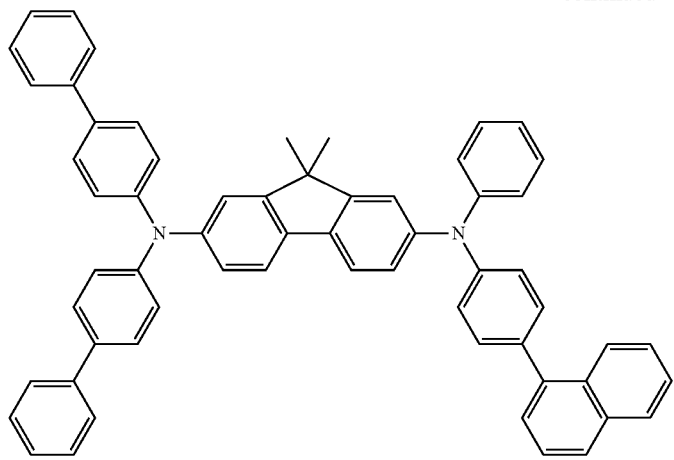
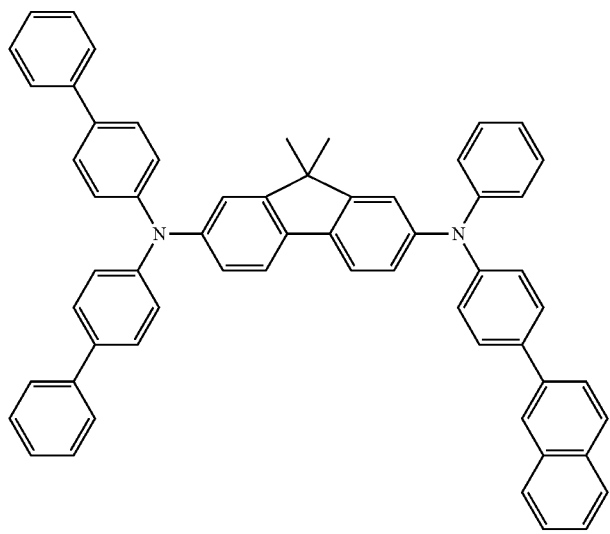
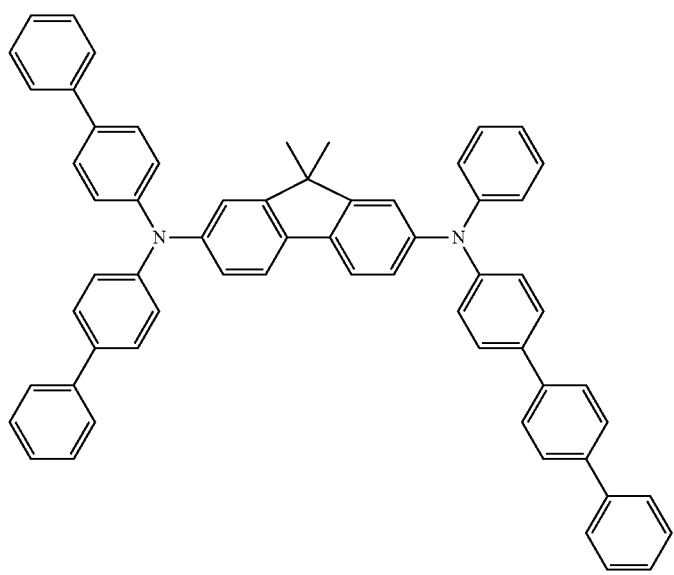

-continued
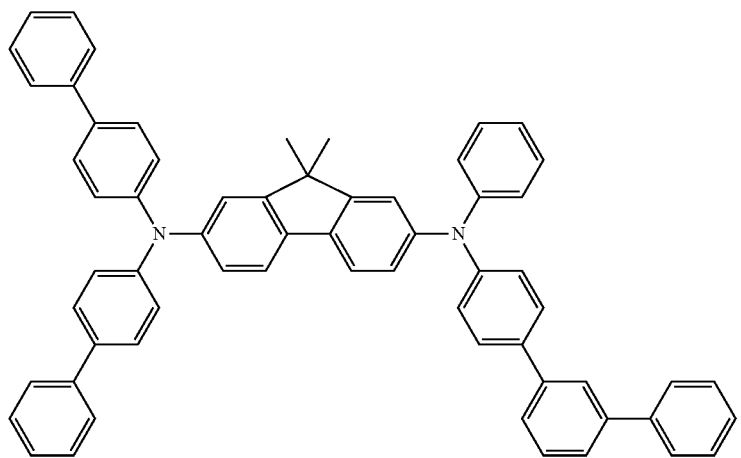
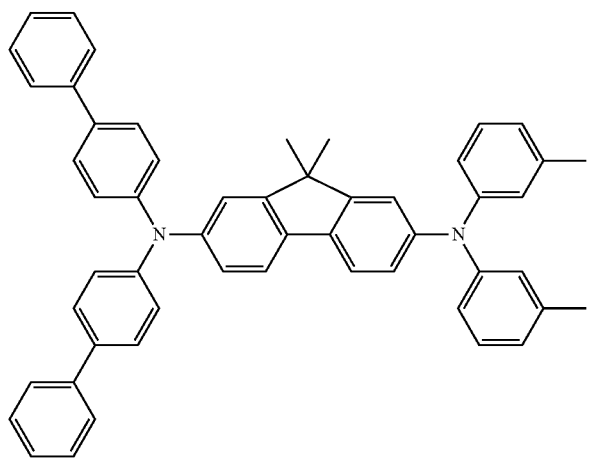
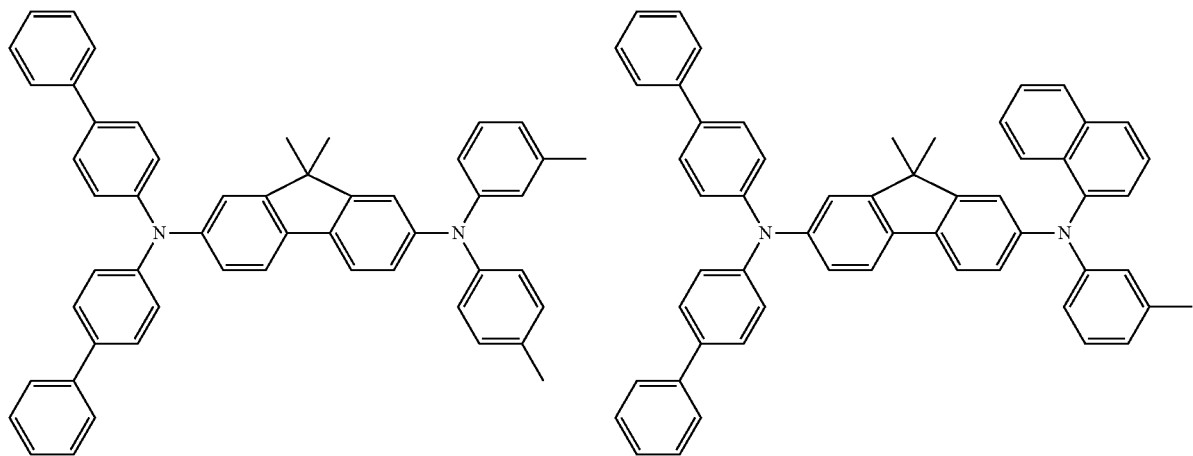

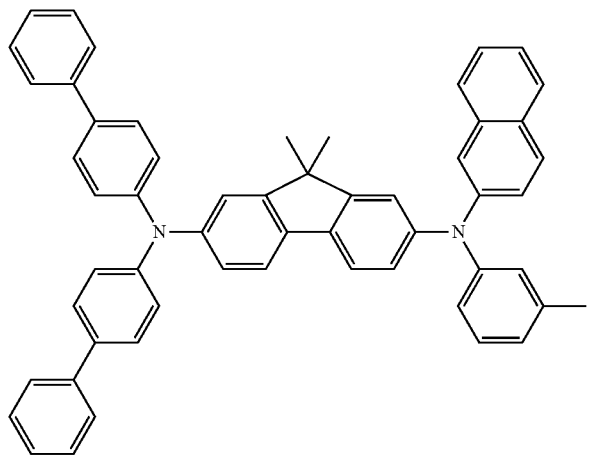
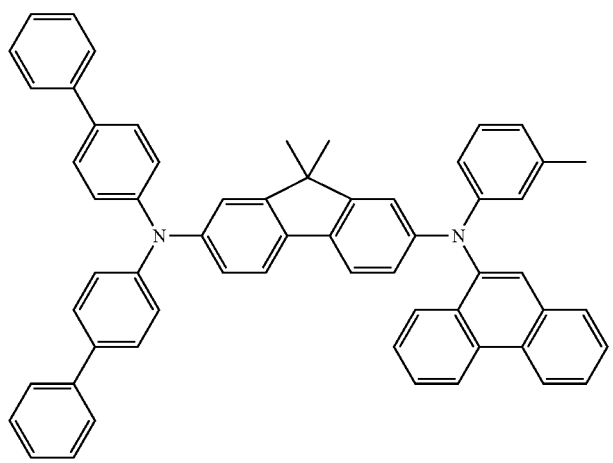
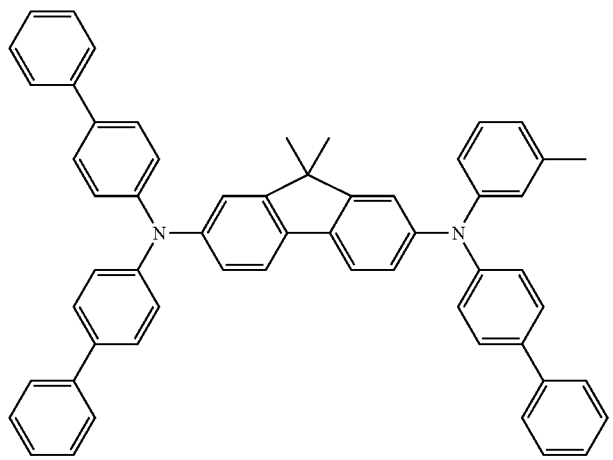

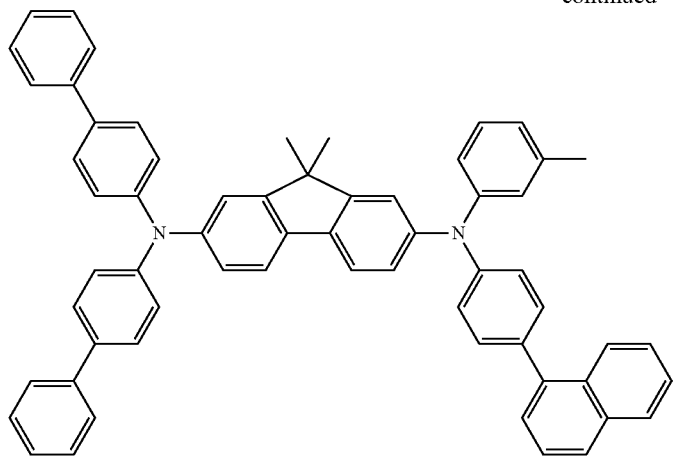
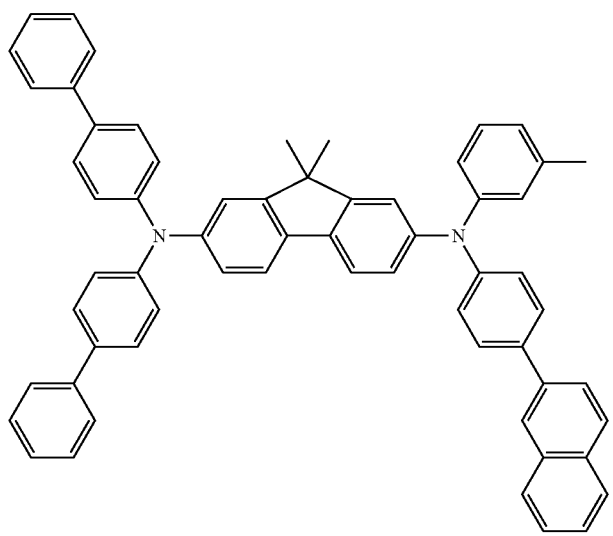
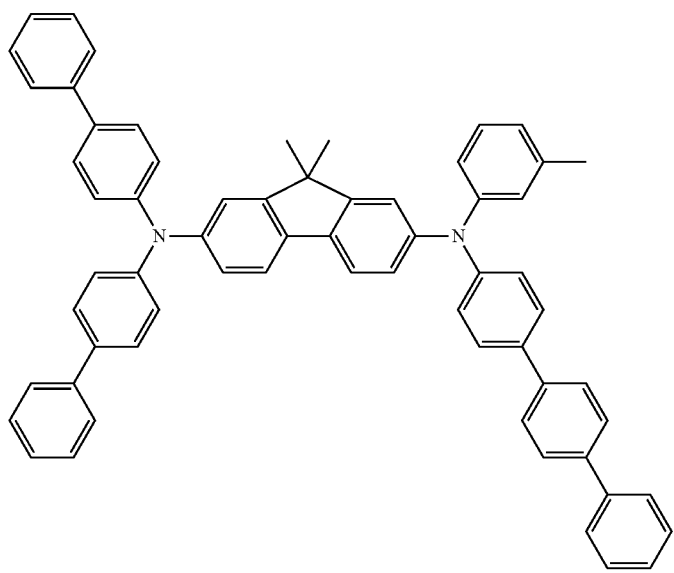

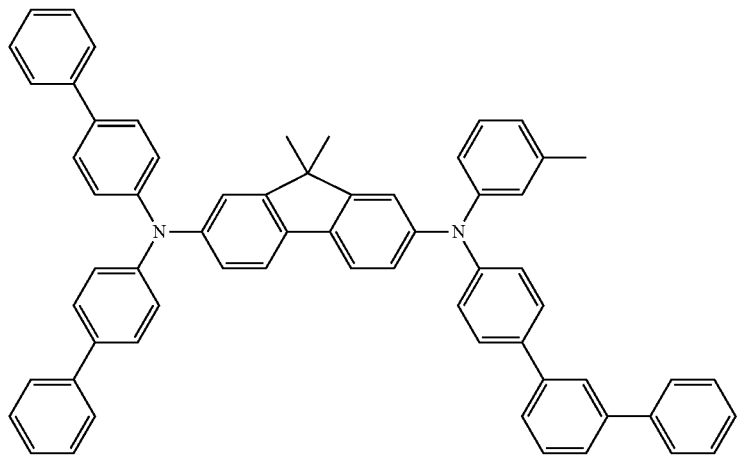
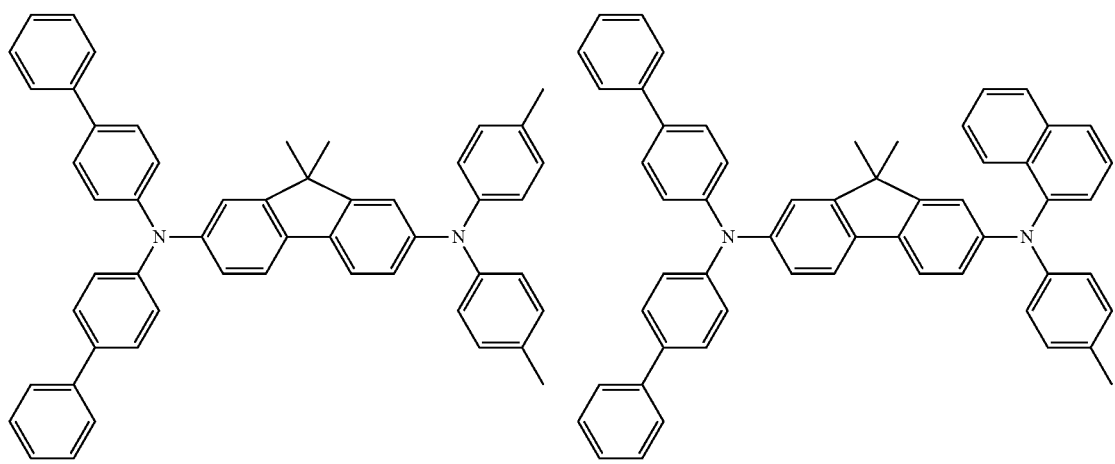
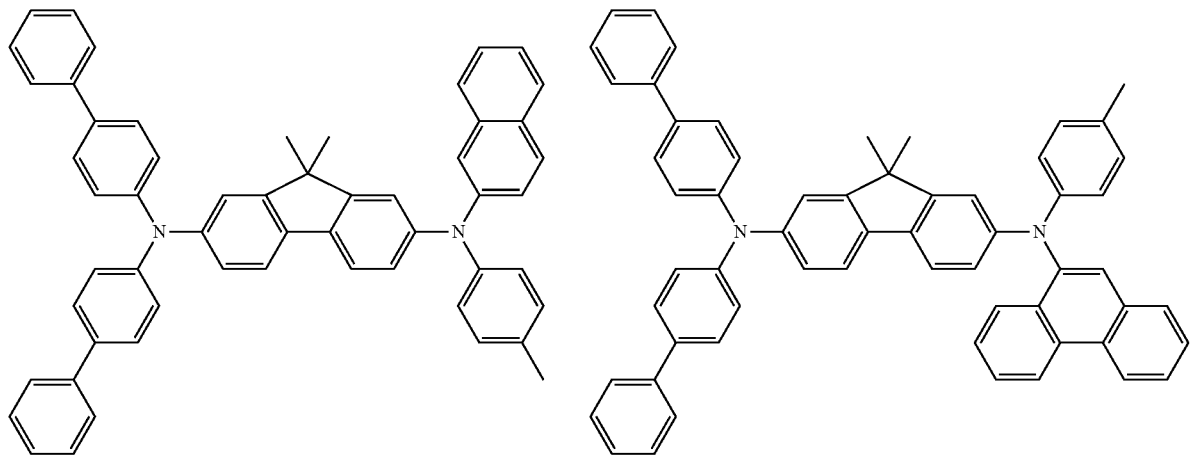

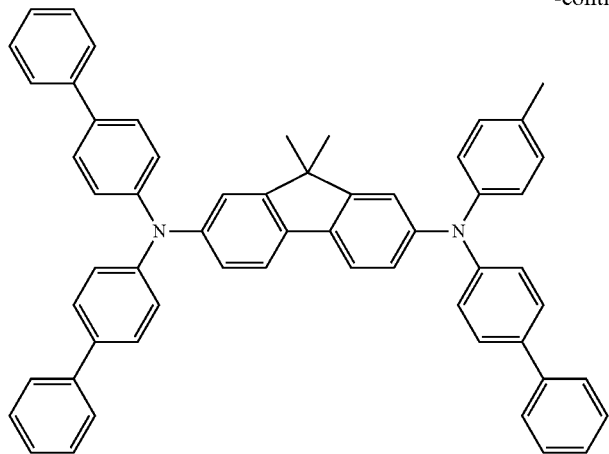
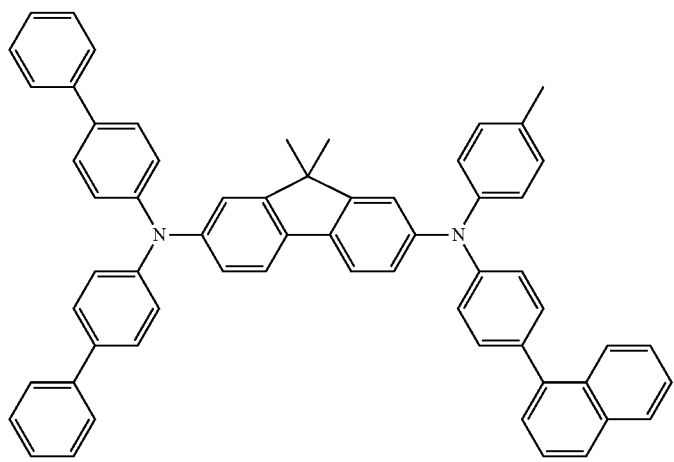
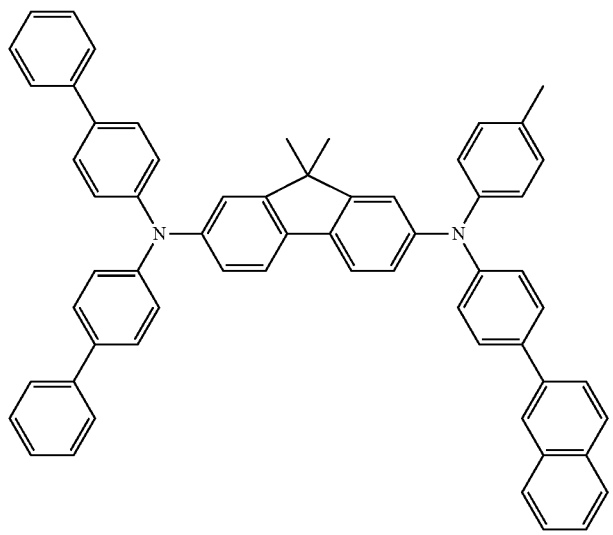

-continued
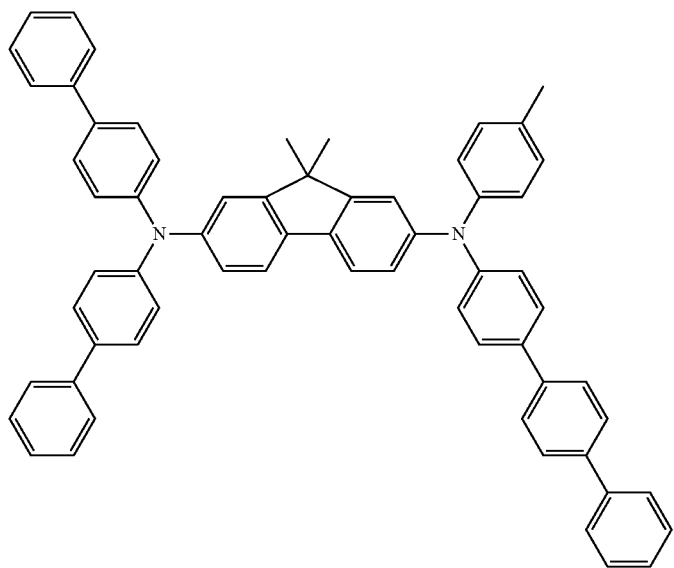
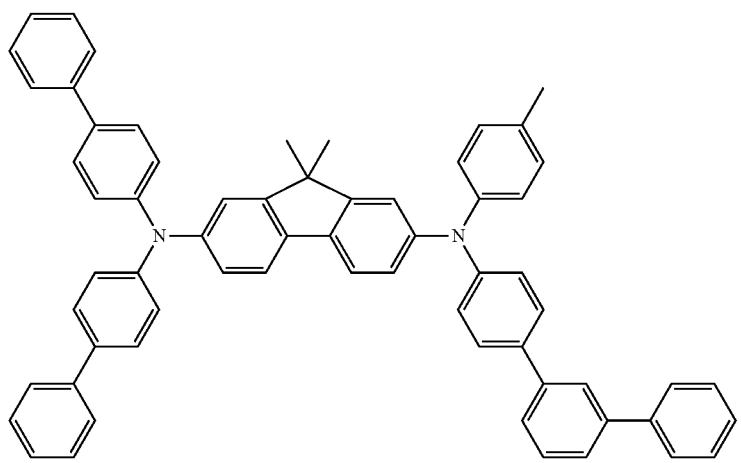
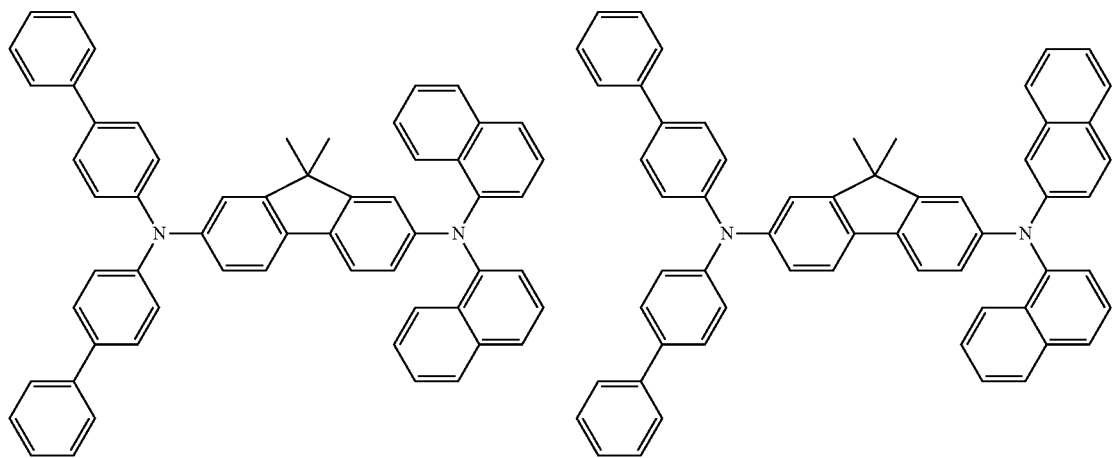

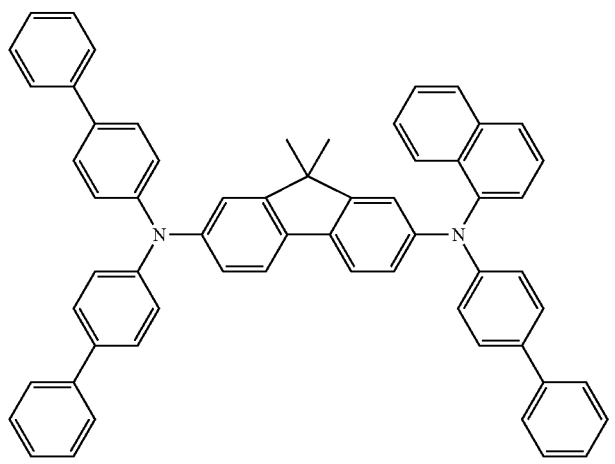
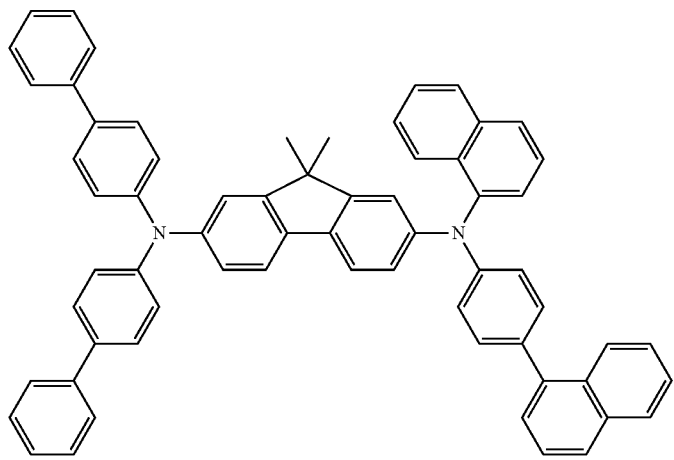

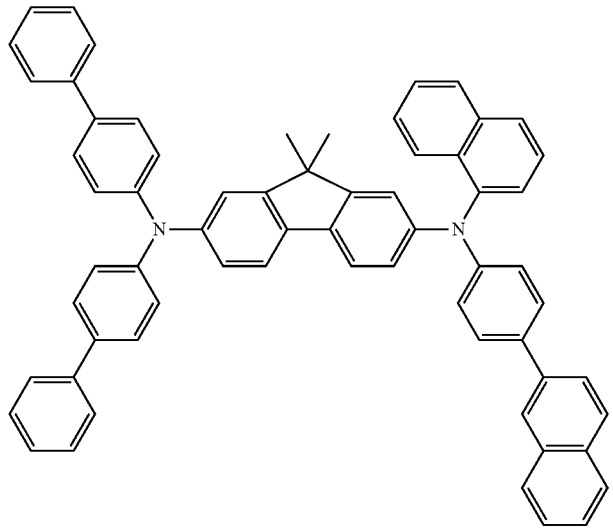
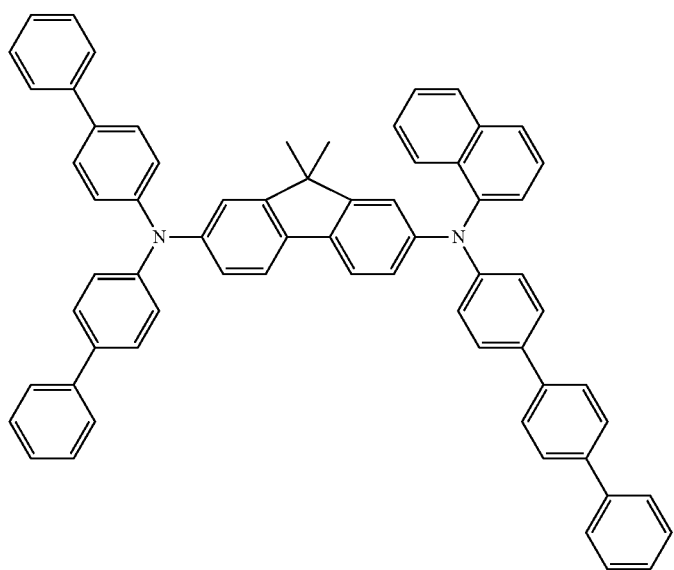
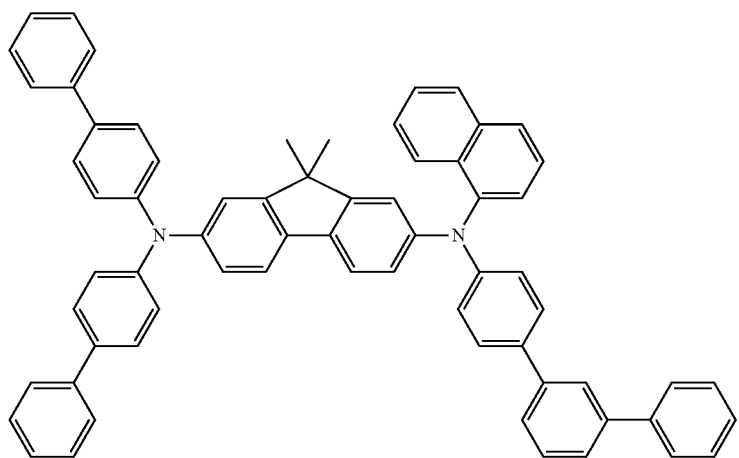

-continued
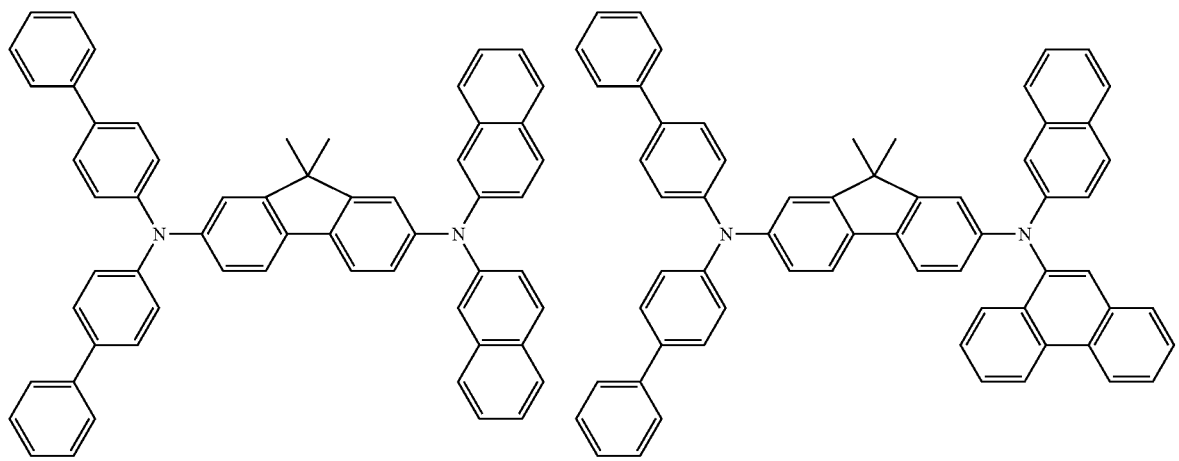
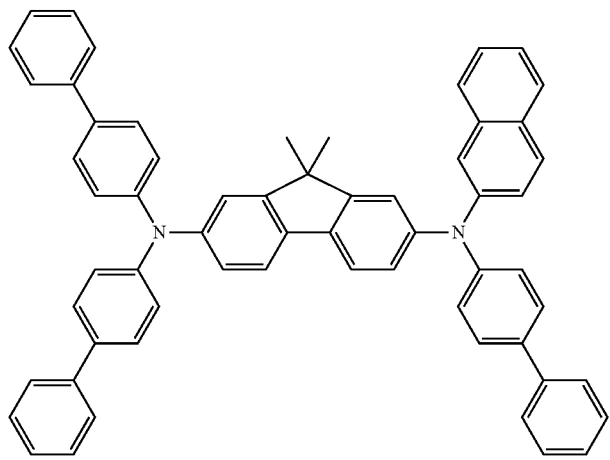
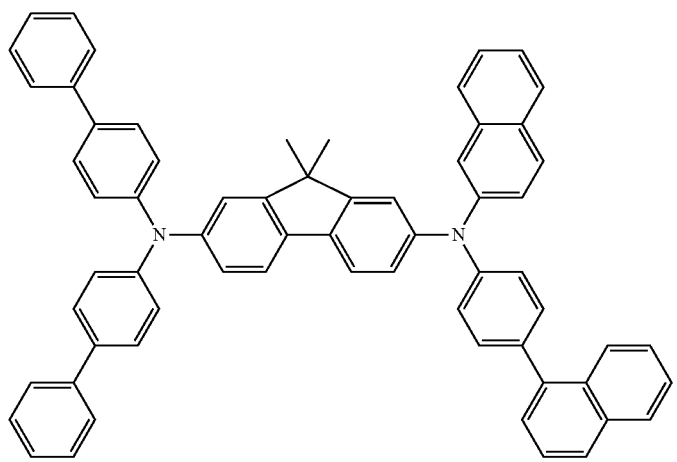

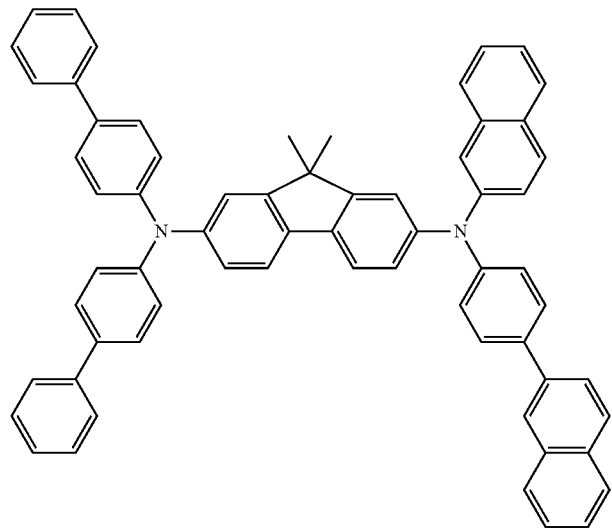
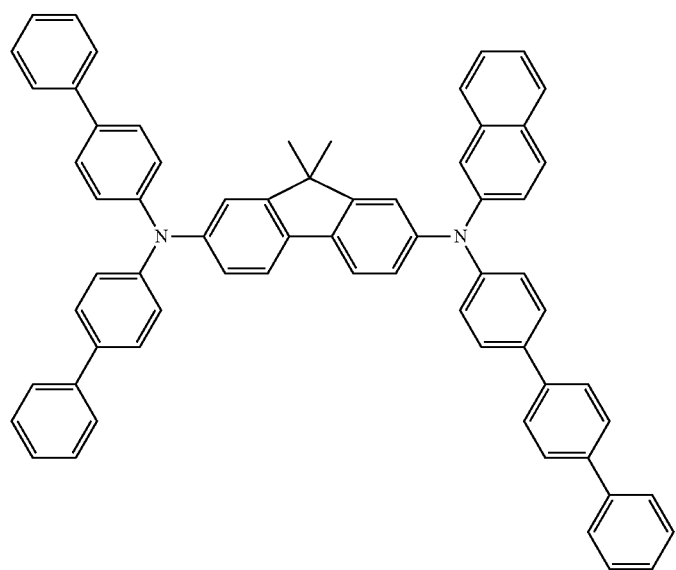
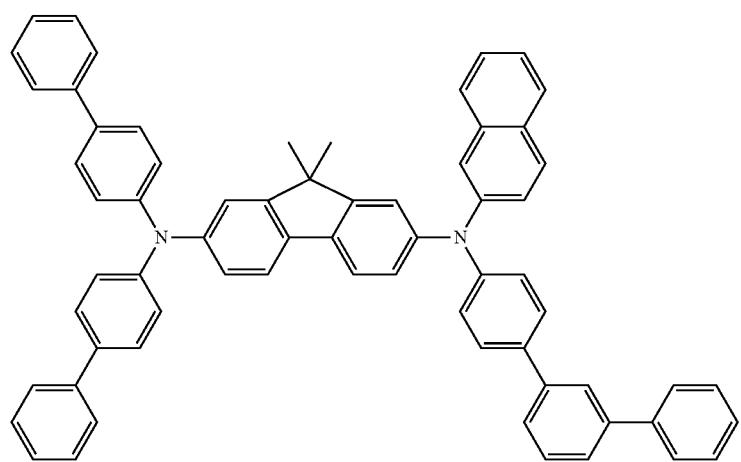

-continued
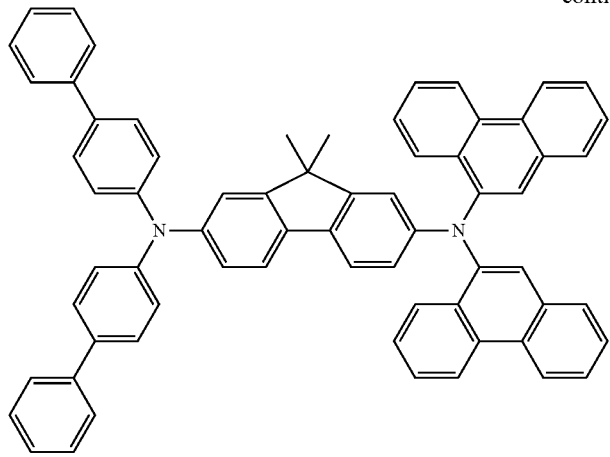
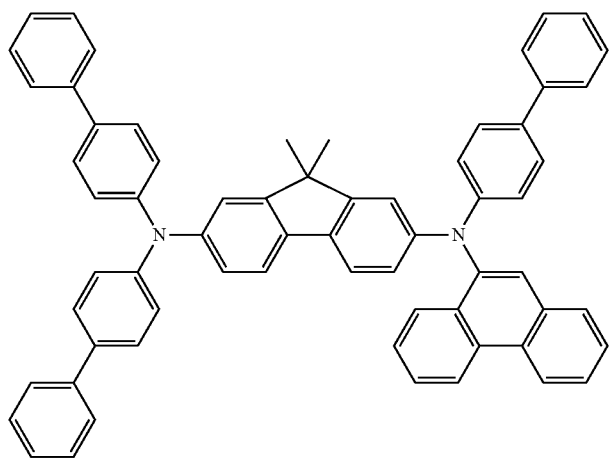
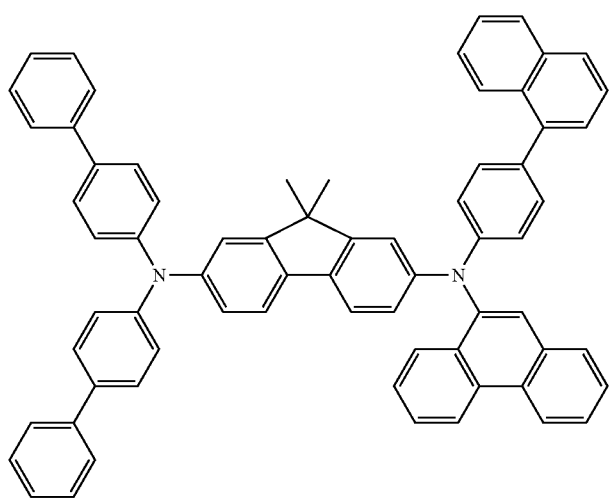

-continued
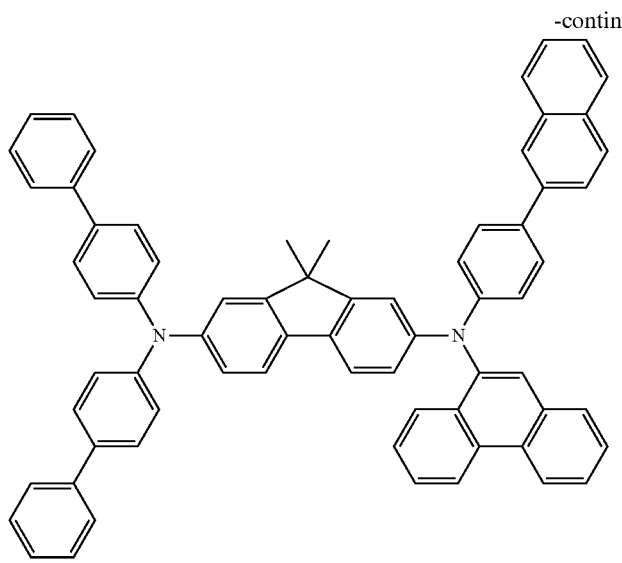
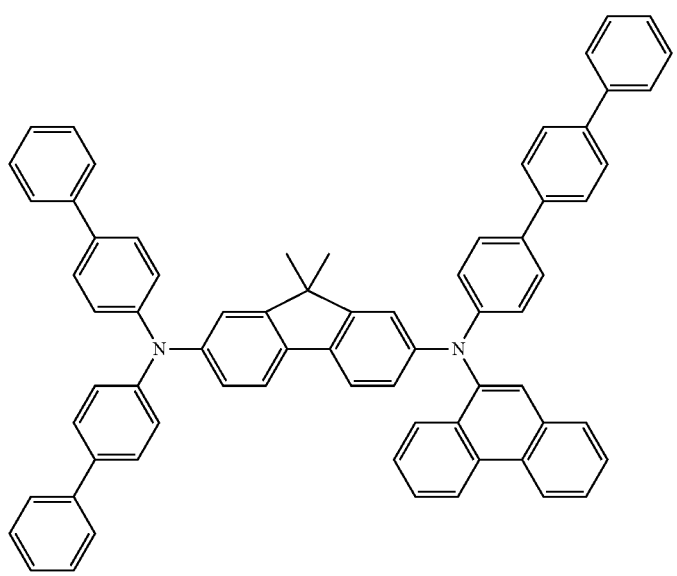
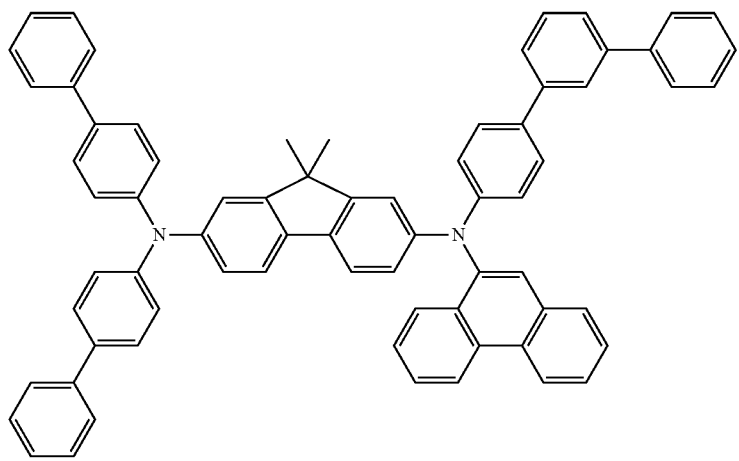

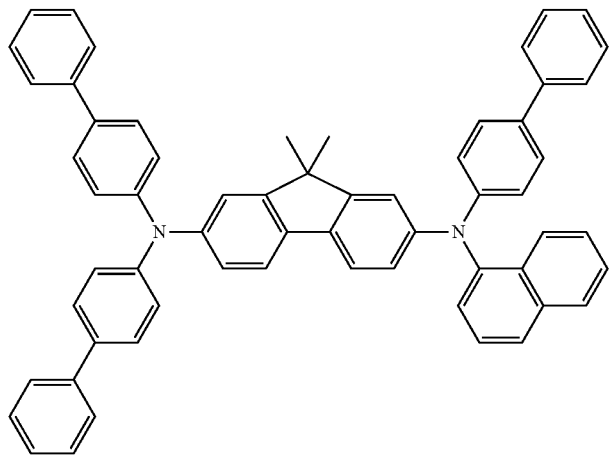
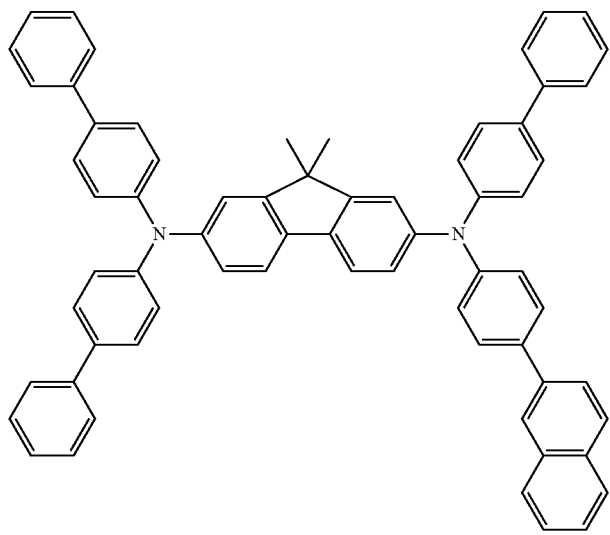
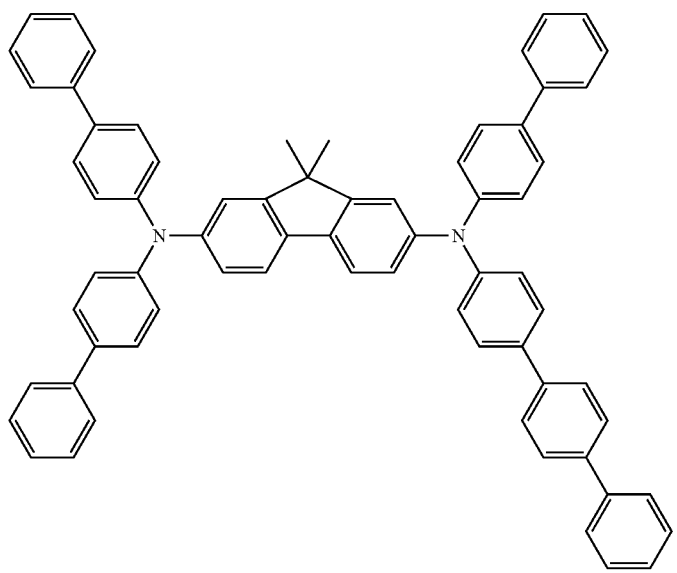

-continued
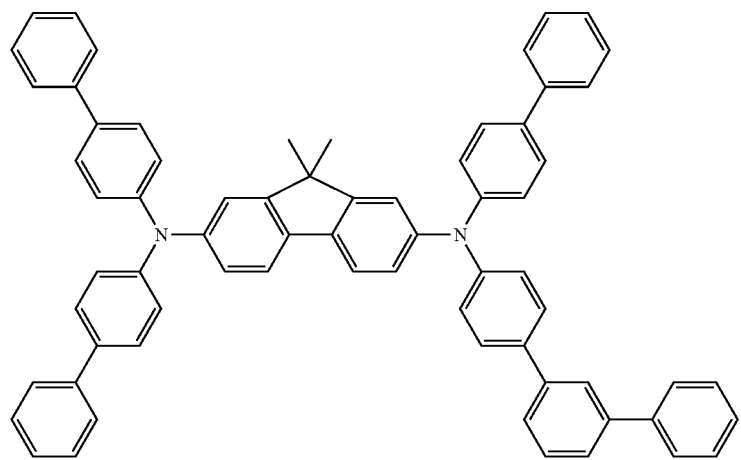
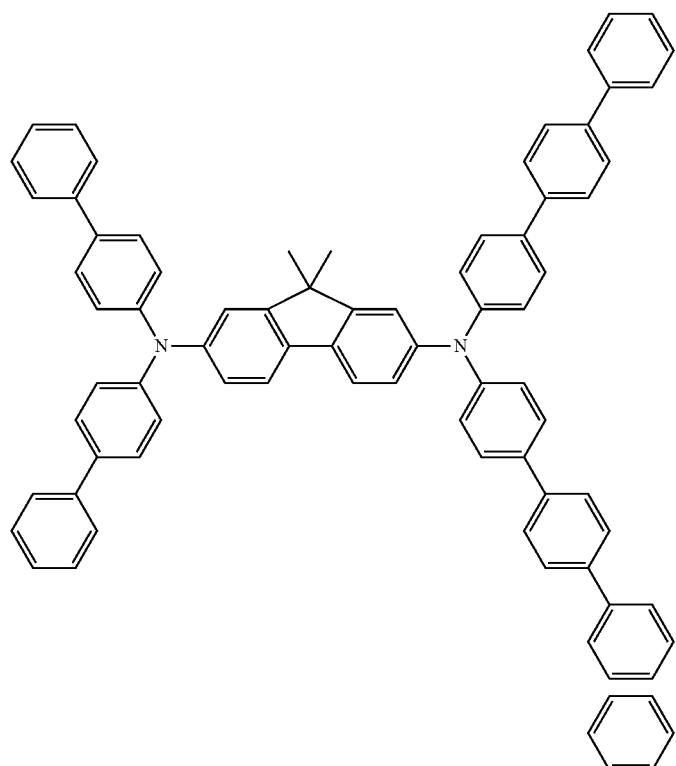
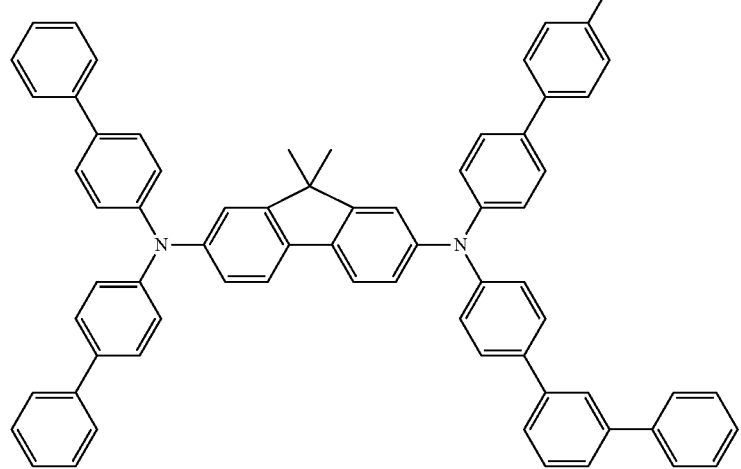

-continued
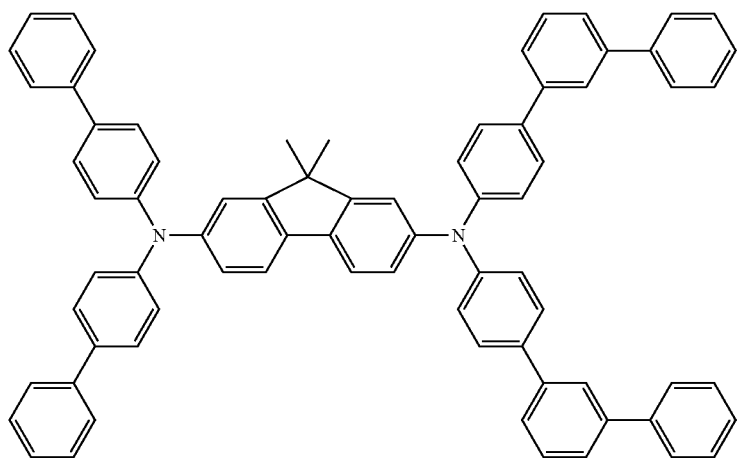
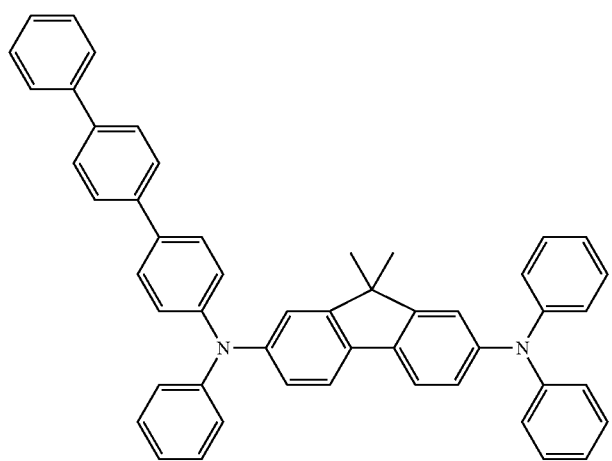
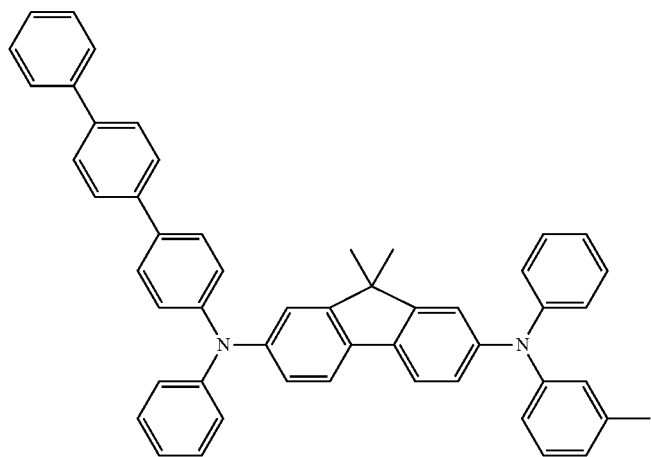

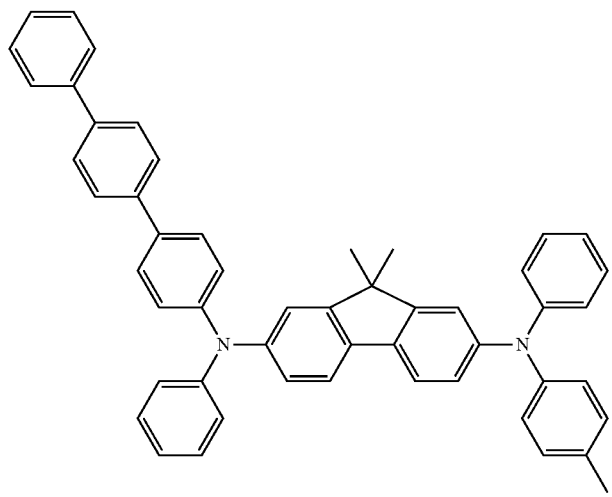
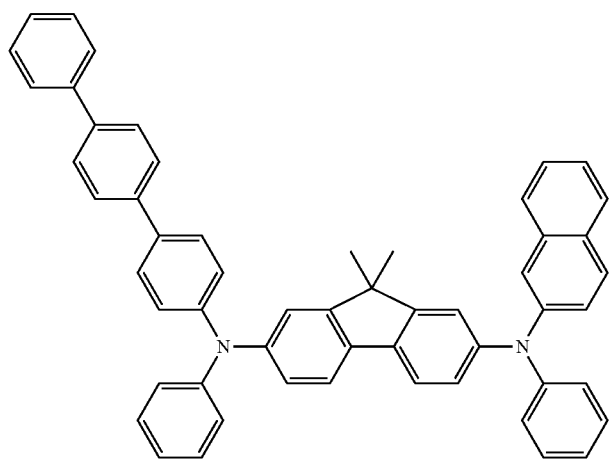
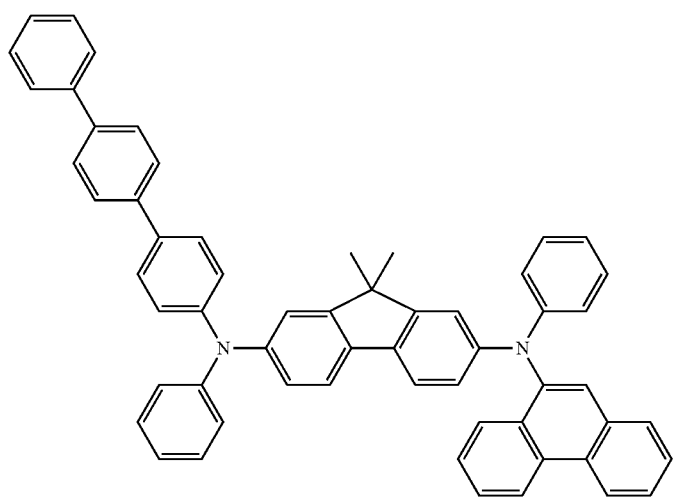

-continued
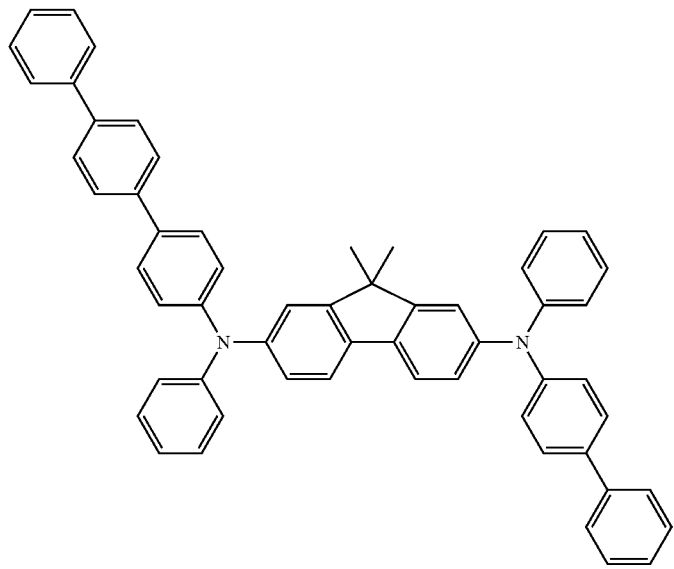
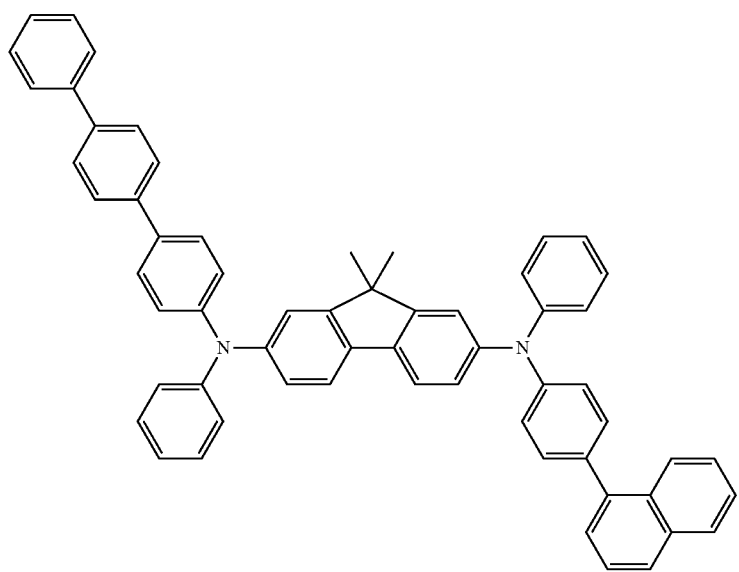

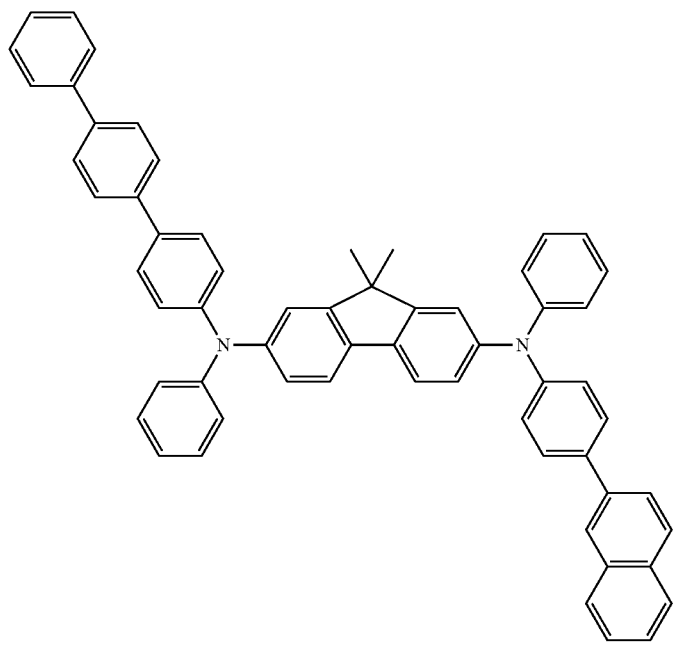
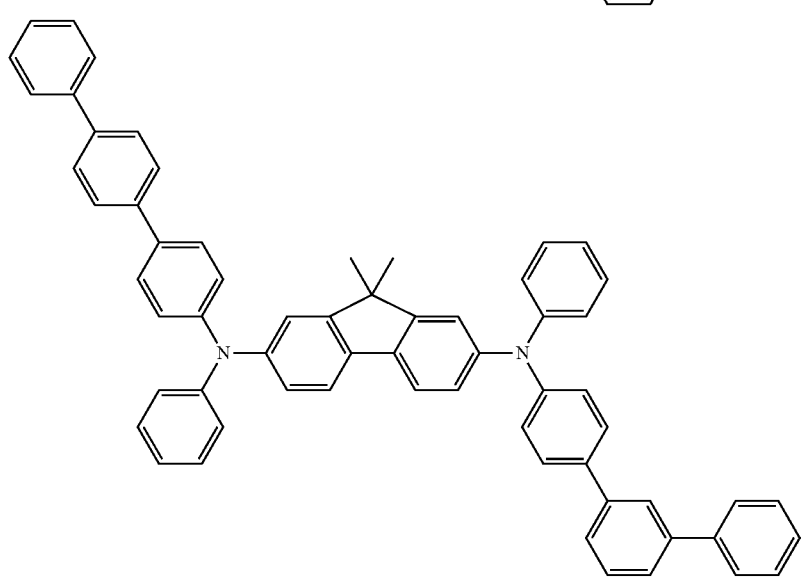
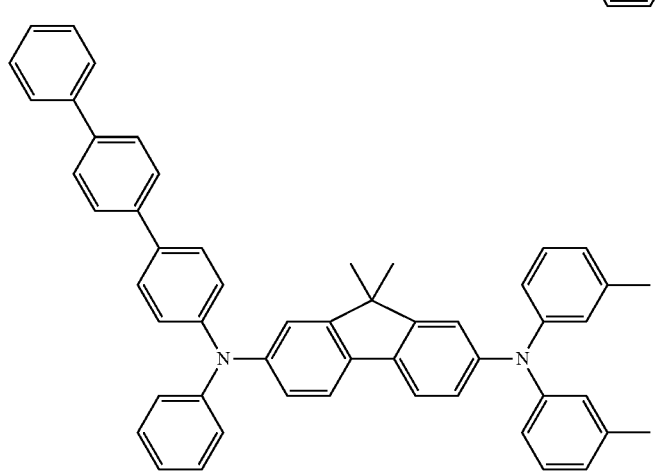

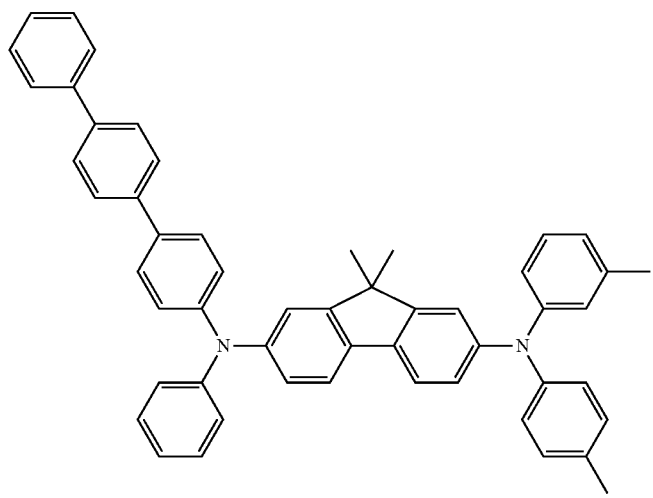
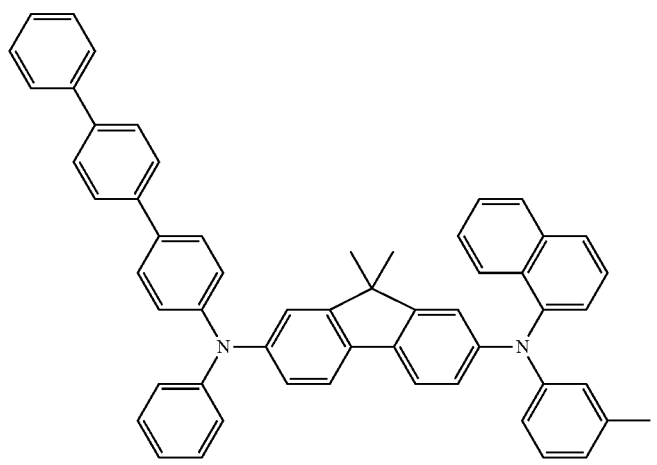

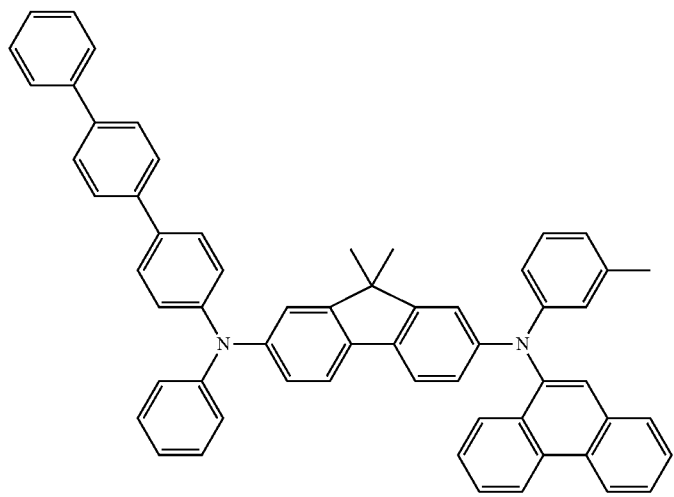
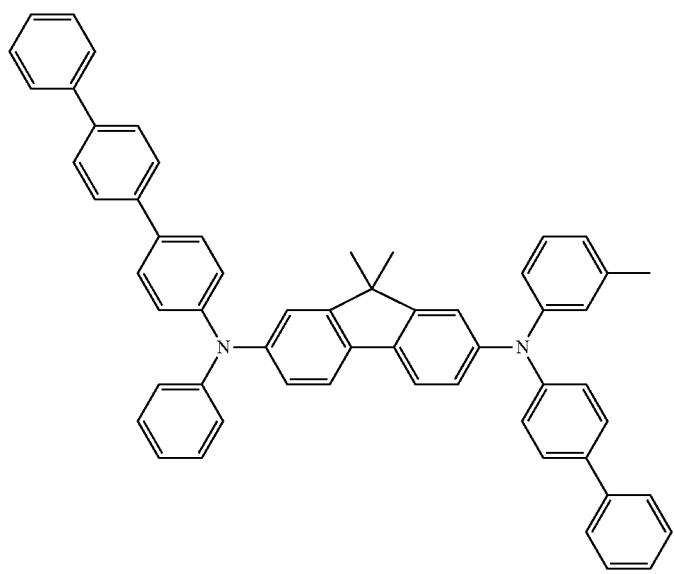
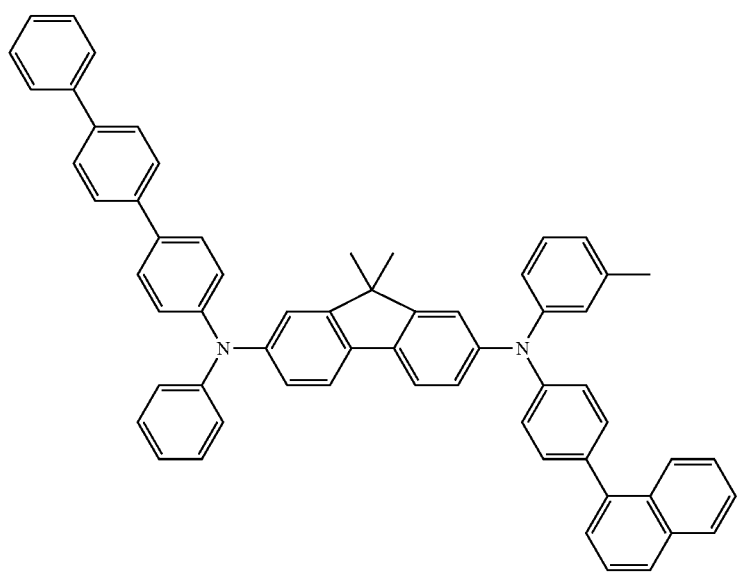

-continued
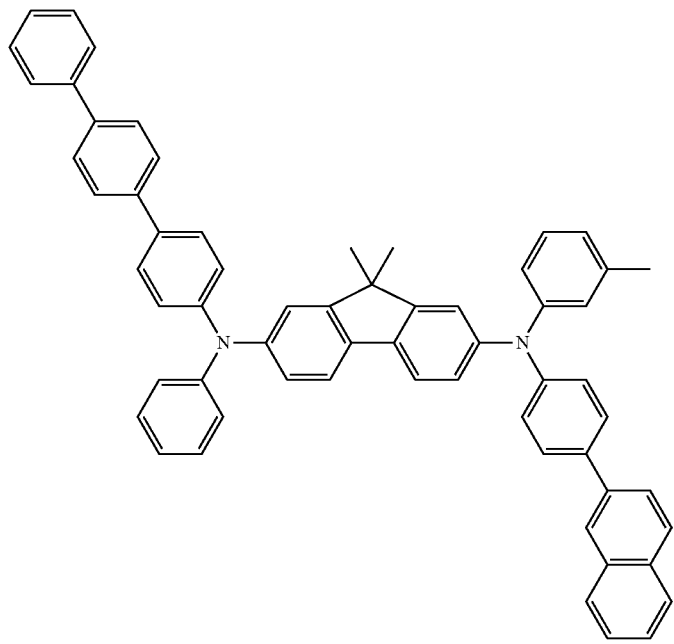
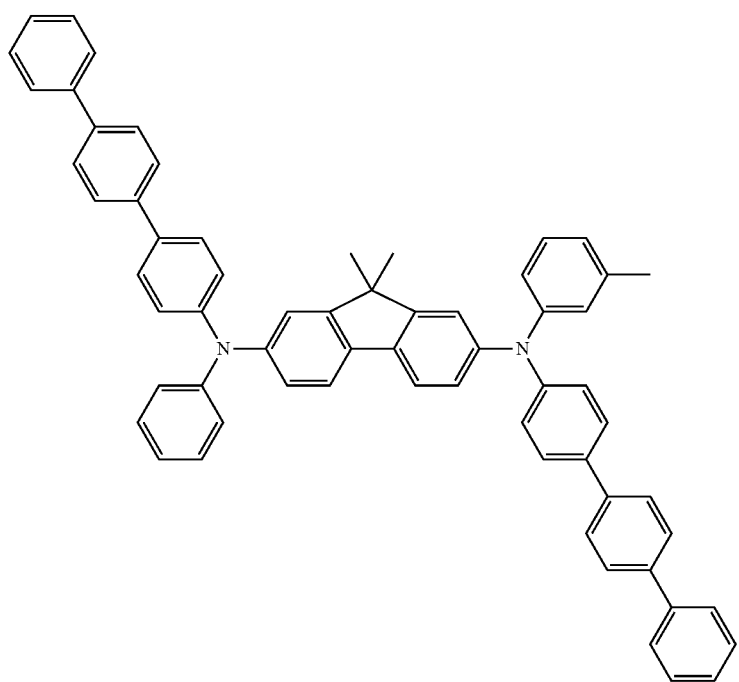

-continued
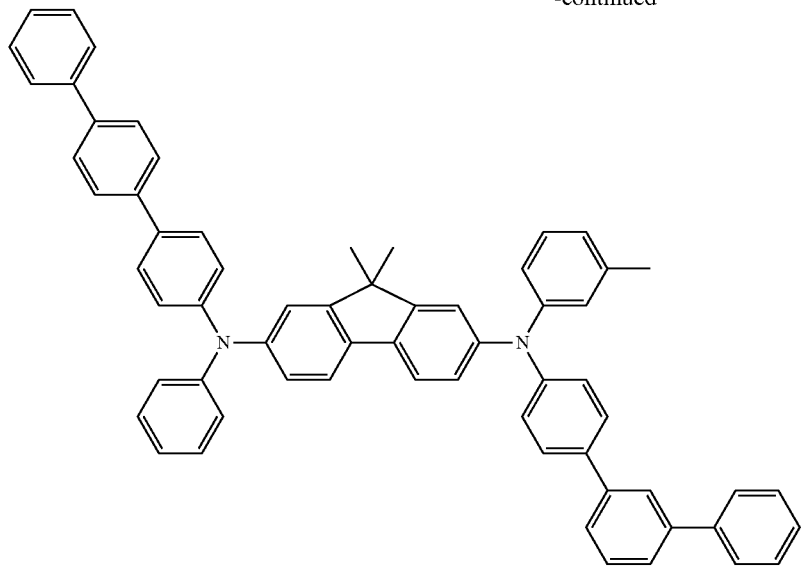
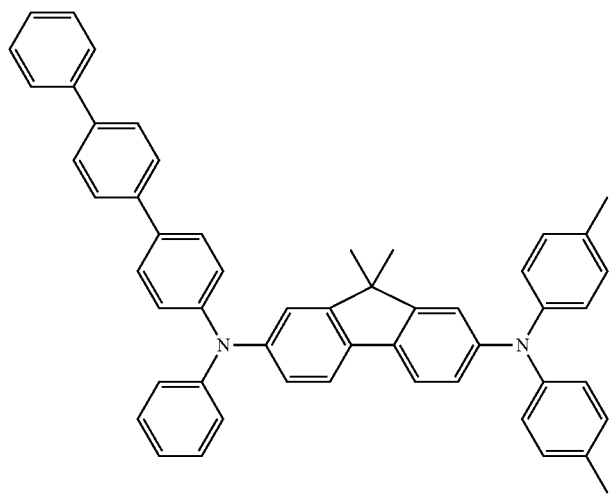
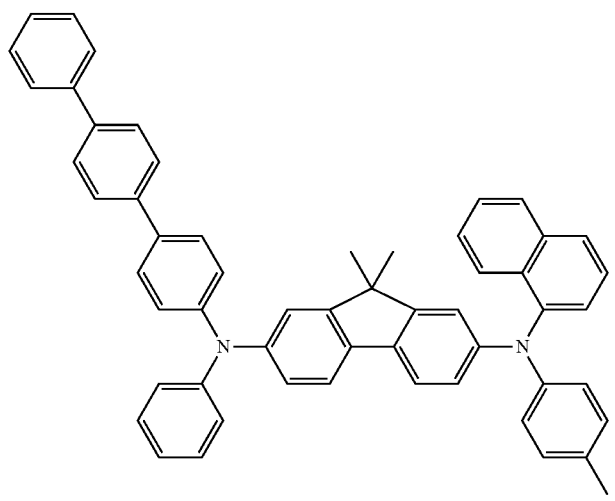

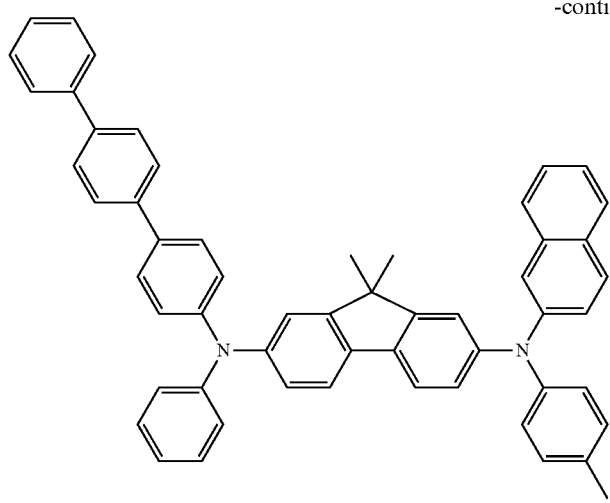
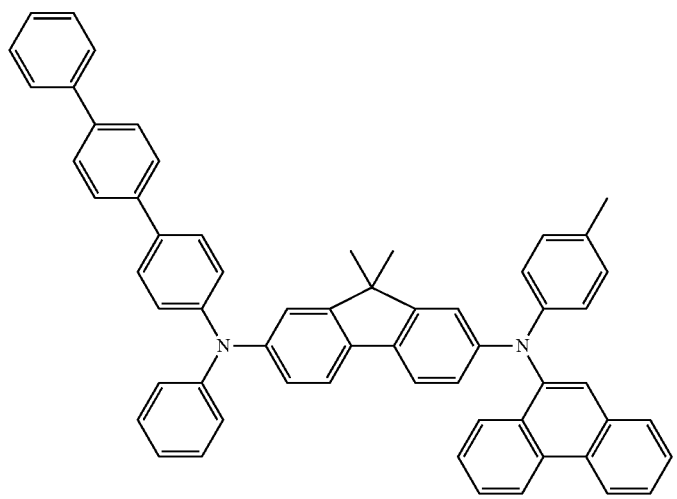
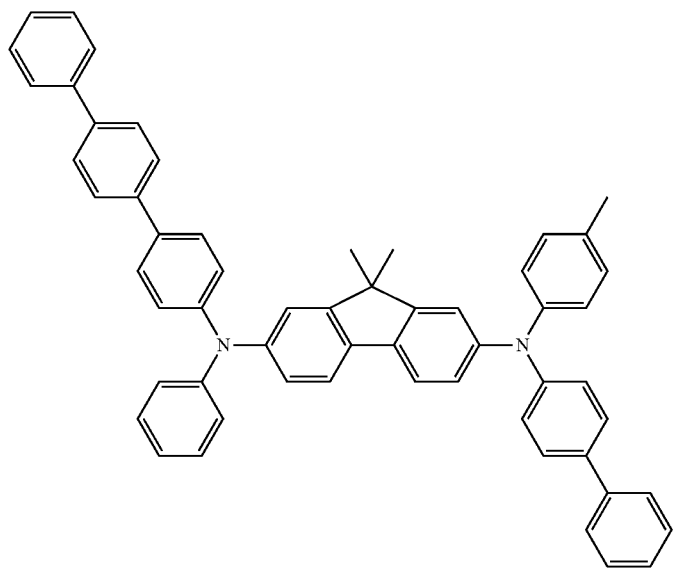

-continued
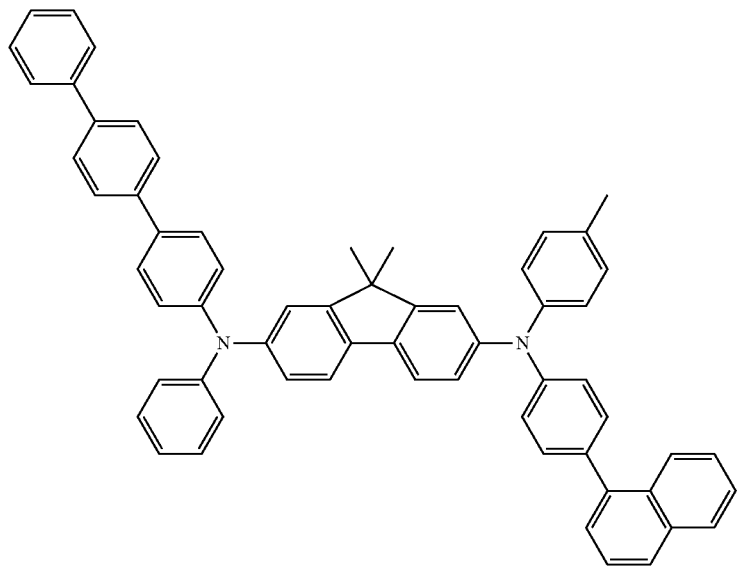
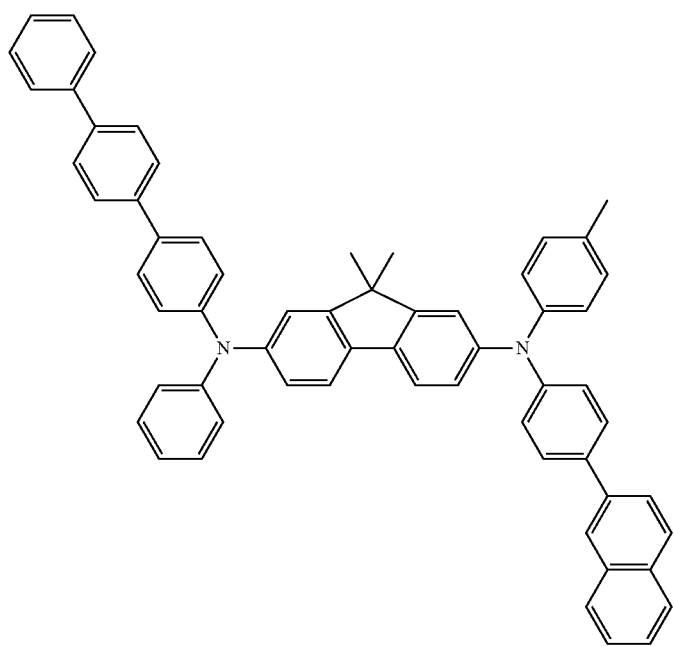

-continued
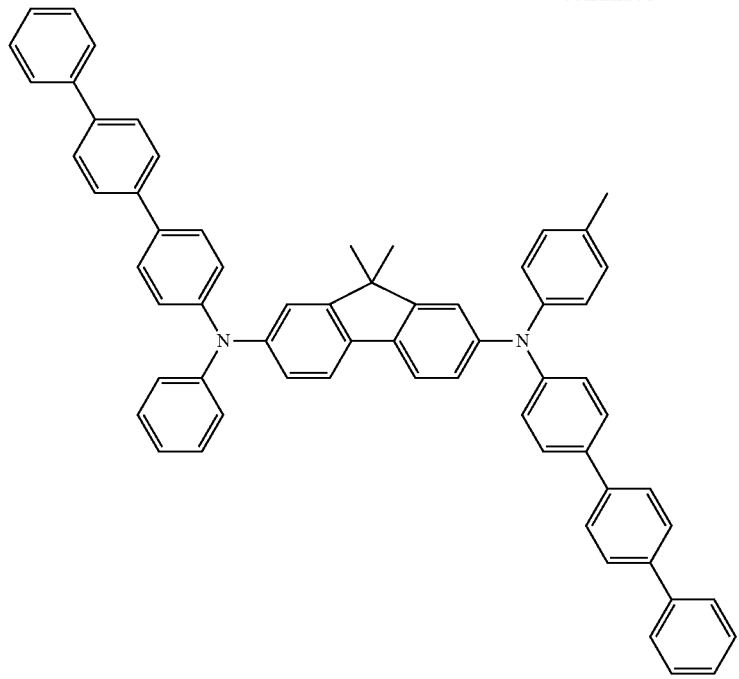
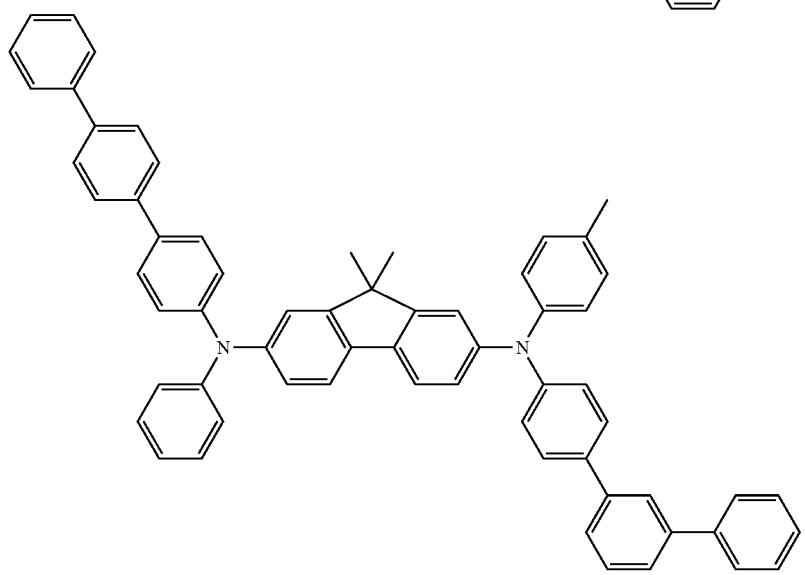
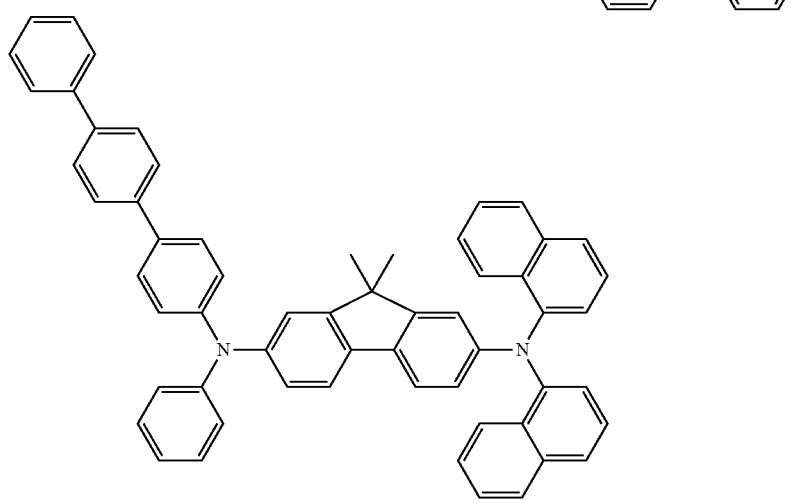

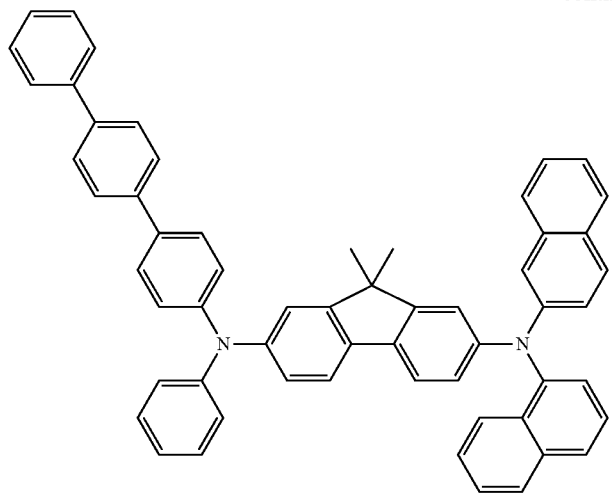
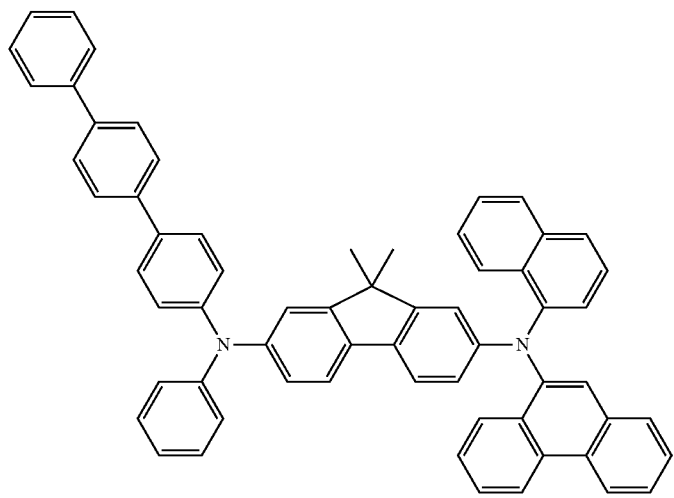
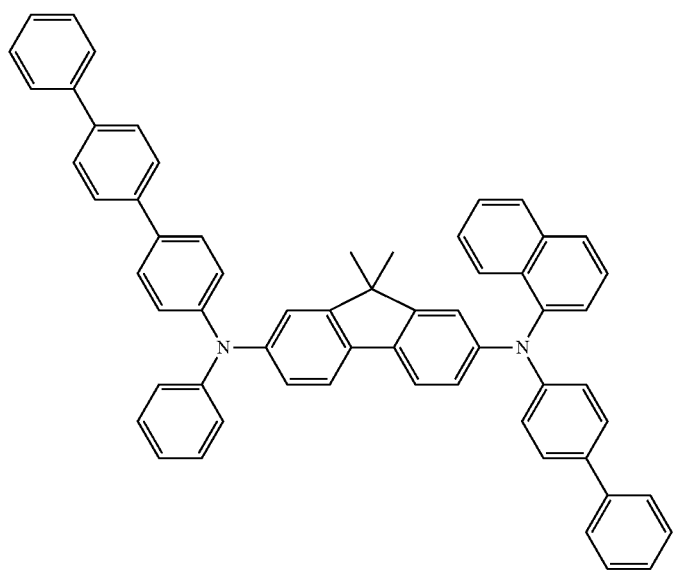

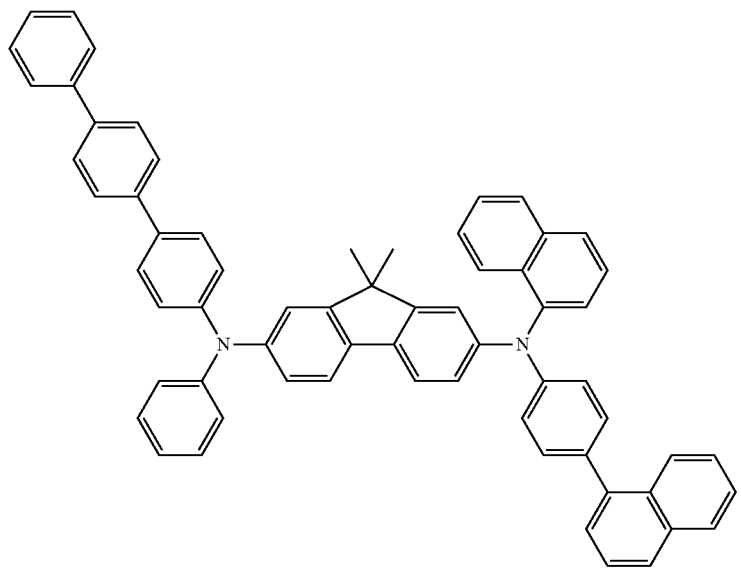
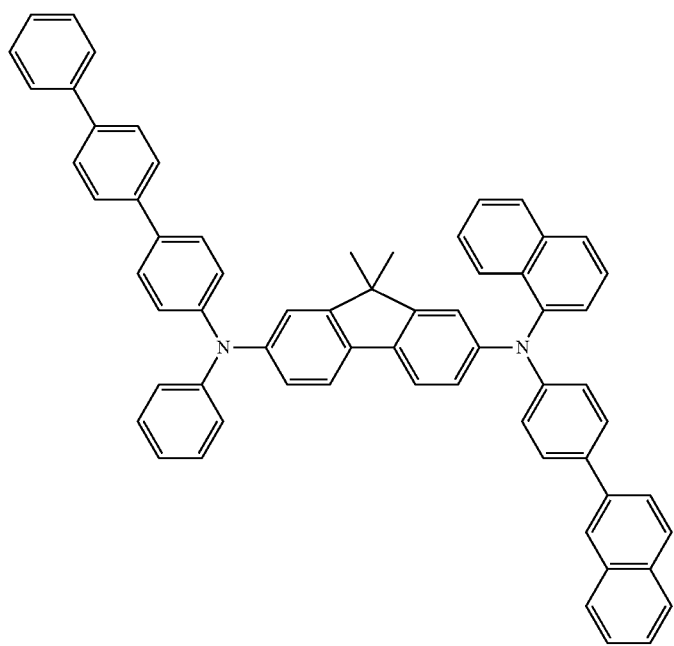

-continued
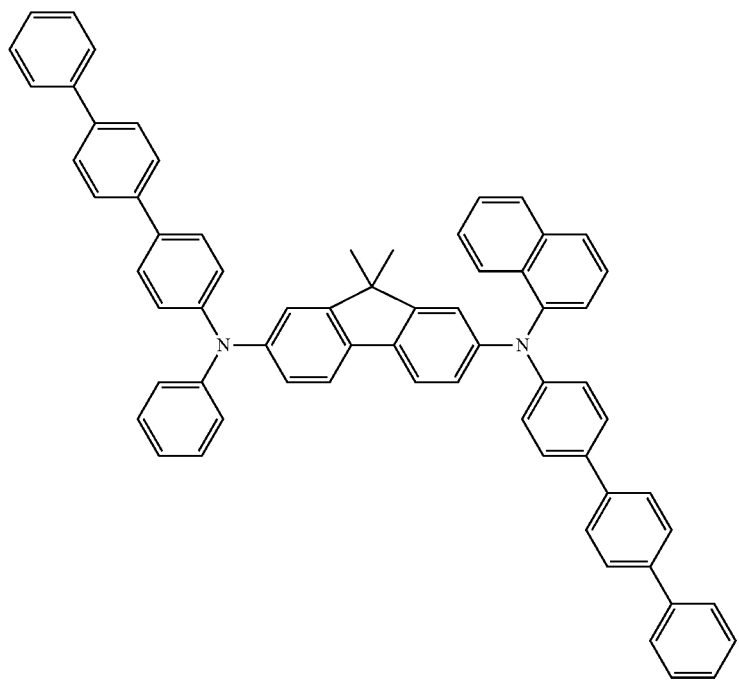
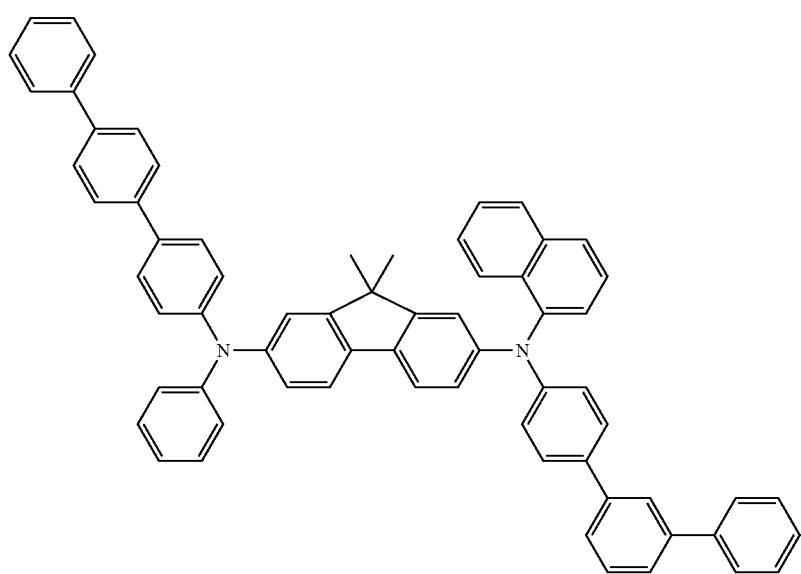

-continued
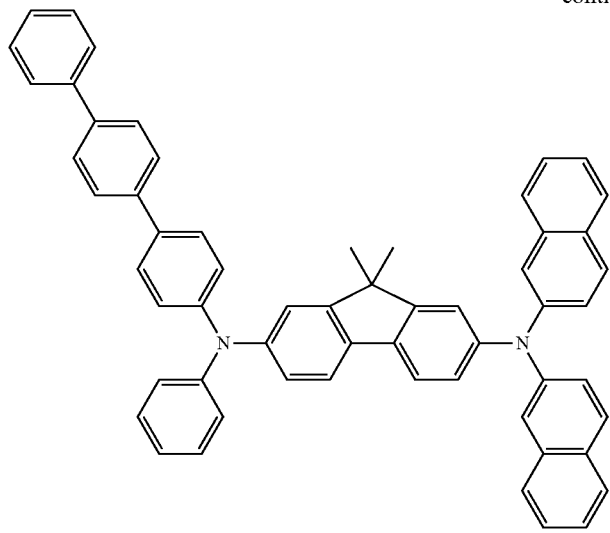
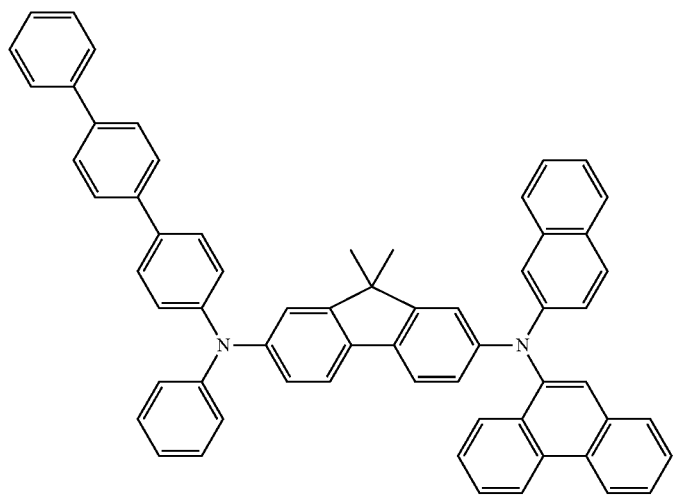
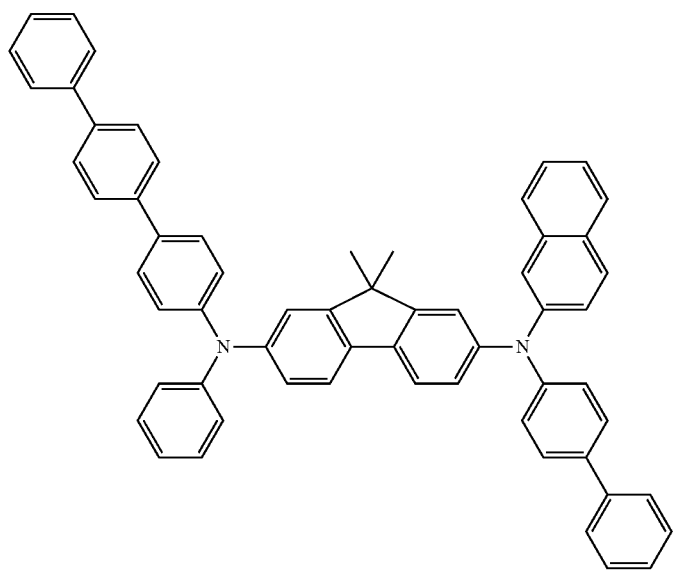

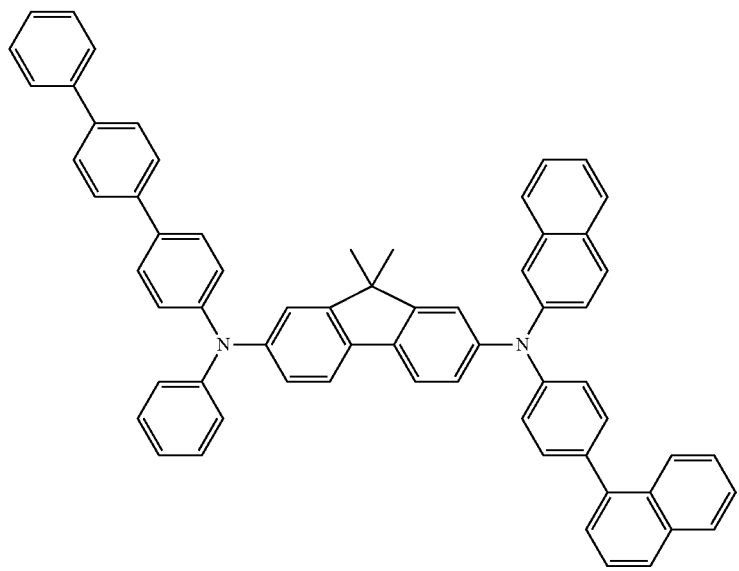
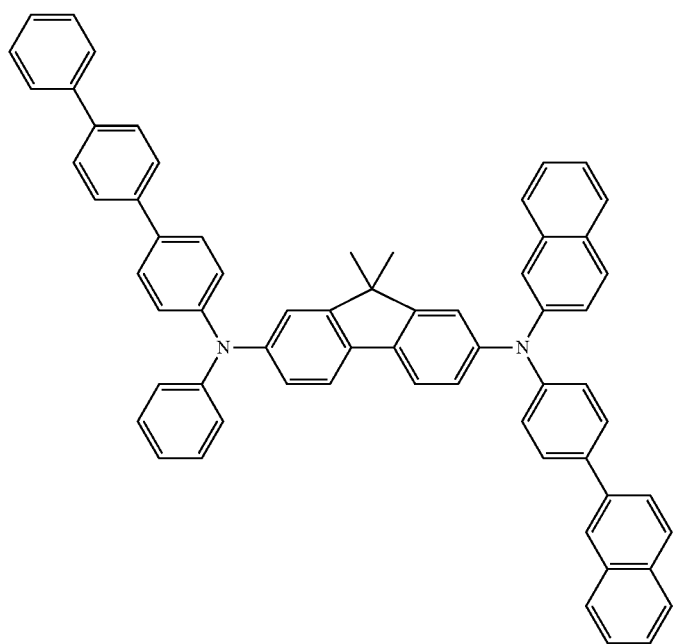

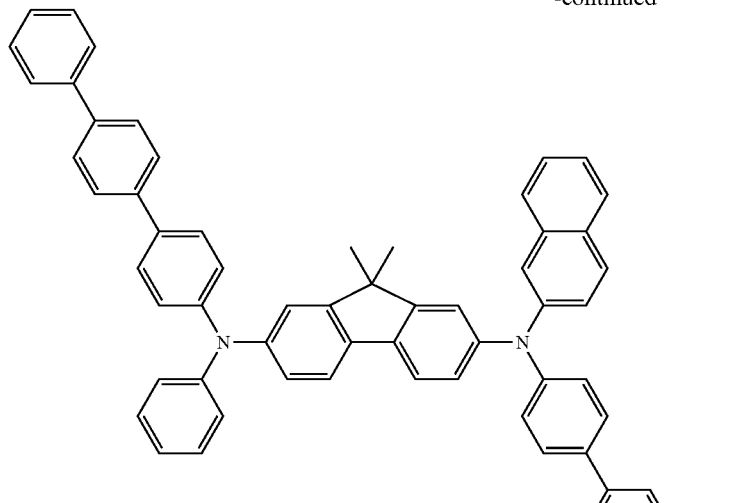
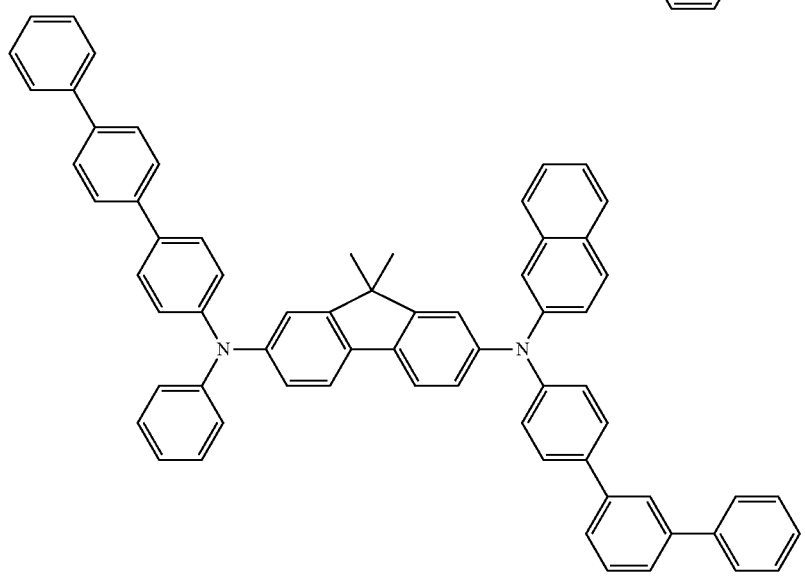
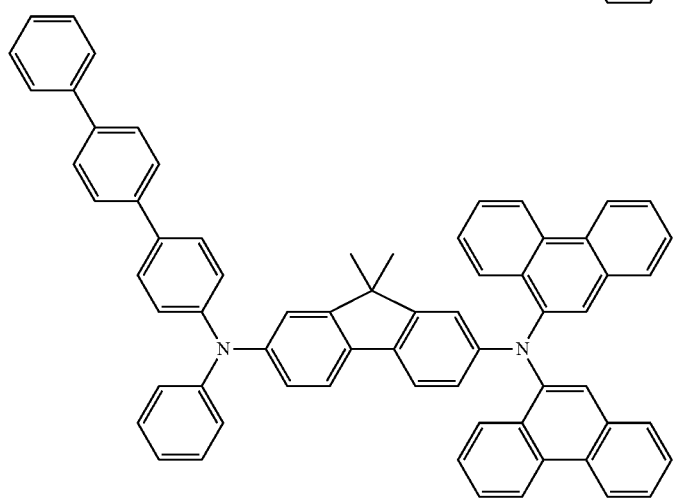

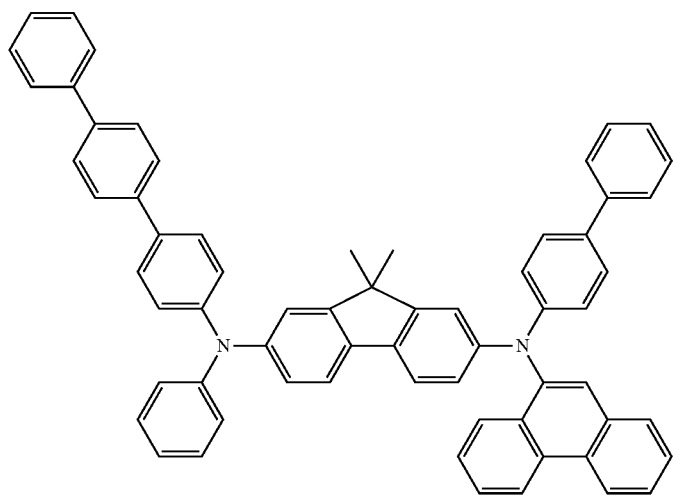
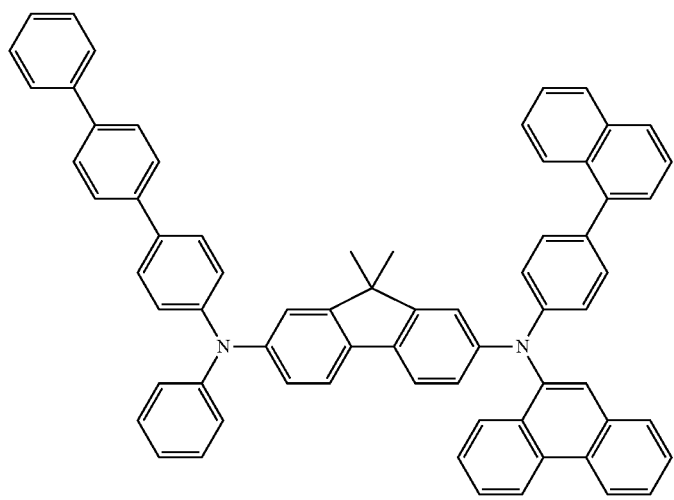
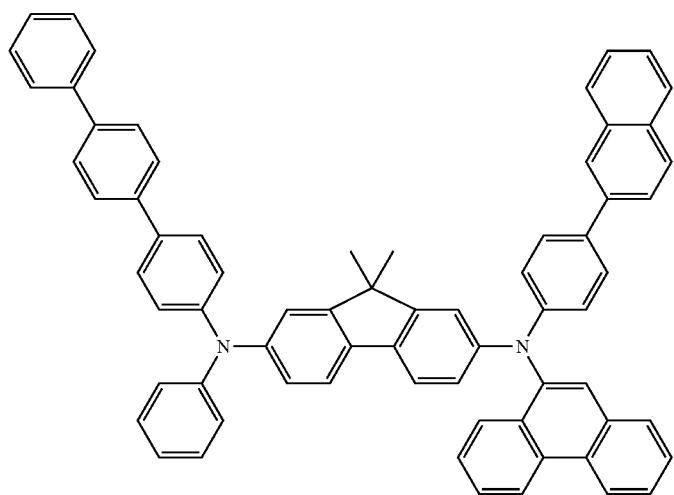

-continued
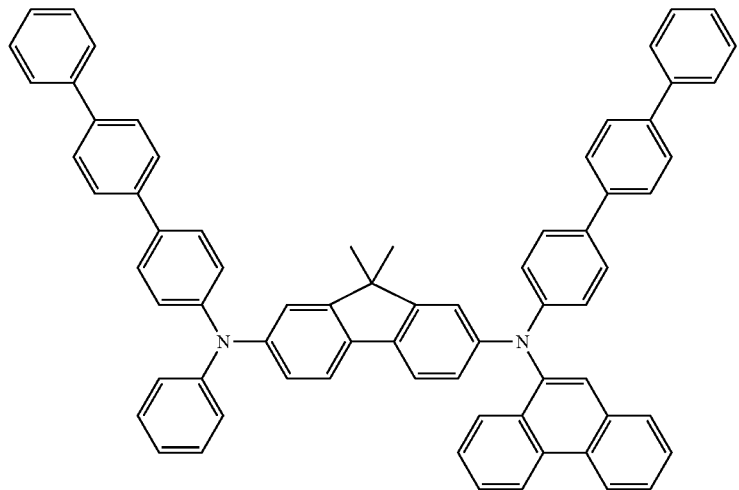
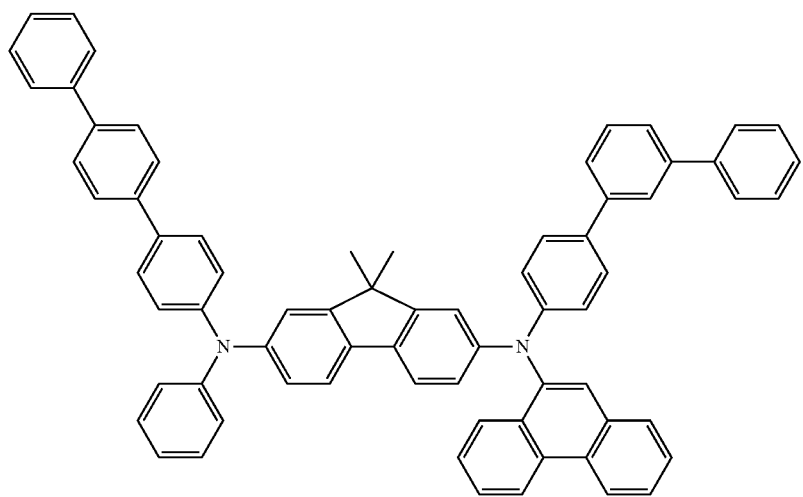
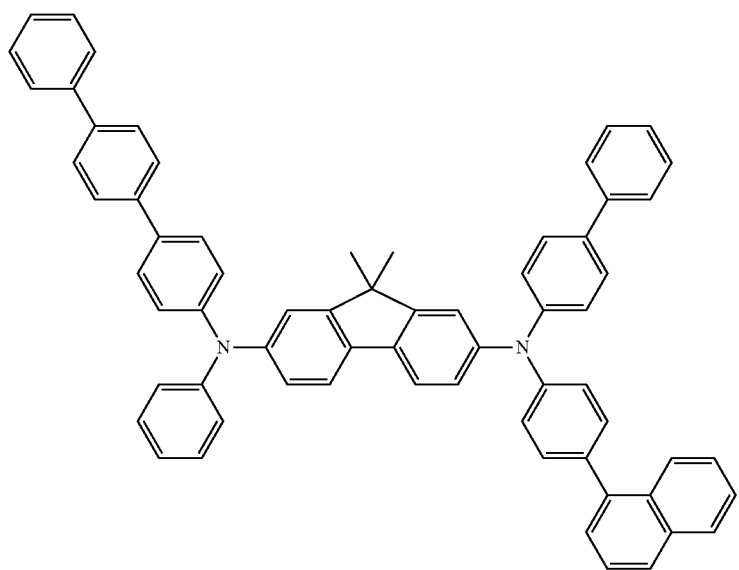

-continued
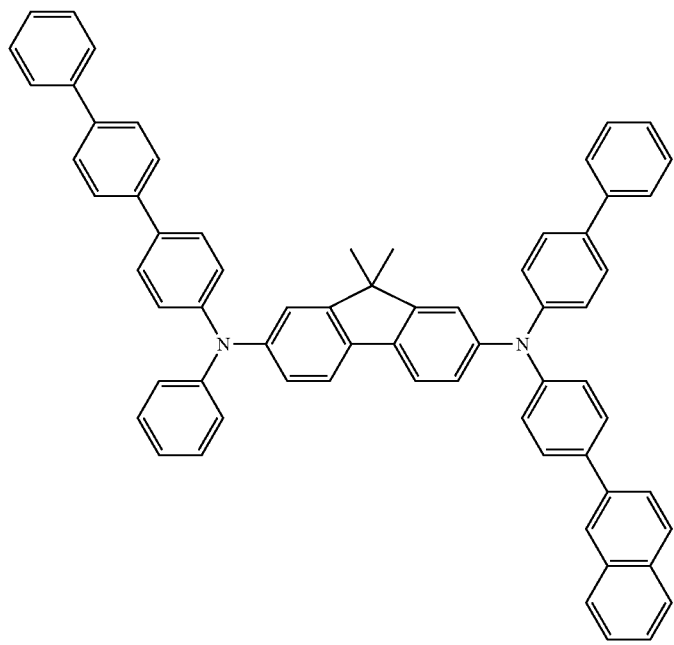
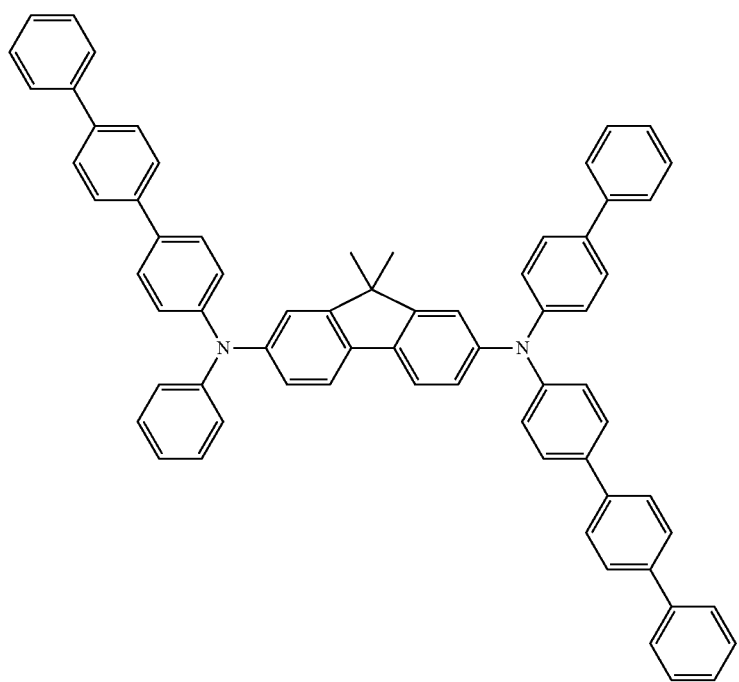

-continued
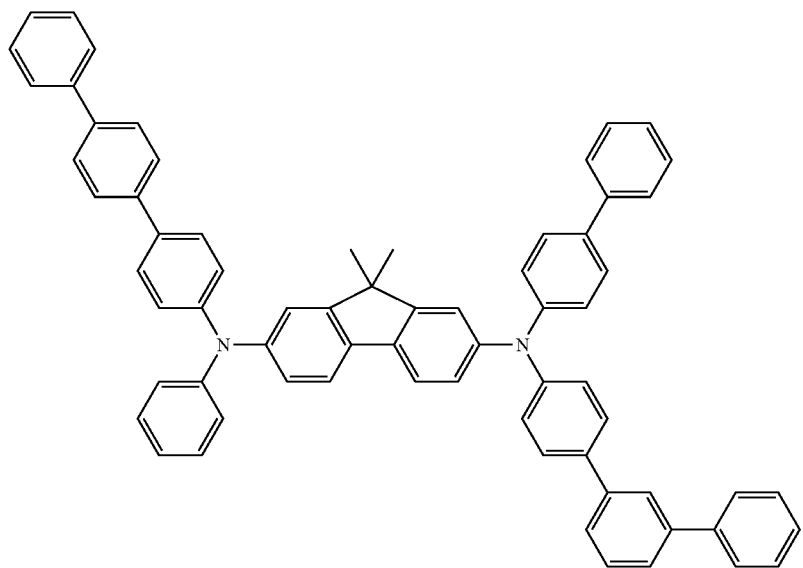
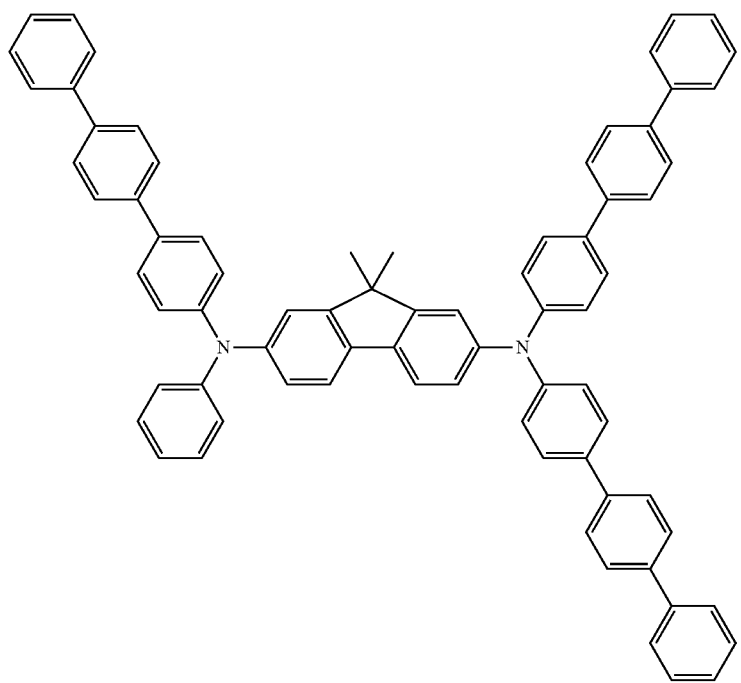

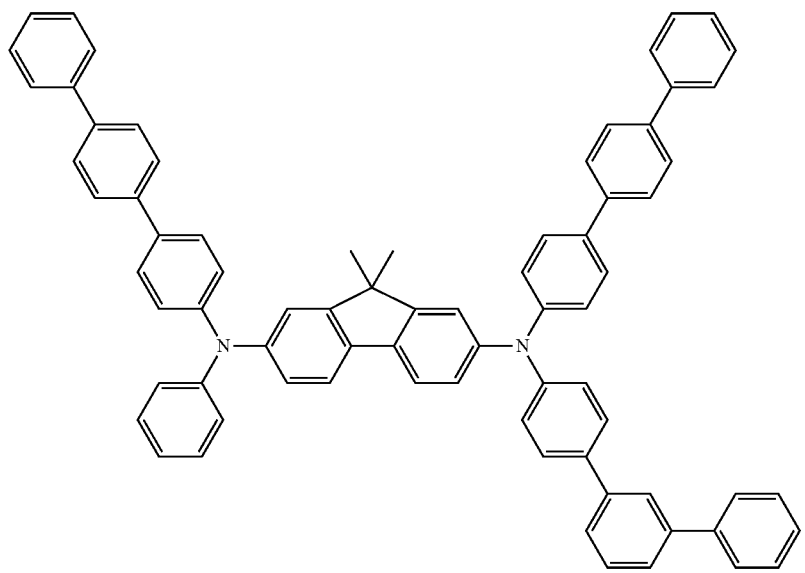
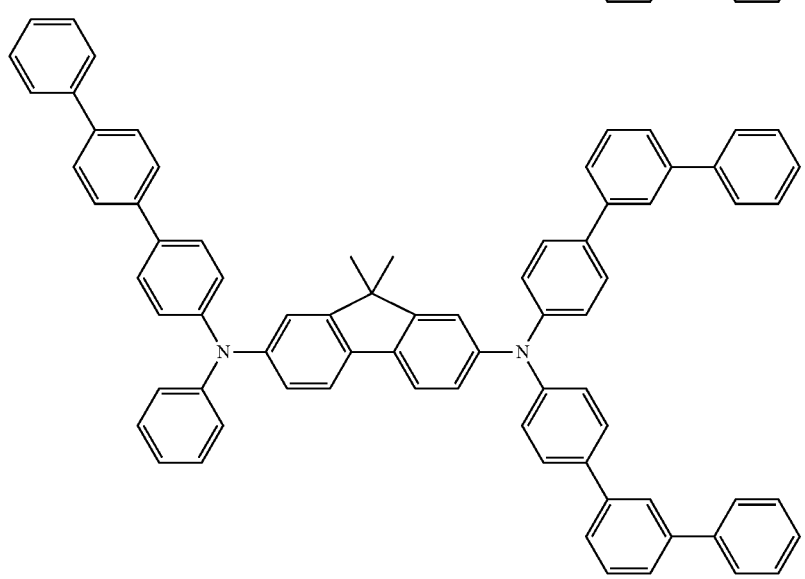
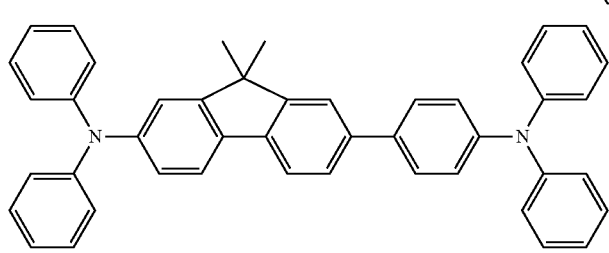
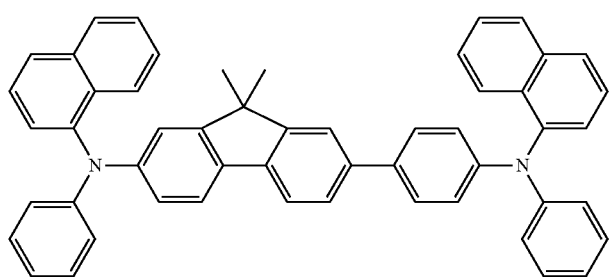

-continued
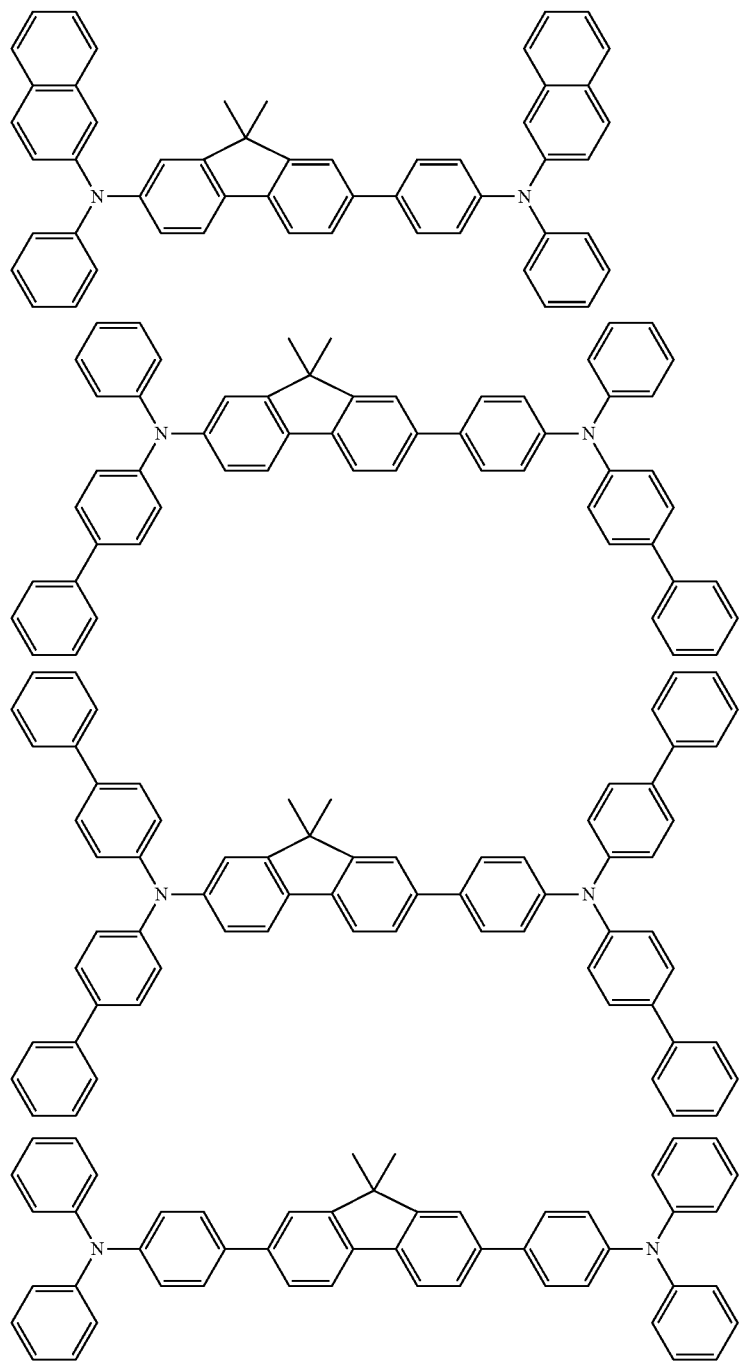
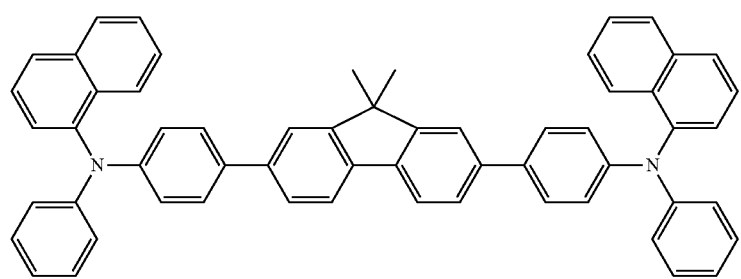

-continued
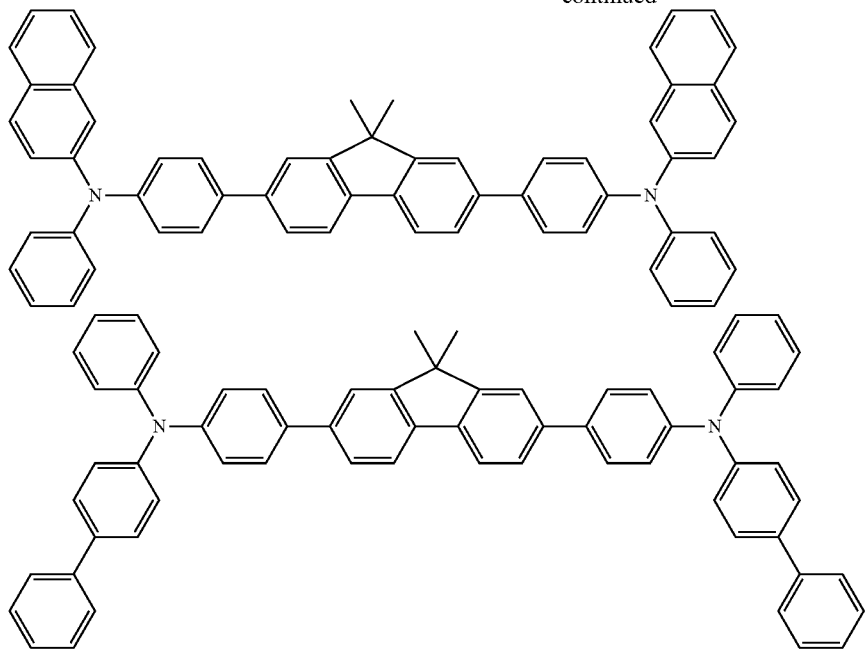
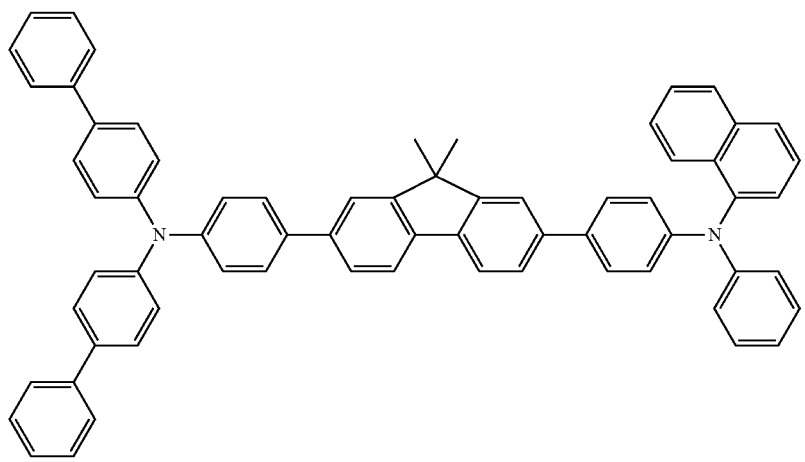
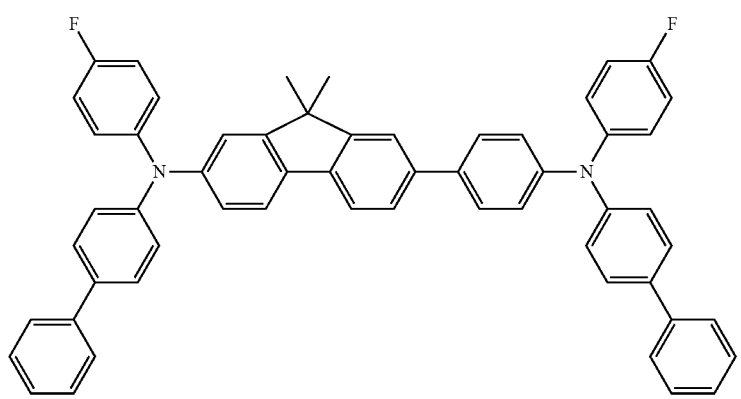

-continued

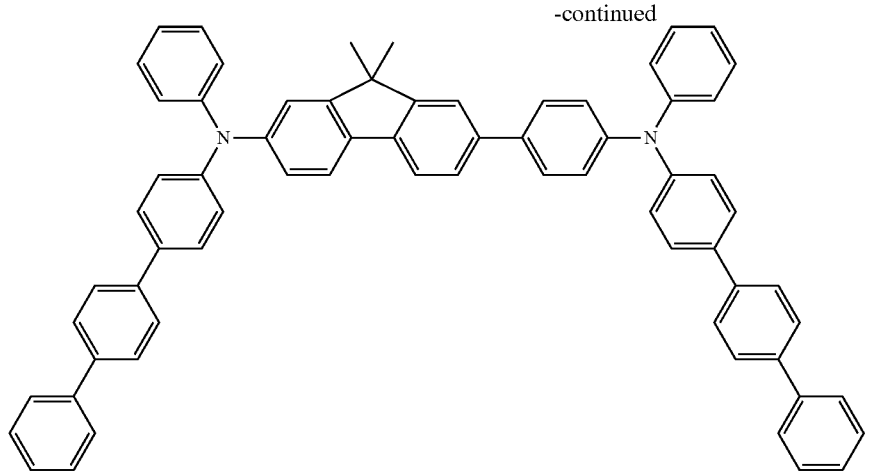

Organic EL Device

Embodiments of the organic EL device of the present invention will be described.

The organic EL device of the present invention contains an anode and a cathode facing each other, and intervening therebetween at least two hole transporting layers and a light emitting layer sequentially, and one of the hole transporting layers contains the compound represented by the formula (1) and is not adjacent to the light emitting layer.

For examples, it is more preferred that the at least two hole transporting layers include a first hole transporting layer on the side of the anode and a second hole transporting layer on the side of the light emitting layer, and the first hole transporting layer contains the compound represented by the formula (1).

In the present invention, the hole transporting layer is constituted by plural layers, and the hole transporting layer that is not adjacent to the light emitting layer among these layers contains the compound having a high mobility represented by the formula (1) as a hole transporting material, whereby the driving voltage may not be increased even when the thickness of the hole transporting layer is increased, the optical path length of the organic EL device may be controlled, and the device may have an increased efficiency and a prolonged service life. The compound represented by the formula (1) has a large affinity with the acceptor material excellent in the hole injection property, and a larger amount of holes may be transported and injected to the light emitting layer by increasing the carrier formation amount, which is considered to derive enhancement of the efficiency of the device. The organic EL device of the present invention is excellent as a phosphorescent organic EL device, and in addition, by using a heteroaryl-substituted amine derivative in the hole transporting layer that is adjacent to the light emitting layer, the organic EL device achieves excellent advantages not only as a phosphorescent organic EL device but also as a fluorescent organic EL device.

The organic EL device of the present invention may be a fluorescent or phosphorescent monochromatic light emitting device or a fluorescent/phosphorescent hybrid type white light emitting device, and may be a simple type having a sole light emitting unit or a tandem type having plural light emitting units. The term "light emitting unit" herein means a minimum unit capable of emitting light through recombination of holes and electrons injected containing one or more organic layers, at least one of which is a light emitting layer.

The structure of the organic EL device of the present invention will be described.

(1) Structure of Organic EL Device

Examples of the representative structure of the organic EL device of the present invention include the following structures:

(1) anode/acceptor material-containing layer (acceptor layer)/first hole transporting layer/second hole transporting layer/light emitting layer/cathode;

(2) anode/acceptor material-containing layer (acceptor layer)/first hole transporting layer/second hole transporting layer/light emitting layer/electron injecting layer/cathode;

(3) anode/acceptor material-containing layer (acceptor layer)/first hole transporting layer/second hole transporting layer/light emitting layer/electron transporting layer/electron injecting layer/cathode;

(4) anode/first hole transporting layer/second hole transporting layer/light emitting layer/electron injecting layer/cathode; and (5) anode/first hole transporting layer/second hole transporting layer/light emitting layer/electron transporting layer/electron injecting layer/cathode.

The organic EL device may further have third, fourth or more hole transporting layers between the second hole transporting layer and the light emitting layer. An electron barrier layer and an exciton barrier layer may be provided between the light emitting layer and the hole transporting layer, and the hole transporting layer that is adjacent to the light emitting layer may be an electron barrier layer or an exciton barrier layer.

The organic EL device of the present invention preferably has an acceptor layer containing an acceptor material between the anode and the at least two hole transporting layers (particularly the hole transporting layer that is closest to the anode). The hole transporting layer that contains the compound represented by the formula (1) may contain the acceptor material.

The acceptor material is preferably a compound having a skeleton having a high planarity, such as compounds represented by the following formulae (A), (B) and (C), since the bonding property with the hole transporting layer that contains the compound represented by the formula (1) is enhanced, by which enhancement of the device capability may be expected.

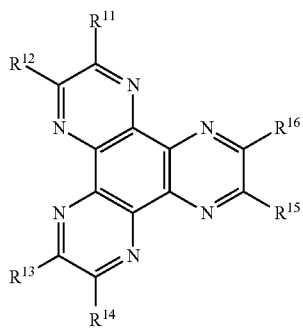
(A)

wherein in the formula (A), $R^{11}$ to $R^{16}$ each independently represent a cyano group, —$CONH_2$, a carboxyl group or —$COOR^{17}$ (wherein $R^{17}$ represents an alkyl group having from 1 to 20 carbon atoms), or $R^{11}$ and $R^{12}$, $R^{13}$ and $R^{14}$, or $R^{15}$ and $R^{16}$ are bonded to each other to form a group represented by —CO—O—CO—.

Examples of the alkyl group represented by $R^{17}$ include a methyl group, an ethyl group, a n-propyl group, an isopropyl group, a n-butyl group, an isobutyl group, a tert-butyl group, a cyclopentyl group and a cyclohexyl group.

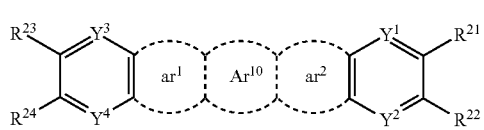
(B)

wherein in the formula (B), $Ar^{10}$ represents a condensed ring having from 6 to 24 ring carbon atoms or a heterocyclic ring having from 6 to 24 ring atoms; and $ar^1$ and $ar^2$, which may be the same as or different from each other, each represent the following formula (i) or (ii):

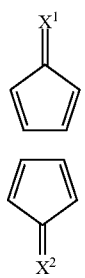
(i)

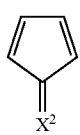
(ii)

wherein $X^1$ and $X^2$, which may be the same as or different from each other, each represent one of divalent groups represented by the following formulae (a) to (g):

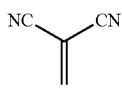
(a)

(b)

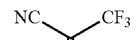
(c)

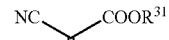
(d)

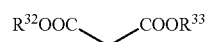
(e)

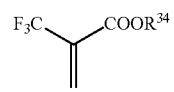
(f)

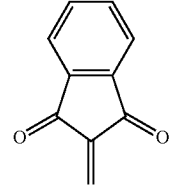
(g)

wherein $R^{31}$ to $R^{34}$, which may be the same as or different from each other, each represent a hydrogen atom, a substituted or unsubstituted fluoroalkyl group having from 1 to 20 carbon atoms, a substituted or unsubstituted alkyl group having from 1 to 20 carbon atoms, a substituted or unsubstituted aryl group having from 6 to 50 carbon atoms or a substituted or unsubstituted heterocyclic group having from 3 to 50 ring atoms, provided that $R^{32}$ and $R^{33}$ may be bonded to each other to form a ring.

In the formula (B), $R^{21}$ to $R^{24}$, which may be the same as or different from each other, each represent a hydrogen atom, a substituted or unsubstituted alkyl group having from 1 to 20 carbon atoms, a substitute or unsubstituted aryl group having from 6 to 50 carbon atoms, a substituted or unsubstituted heterocyclic group having from 3 to 50 ring atoms, a halogen atom, a substituted or unsubstituted fluoroalkyl group having from 1 to 20 carbon atoms, a substituted or unsubstituted alkoxy group having from 1 to 20 carbon atoms, a substituted or unsubstituted fluoroalkoxy group having from 1 to 20 carbon atoms, a substituted or unsubstituted aryloxy group having from 6 to 50 carbon atoms or a cyano group. The adjacent groups in $R^{21}$ to $R^{24}$ may be bonded to each other to form a ring. $Y^1$ to $Y^4$, which may be the same as or different from each other, each represent —N=, —CH= or C($R^{25}$)=, wherein $R^{25}$ represents a substituted or unsubstituted alkyl group having from 1 to 20 carbon atoms, a substituted or unsubstituted aryl group having from 6 to 50 carbon atoms, a substituted or unsubstituted heterocyclic group having from 3 to 50 ring atoms, a halogen atom, a substituted or unsubstituted fluoroalkyl group having from 1 to 20 carbon atoms, a substituted or unsubstituted alkoxy group having from 1 to 20 carbon atoms, a substituted or unsubstituted fluoroalkoxy group having from 1 to 20 carbon atoms, a substituted or unsubstituted aryloxy group having from 6 to 50 carbon atoms or a cyano group.

Examples of the groups represented by $R_{21}$ to $R_{24}$ and $R_{31}$ to $R_{34}$ are as follows.

Examples of the alkyl group include a methyl group, an ethyl group, a n-propyl group, an isopropyl group, a n-butyl group, an isobutyl group, a tert-butyl group, a cyclopentyl group and a cyclohexyl group.

Examples of the aryl group include a phenyl group, a biphenyl group, a naphthyl group, a fluorophenyl group and a trifluoromethylphenyl group.

Examples of the heterocyclic ring group include residual groups of pyridine, pyrazine, furan, imidazole, benzimidazole and thiophene.

Examples of the halogen atom include a fluorine atom, a chlorine atom, a bromine atom and an iodine atom.

Examples of the fluoroalkyl group include a trifluoromethyl group, a pentafluoroethyl group, a perfluorocyclohexyl group and a perfluoroadamantyl group.

Examples of the alkoxy group and the fluoroalkoxy group include a methoxy group, an ethoxy group and a trifluoromethoxy group.

Examples of the aryloxy group include a phenyloxy group.

These groups may have a substituent, and examples of the substituted aryl group include an aryl group having a halogen atom substituted, such as a monofluorophenyl group and a trifluoromethylphenyl group, and an aryl group having an alkyl group having from 1 to 10 (preferably from 1 to 5) carbon atoms substituted, such as a tolyl group and a 4-t-butylphenyl group. Examples of the substituted alkyl group include an alkyl group having a halogen atom substituted, such as a trifluoromethyl group, a pentafluoroethyl group, a perfluorocyclohexyl group and a perfluoroadamantyl group. Examples of the substituted aryloxy group include an aryloxy group having a halogen atom substituted or having a halogen atom-containing alkyl group (having from 1 to 5 carbon atoms) substituted, such as 4-trifluoromethylphenyloxy group and a pentafluorophenyloxy group, and an aryloxy group having an alkyl group having from 1 to 10 (preferably from 1 to 5) carbon atoms substituted, such as a 4-t-butylphenoxy group.

The adjacent groups in $R^{21}$ to $R^{24}$ may be bonded to each other to form a ring. Examples of the ring include a benzene ring, a naphthalene ring, a pyrazine ring, a pyridine ring and a furan ring.

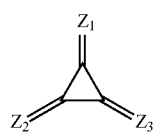

(C)

wherein $Z_1$ to $Z_3$ each independently represent a divalent group represented by the following formula (h):

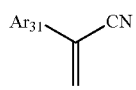

(h)

wherein $Ar_{31}$ represents a substituted or unsubstituted aryl group having from 6 to 50 carbon atoms or a substituted or unsubstituted heteroaryl group having from 3 to 50 ring atoms.

Examples of the aryl group include a phenyl group and a naphthyl group.

Examples of the heteroaryl group include pyridine, pyradine, pyrimidine, quinoline and isoquinoline.

Examples of the substituent on these groups include an electron withdrawing group, such as a cyano group, a fluoro group, a trifluoromethyl group, a chloro group and a bromo group.

(2) Light Transmissive Substrate

The organic EL device of the present invention may be formed on a light transmissive substrate. The light transmissive substrate referred herein is a substrate that supports the organic EL device and is preferably a flat and smooth substrate having a transmittance to light in the visible range of from 400 to 700 nm of 50% or more.

Specific examples thereof include a glass plate and a polymer plate. Examples of the glass plate include particularly soda-lime glass, barium-strontium-containing glass, lead glass, aluminosilicate glass, borosilicate glass, barium-borosilicate glass and quartz. Examples of the polymer plate include polycarbonate, acrylic, polyethylene terephthalate, polyether sulfide and polysulfone.

(3) Anode

The anode of the organic EL device of the present invention has a function of injecting holes to the hole transporting layer or the light emitting layer, and may effectively has a work function of 4.5 eV or more. Specific examples of the material of the anode used in the present invention include indium tin oxide alloy (ITO), tin oxide (NESA), indium zinc oxide (IZO), gold, silver, platinum and copper.

The anode may be produced by forming a thin film of these electrode materials by such a method as a vapor deposition method and a sputtering method.

In the case where light emitted from the light emitting layer is taken out from the anode, the transmittance of the anode to the emitted light is preferably 10% or more. The sheet resistance of the anode is preferably several hundred Ω per square or less. The thickness of the anode may be selected from a range of generally from 10 nm to 1 μm, and preferably from 10 to 200 nm, while depending on the material thereof.

(4) Hole Transporting Layer

As having been described above, the organic EL device of the present invention has two or more layers of the hole transporting layers.

The hole transporting layer that is not adjacent to the light emitting layer may often be used with a large thickness for optical control of the organic EL device, and is demanded to have a high hole mobility from the standpoint of reduction of the operation voltage. Furthermore, the layer may often be used with an acceptor layer laminated therewith for generating the carrier efficiently, and is required to exhibit high interaction with the acceptor layer.

The compound represented by the formula (1) has a high planarity due to the fluorene structure thereof, as compared to a biphenyl structure, and thus has a large hole mobility. Furthermore, the compound is excellent in interaction with an acceptor material, which generally has a high planarity, and thus may transport and inject a larger amount of holes to the light emitting layer. In other words, the compound represented by the general formula (1) satisfies the characteristics that are demanded for the hole transporting layer that is not adjacent to the light emitting layer, and thus is preferably used as the material for the hole transporting layer that is not adjacent to the light emitting layer.

On the other hand, as the characteristics demanded for the hole transporting layer that is adjacent to the light emitting layer, it is demanded to be an organic layer that has higher triplet energy (preferably 2.6 eV or more) for preventing the excitation energy of the light emitting layer from being diffused, has electroresistance since the layer is adjacent to the light emitting layer, and has a small affinity (preferably 2.4 eV or less) for preventing electrons from leaking from the light emitting layer, and an organic layer that has a large ionization potential (preferably 5.5 eV or more) for accelerating injection of holes to the light emitting layer. As a material satisfying these requirements, a heteroaryl-substituted amine derivative is preferred, and more preferred examples thereof include compounds represented by the following formulae (4) to (8), for providing not only an excellent phosphorescent organic EL device but also an excellent fluorescent organic EL device.

Example of Material for Hole Transporting Layer Adjacent to Light Emitting Layer (Second Hole Transporting Material);

Formula (4)

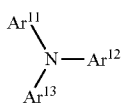

(4)

wherein in the formula (4), at least one of $Ar^{11}$ to $Ar^{13}$ is a group represented by the following formula (4-2) or (4-3), provided that the group that is not a group represented by the formula (4-2) is a group represented by the following formula (4-3) or (4-4) or a substituted or unsubstituted aryl group having from 6 to 40 carbon atoms, and the group that is not a group represented by the formula (4-3) is a group represented by the following formula (4-2) or (4-4) or a substituted or unsubstituted aryl group having from 6 to 40 carbon atoms.

A compound wherein at least one of $Ar^{11}$ to $Ar^{13}$ is the group (4-2) is particularly preferred.

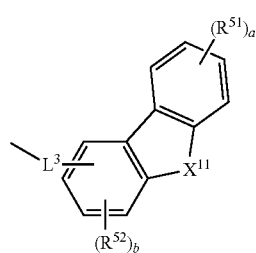

(4-2)

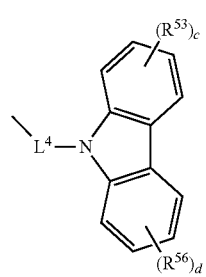

(4-3)

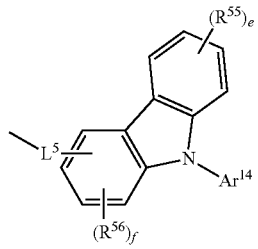

(4-4)

wherein $X^{11}$ represents an oxygen atom or a sulfur atom;

$L^3$ to $L^5$ each independently represents a single bond or a substituted or unsubstituted arylene group having from 6 to 50 ring carbon atoms, wherein a substituent that may be substituted on $L^3$ to $L^5$ is a linear or branched alkyl group having from 1 to 10 carbon atoms, a cycloalkyl group having from 3 to 10 ring carbon atoms, a trialkylsilyl group having from 3 to 10 carbon atoms, a triarylsilyl group having from 18 to 30 ring carbon atoms, an alkylarylsilyl group having from 8 to 15 carbon atoms (in which the alkyl group has from 1 to 5 carbon atoms, and the aryl group has from 6 to 14 ring carbon atoms), an aryl group having from 6 to 50 ring carbon atoms, a halogen atom or a cyano group;

$Ar^{14}$ represents a substituted or unsubstituted aryl group having from 6 to 50 ring carbon atoms, in which examples of the substituent that may be substituted on $Ar^{14}$ is a linear or branched alkyl group having from 1 to 10 carbon atoms, a cycloalkyl group having from 3 to 10 ring carbon atoms, a trialkylsilyl group having from 3 to 10 carbon atoms, a triarylsilyl group having from 18 to 30 ring carbon atoms, an alkylarylsilyl group having from 8 to 15 carbon atoms (in which the alkyl group has from 1 to 5 carbon atoms, and the aryl group has from 6 to 14 ring carbon atoms), an aryl group having from 6 to 50 ring carbon atoms, a halogen atom or a cyano group;

$R^{51}$ to $R^{56}$ each independently represents a substituted or unsubstituted linear or branched alkyl group having from 1 to 10 carbon atoms, a substituted or unsubstituted cycloalkyl group having from 3 to 10 ring carbon atoms, a substituted or unsubstituted trialkylsilyl group having from 3 to 10 carbon atoms, a substituted or unsubstituted triarylsilyl group having from 18 to 30 ring carbon atoms, a substituted or unsubstituted alkylarylsilyl group having from 8 to 15 carbon atoms (in which the alkyl group has from 1 to 5 carbon atoms, and the aryl group has from 6 to 14 ring carbon atoms), a substituted or unsubstituted aryl group having from 6 to 50 ring carbon atoms, a halogen atom or a cyano group, provided that the adjacent groups in $R^{51}$ to $R^{56}$ may be bonded to each other to form a ring; and b and f each independently represent an integer of from 0 to 3, and a, c, d and e each independently represent an integer of from 0 to 4.

Examples of the arylene group represented by $L^3$ to $L^5$ include a phenylene group, a naphthylene group, a biphenylene group, an anthrylene group, an acenaphtylenyl group, an anthranylene group, a phenanthrenylene group, a phenalenyl group, a quinolylene group, an isoquinolylene group, an s-indacenylene group, an as-indacenylene group and a chrysenylene group. Among these, an arylene group having from 6 to 30 ring carbon atoms is preferred, an arylene group having from 6 to 20 ring carbon atoms is more preferred, an arylene group having from 6 to 12 ring carbon atoms is further preferred, and a phenylene group is particularly preferred.

The other groups are described below, and the same description may be applied to the same group.

The alkyl group is preferably an alkyl group having from 1 to 5 carbon atoms, and more preferably an alkyl group having from 1 to 3 carbon atoms. Examples of the alkyl group include a methyl group, an ethyl group, a n-propyl group, an isopropyl group, a n-butyl group, an isobutyl group, a t-butyl group and a n-hexyl group.

The alkyl group in the trialkylsilyl group is the same as above, and the preferred examples thereof are also the same. Examples of the aryl group in the triarylsilyl group include a phenyl group, a naphthyl group and a biphenyl group.

Examples of the alkylaryl group in the alkylarylsilyl group include a dialkylmonoarylsilyl group. The alkyl group may have from 1 to 5 carbon atoms, and preferably from 1 to 3 carbon atoms, and the aryl group may have from 6 to 14 ring carbon atoms, and preferably from 6 to 10 ring carbon atoms.

Examples of the aryl group having from 6 to 50 ring carbon atoms include a phenyl group, a naphthyl group, a biphenylyl group, an anthryl group, a phenanthryl group and a terphenylyl group. Among these, an aryl group having from 6 to 30 ring carbon atoms is preferred, an aryl group having from 6 to 20 ring carbon atoms is more preferred, and an aryl group having from 6 to 12 ring carbon atoms is further preferred.

Examples of the halogen atom include a fluorine atom, a chlorine atom and a iodine atom.

a to f each is preferably 0 or 1, and more preferably 0.

Preferred examples of the formula (4-2) include the following formulae (4-2') and (4-2") (wherein the definitions of the groups are the same as above).

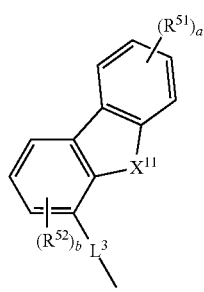

(4-2')

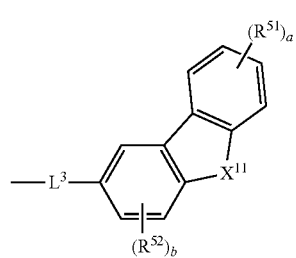

(4-2")

Preferred examples of the formula (4-4) include the following formula (4-4') (wherein the definitions of the groups are the same as above).

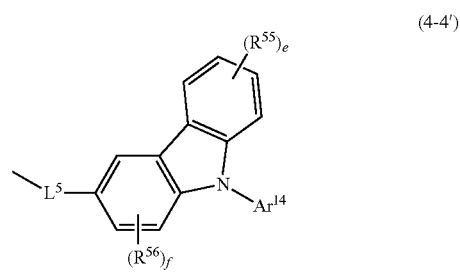

(4-4')

In the formula (4), at least one of $Ar^{11}$ to $Ar^{13}$ preferably represents a group represented by the formula (4-2). In the formula (4-2), $X^{11}$ preferably represents an oxygen atom.

In $Ar^{11}$ to $Ar^{13}$, it is also preferred that two groups are each a group represented by the formula (4-2); it is also preferred that one group is a group represented by the formula (4-2), and another one group is a group represented by the formula (4-3); and it is also preferred that three groups are each a group represented by the formula (4-2).

In the case where $L^3$ in the formula (4-2) or $L^5$ in the formula (4-4) is an arylene group, the electron density of the compound represented by the formula (4) is suppressed from being increased, the Ip thereof is increased, and the hole injection to the light emitting layer is accelerated, thereby making the driving voltage of the device advantageously low. Furthermore, when the dibenzofuran structure or the carbazole structure is bonded to the nitrogen atom through the arylene group, the amine is suppressed from being oxidized to make the compound stable in many cases, thereby prolonging the service life of the device. In the case where $L^5$ in the formula (4-4) is an arylene group, the compound becomes stable to facilitate synthesis of the compound. The arylene group is particularly preferably a phenylene group.

In the case where $Ar^{11}$ to $Ar^{13}$ in the formula (4) are not a group represented by the formulae (4-2) to (4-4), $Ar^{11}$ to $Ar^{13}$ each represent a substituted or unsubstituted aryl group having from 6 to 40 carbon atoms. The aryl group is preferably represented by the following formulae (4-5) to (4-7).

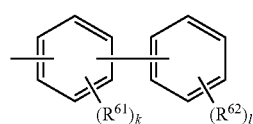

(4-5)

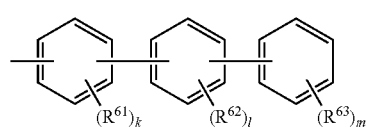

(4-6)

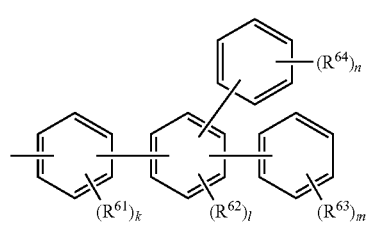

(4-7)

wherein $R^{61}$ to $R^{64}$ each independently represent a linear or branched alkyl group having from 1 to 10 carbon atoms, a cycloalkyl group having from 3 to 10 ring carbon atoms, a trialkylsilyl group having from 3 to 10 carbon atoms, a triarylsilyl group having from 18 to 30 ring carbon atoms, an alkylarylsilyl group having from 8 to 15 carbon atoms (in which the aryl moiety has from 6 to 14 ring carbon atoms), an aryl group having from 6 to 50 ring carbon atoms, a halogen atom or a cyano group, provided that the plural adjacent groups in $R^{61}$ to $R^{64}$ may be bonded to each other to form a saturated or unsaturated ring; and k, l, m and n each independently represent an integer of from 0 to 4.

The formulae (4-5) to (4-7) are preferably the following formulae (4-5') to (4-7') (wherein the definitions of the groups are the same as above).

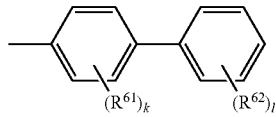
(4-5')

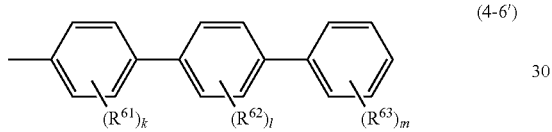
(4-6')

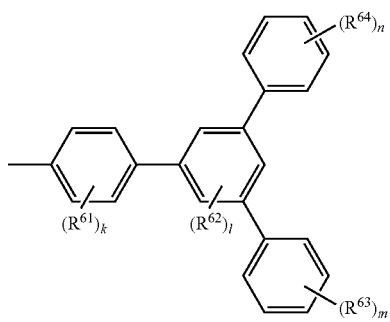
(4-7')

The formula (4-5') also includes the following groups.

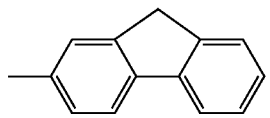

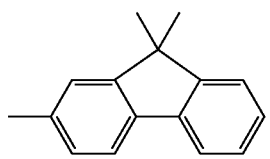

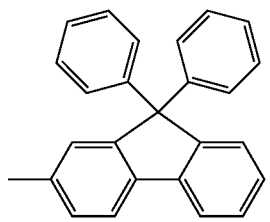

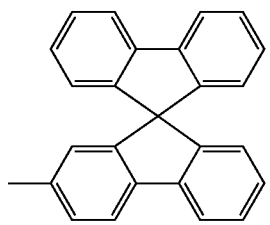

Specific examples of the compound represented by the formula (4) are shown below, but the compound is not particularly limited thereto.

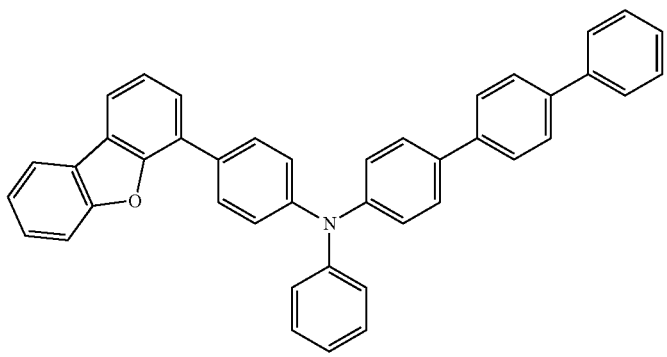

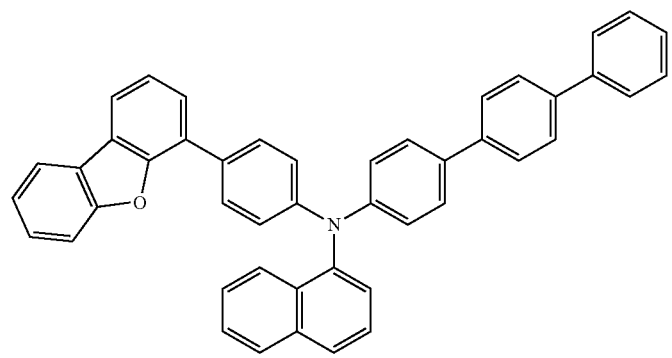
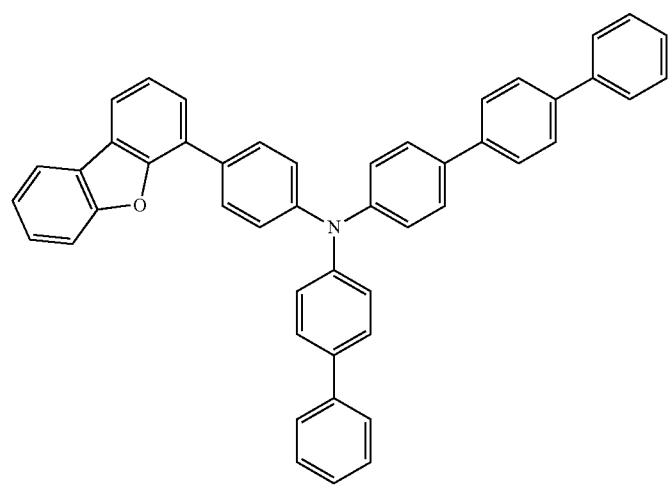
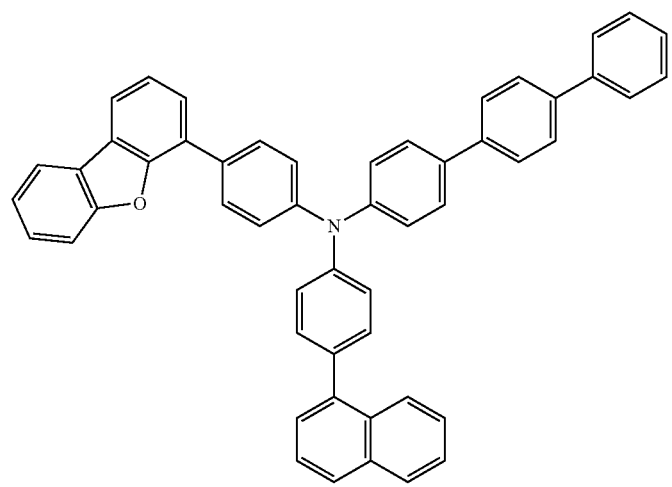

-continued
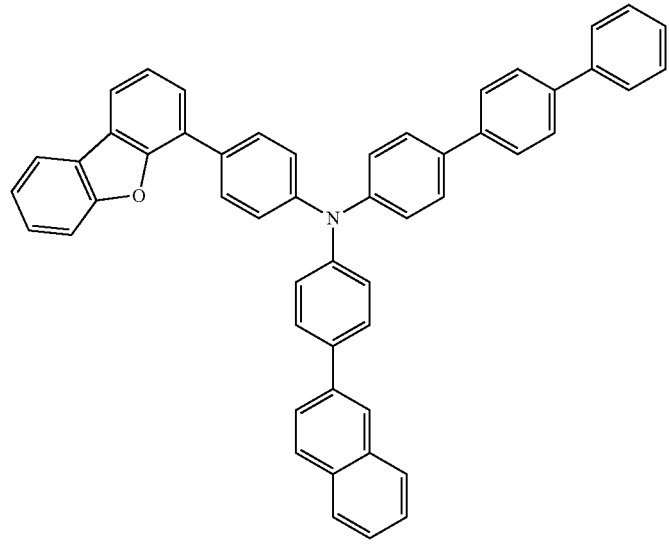
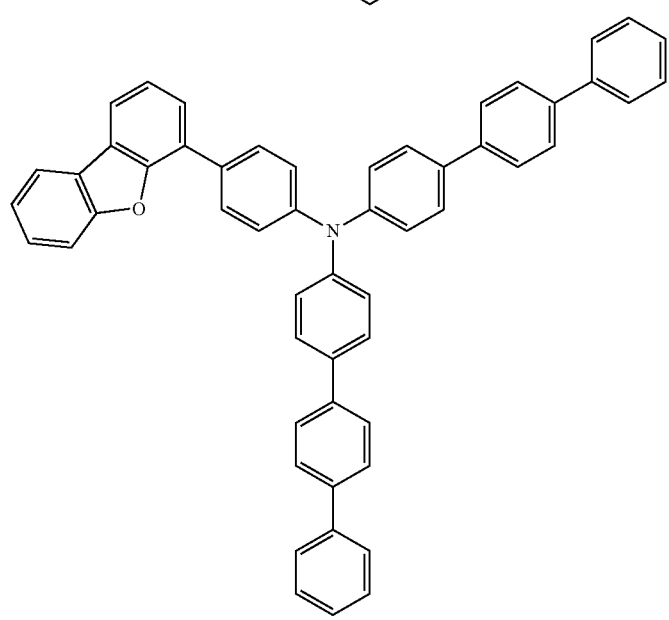
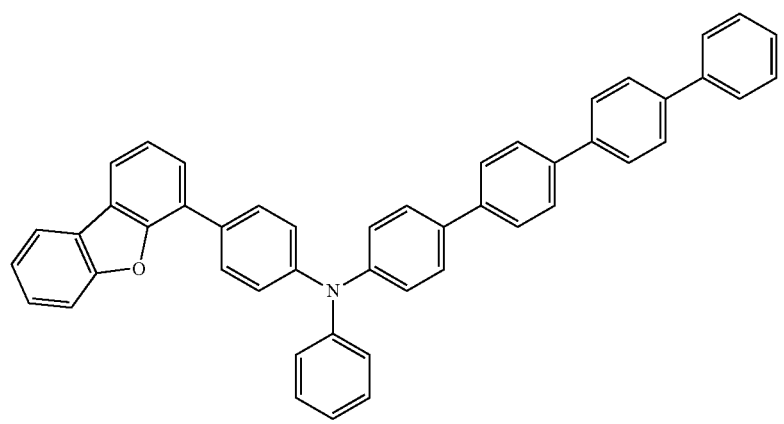

-continued
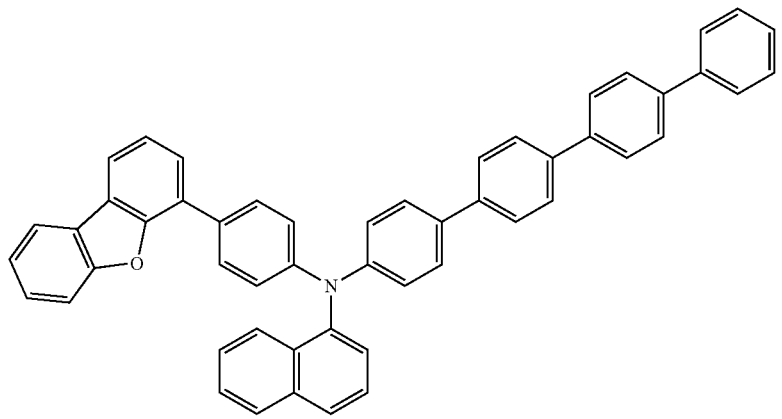
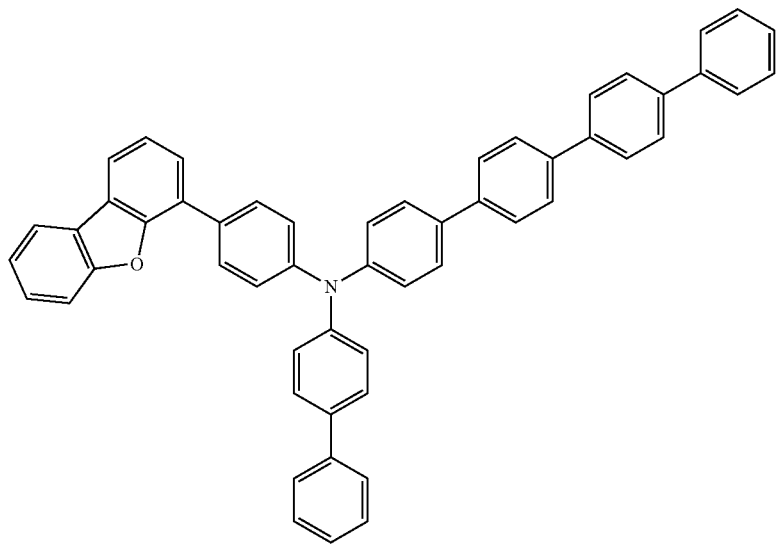
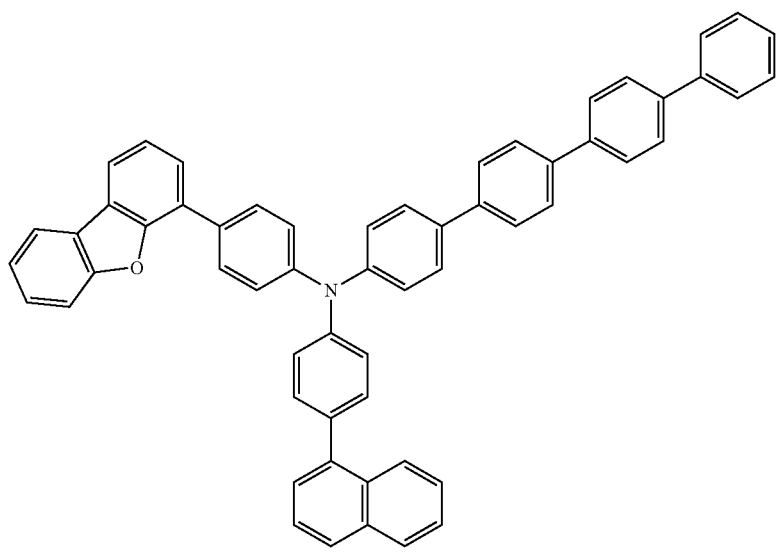

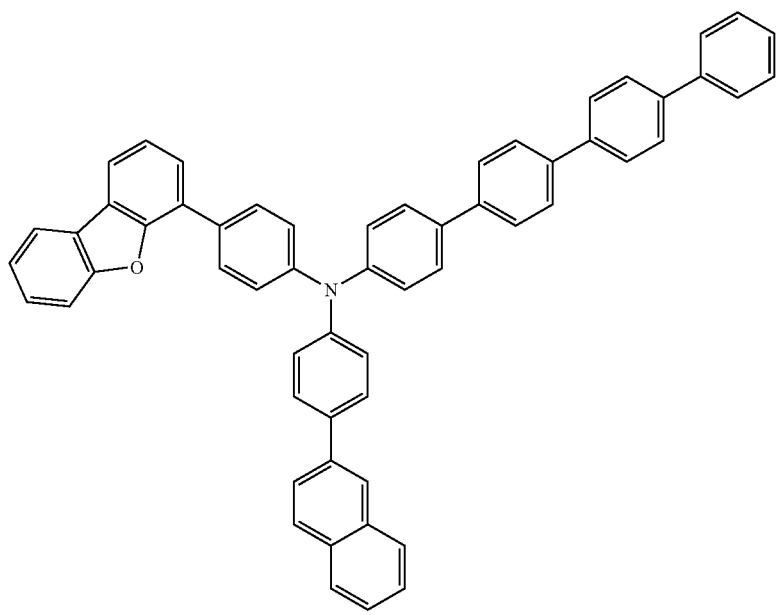
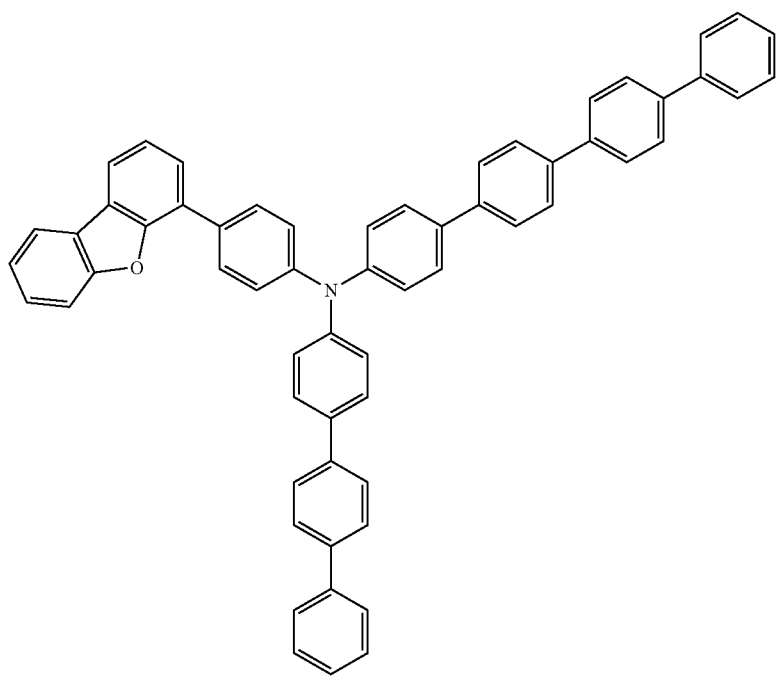
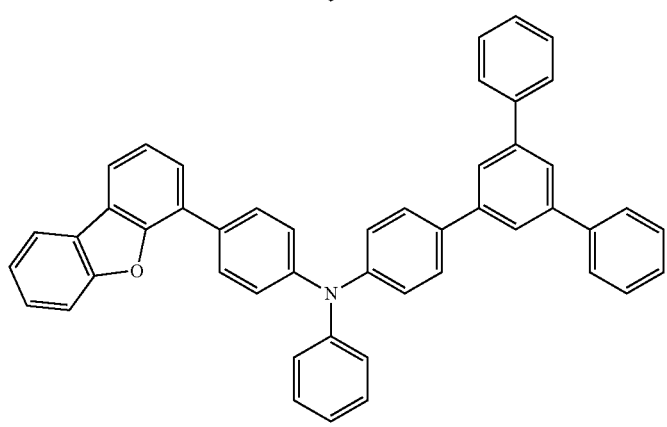

-continued
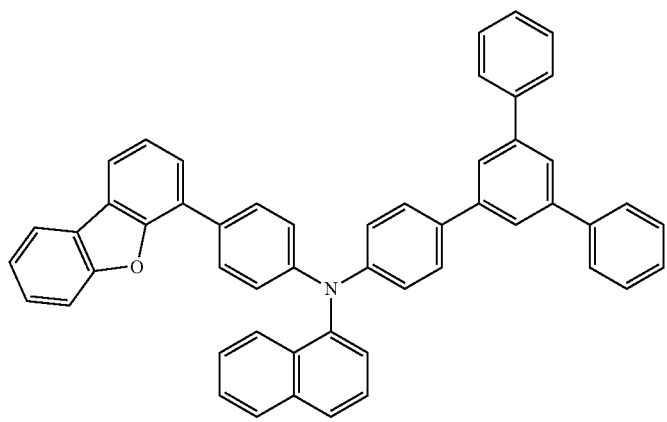
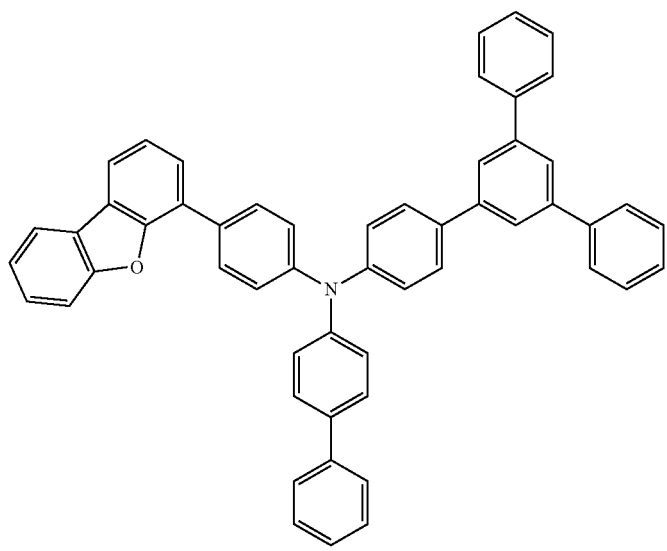
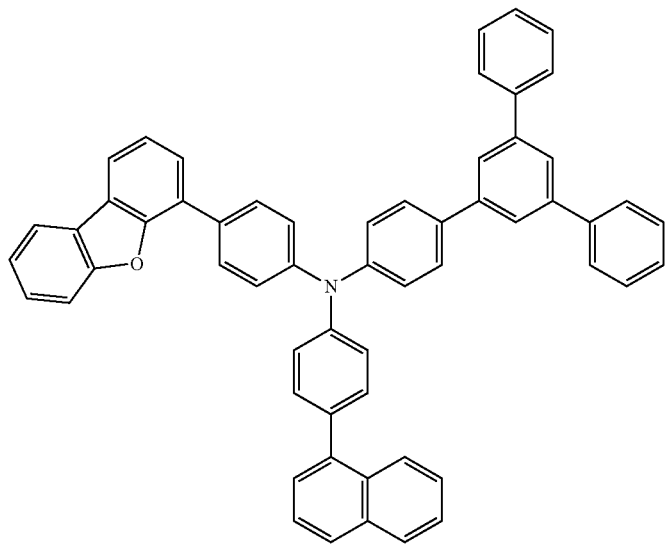

-continued
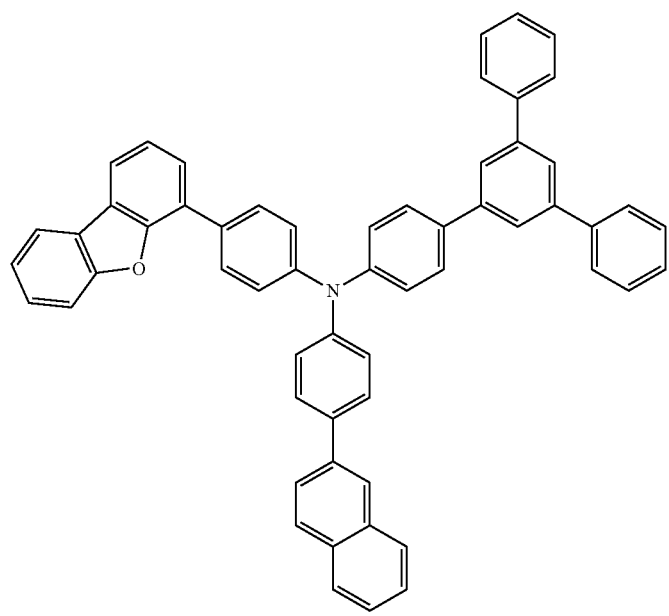
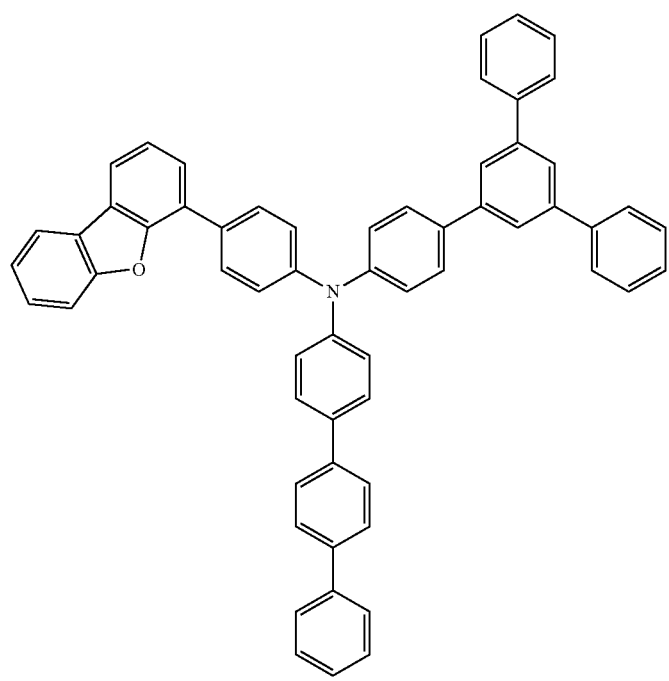

-continued
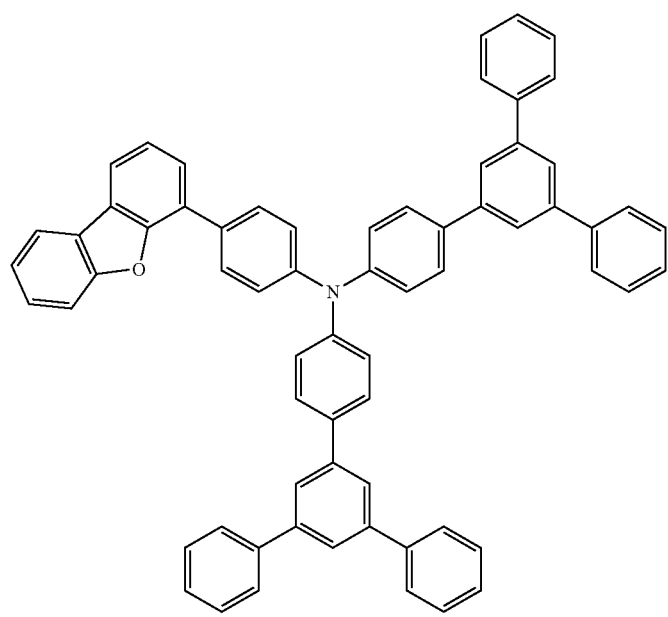
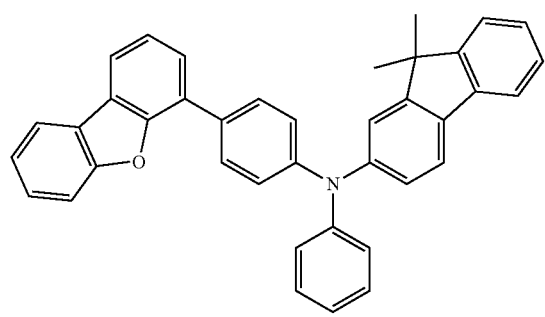
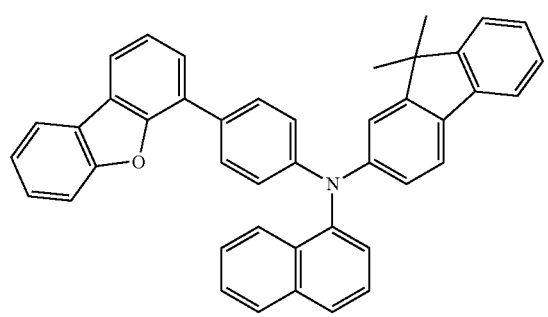
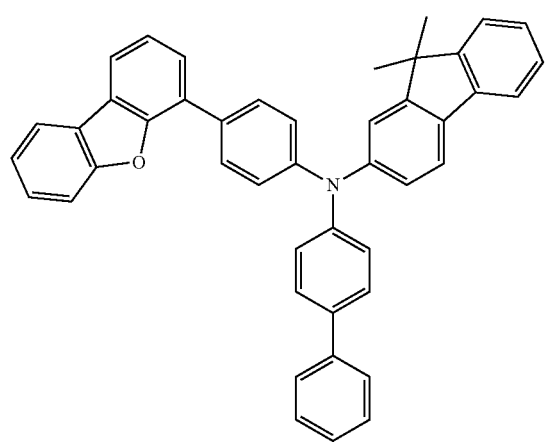
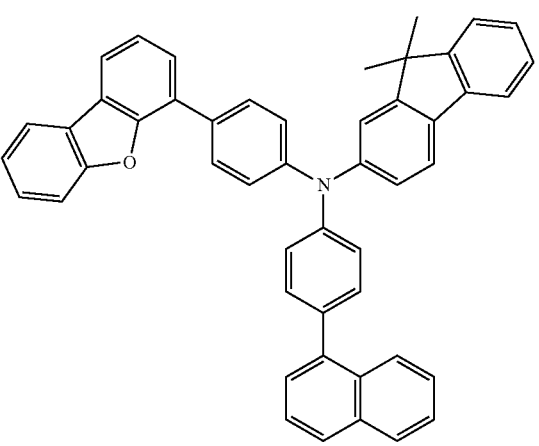

-continued
159
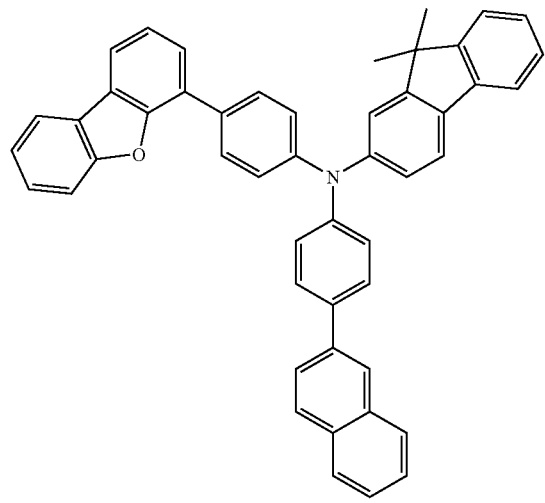
160
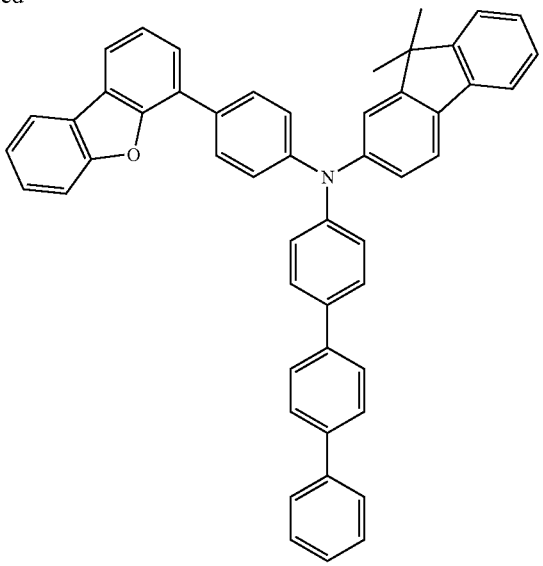
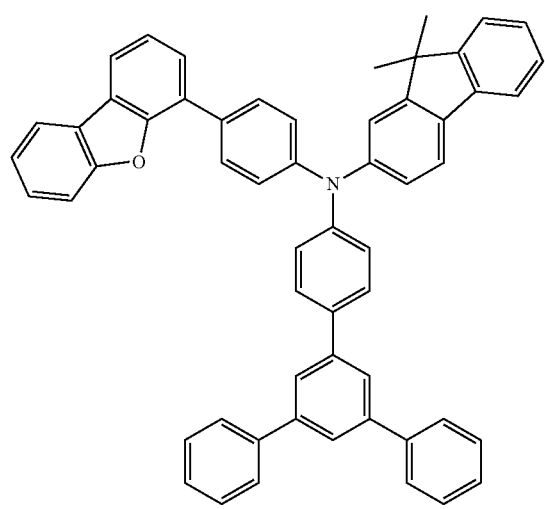
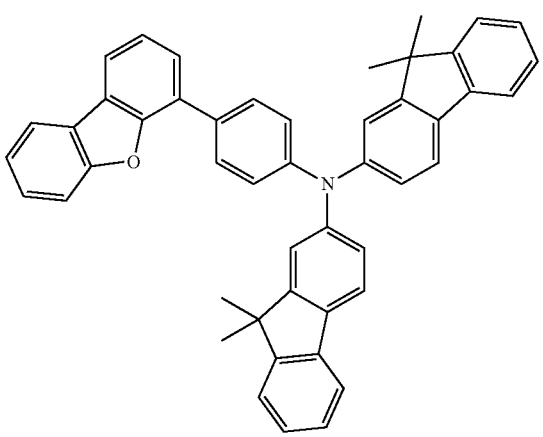
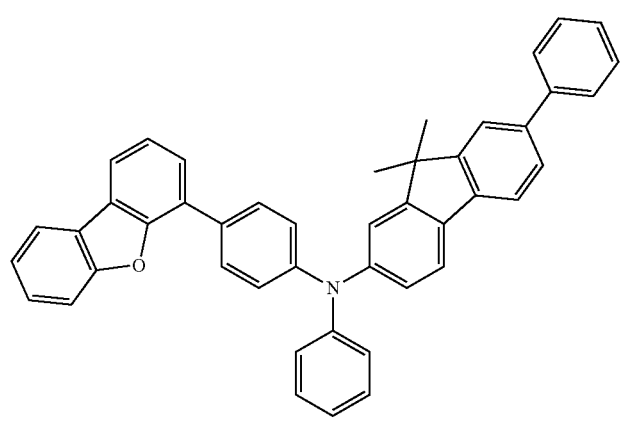

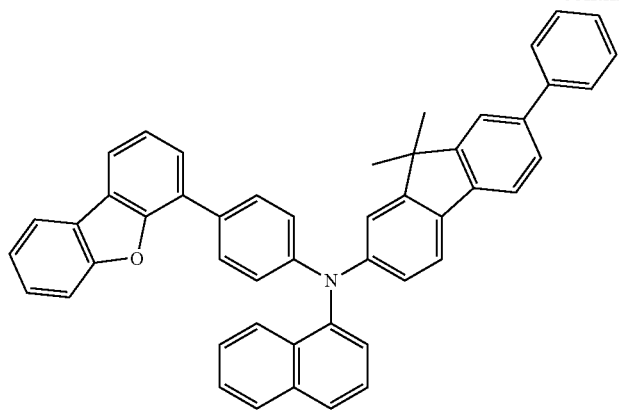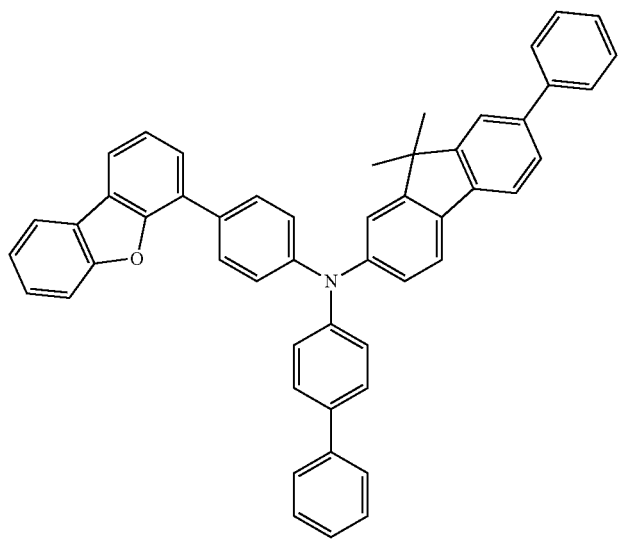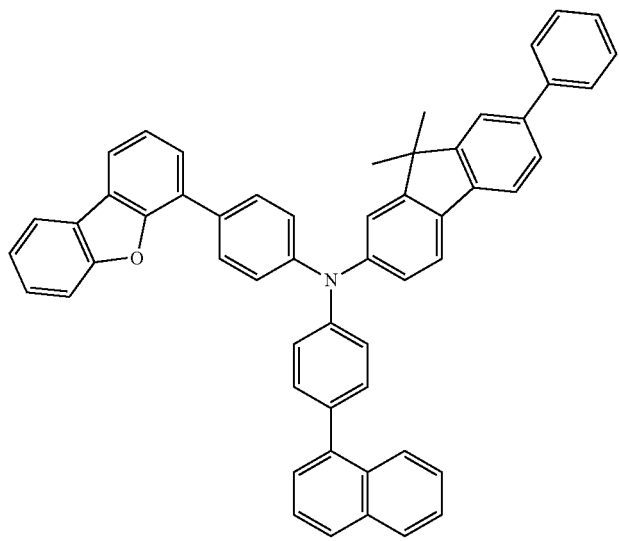

-continued
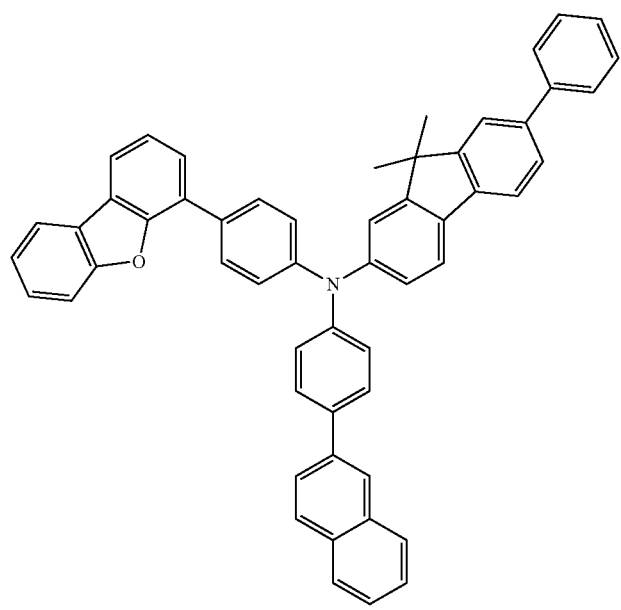
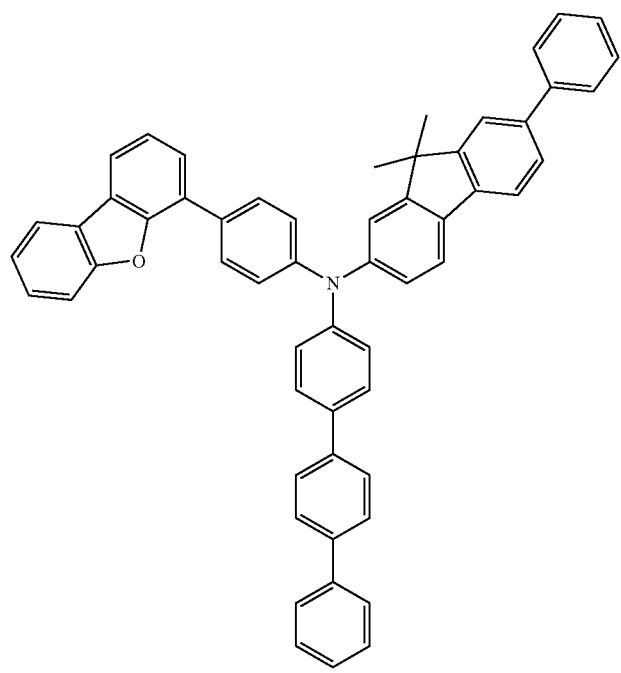

-continued
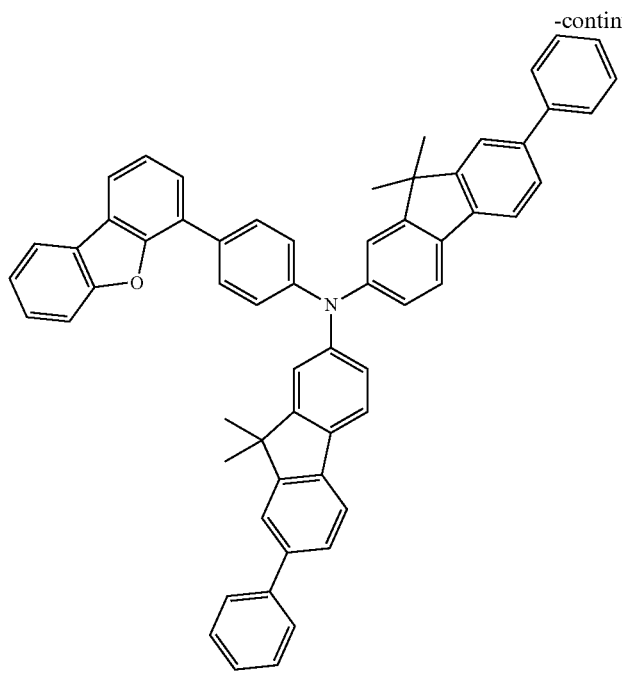
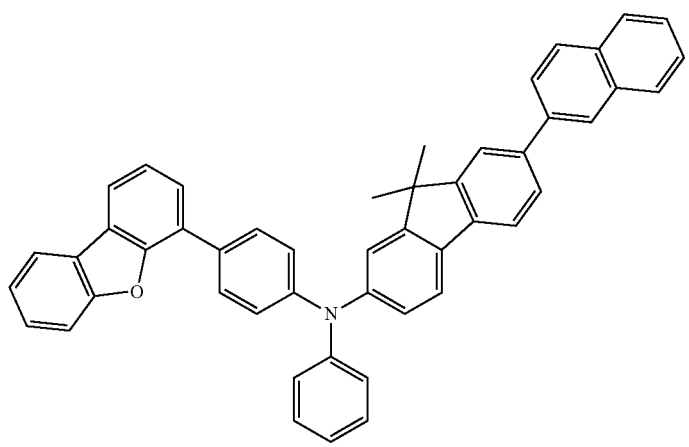
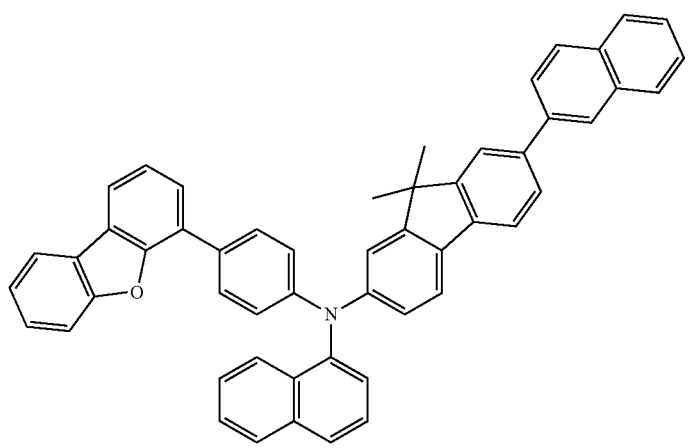

-continued
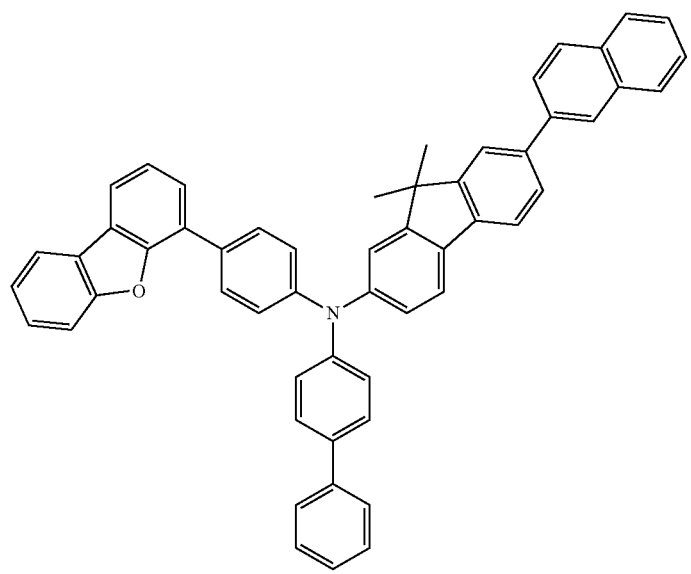
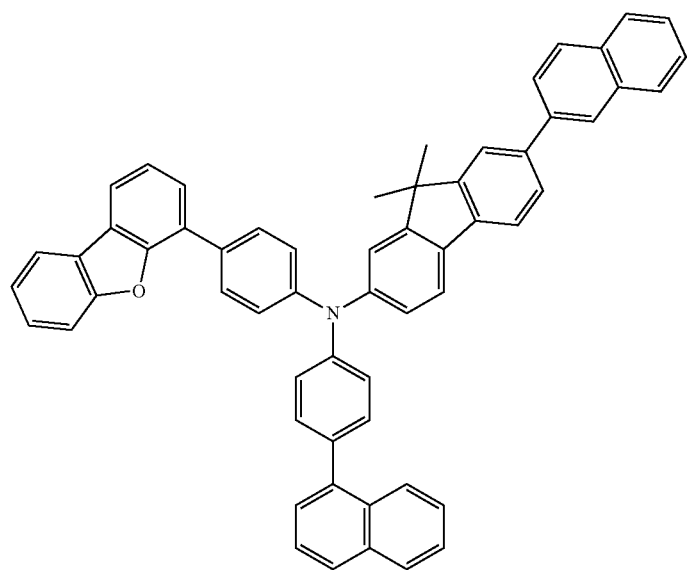

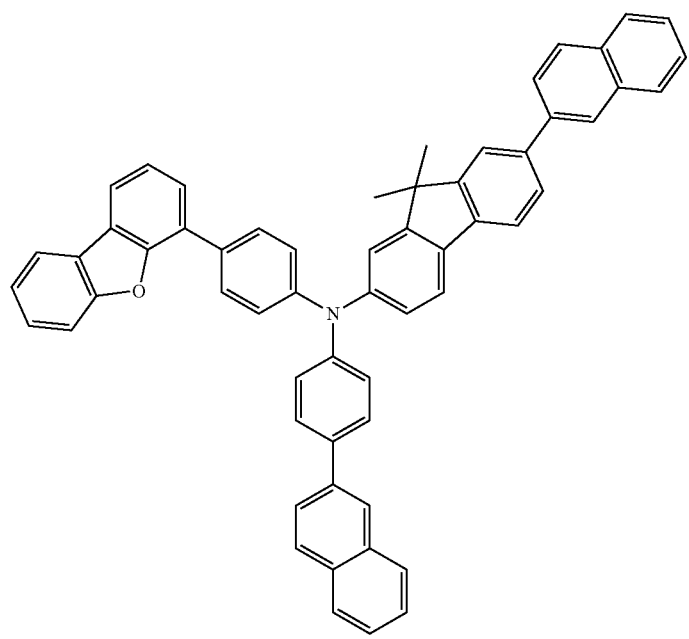
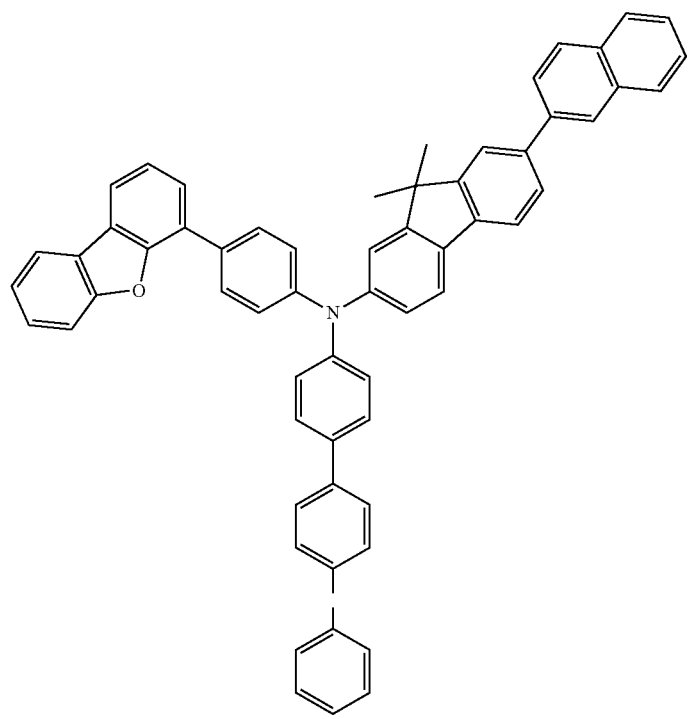
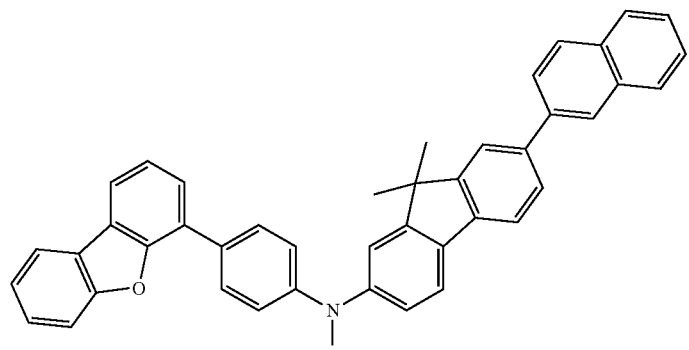

171 172
-continued
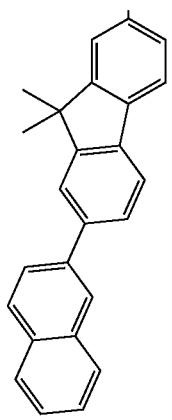
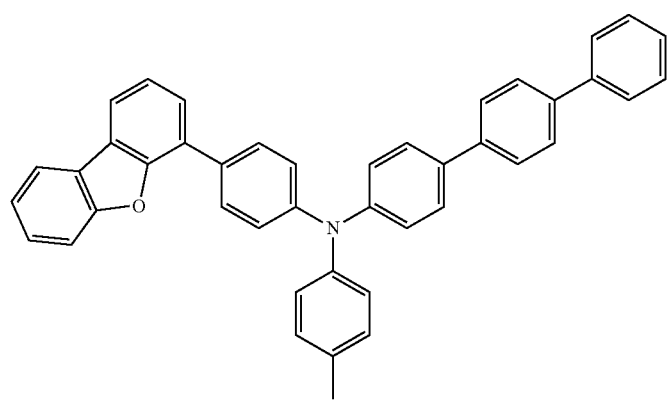
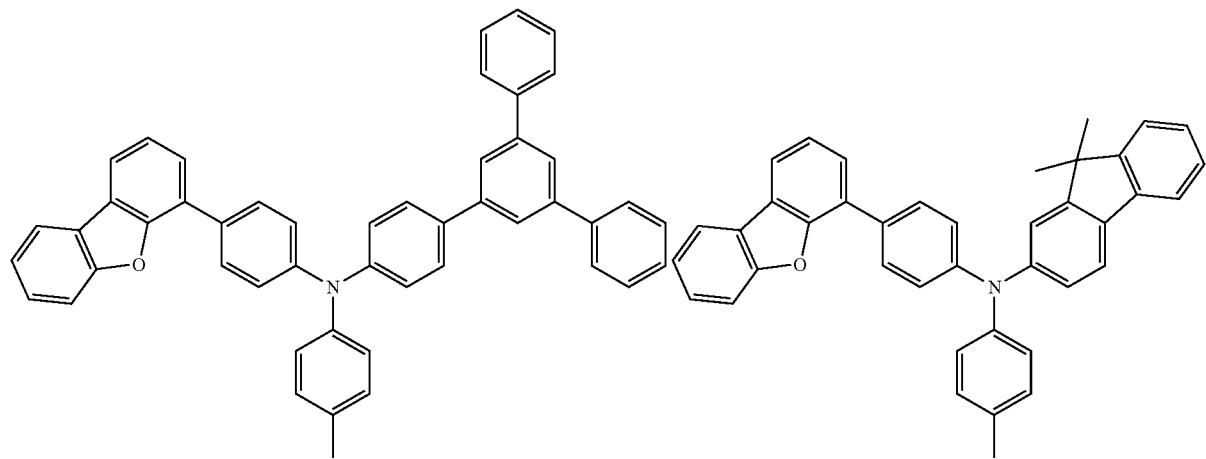

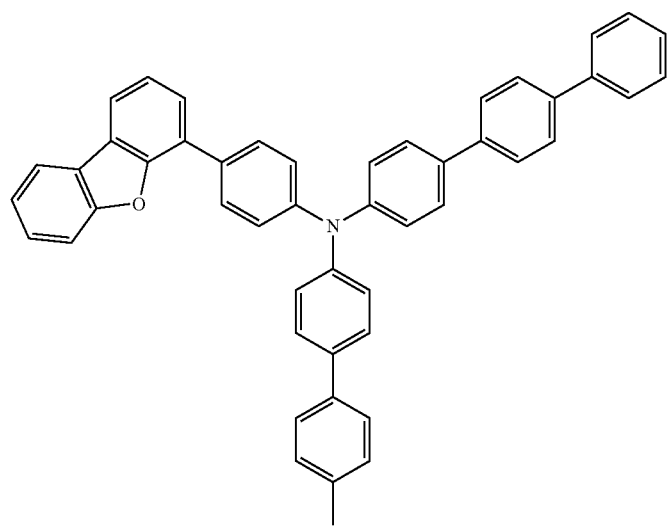
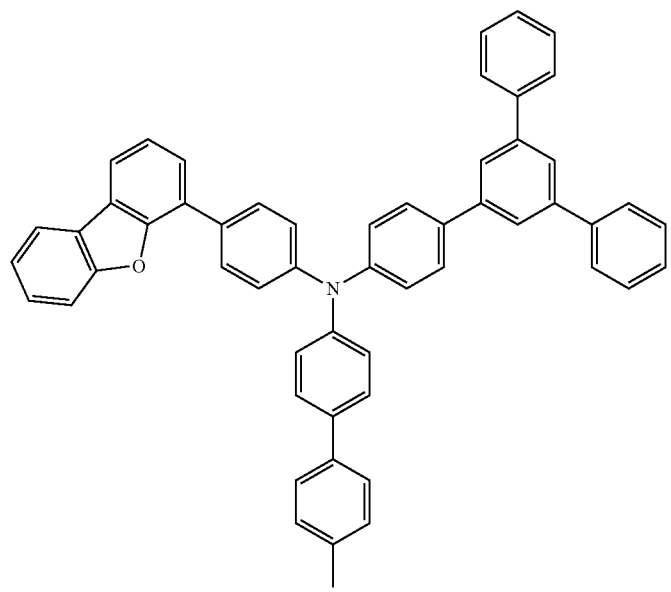
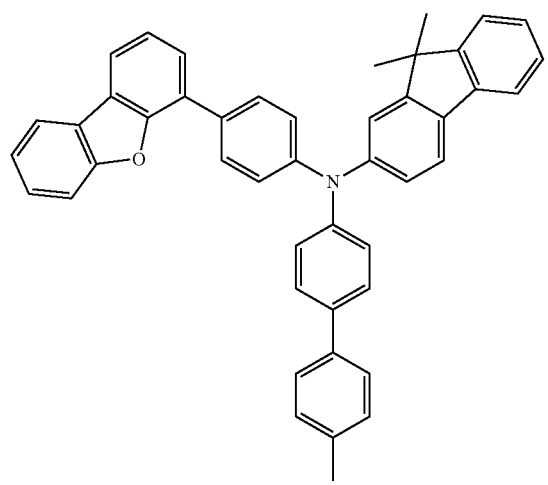

-continued
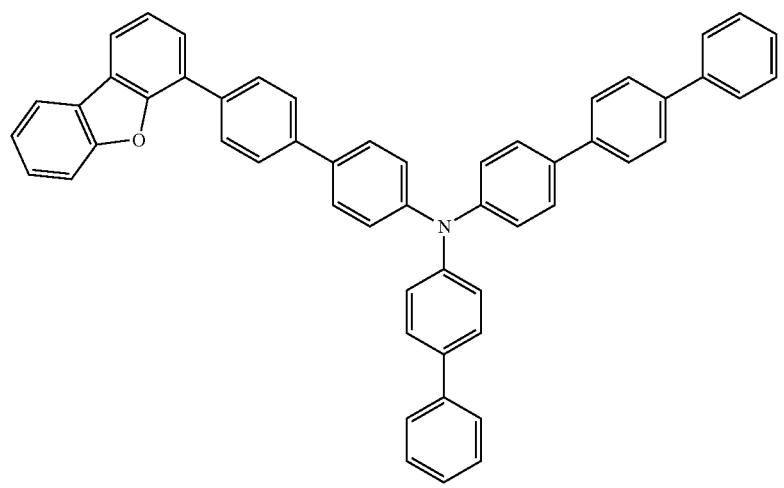
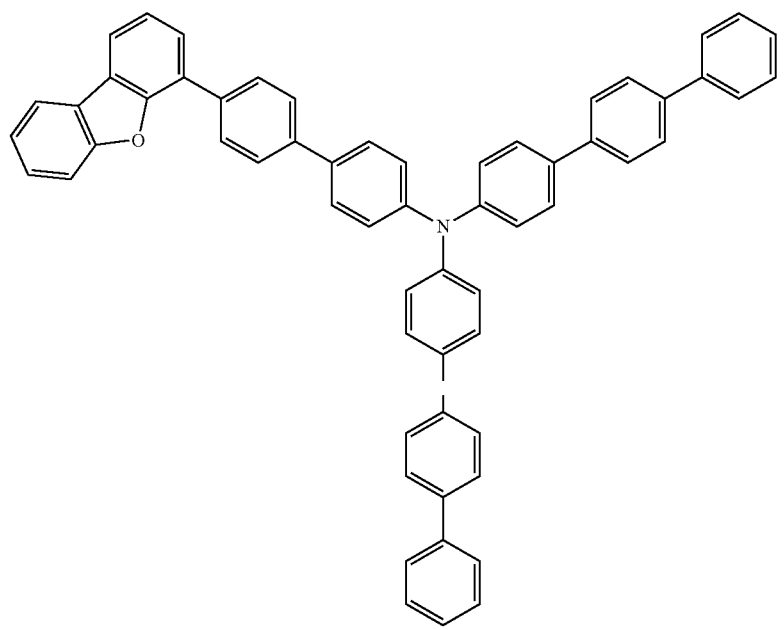
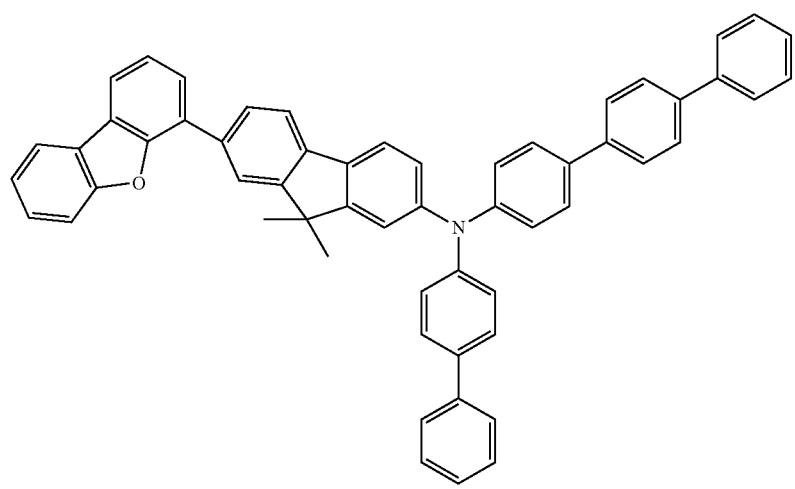

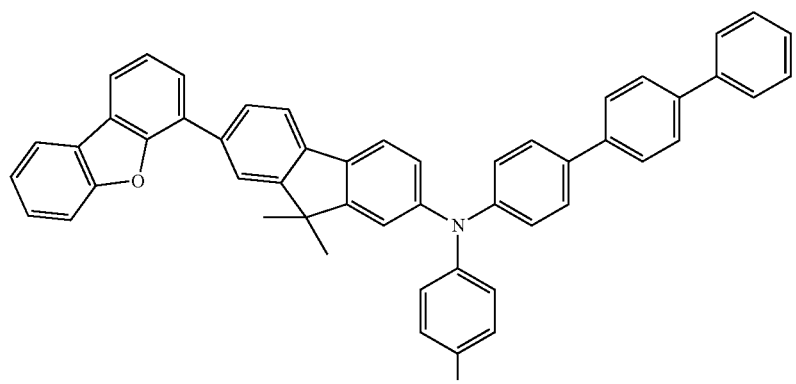
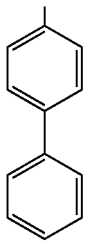
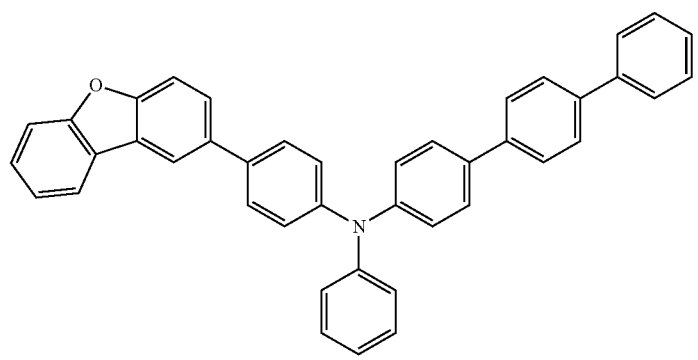
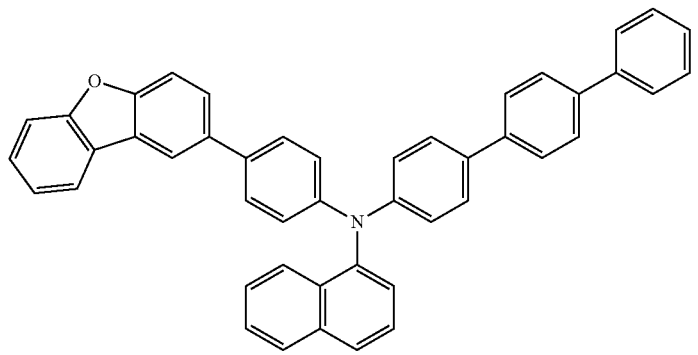

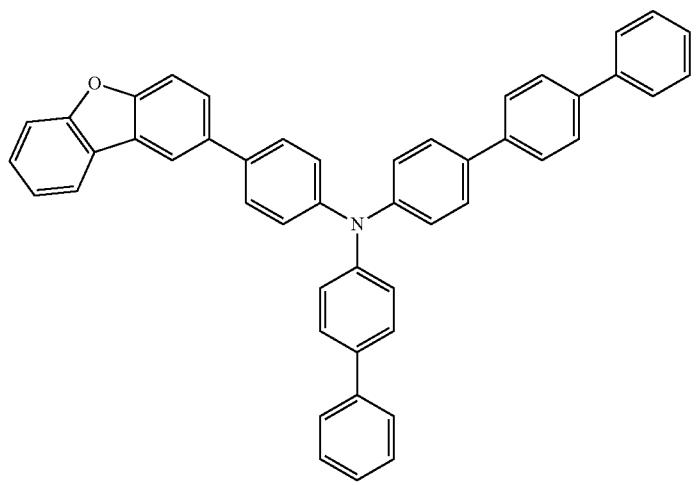
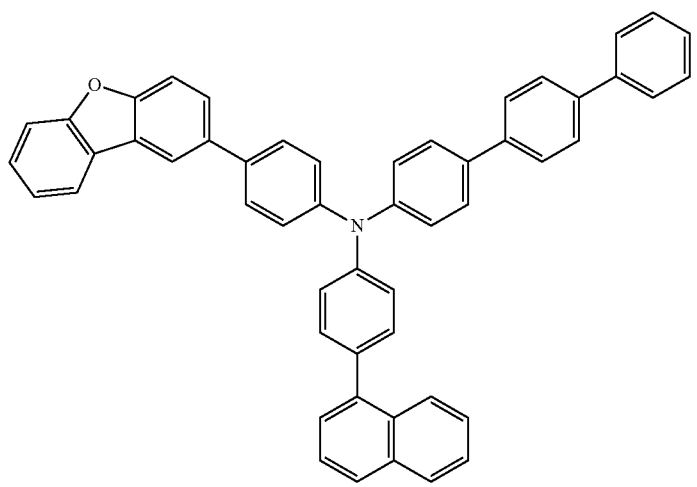
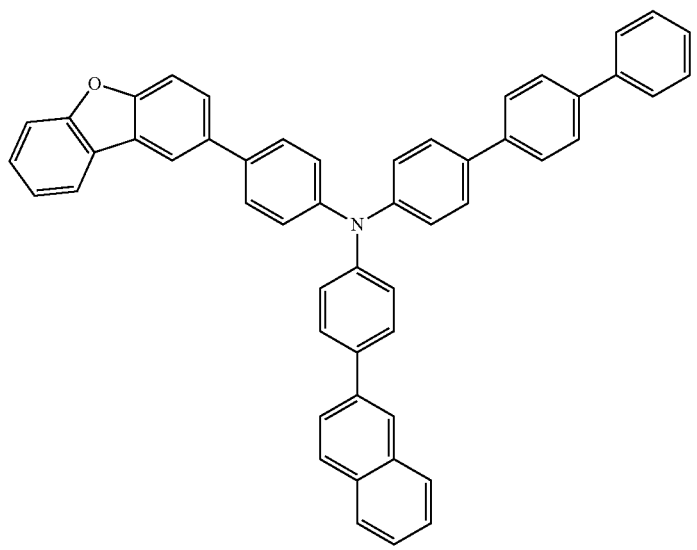

-continued
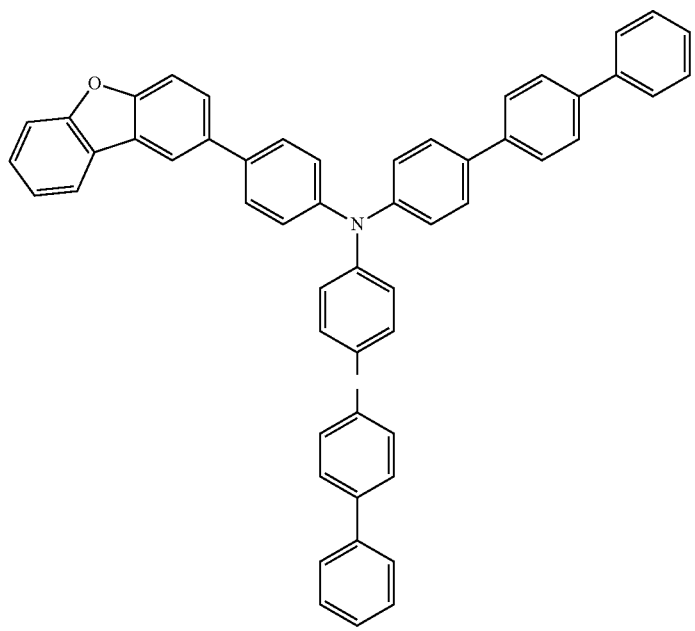
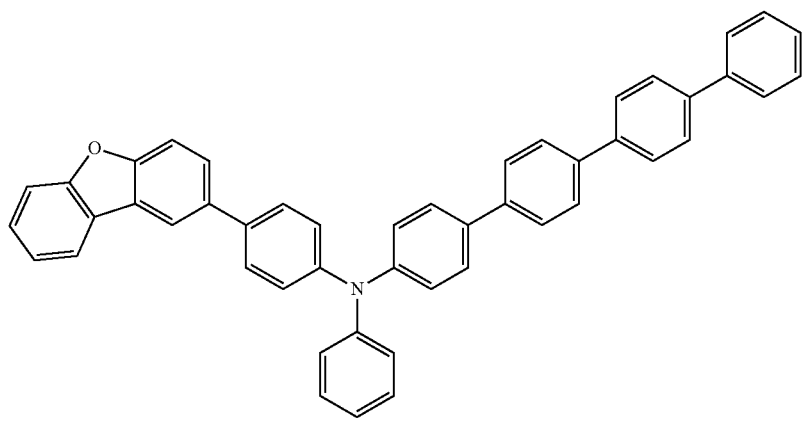
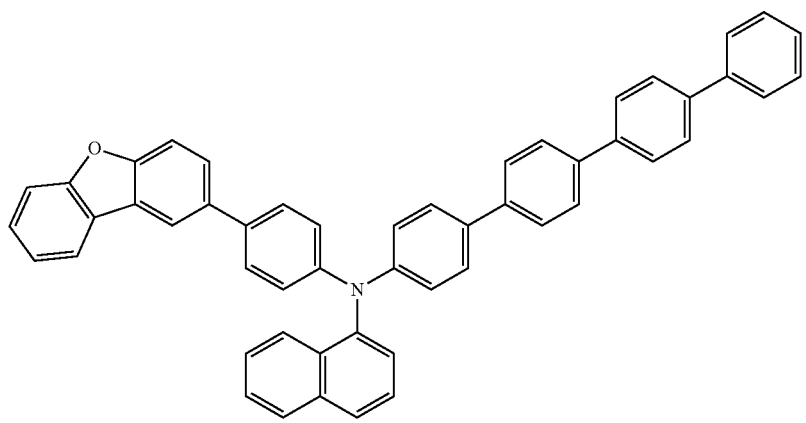

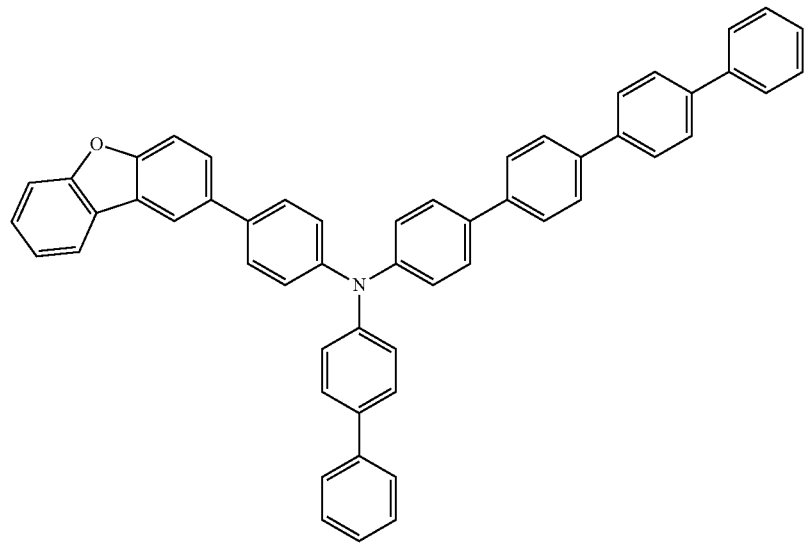
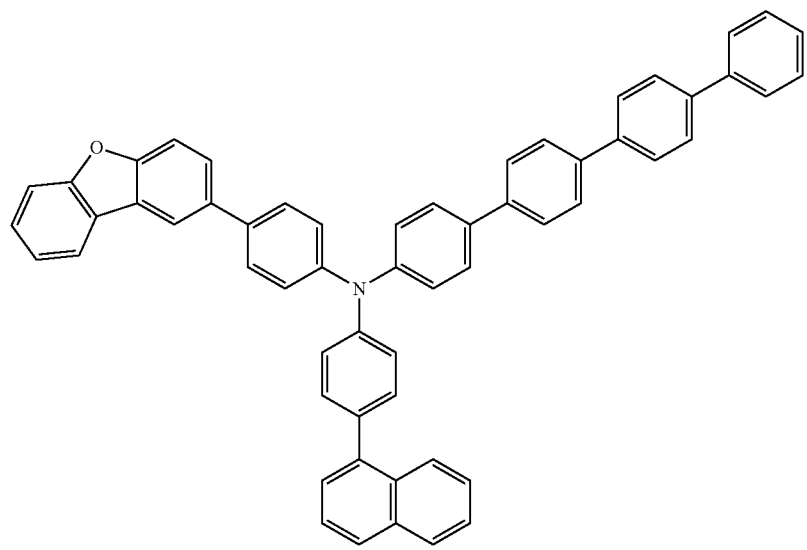
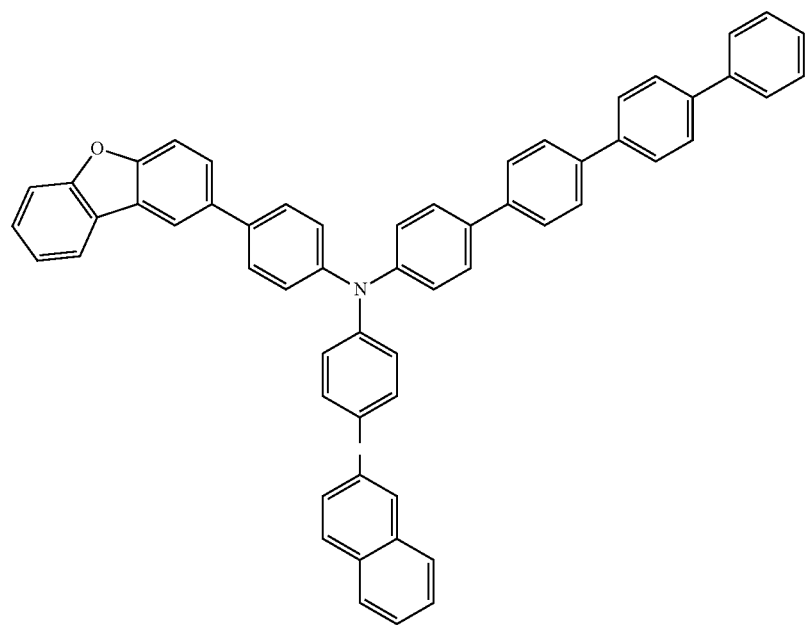

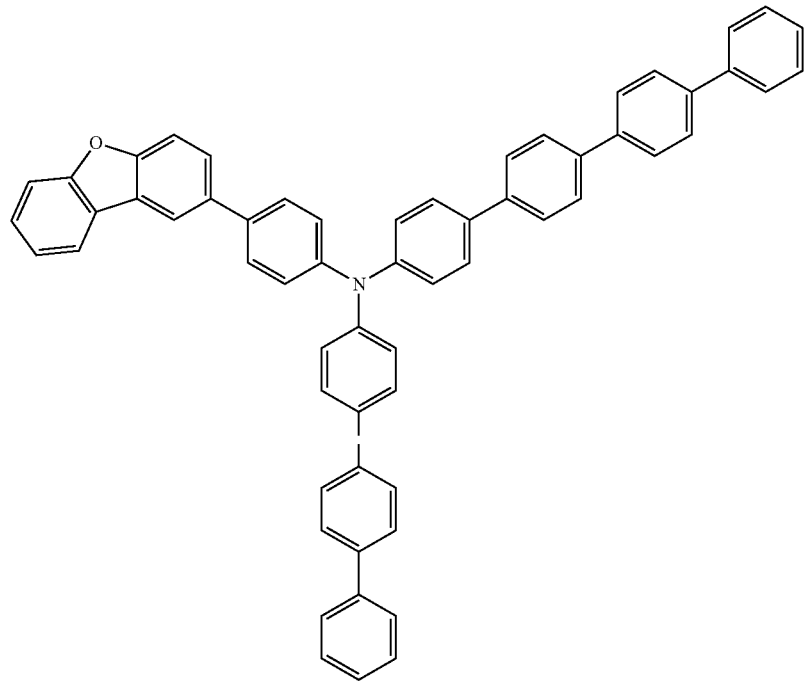
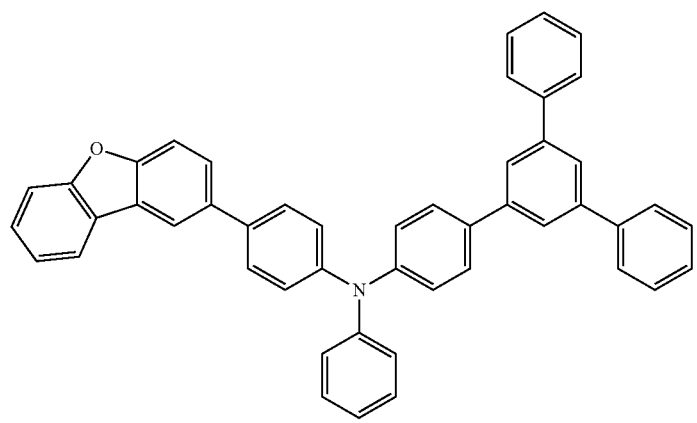
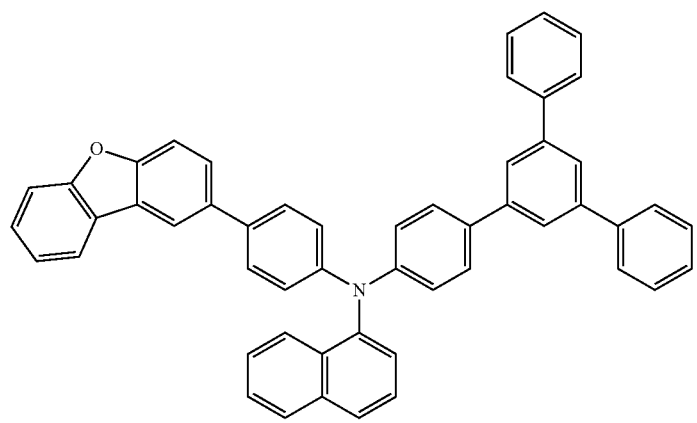

-continued
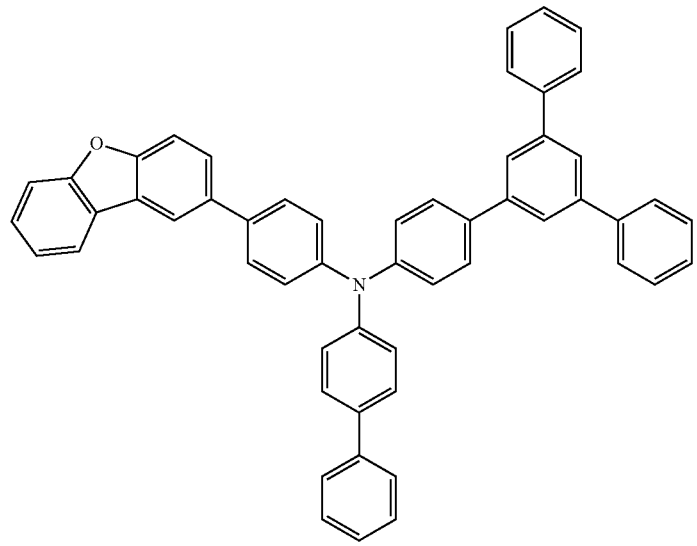
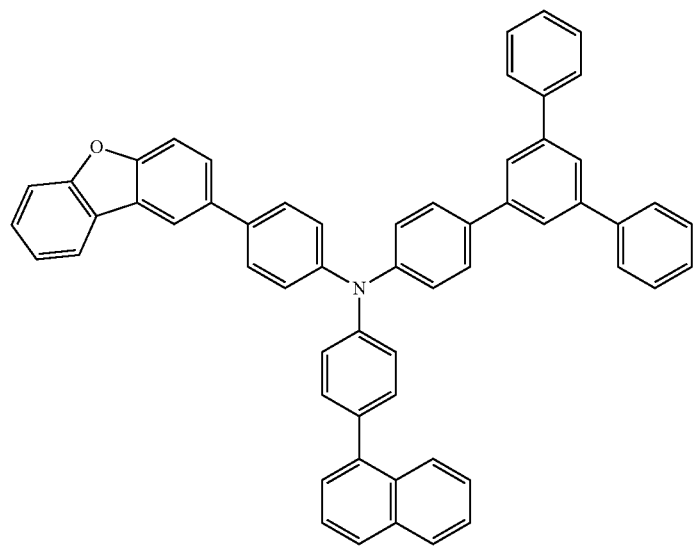
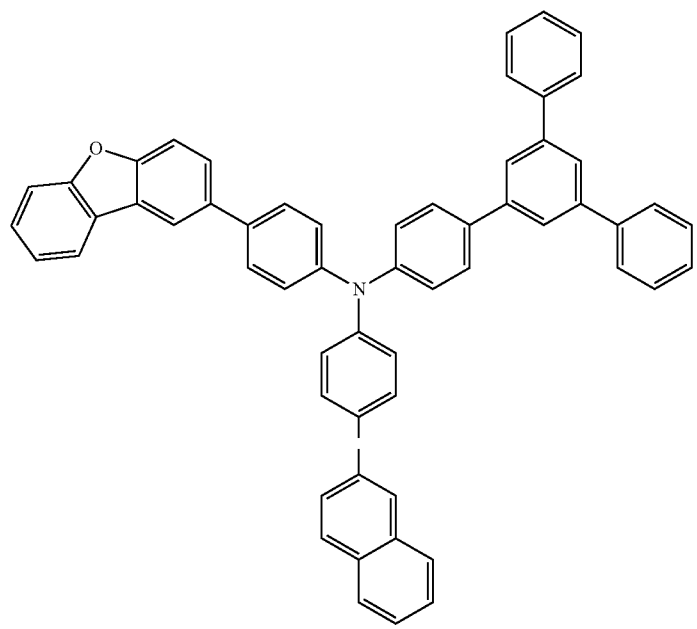

-continued
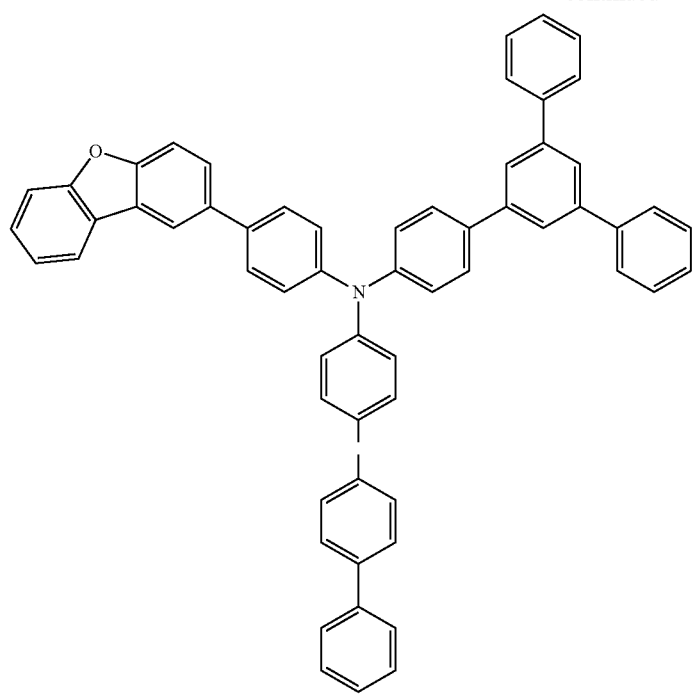
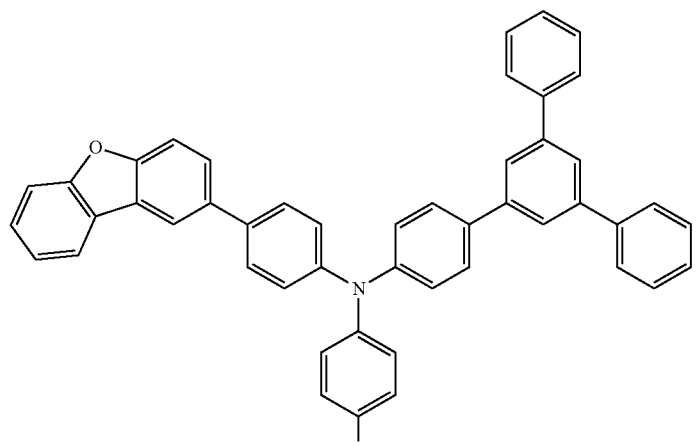
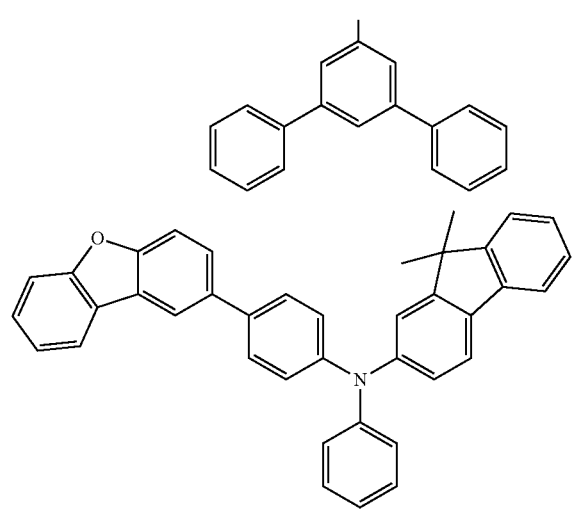

-continued
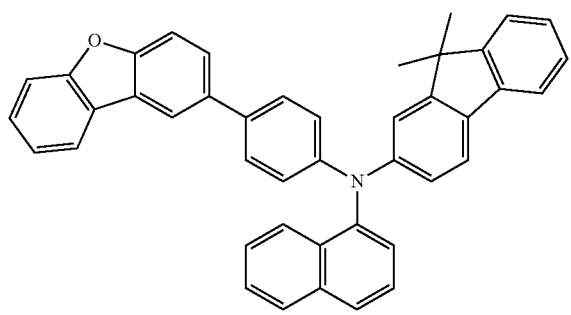
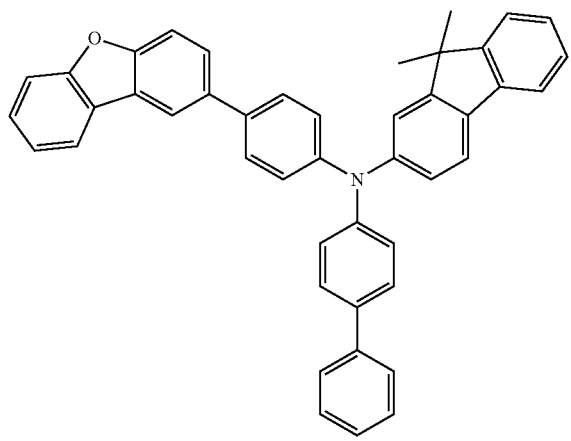
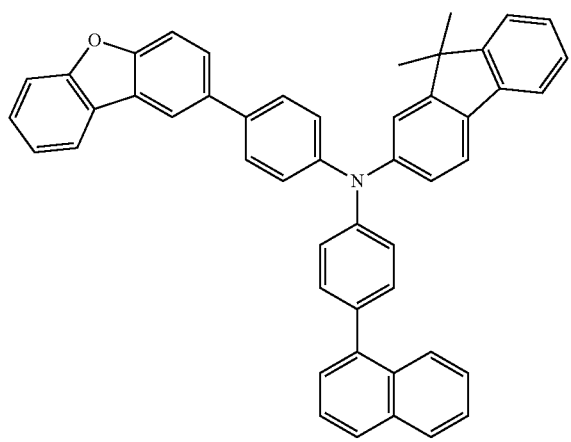
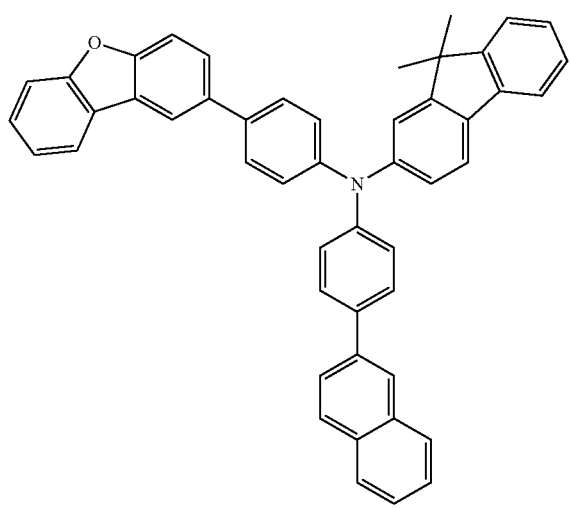

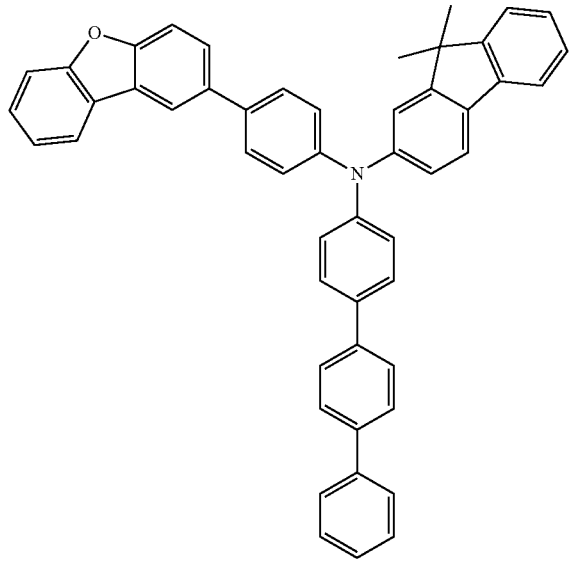
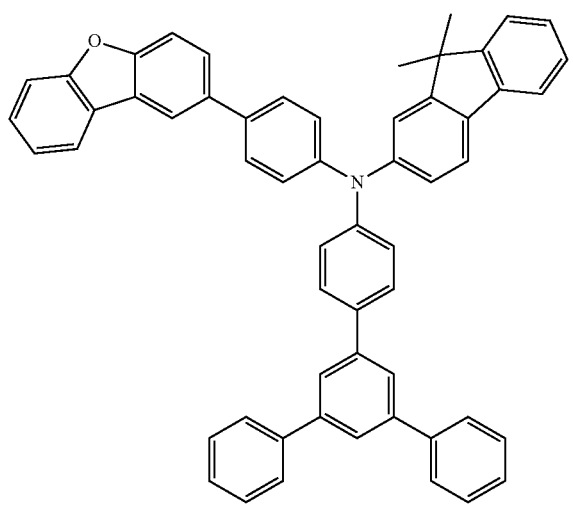
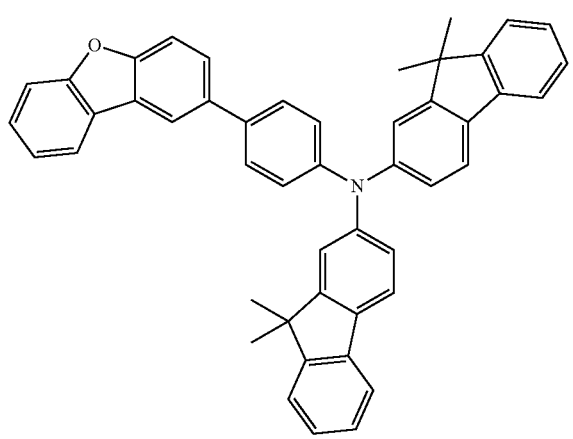

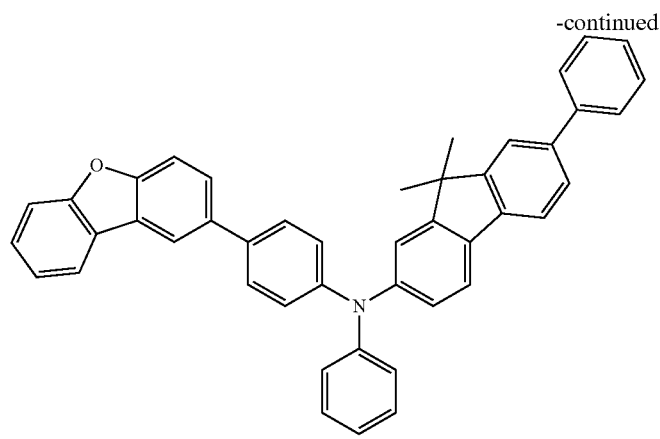
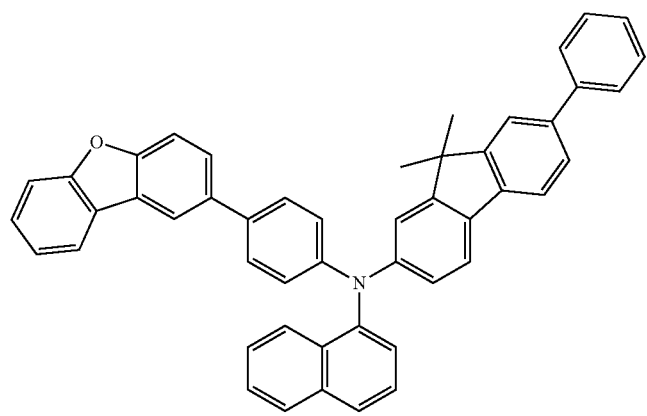
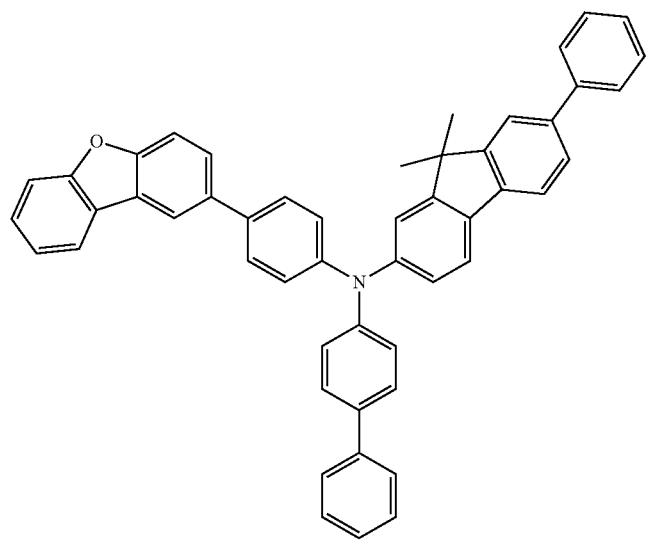

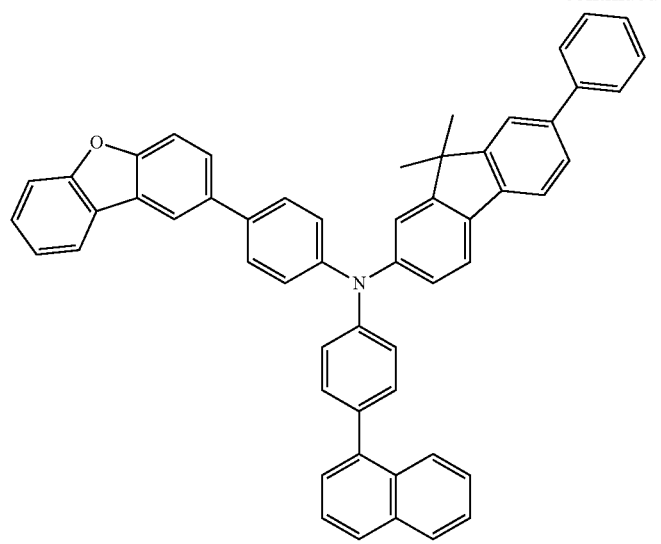
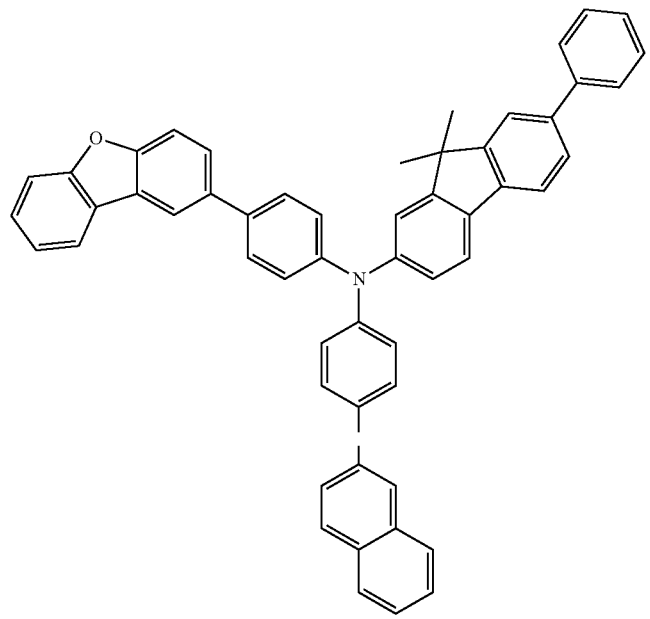
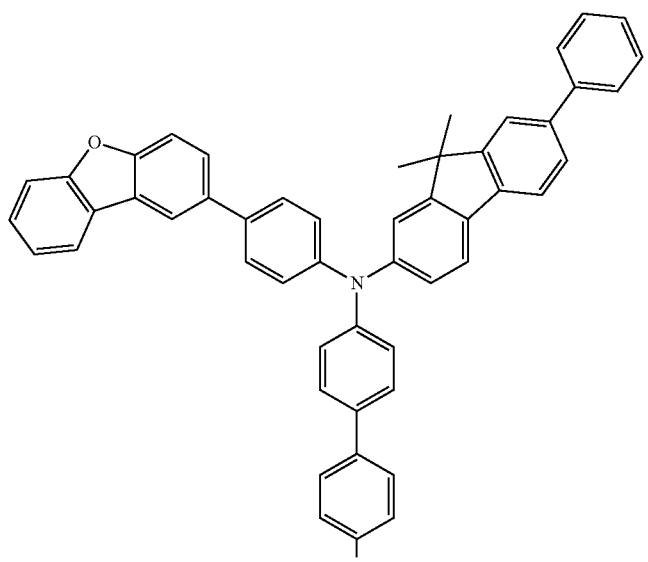

-continued
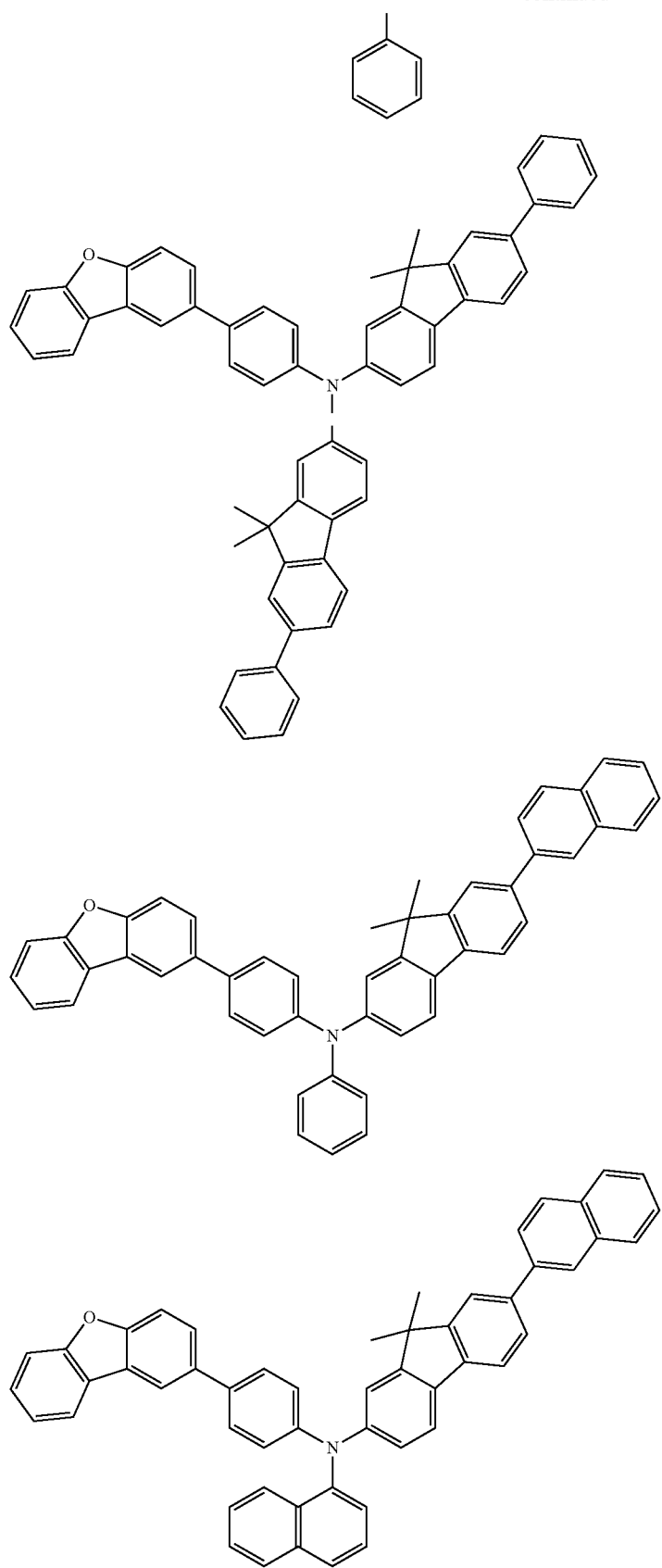

-continued
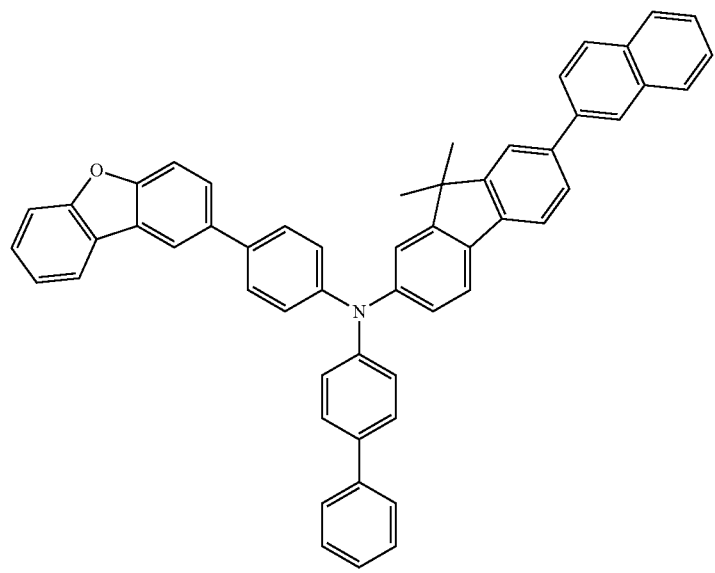
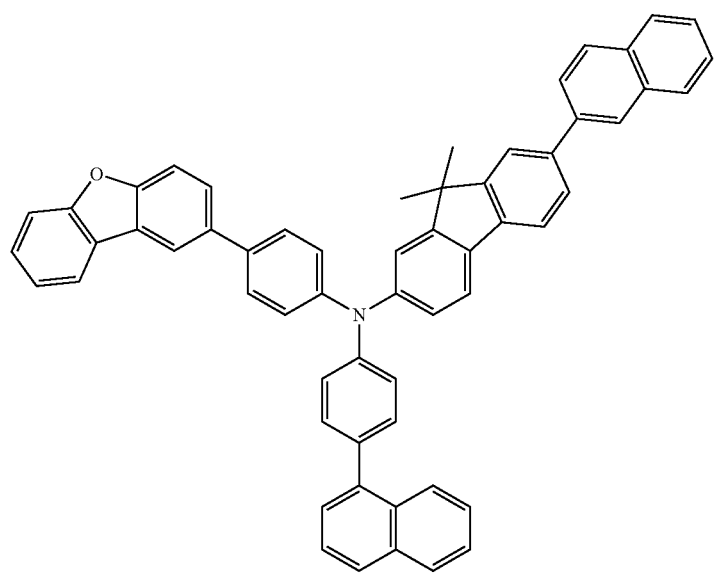

-continued
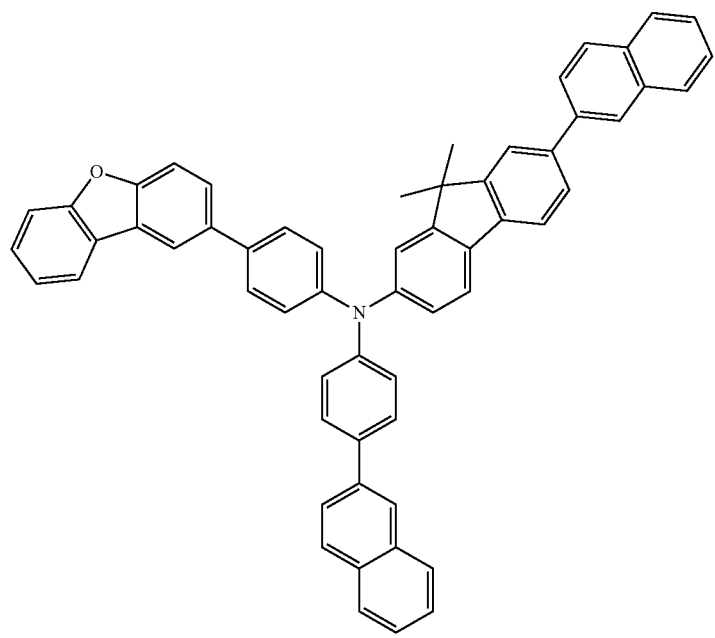
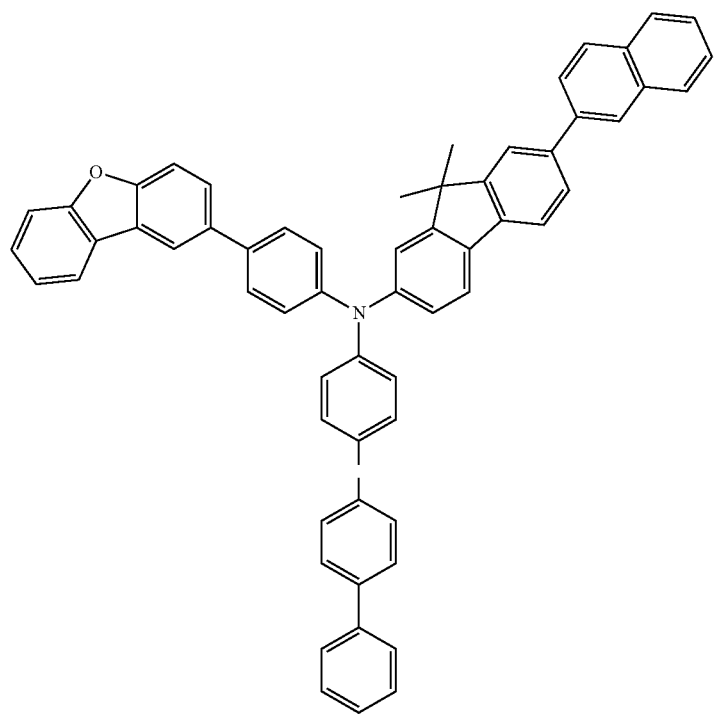

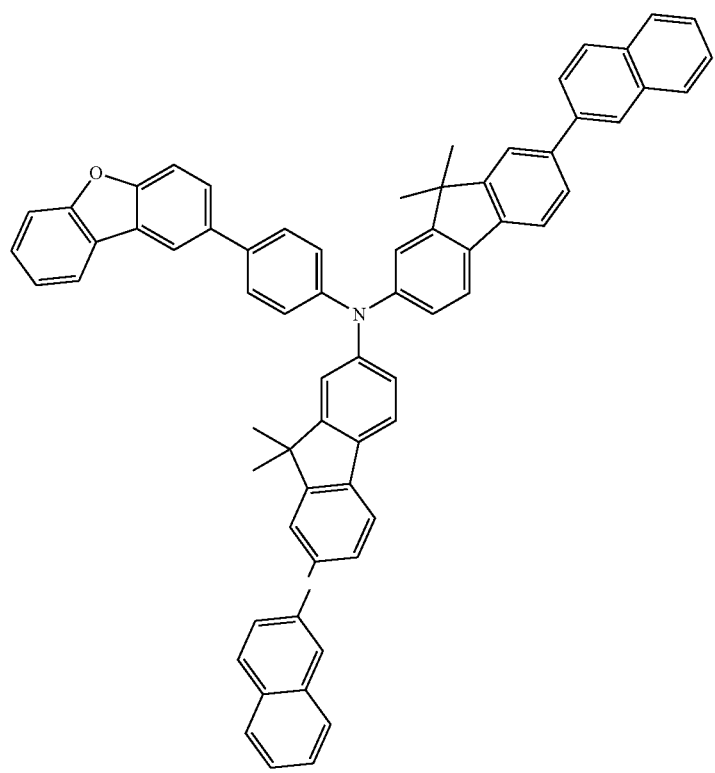
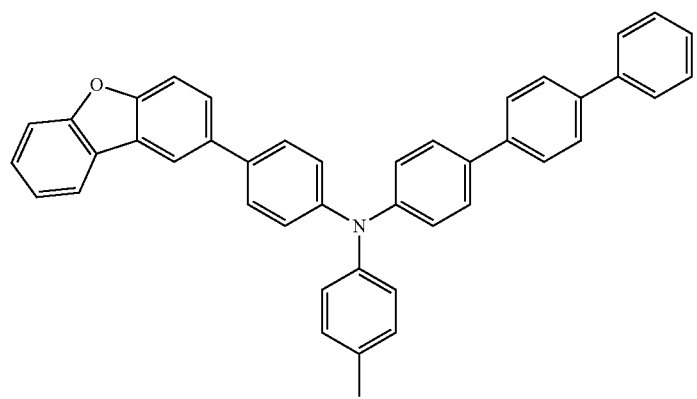
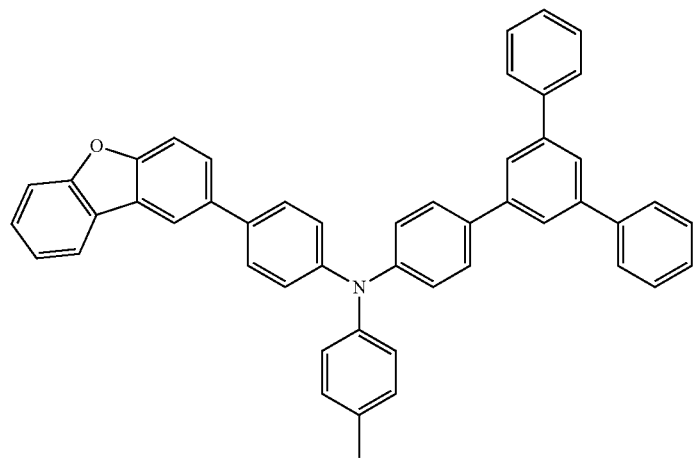

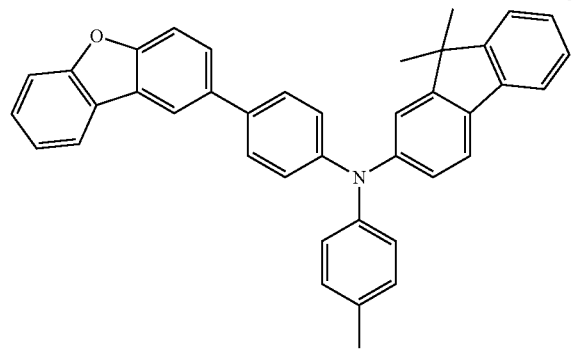
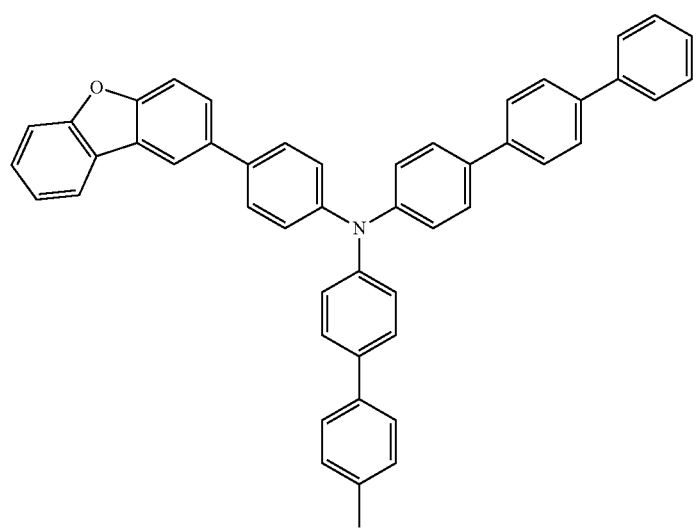
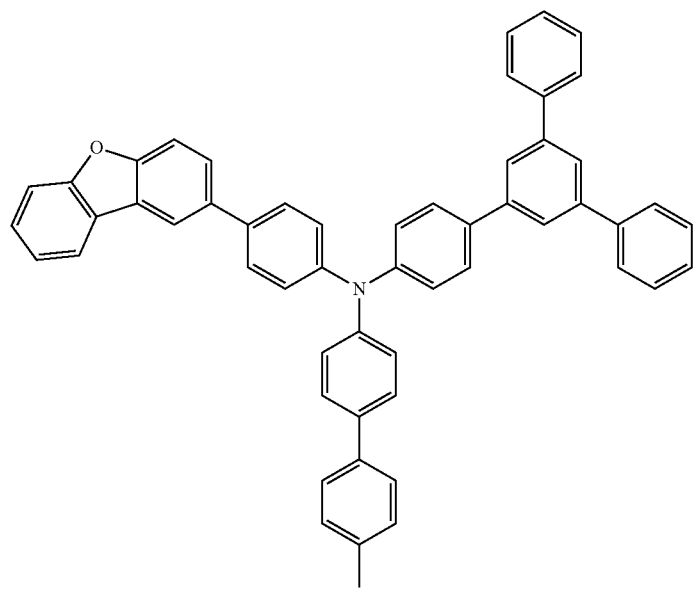

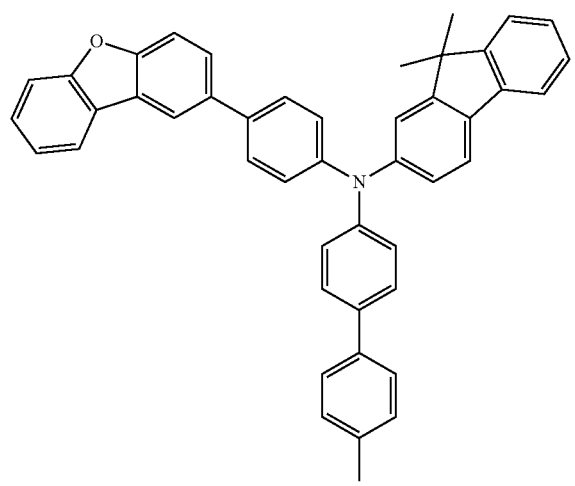
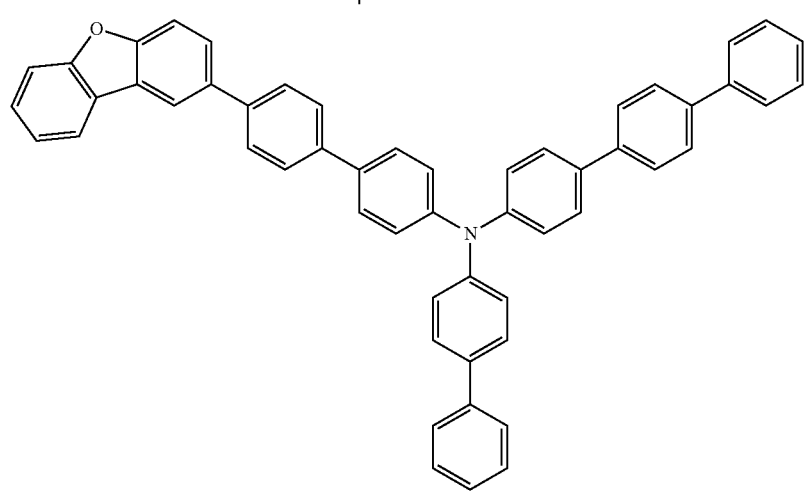
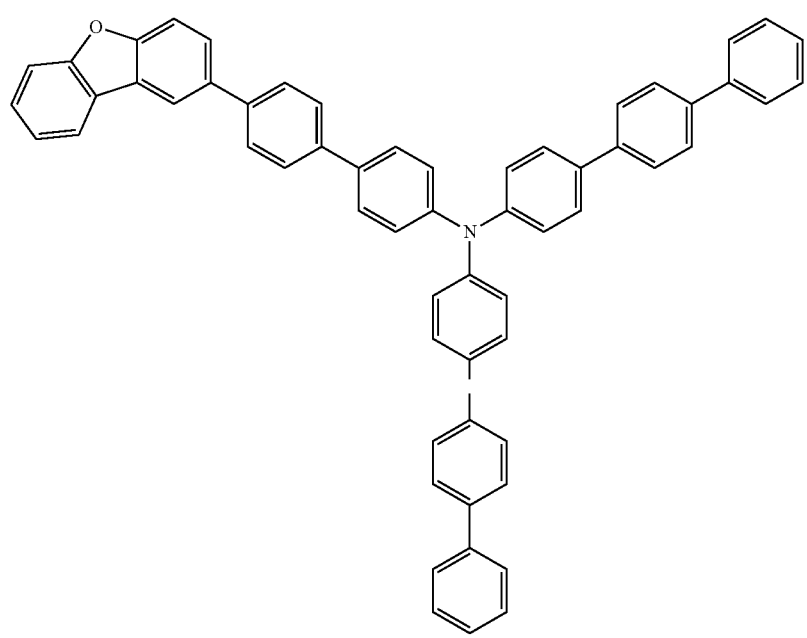

-continued
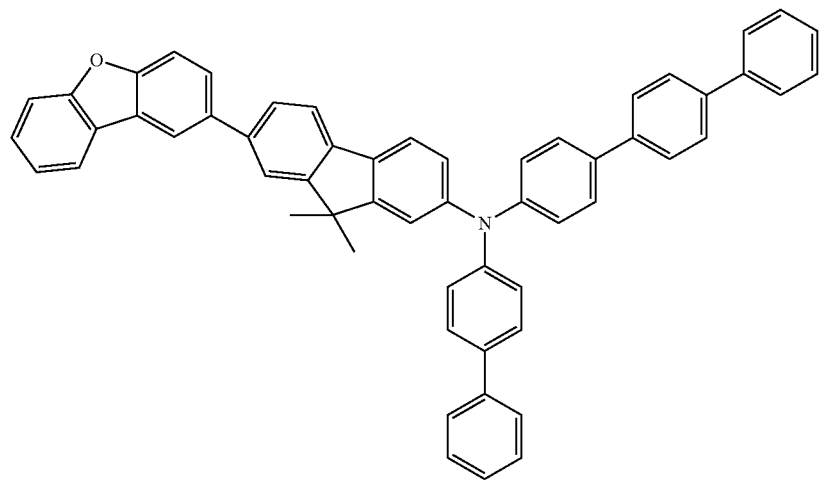
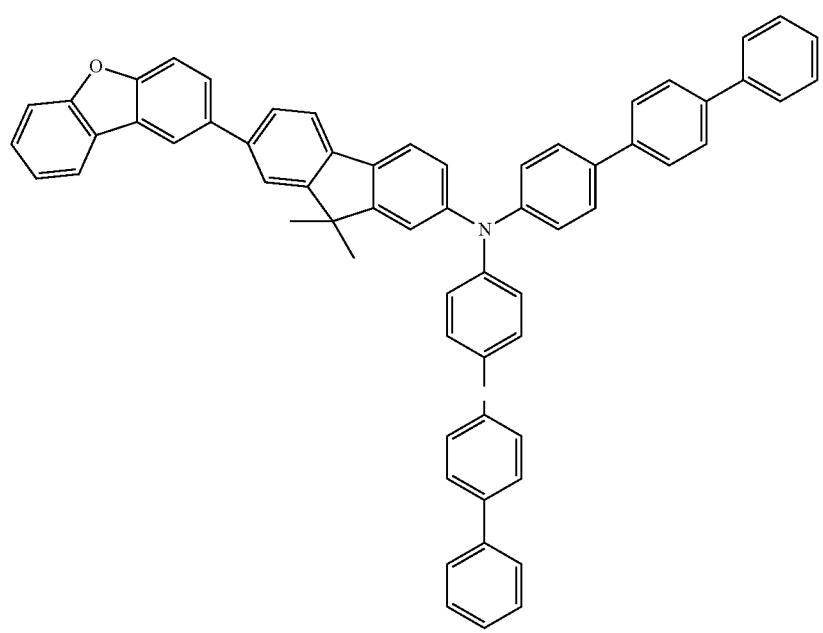
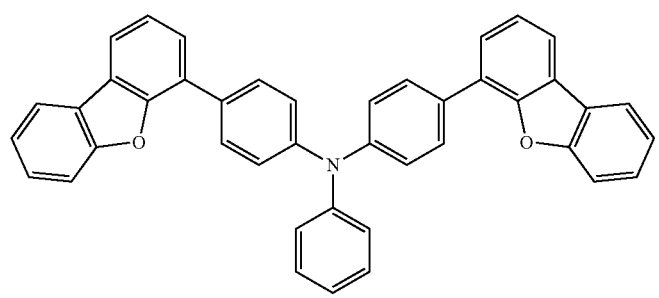
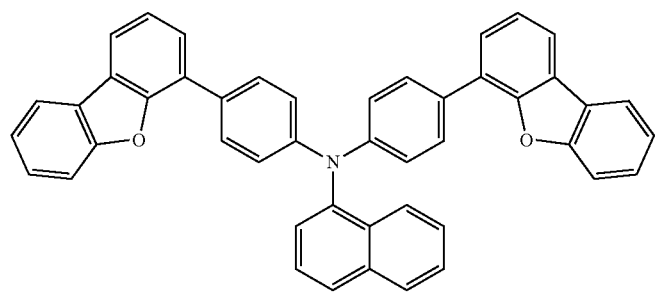

-continued
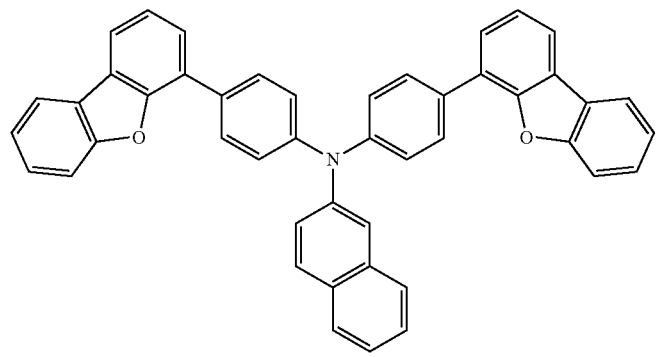
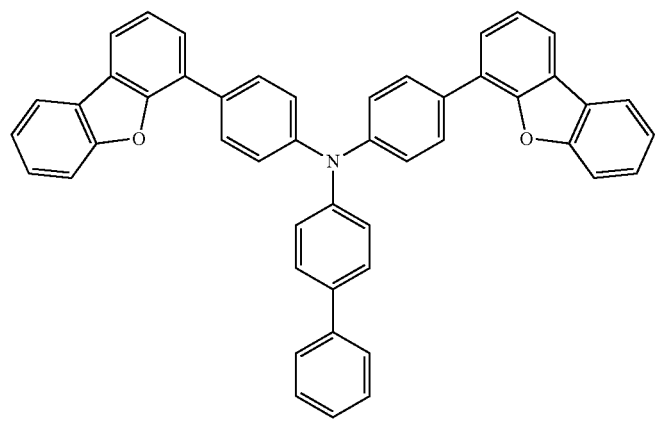
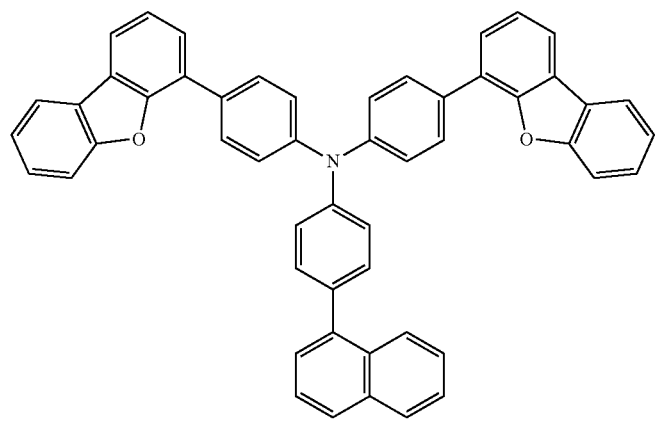
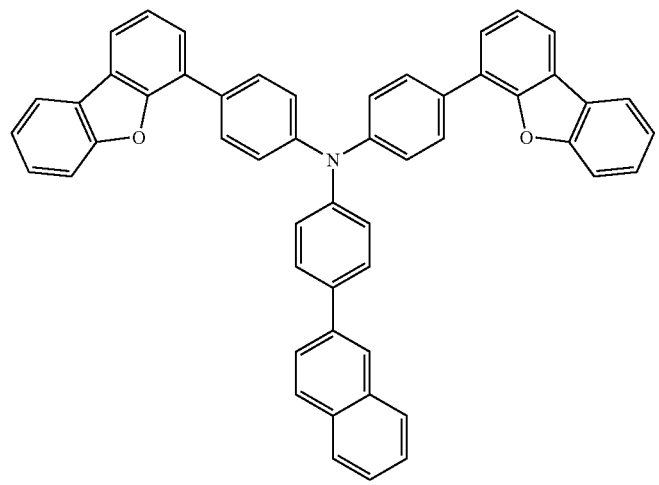

-continued
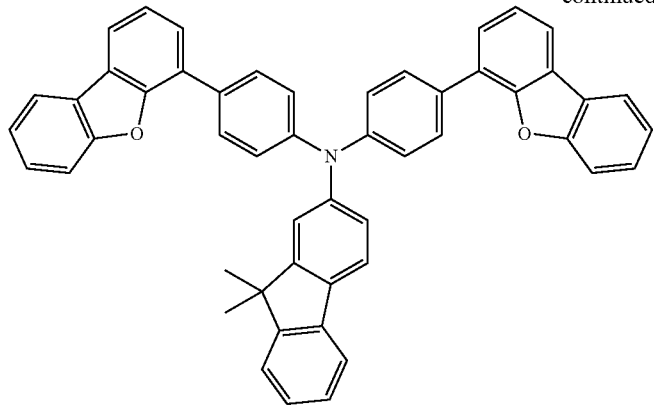
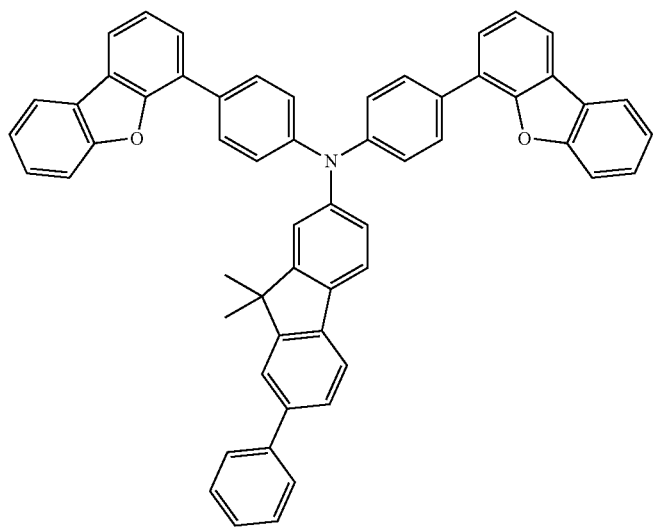
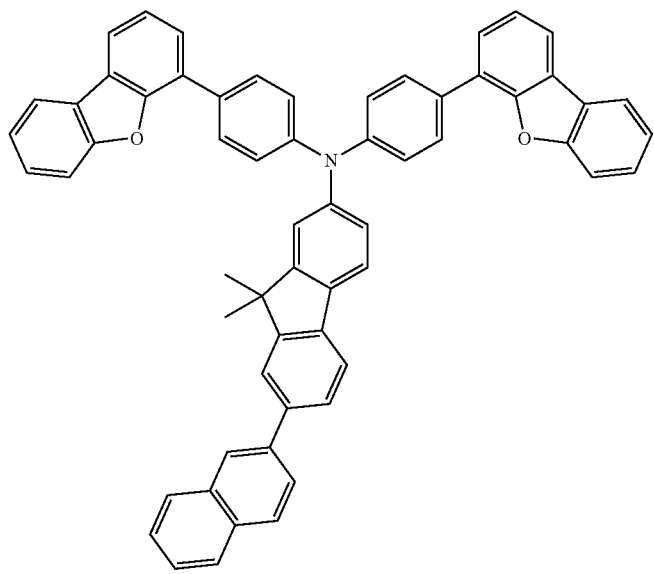

-continued
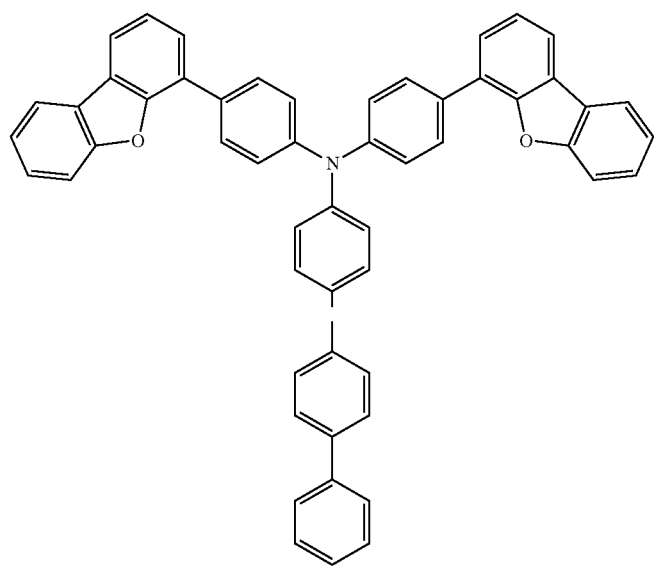
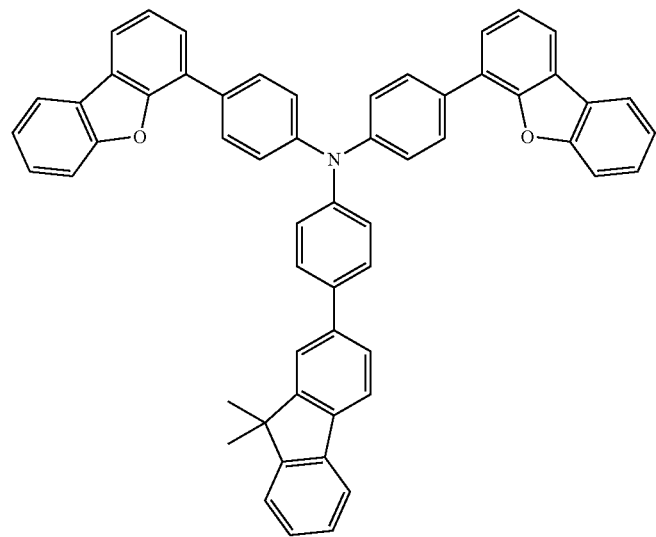
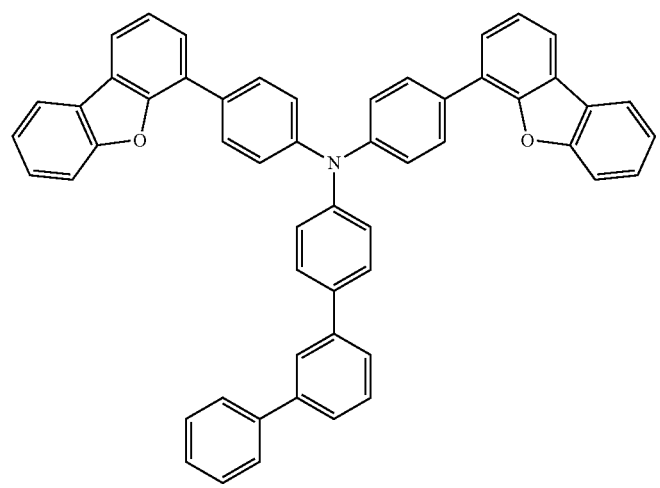

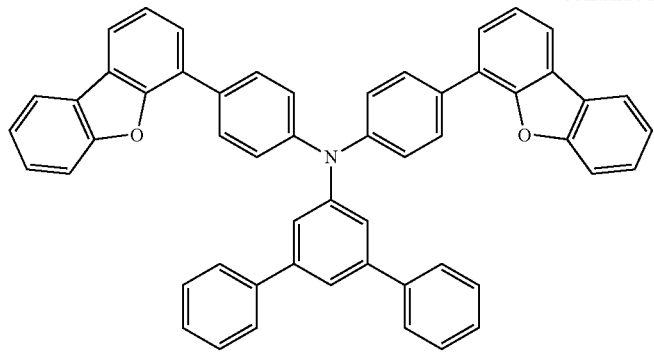
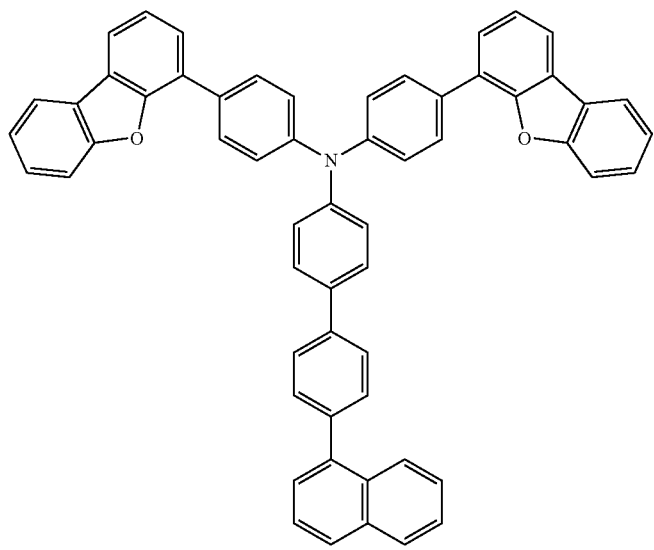
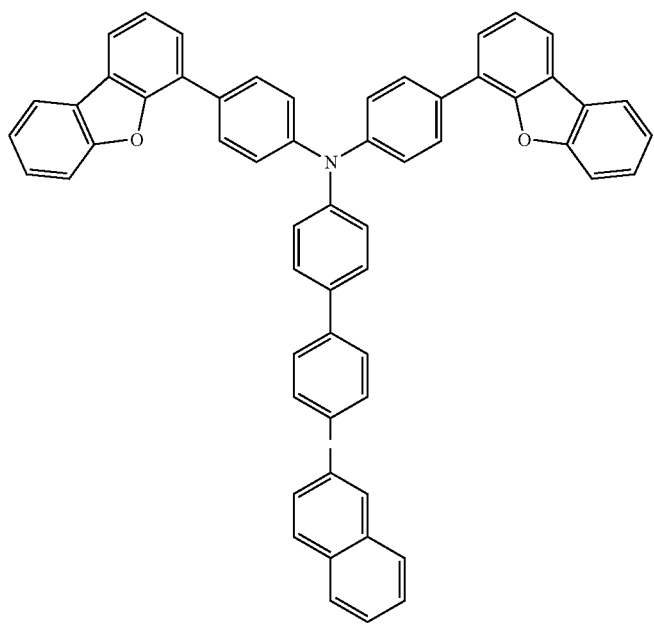

221 222
-continued
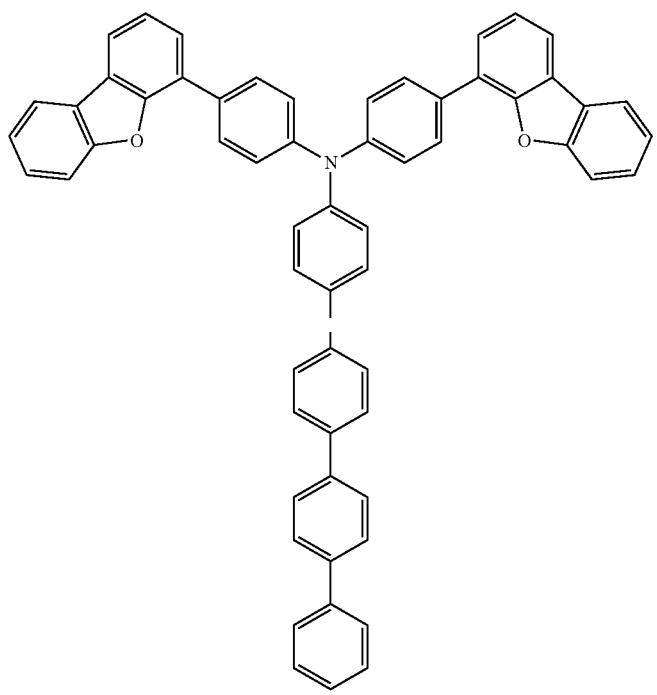
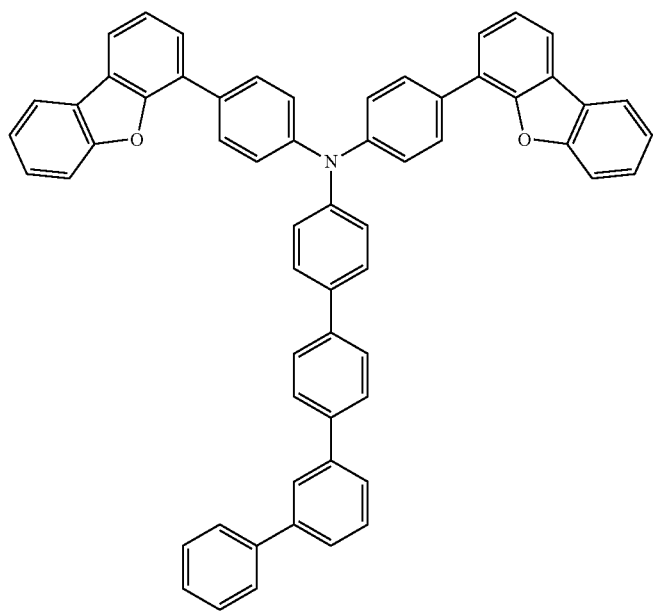

-continued
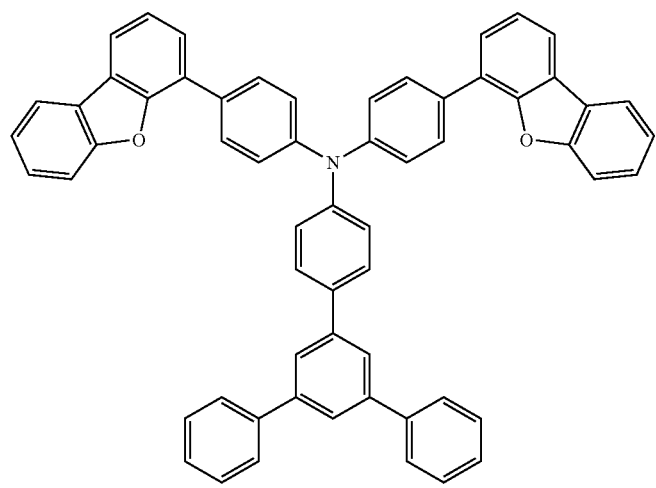
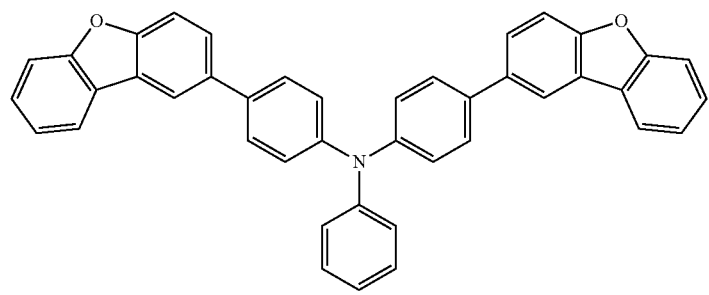
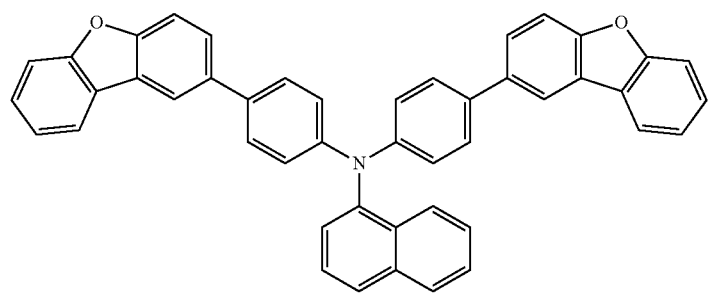
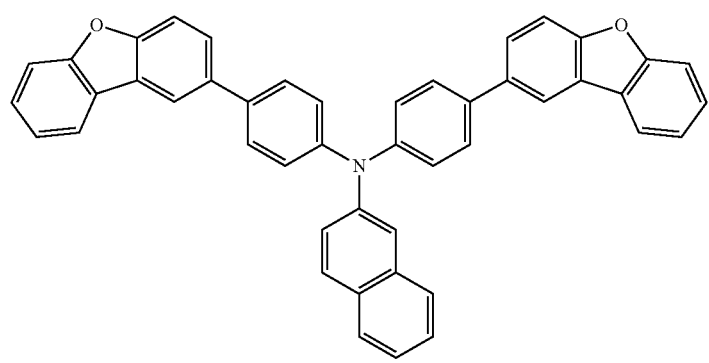

-continued
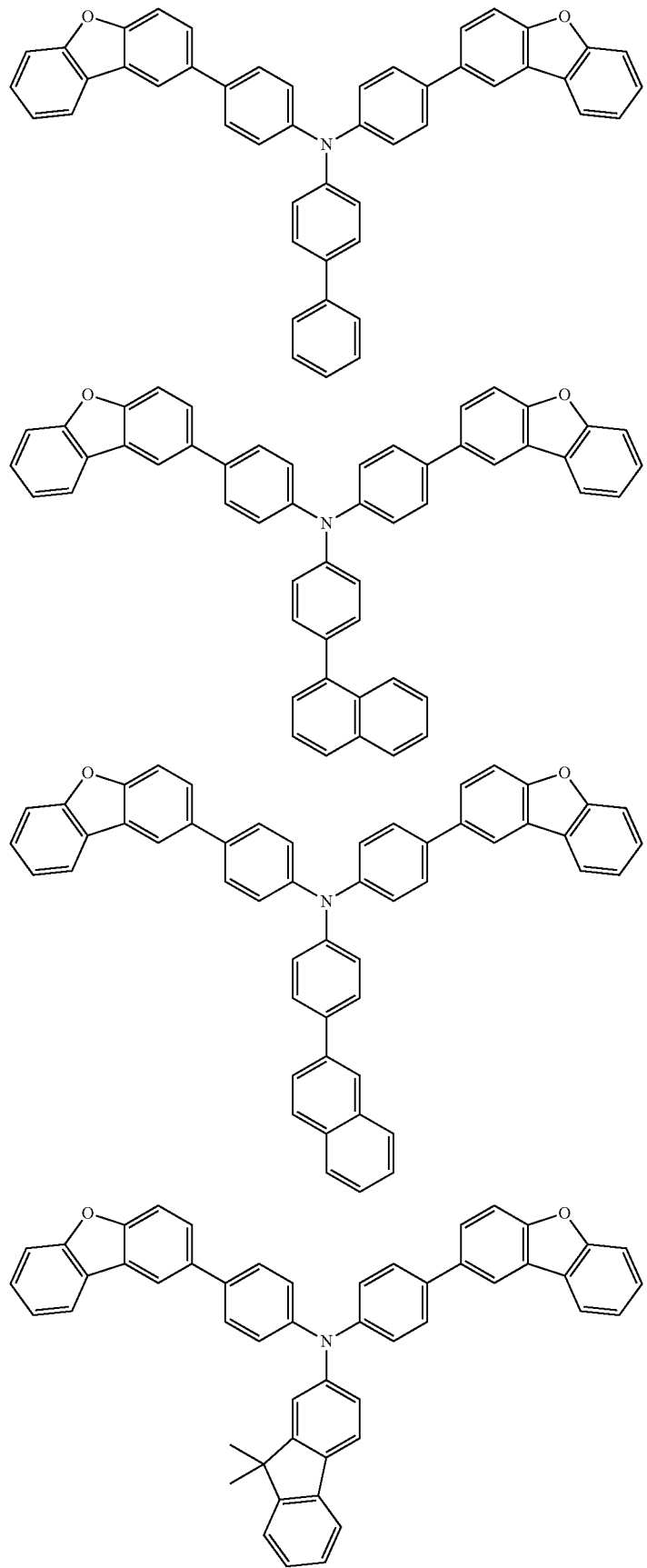

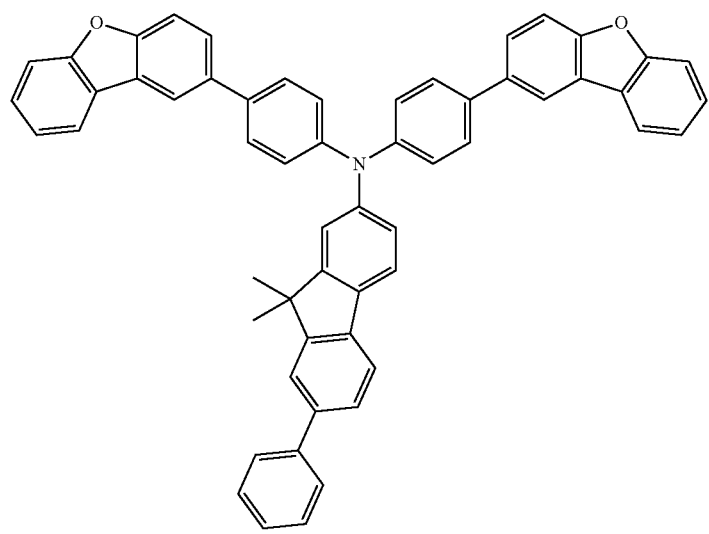
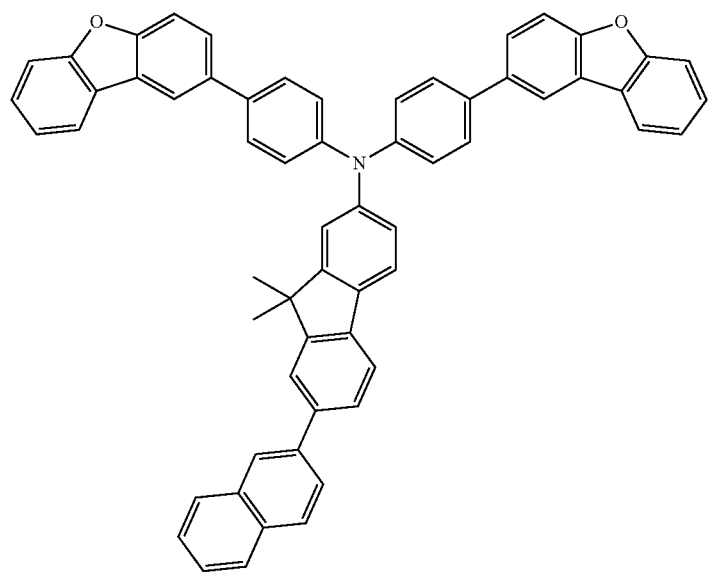
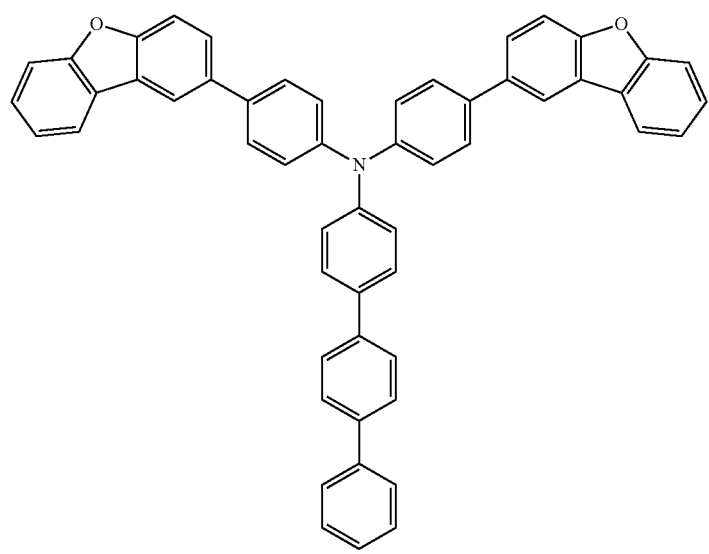

-continued
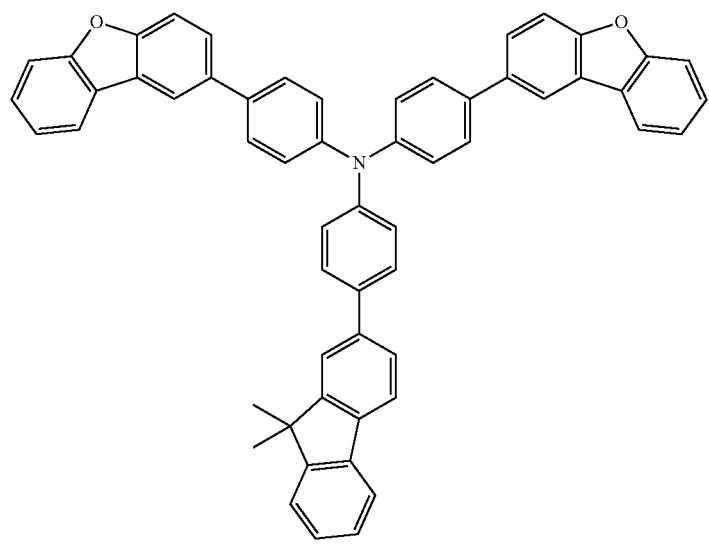
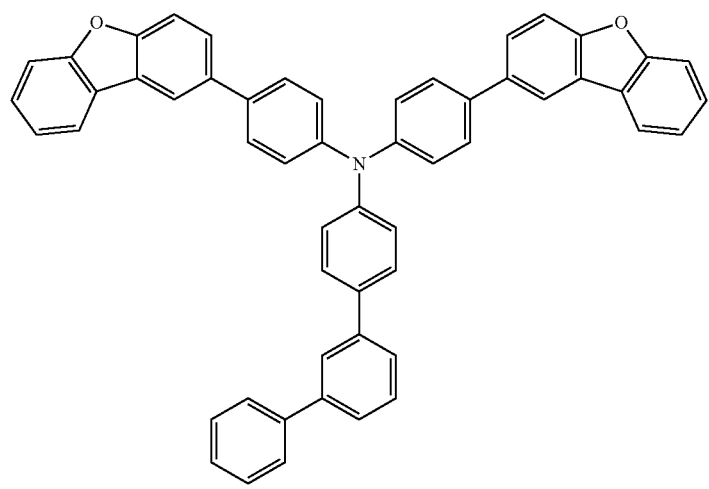
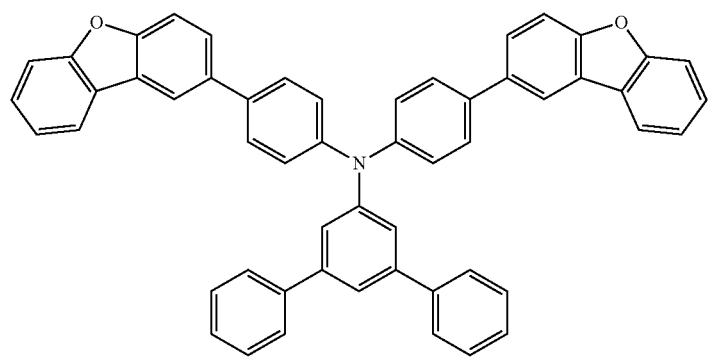

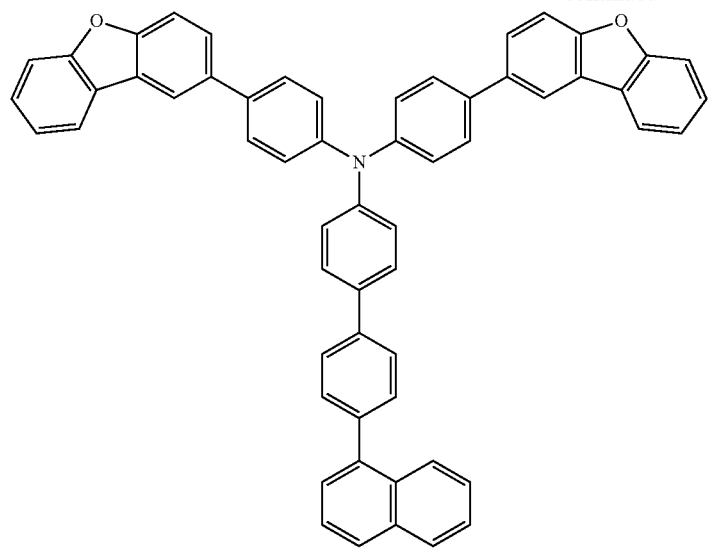
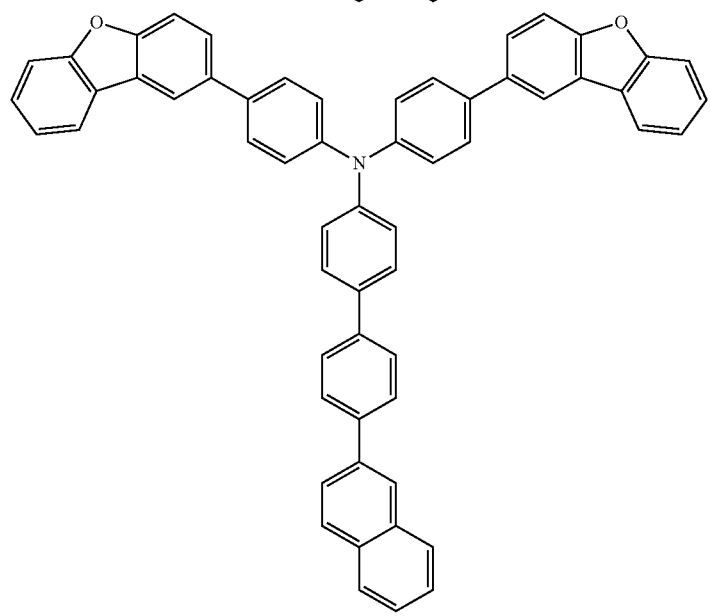
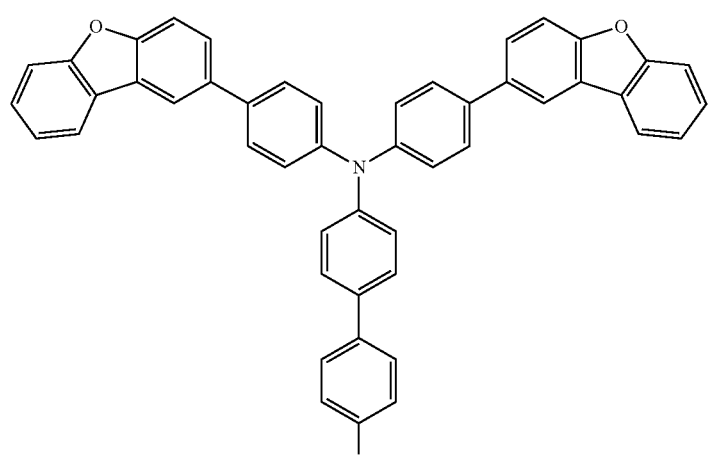

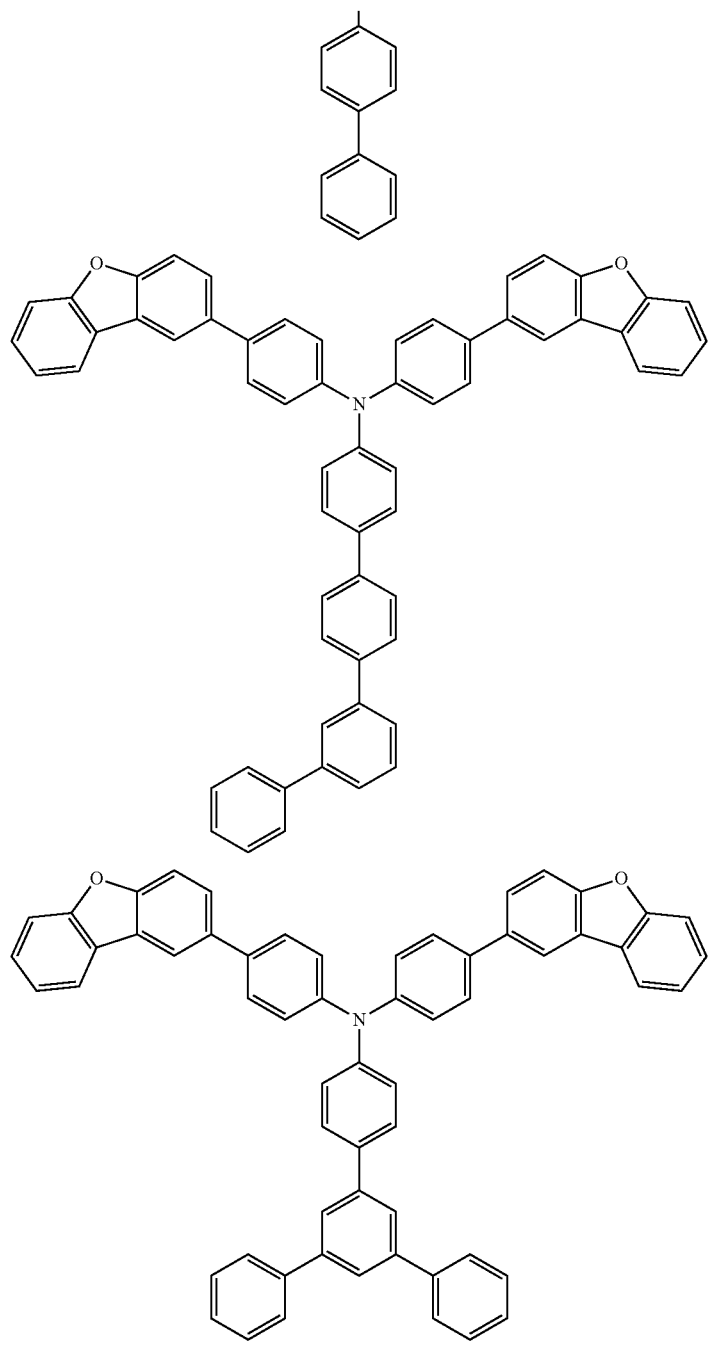
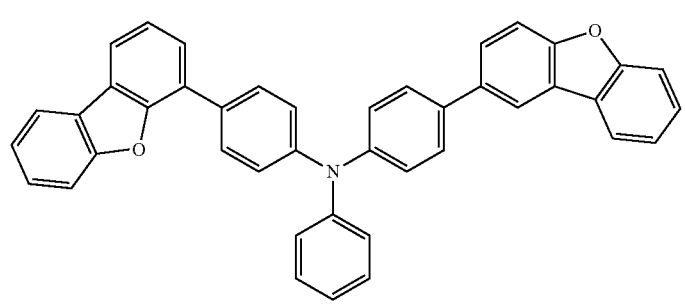

-continued
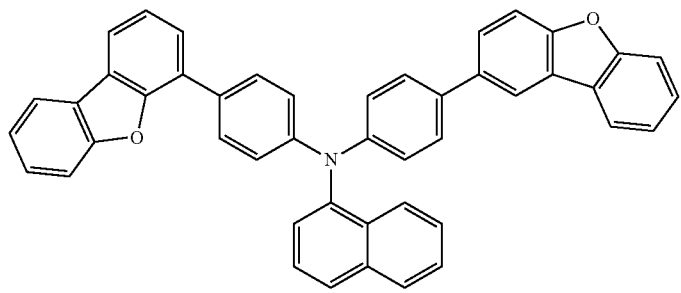
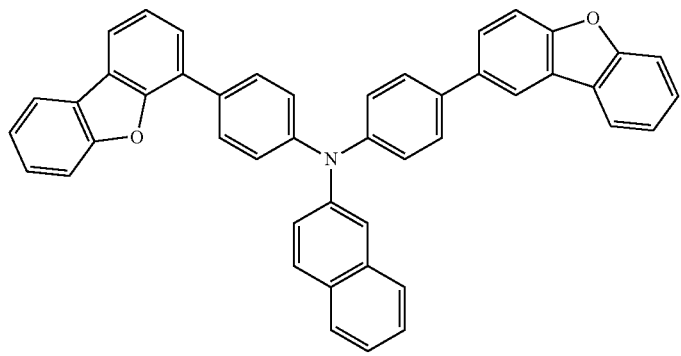
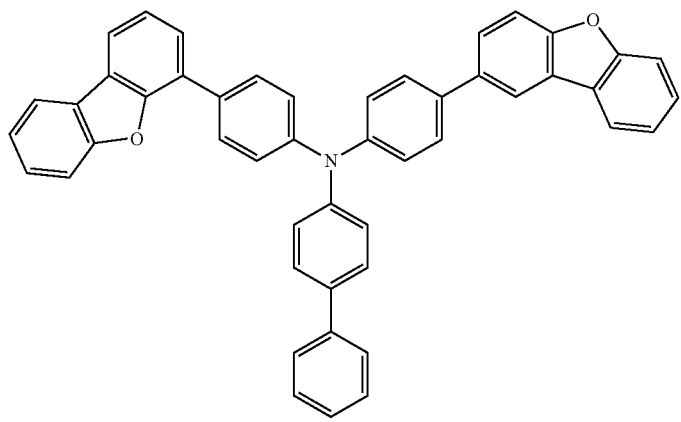
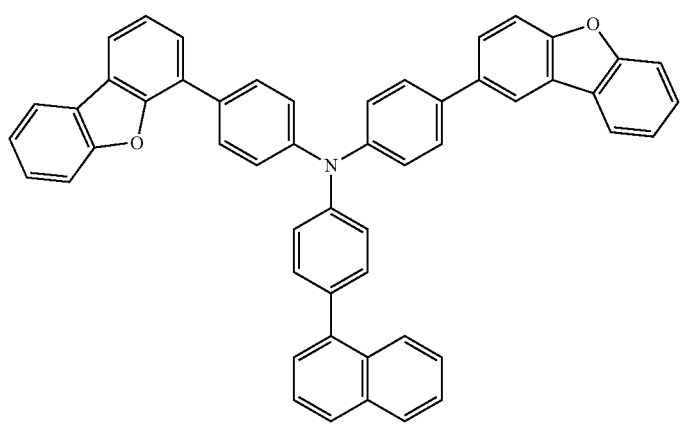

-continued
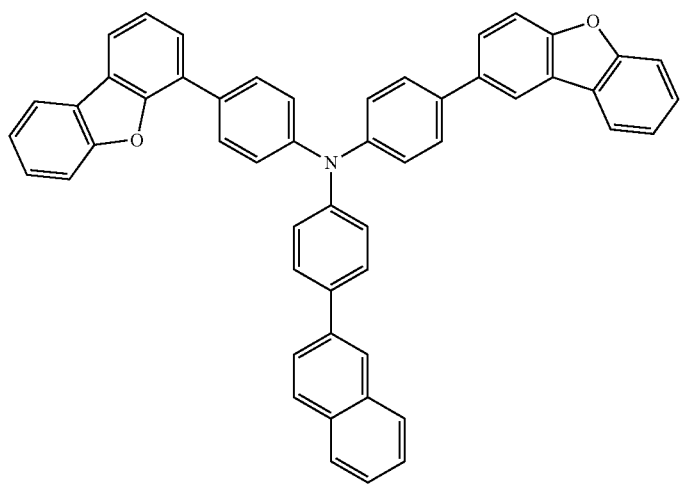
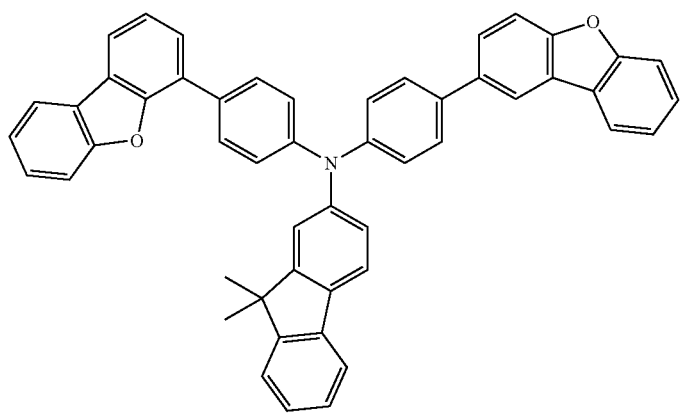
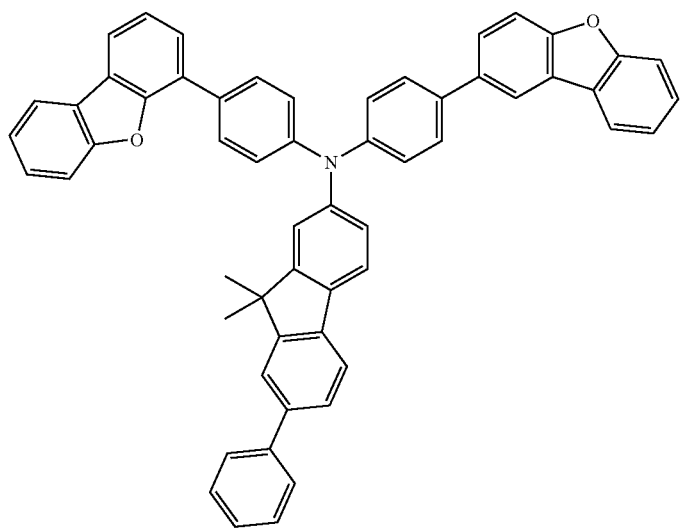

-continued
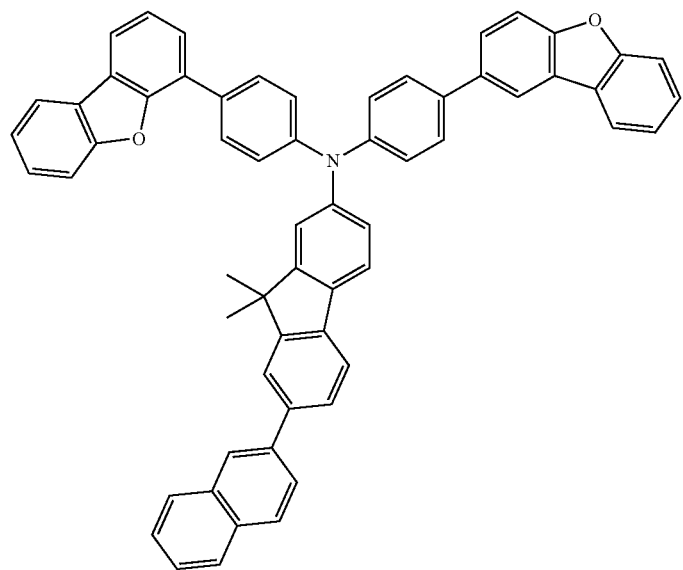
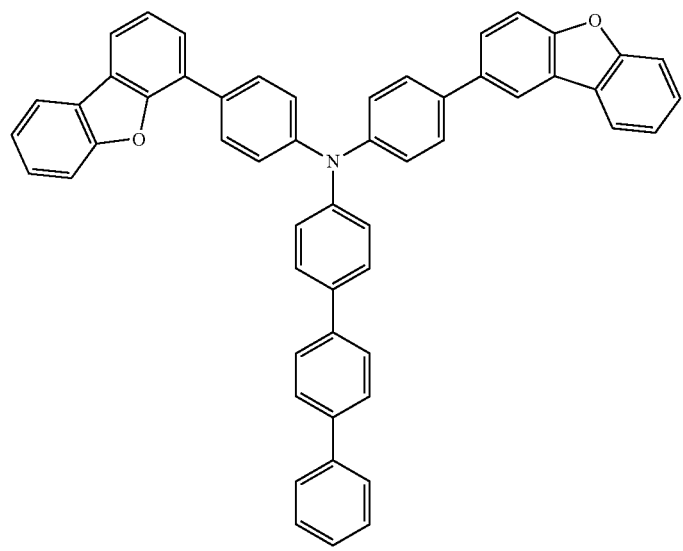
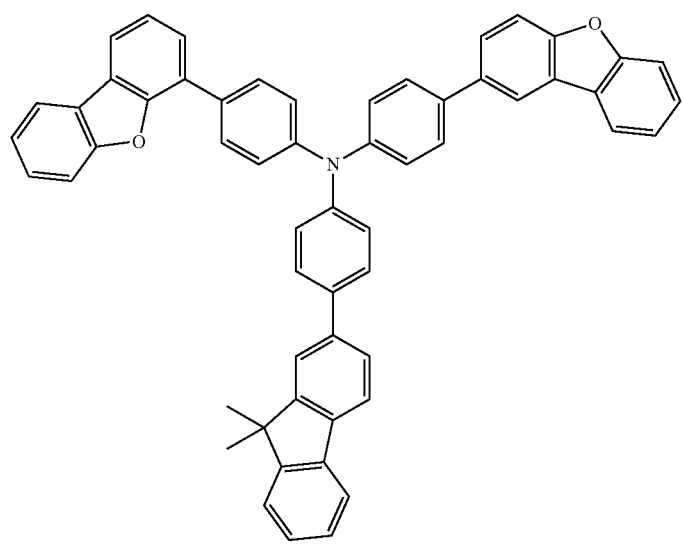

-continued
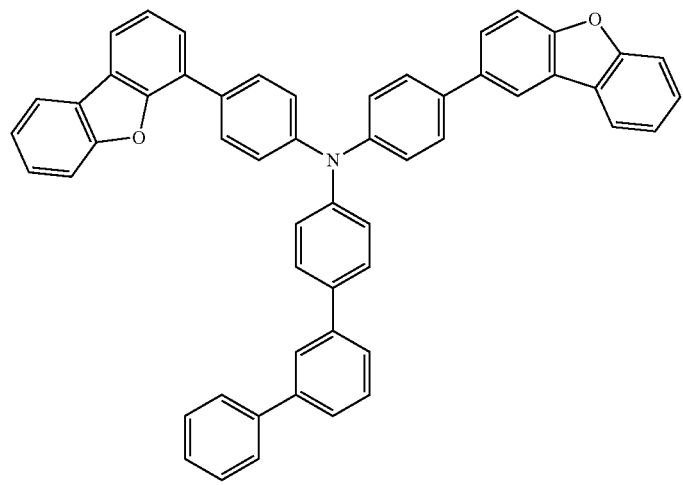
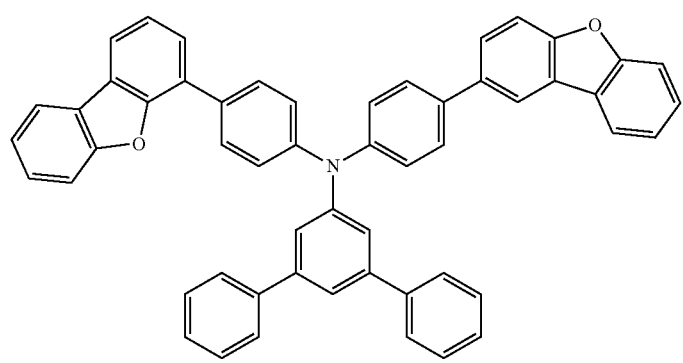
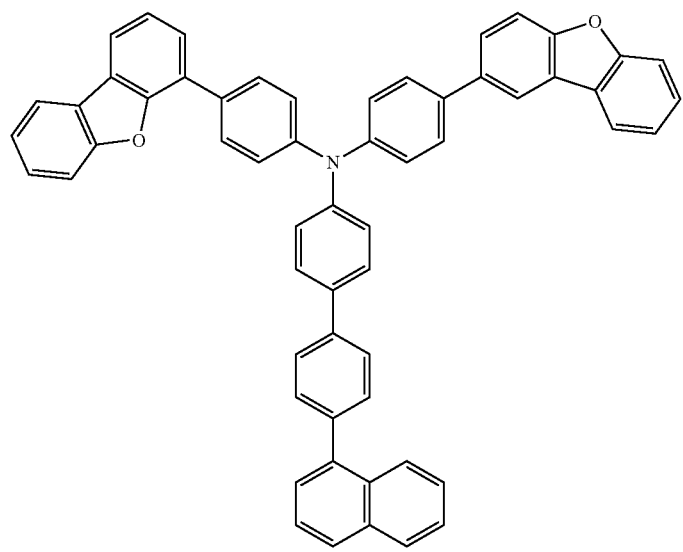

-continued
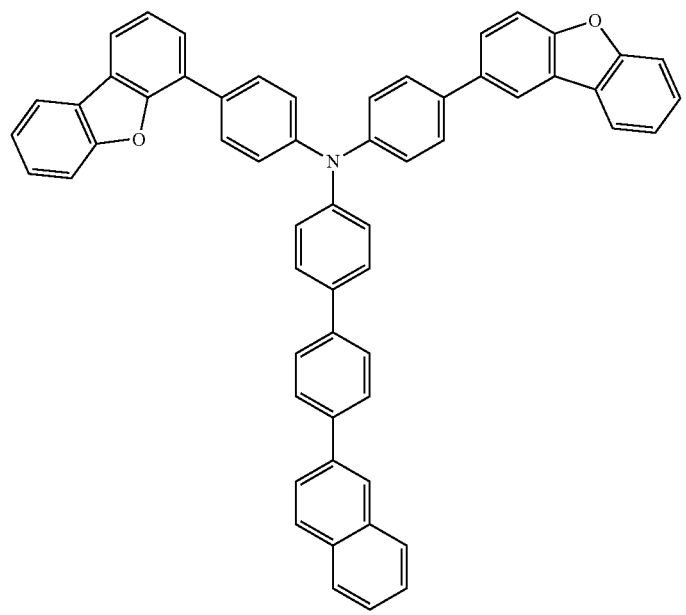
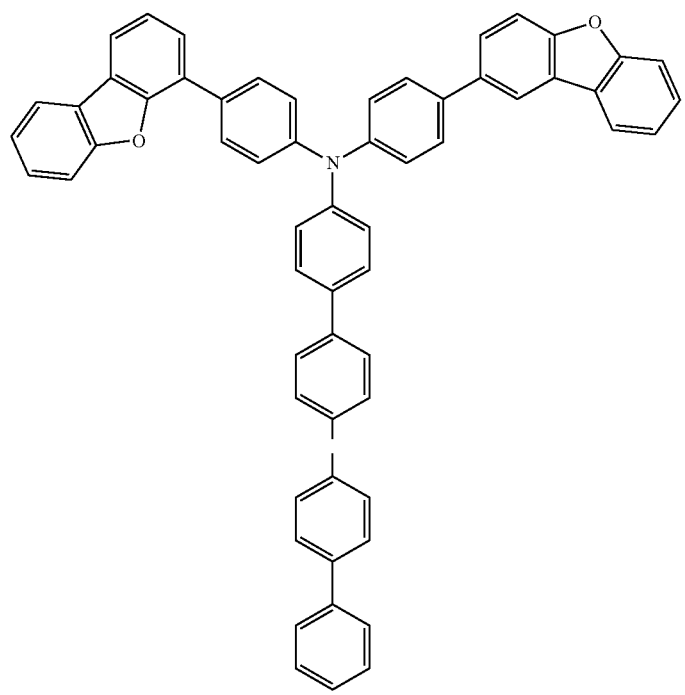

245
246
-continued
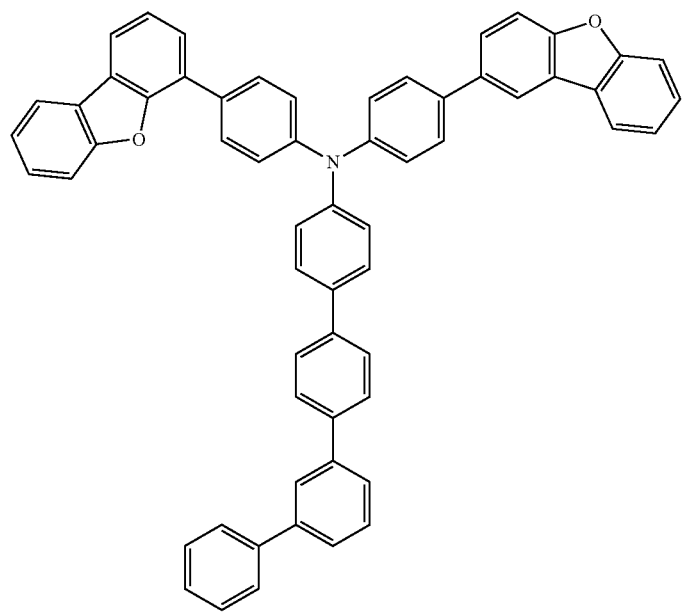
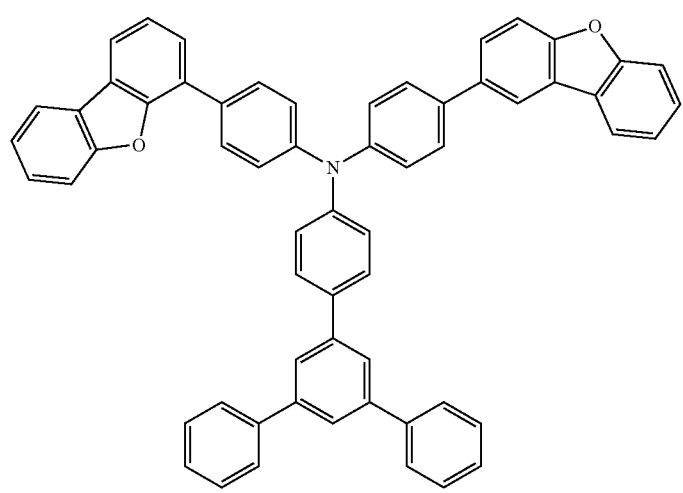
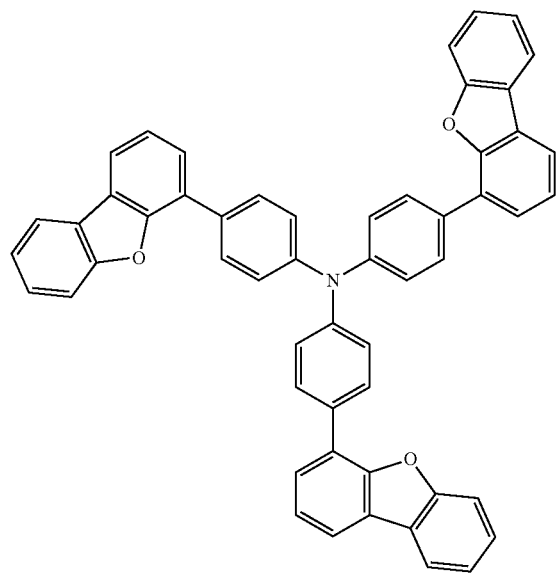

-continued
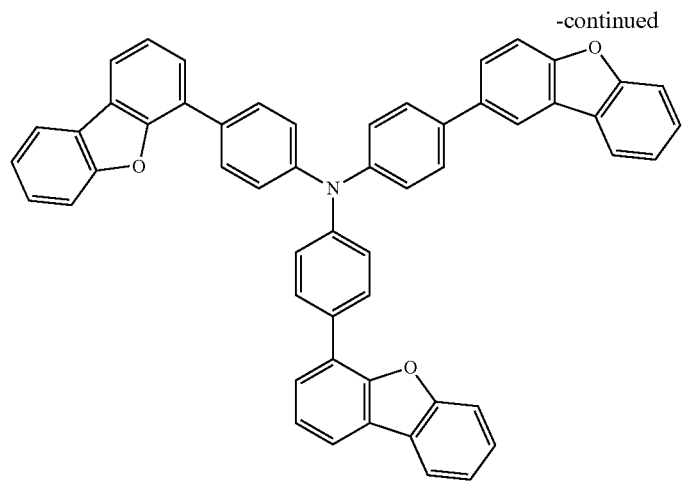
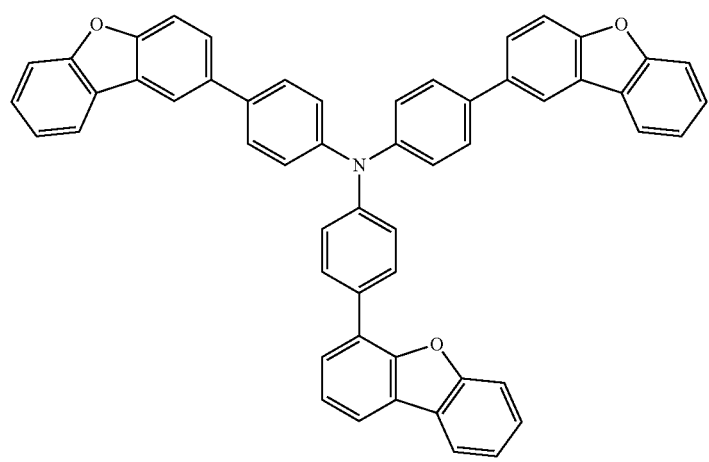
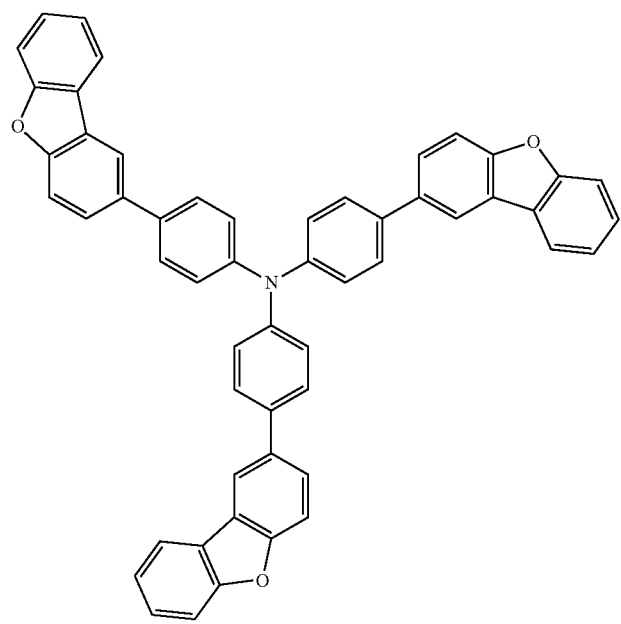

-continued
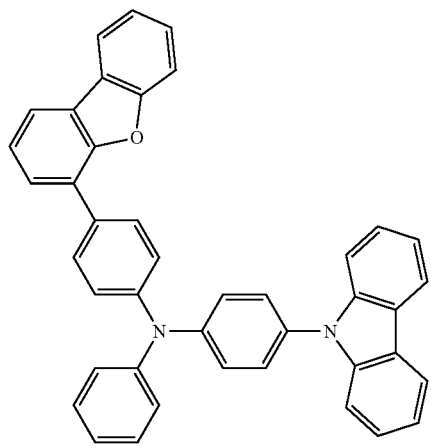
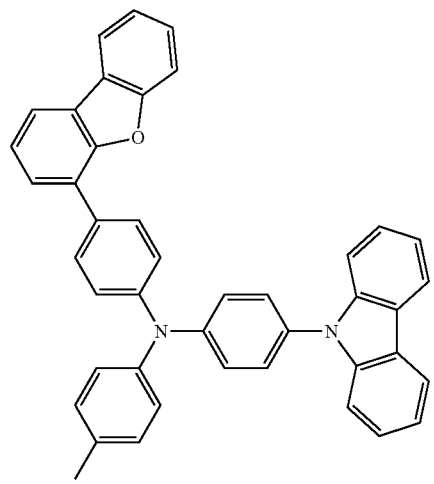
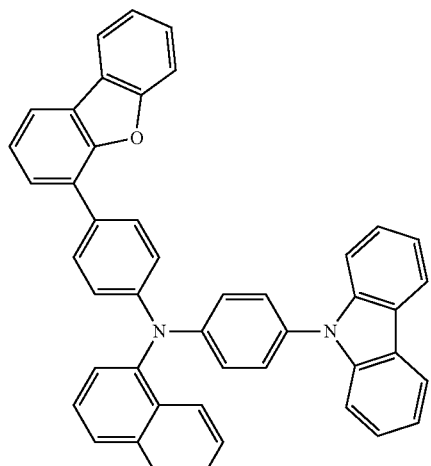
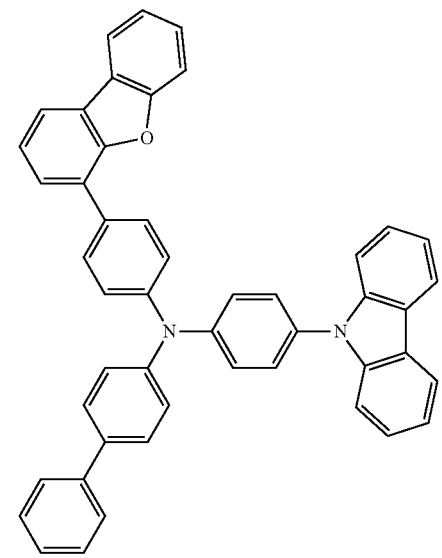
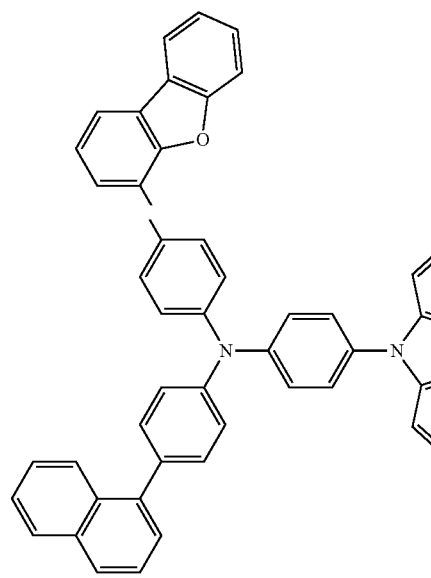
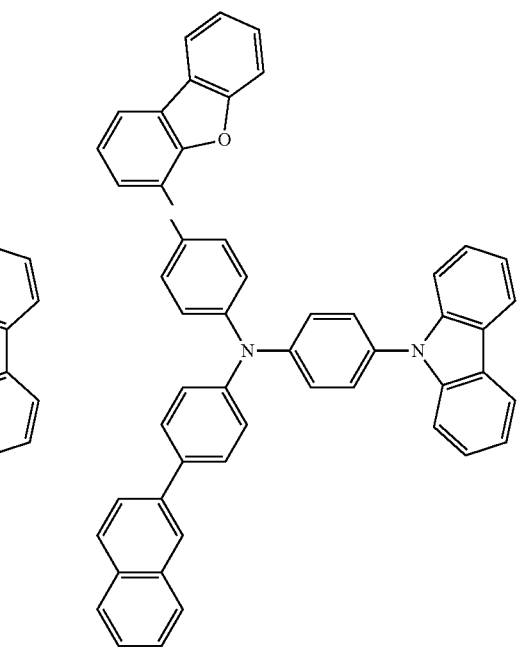

251
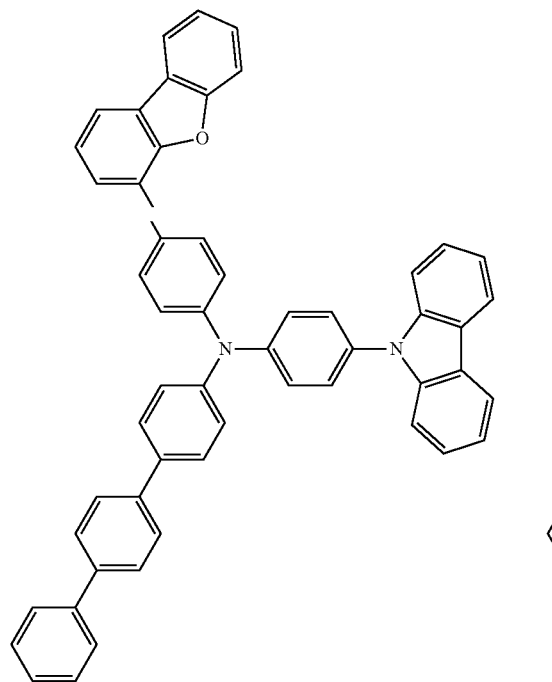
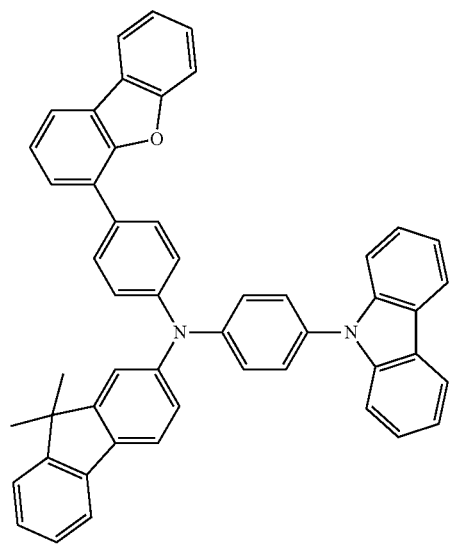
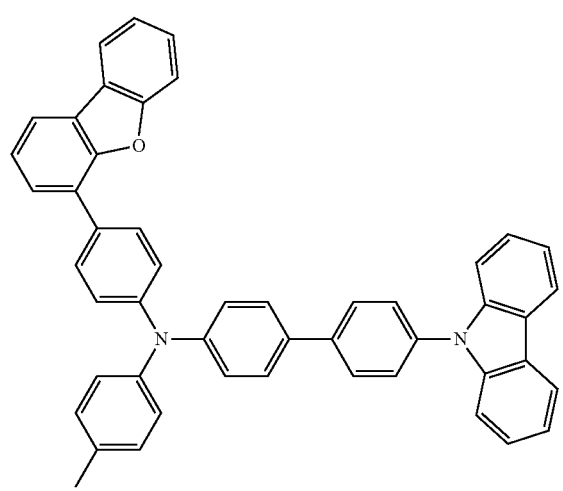
252
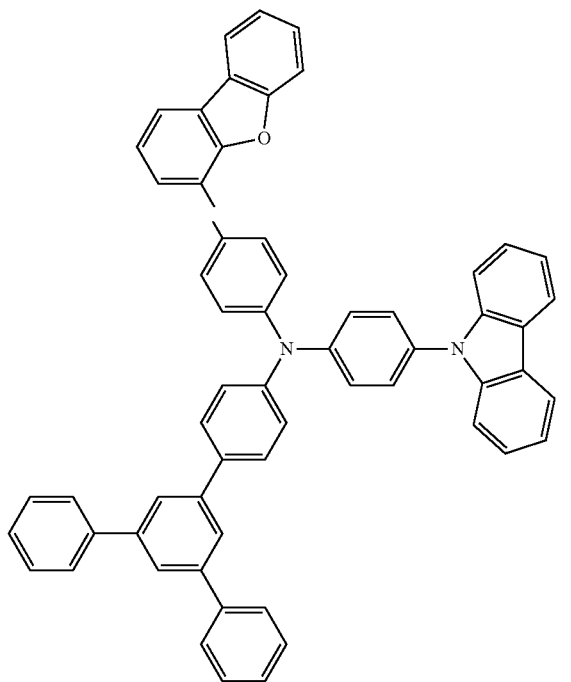
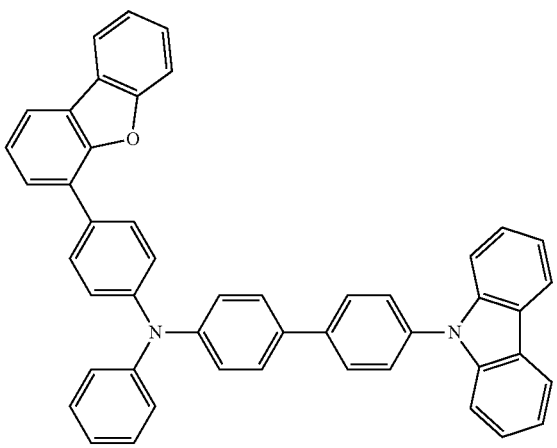
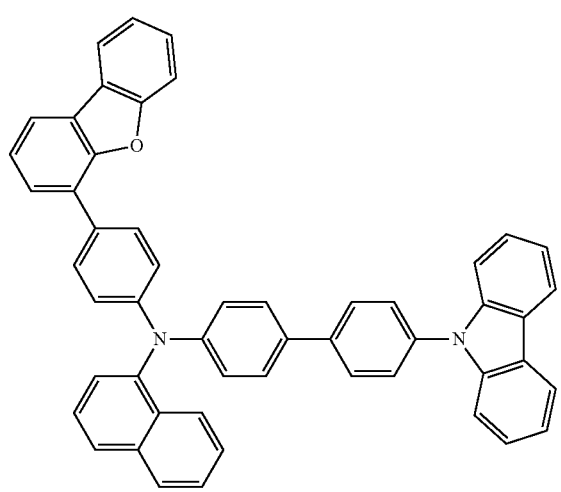

253
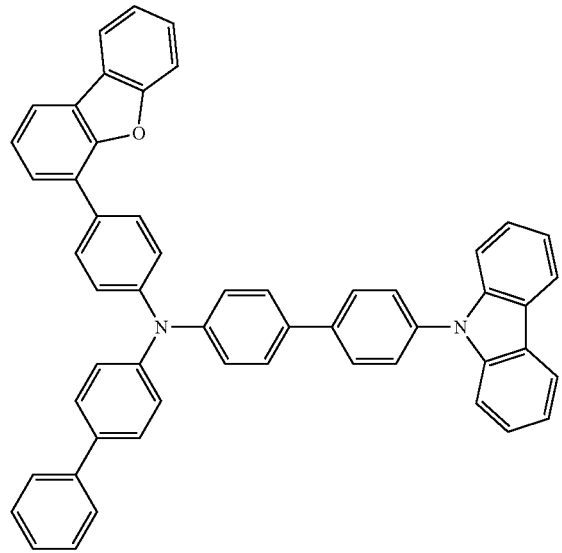
254
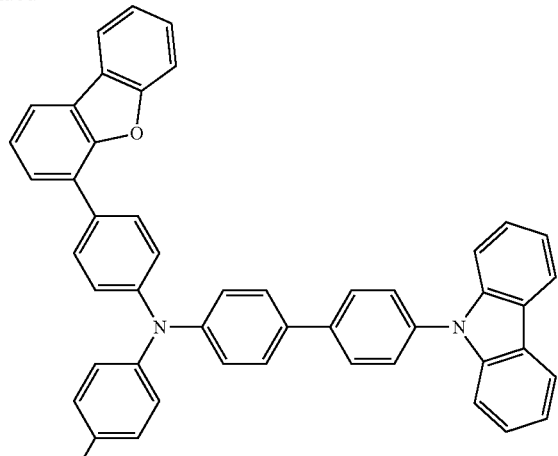
-continued
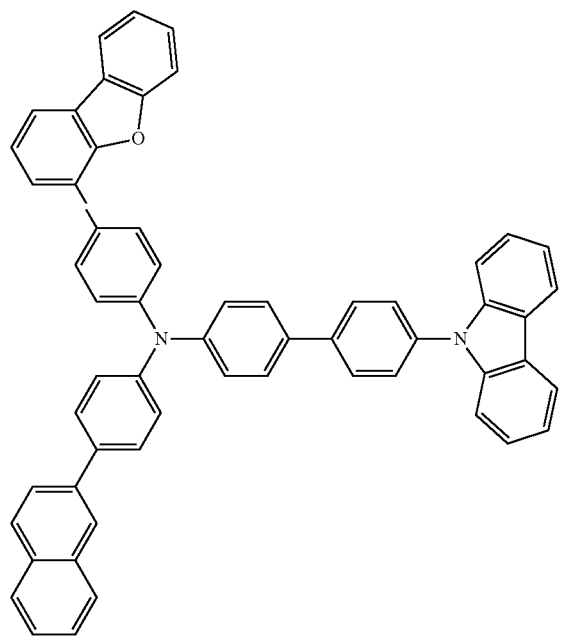
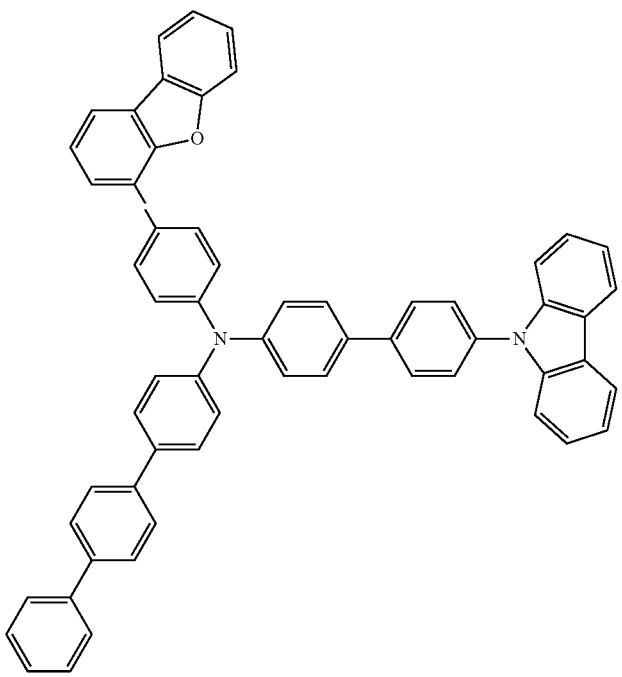
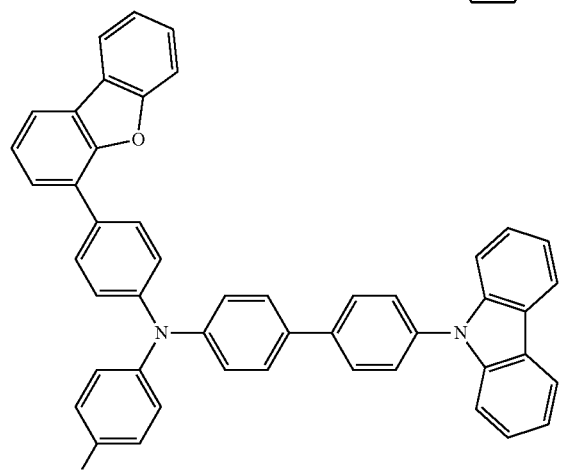

255
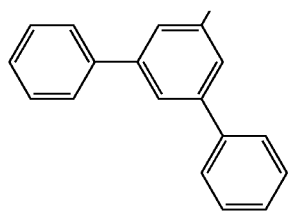
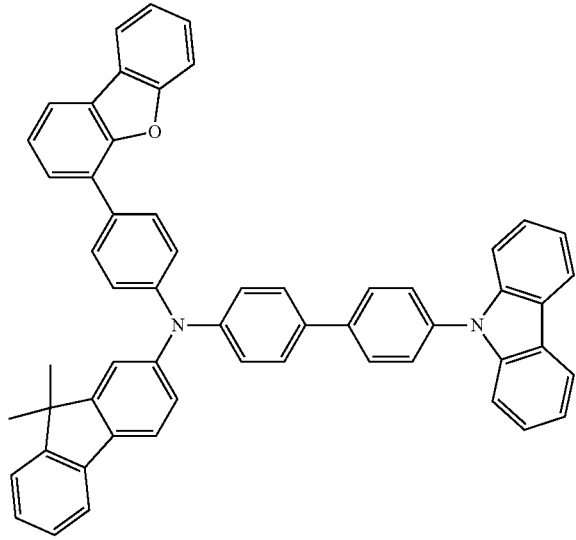
256
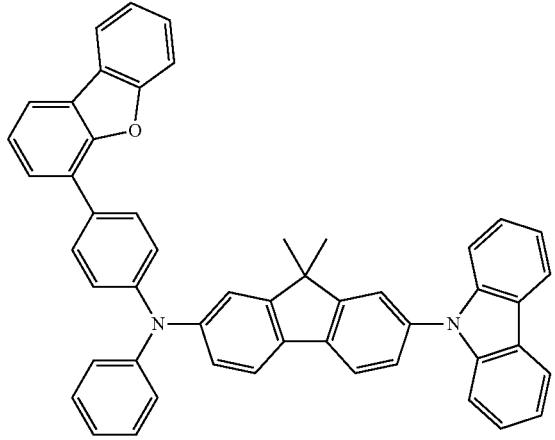
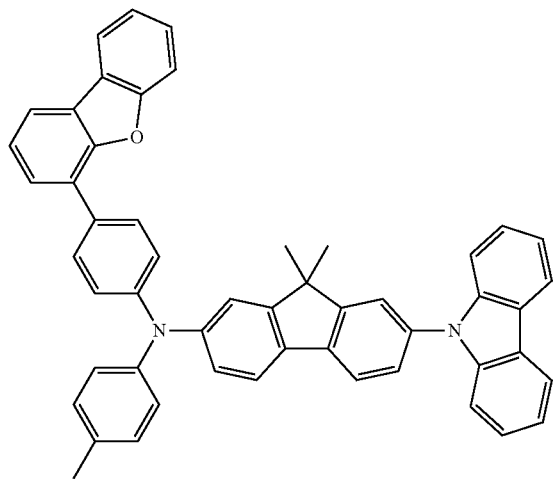
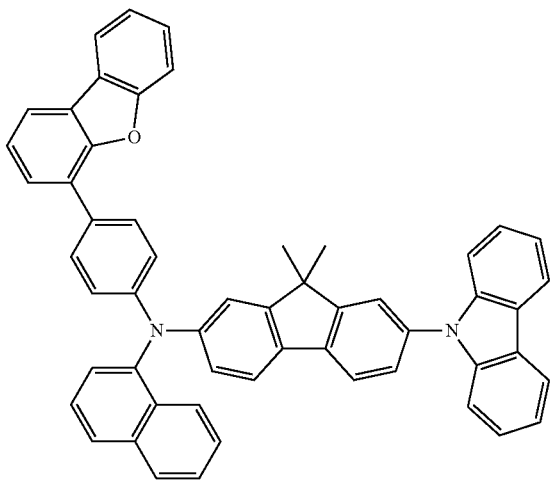
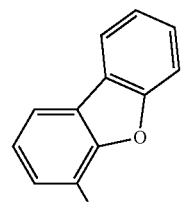
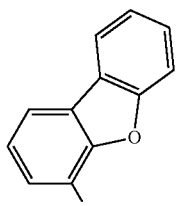

-continued
257
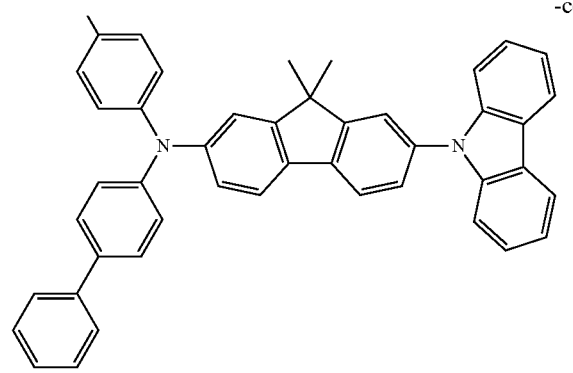
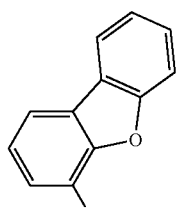
258
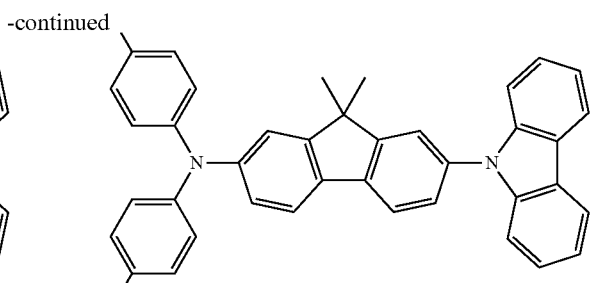
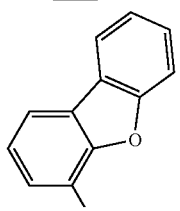
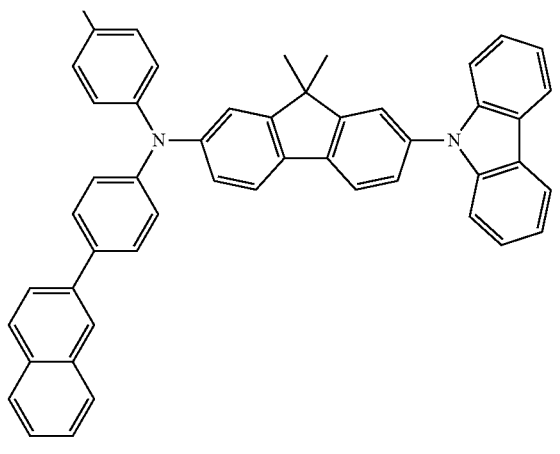
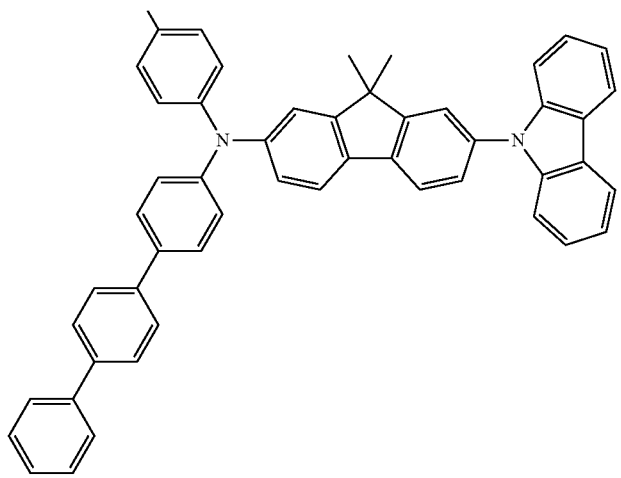
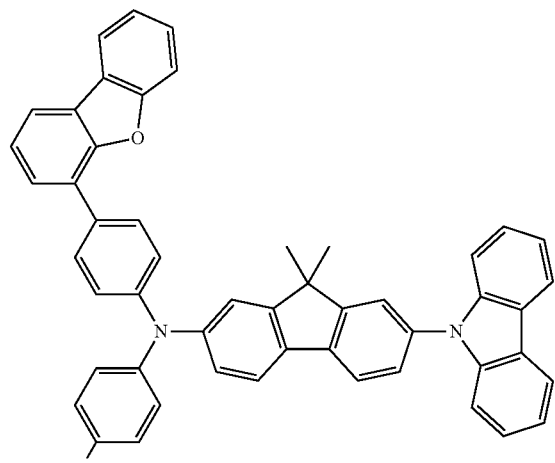

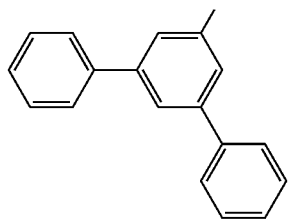
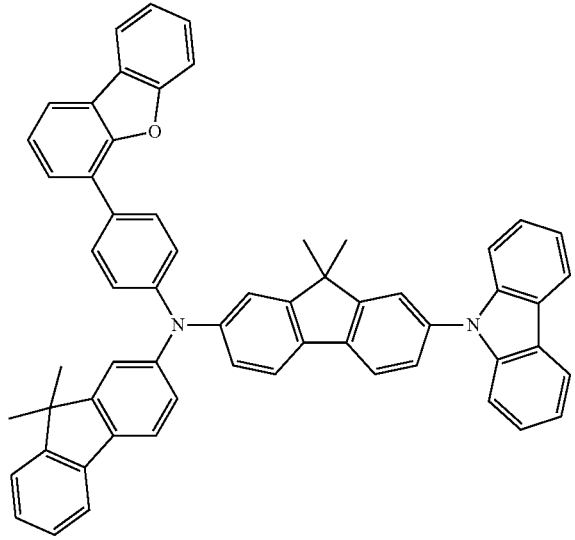
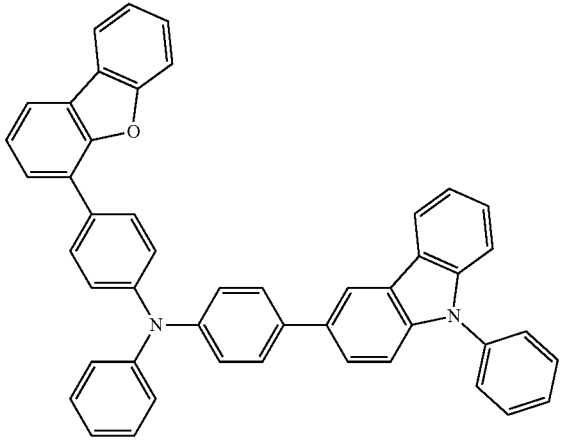
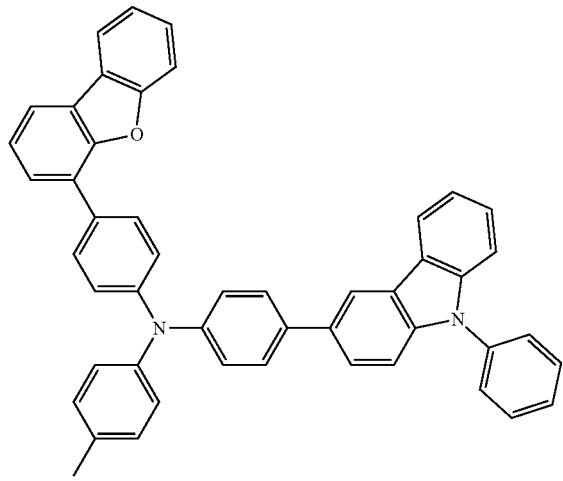
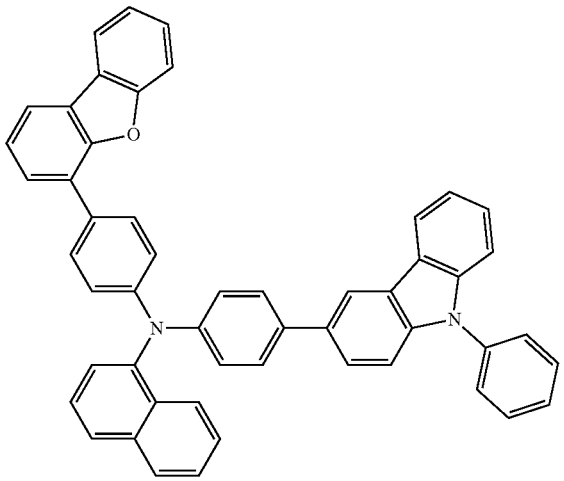
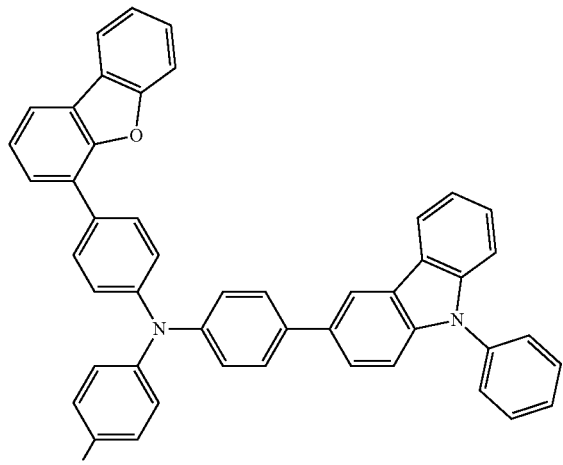
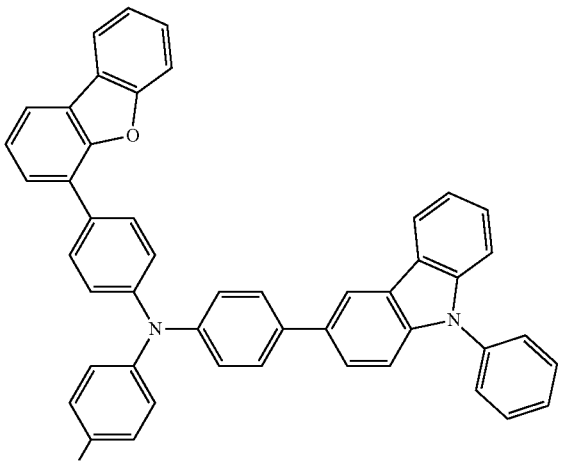

261
262
-continued
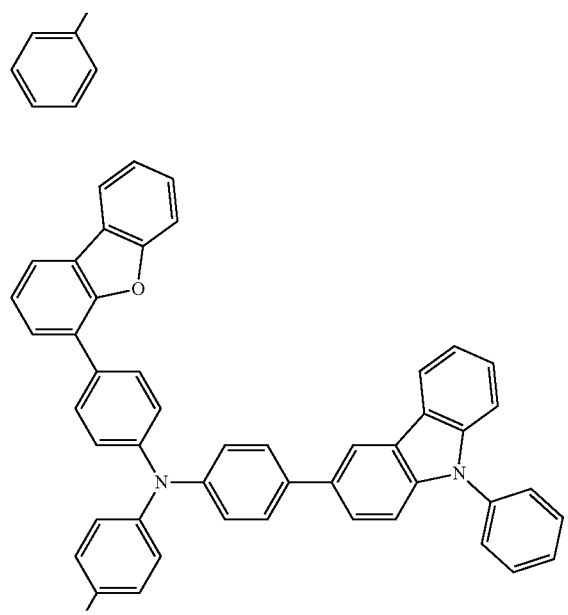
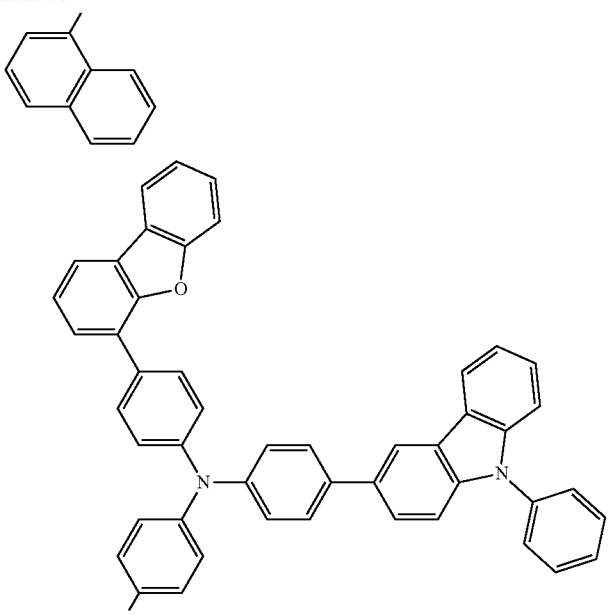
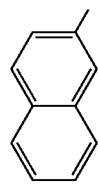
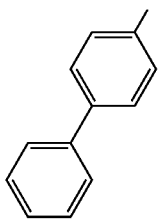
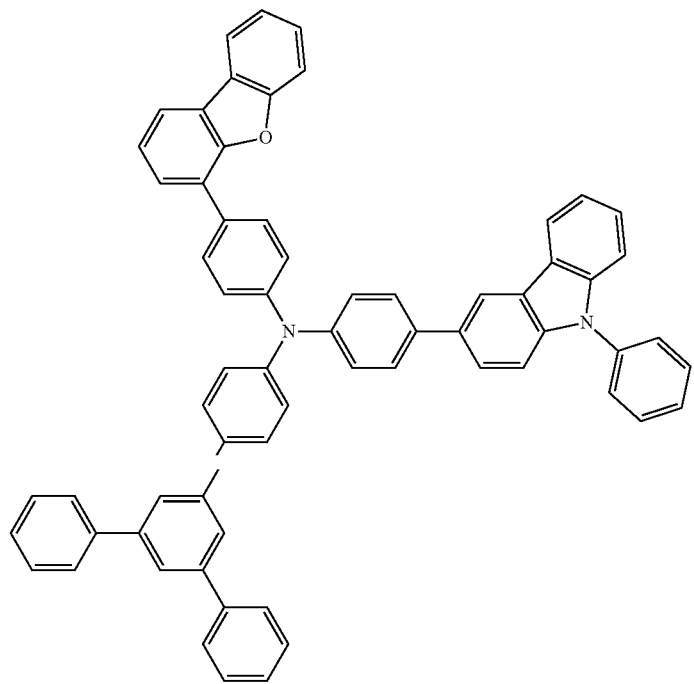

-continued
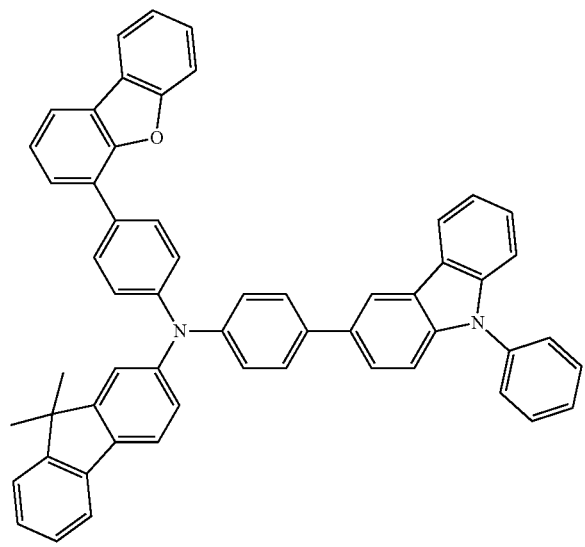
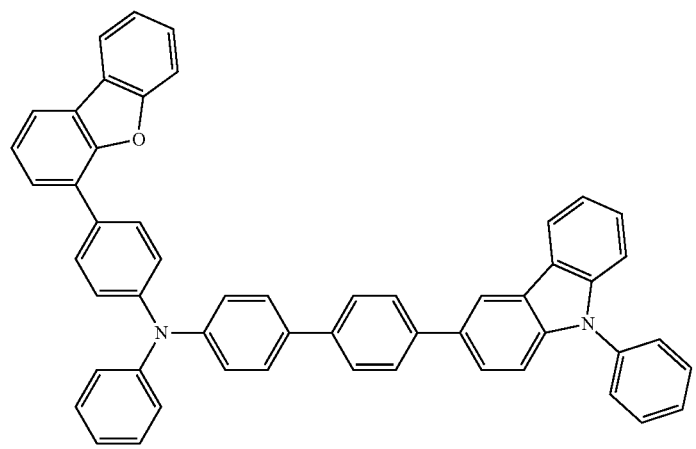
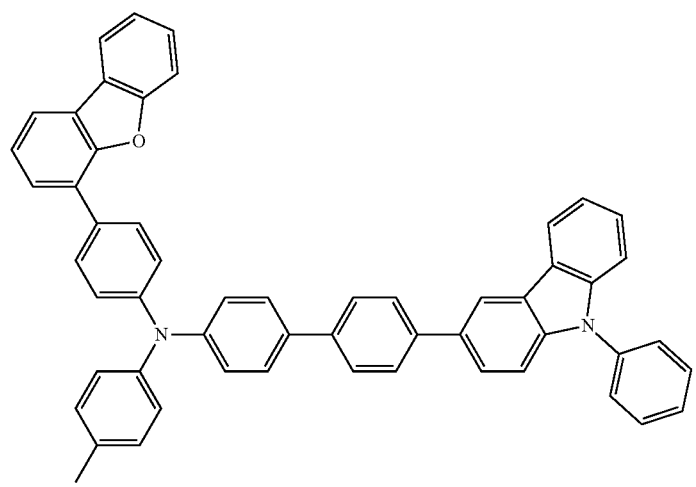

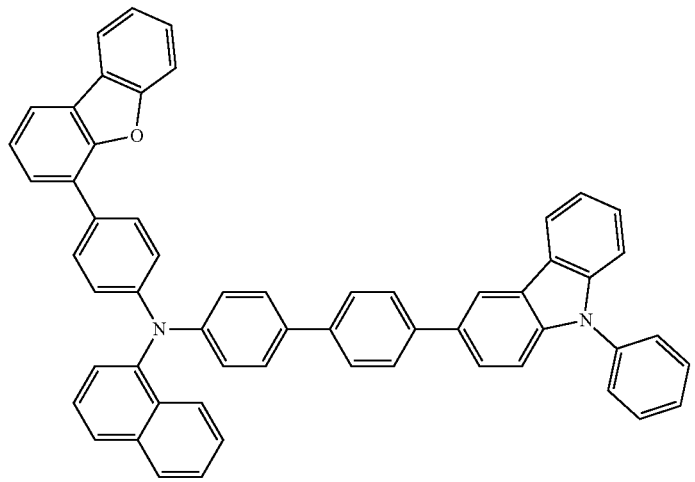
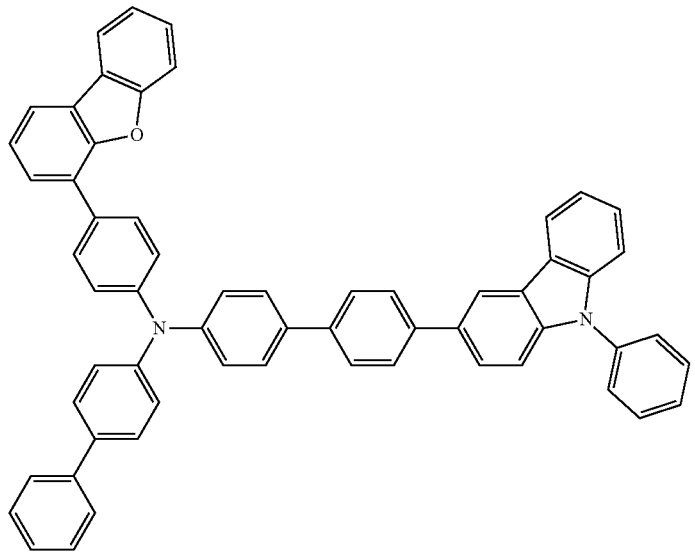
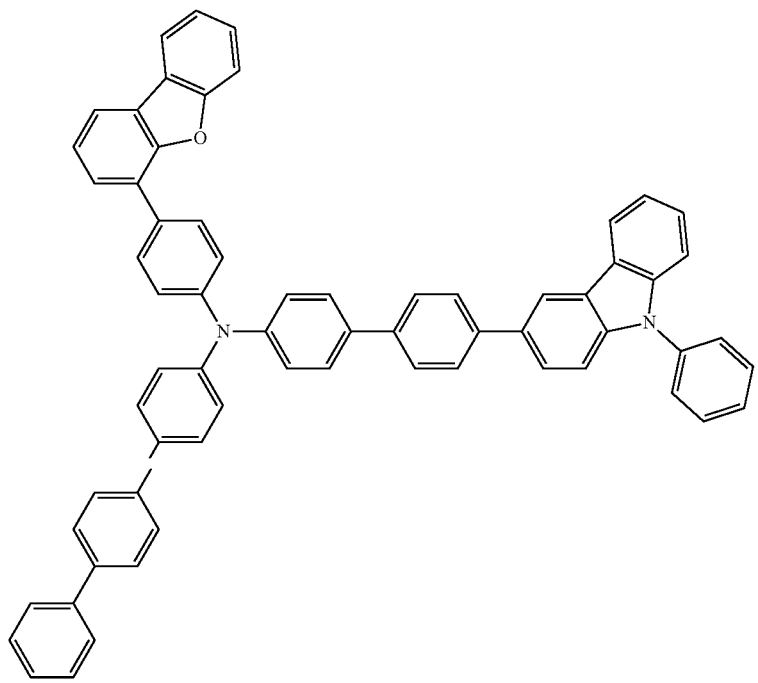

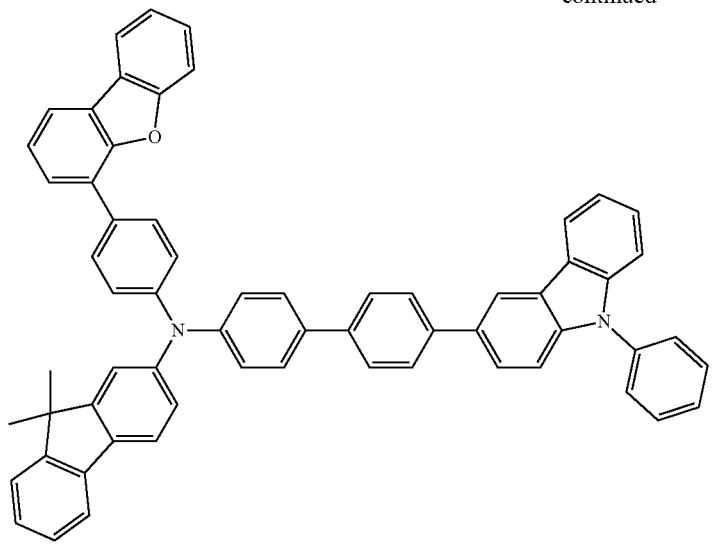
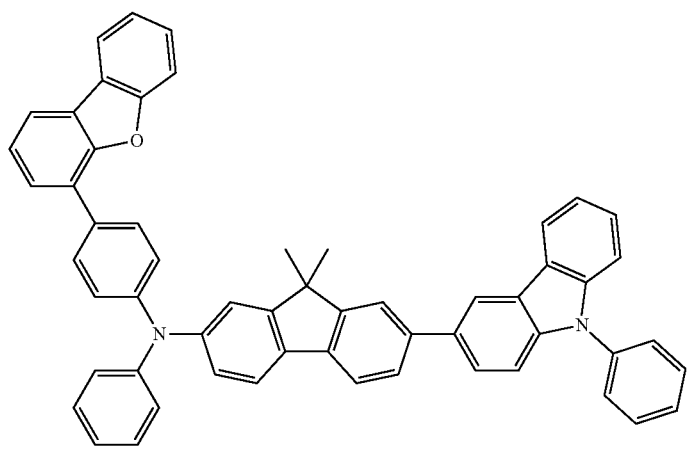
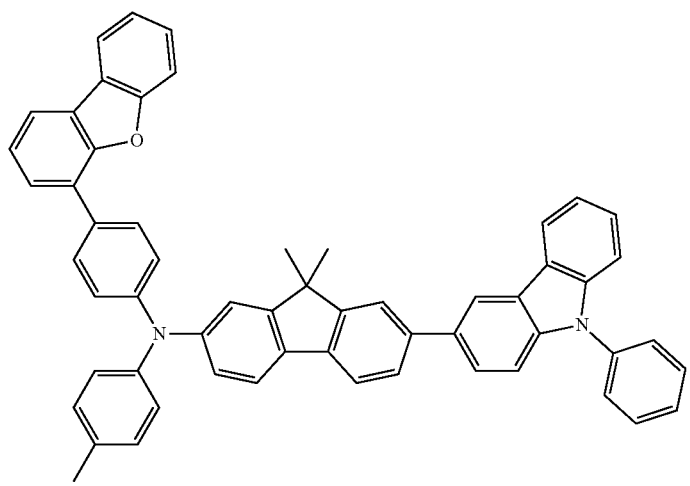

-continued
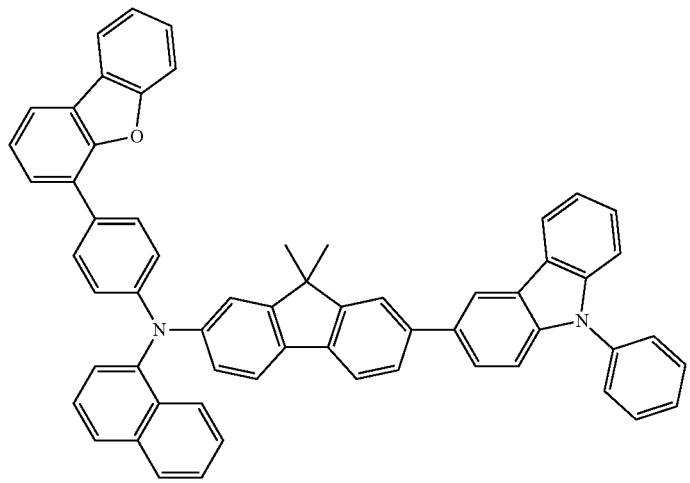
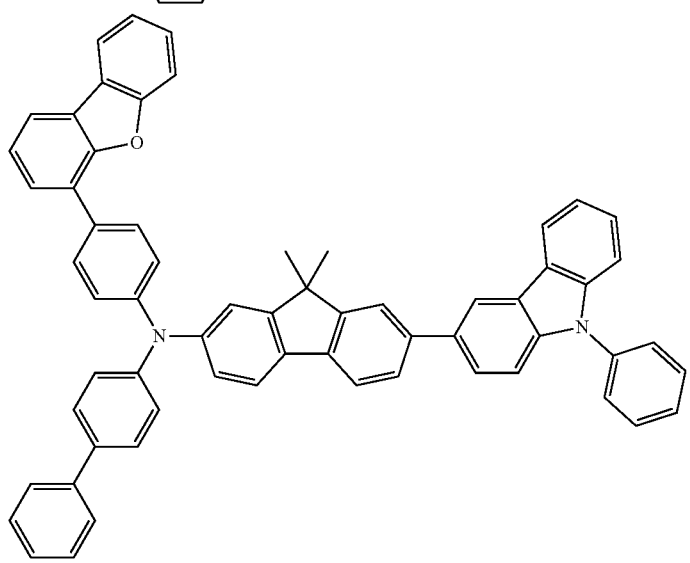
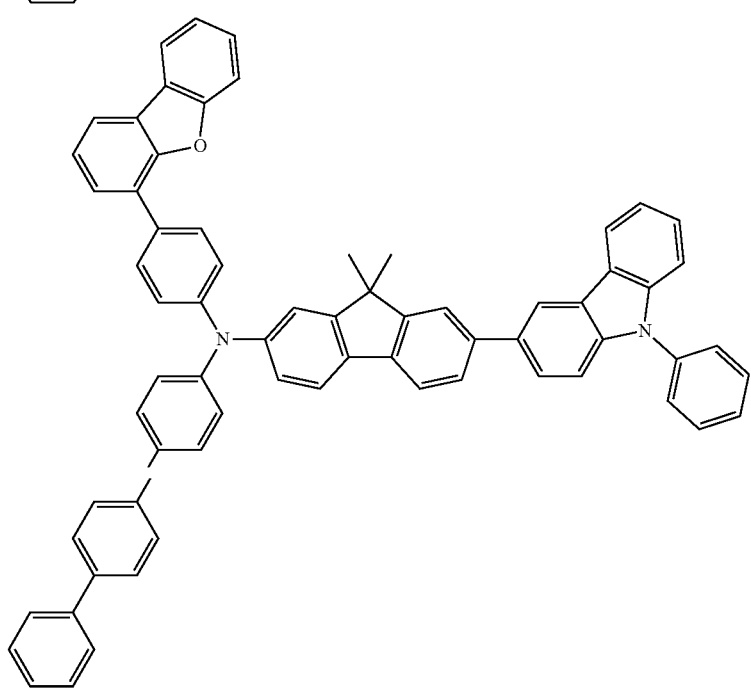

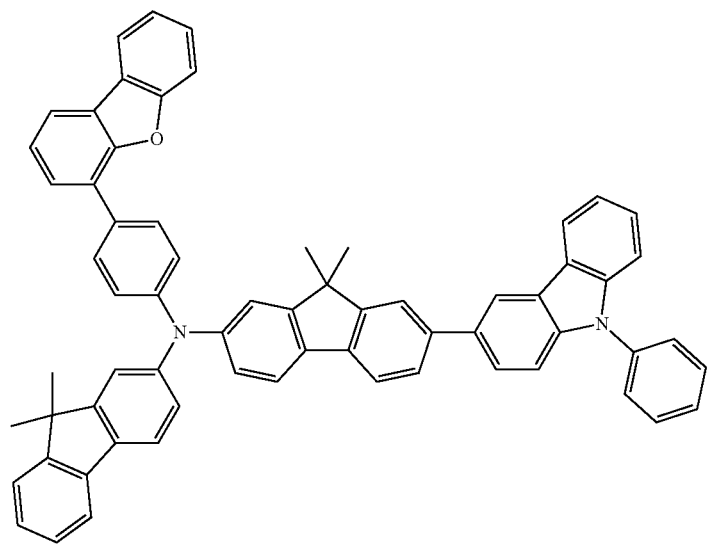
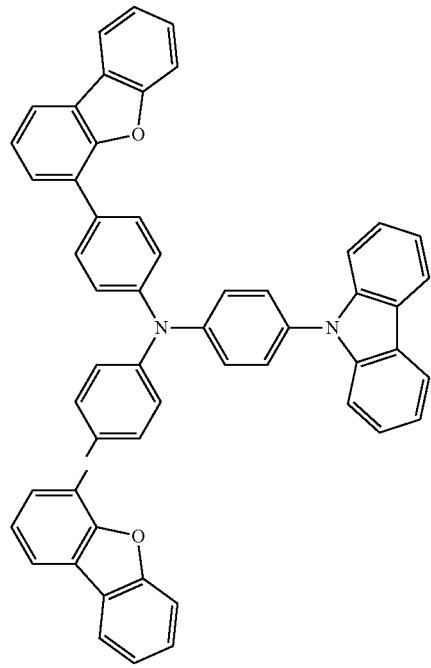
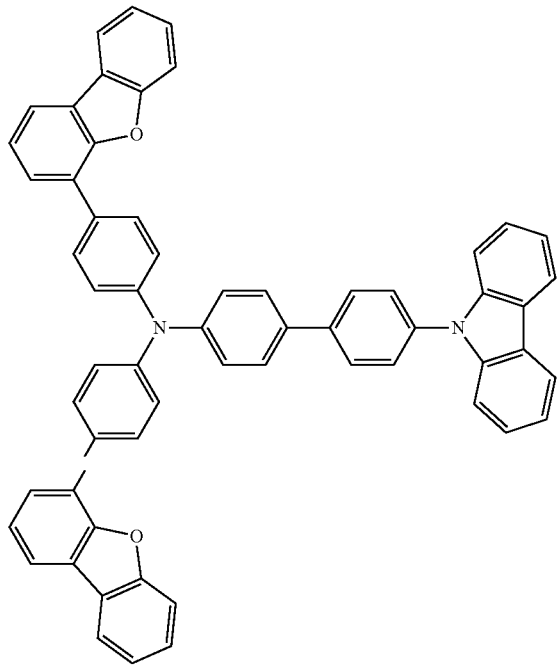
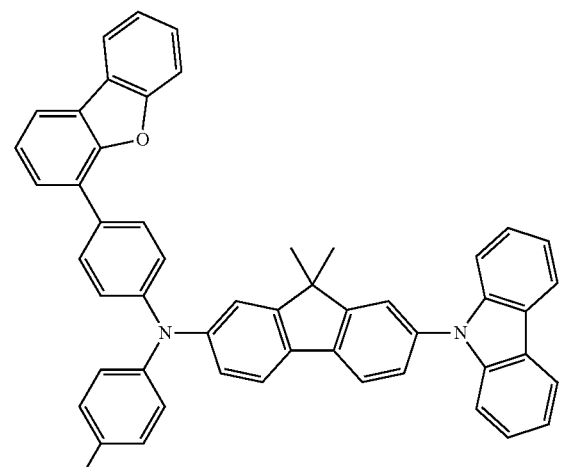
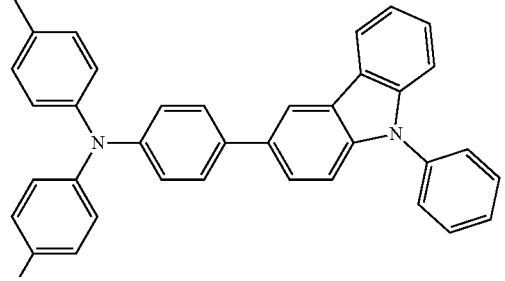

273
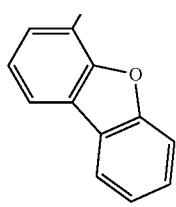
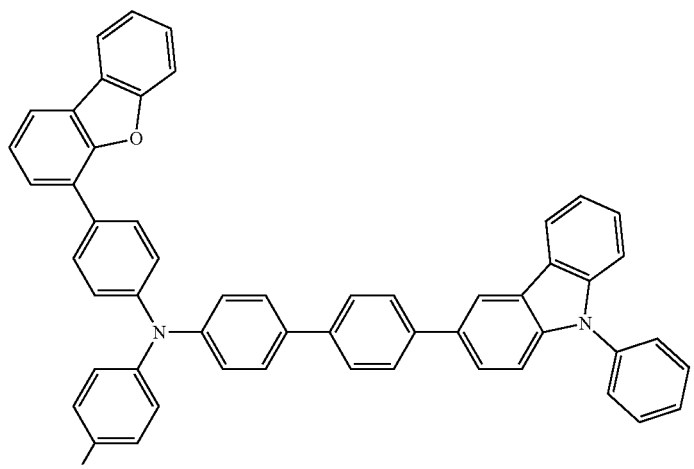
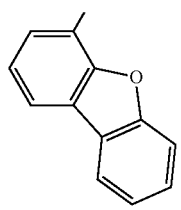
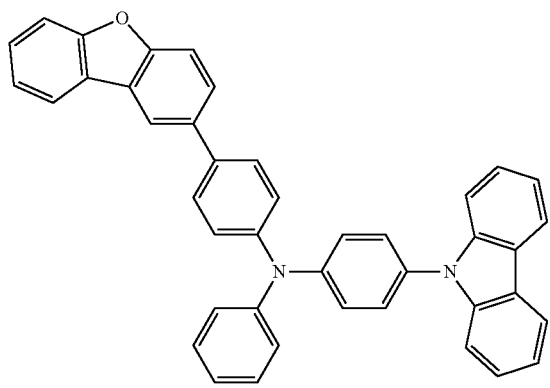
-continued
274
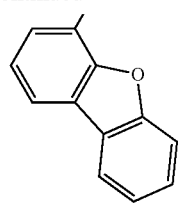
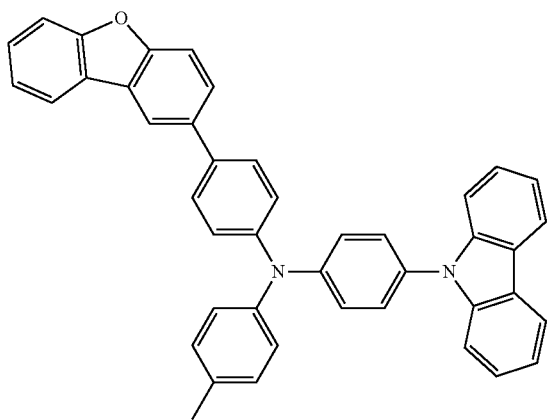

-continued
| 275 | 276 |
|---|---|
| 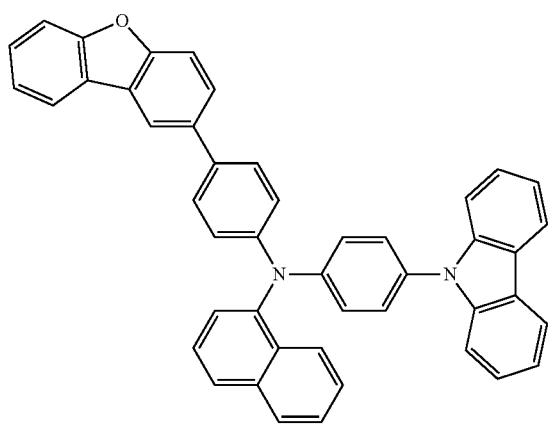 | 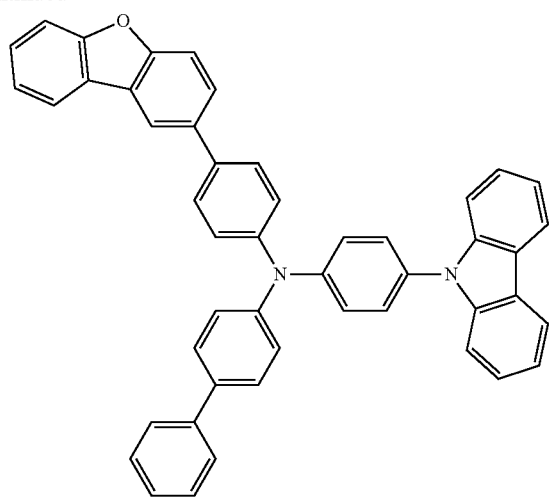 |
| 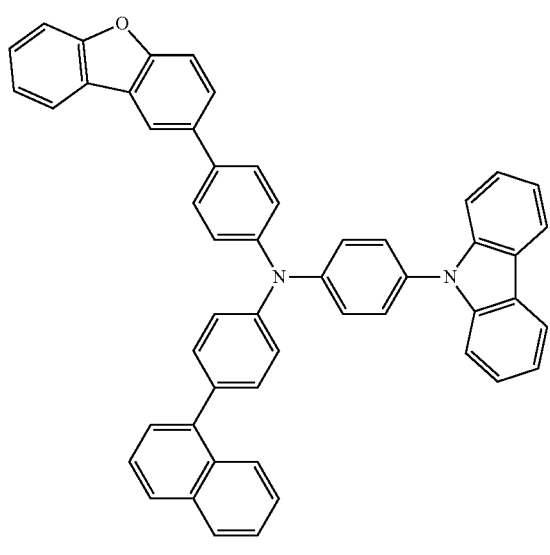 | 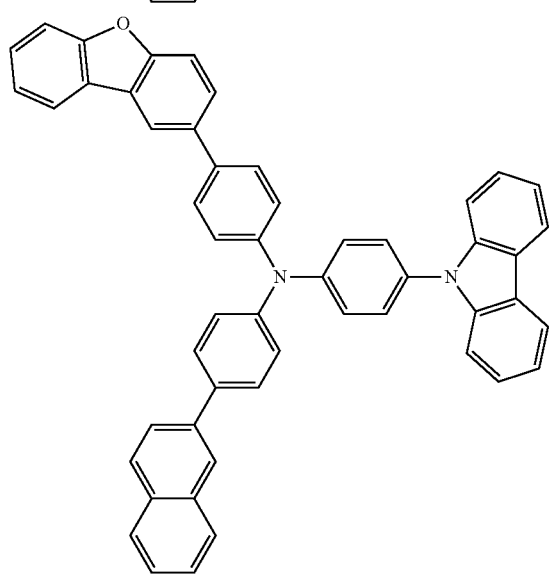 |
| 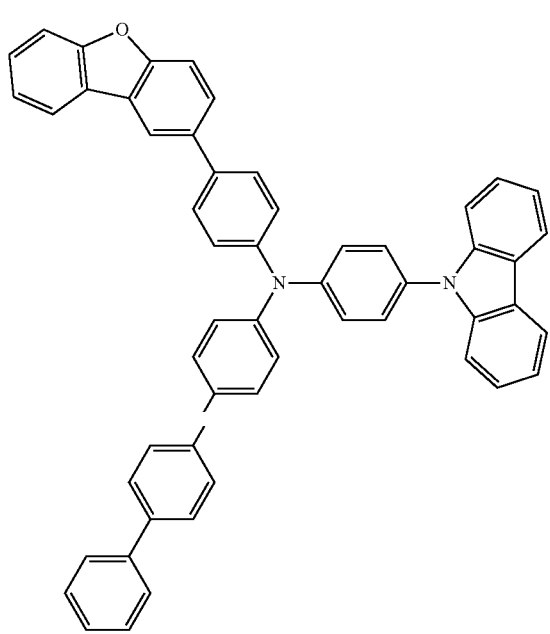 | 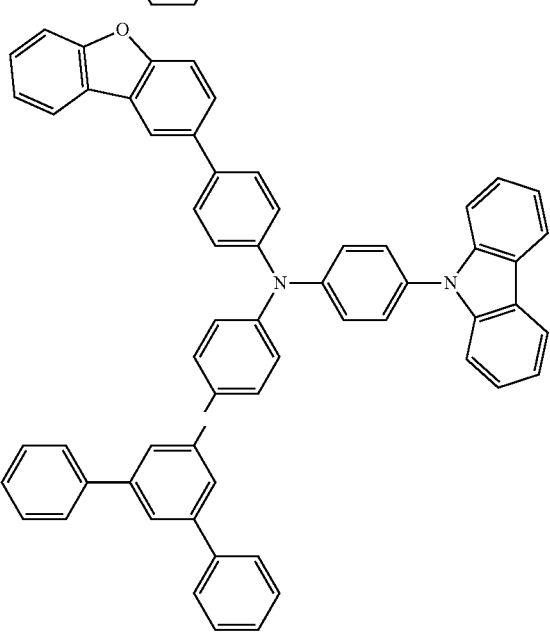 |

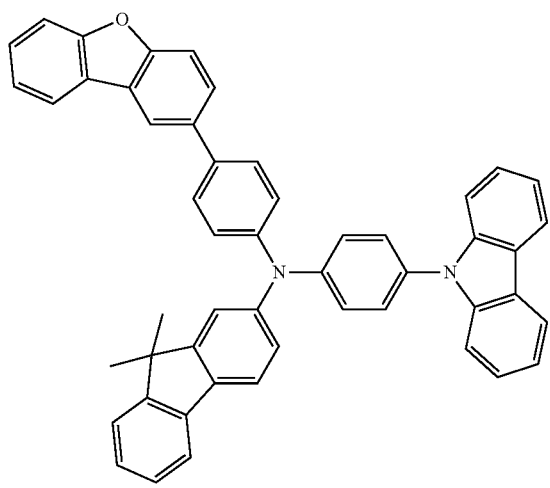
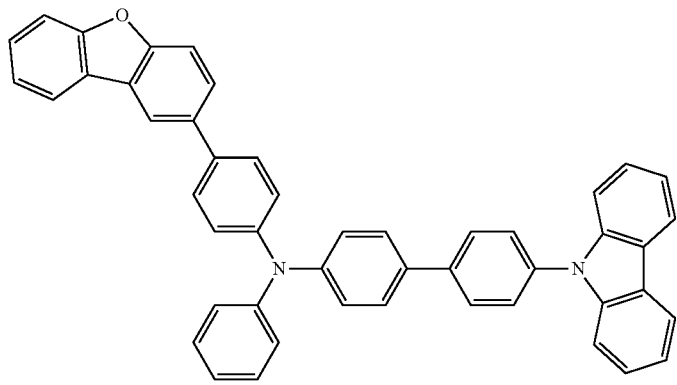
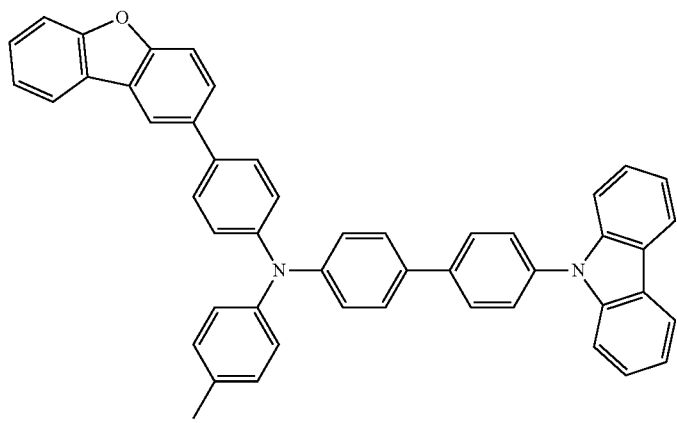
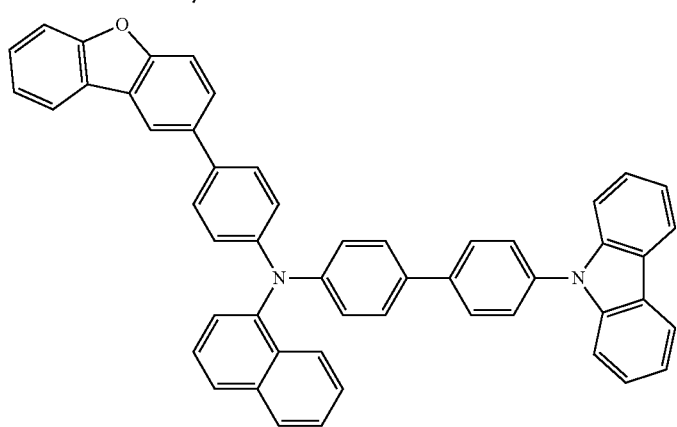

-continued
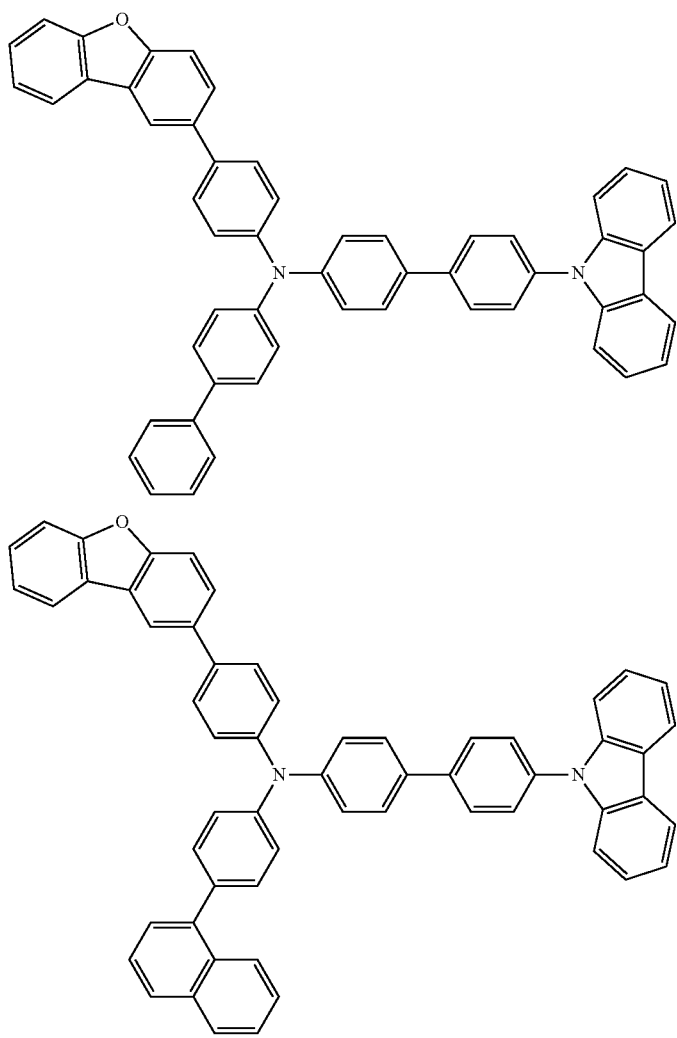
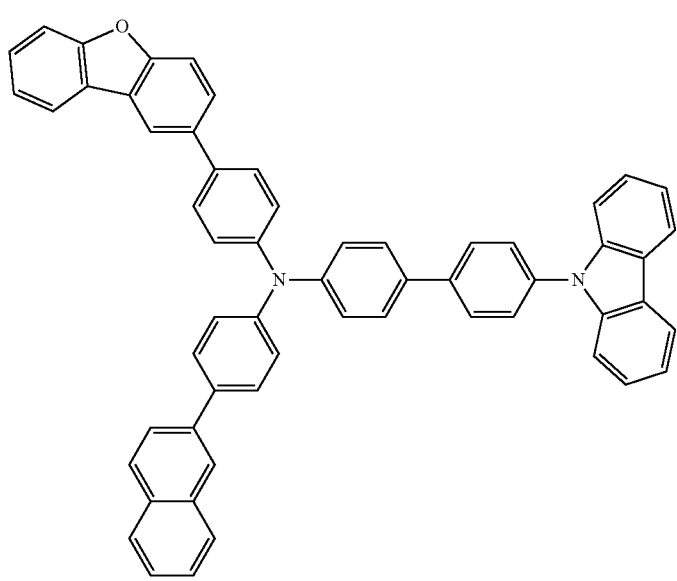

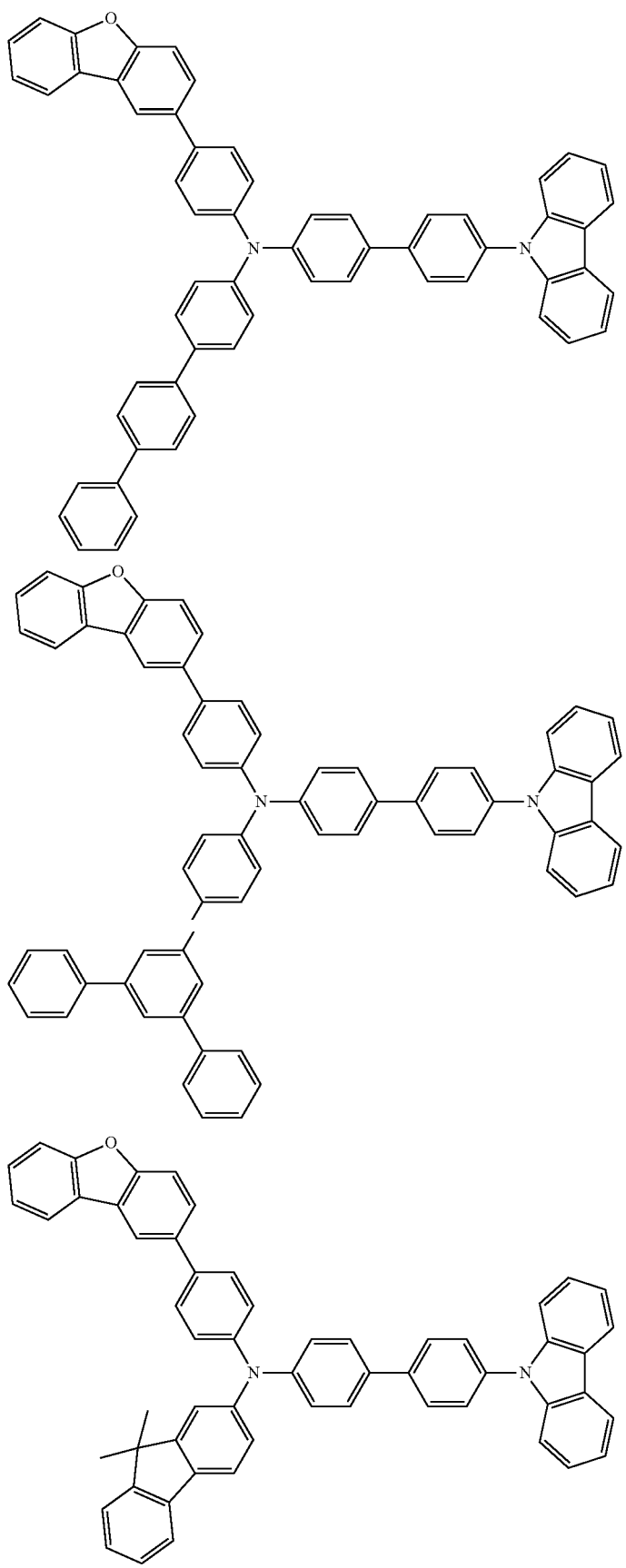

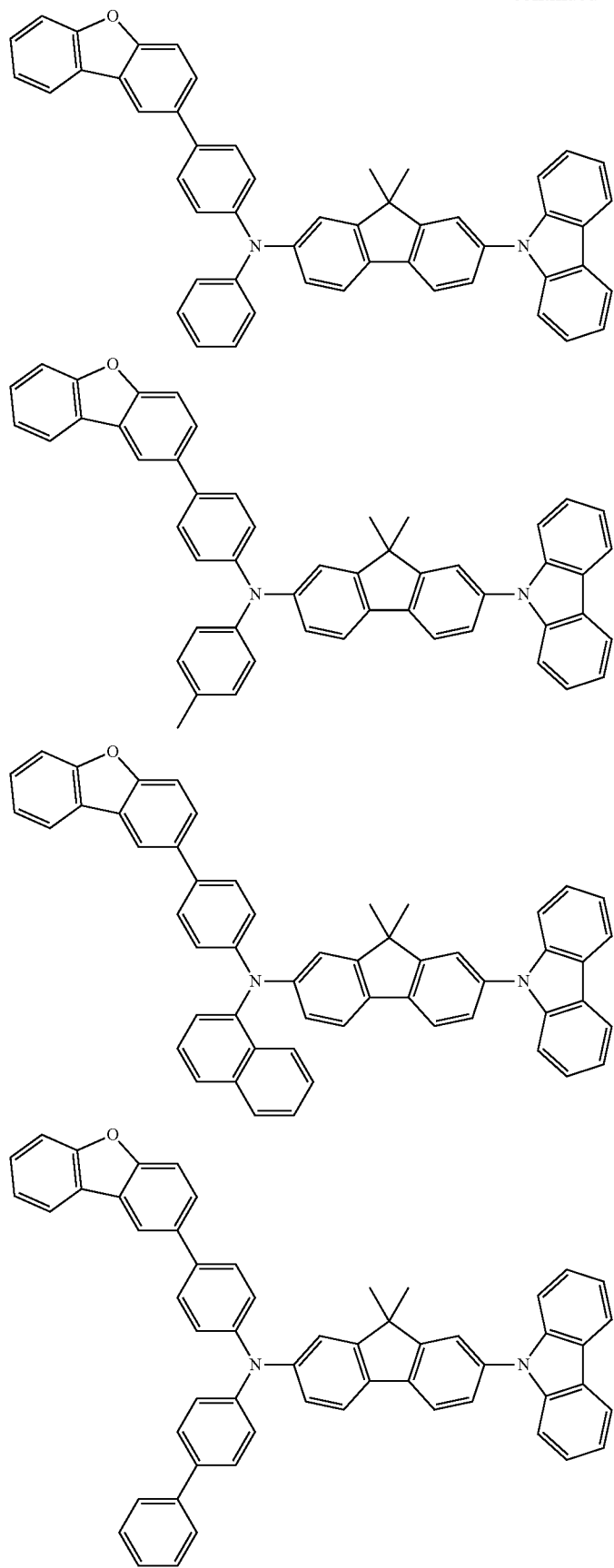

-continued
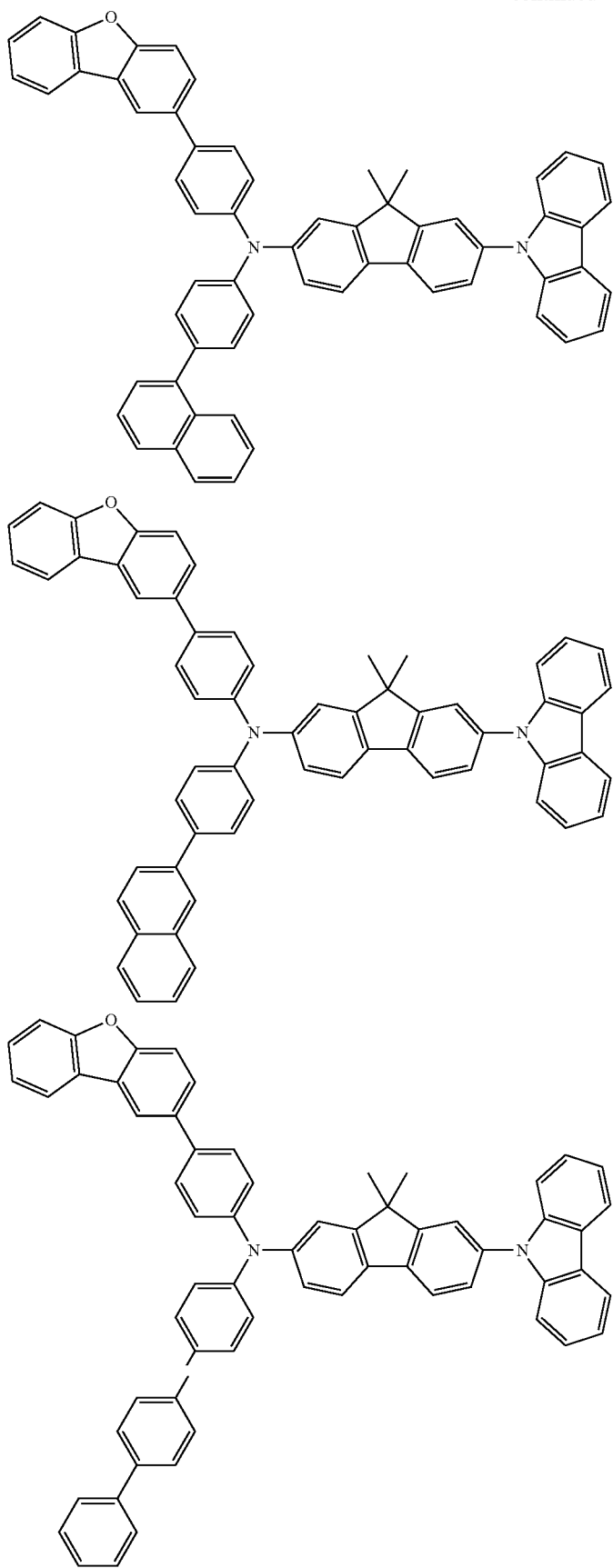

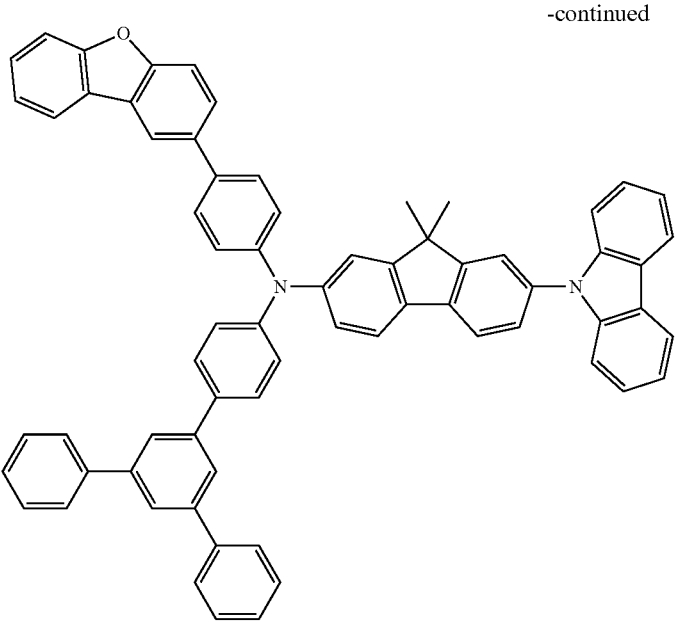
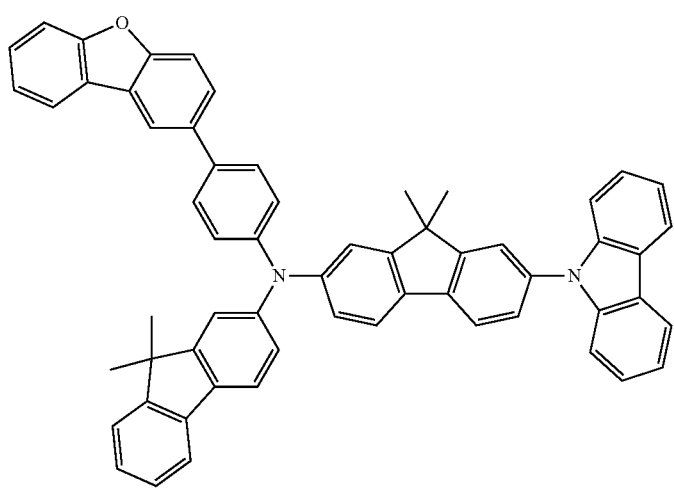
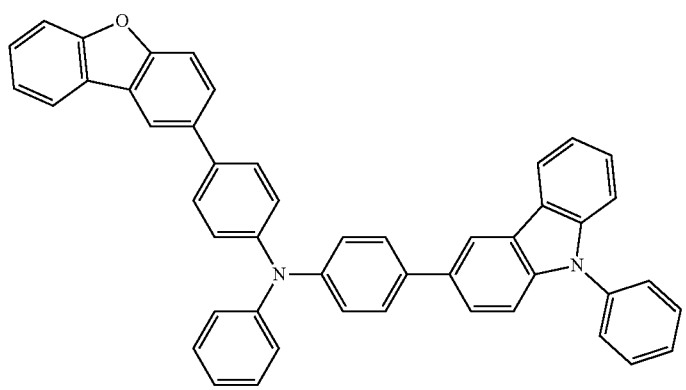

-continued
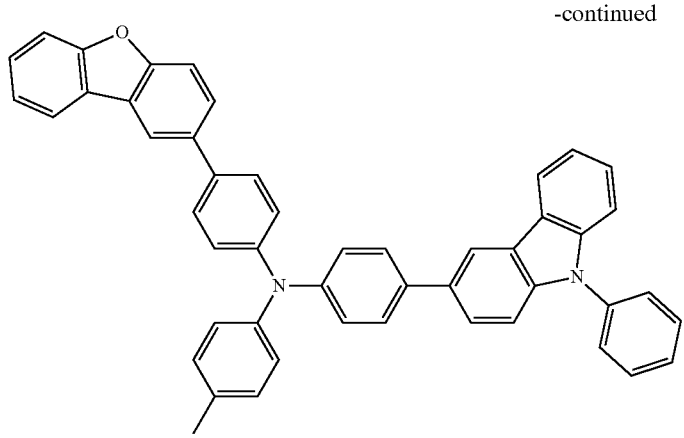
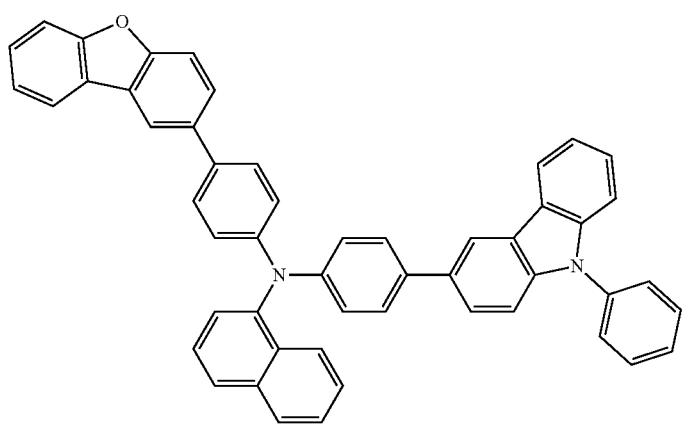
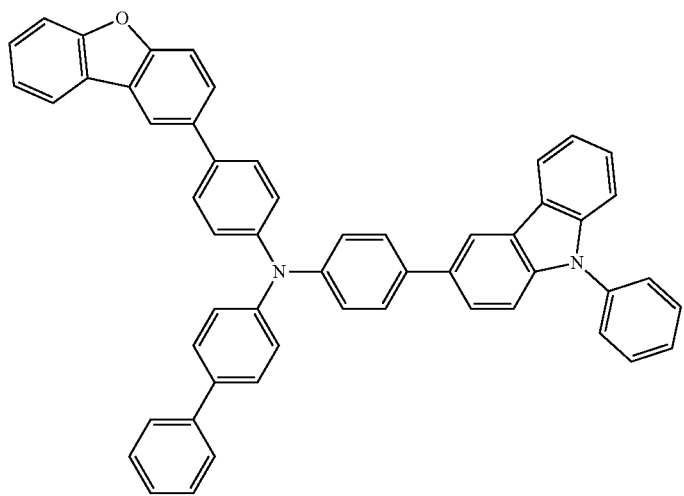

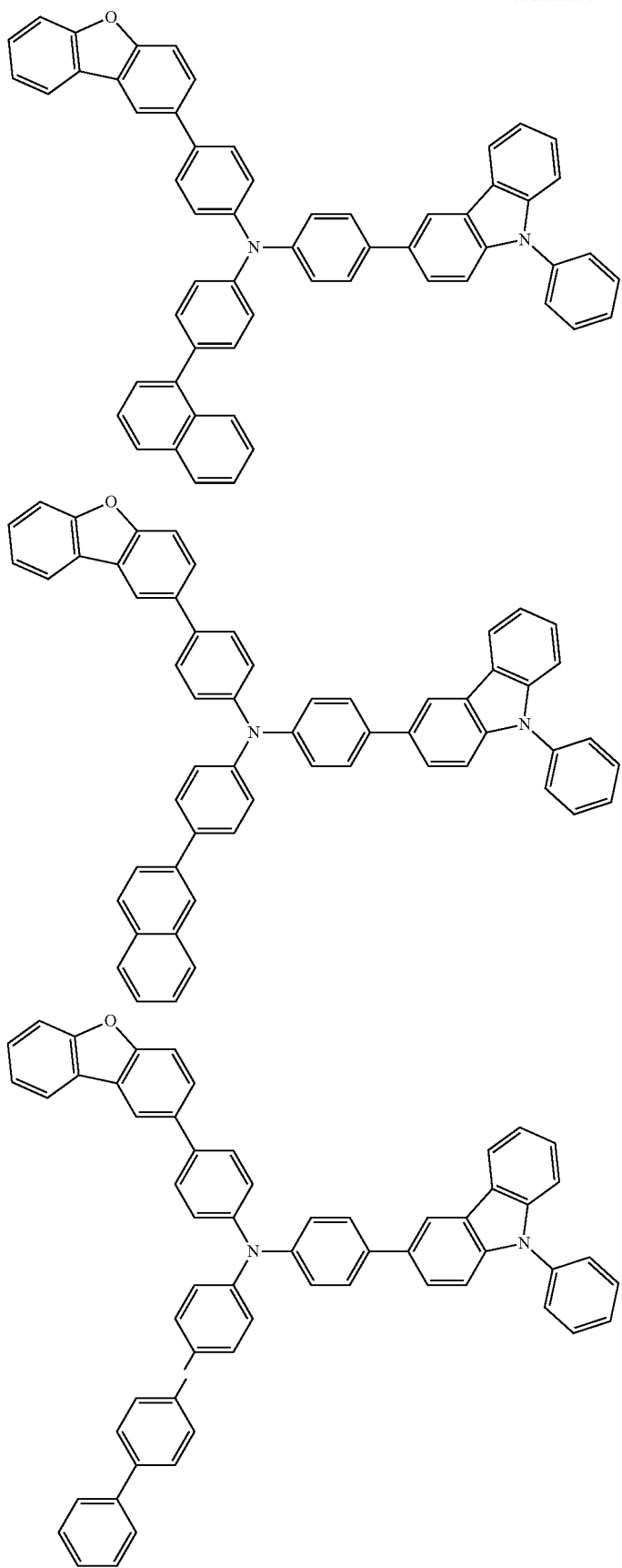

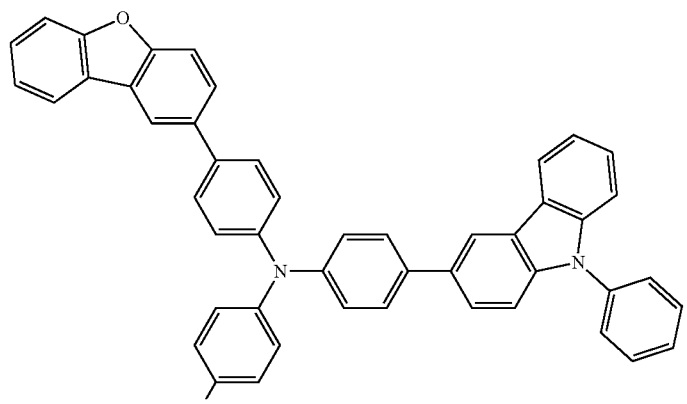
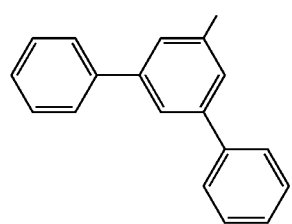
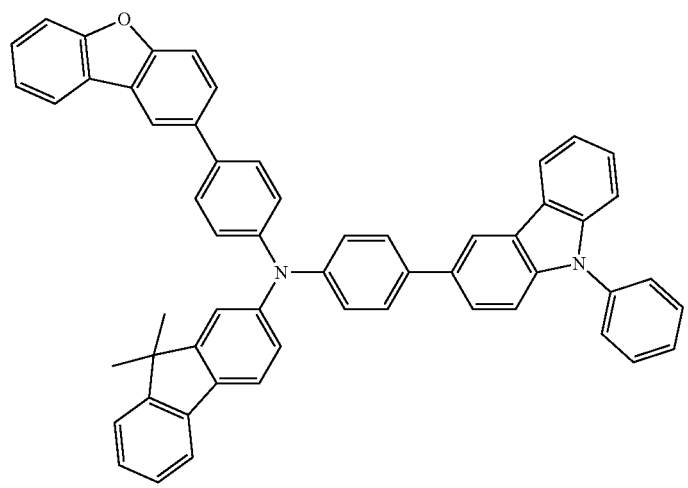
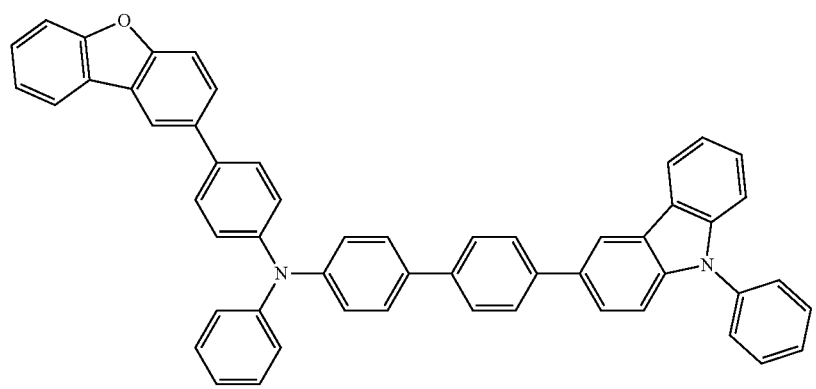

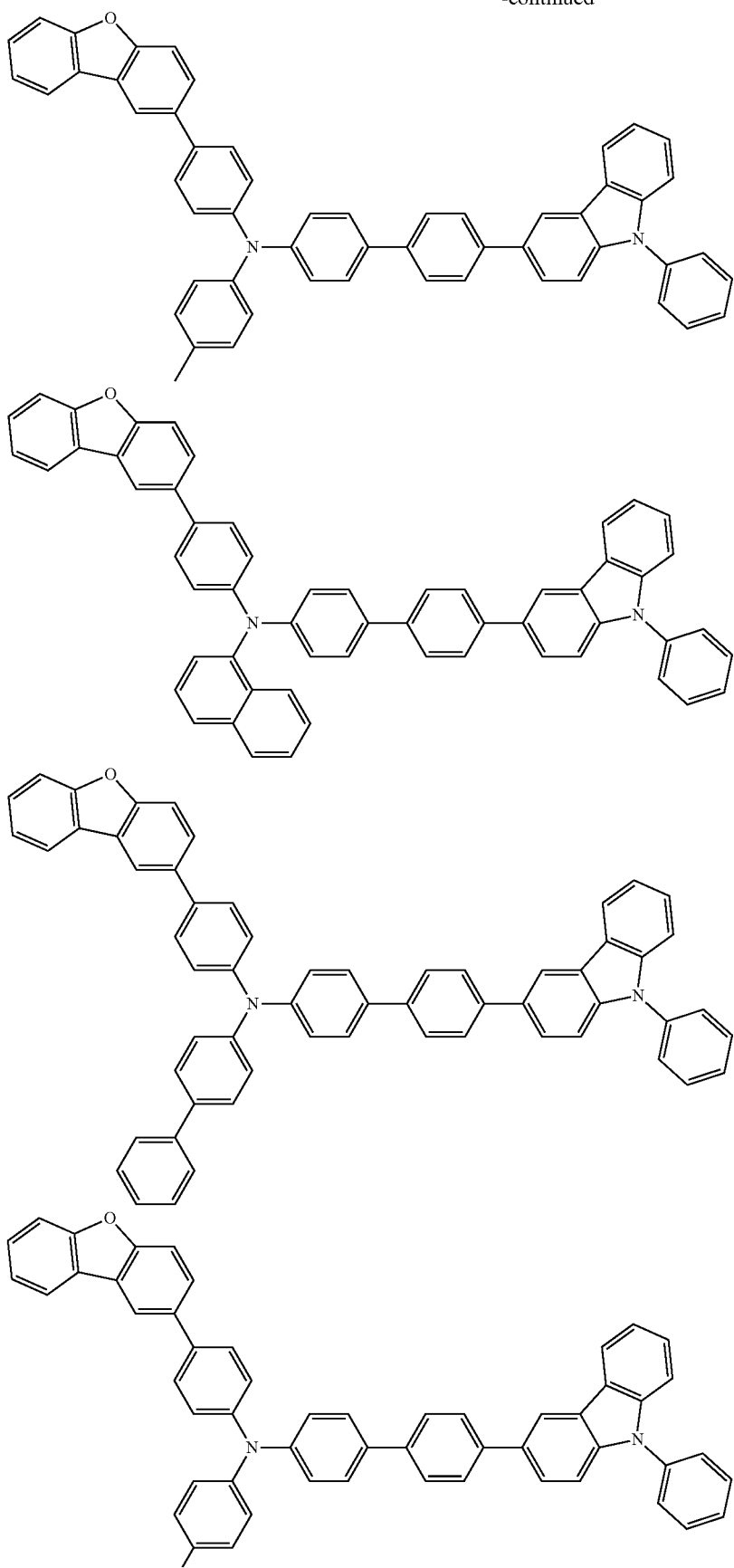

-continued
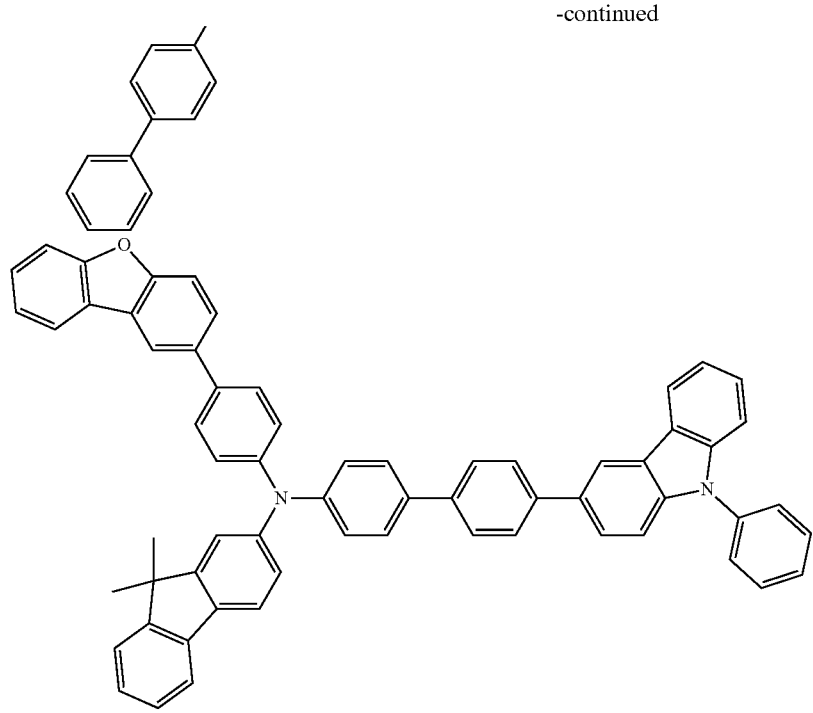
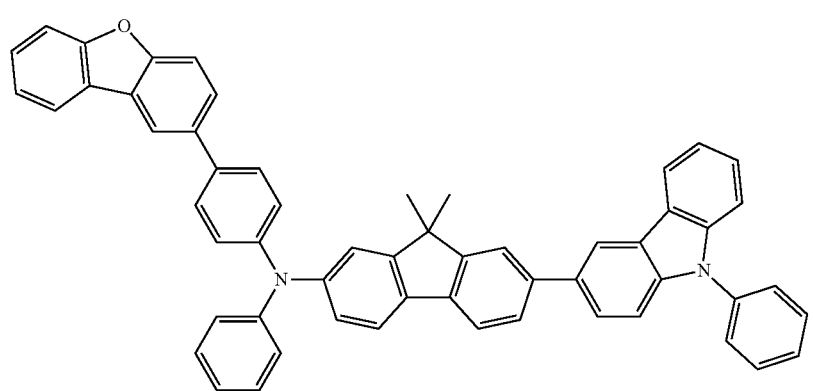
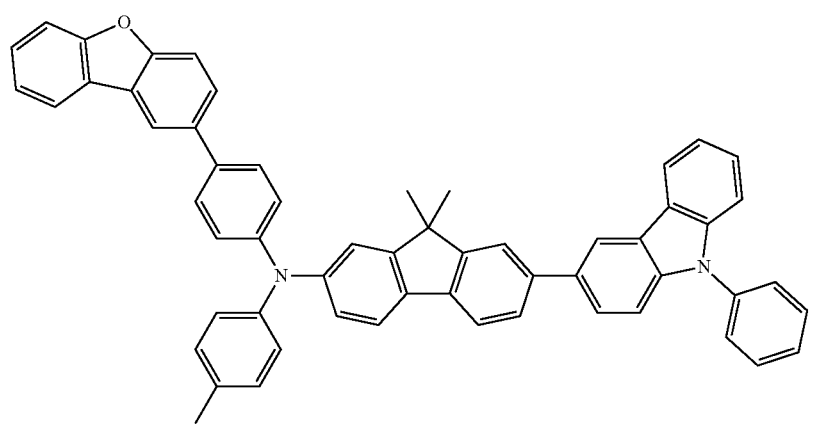

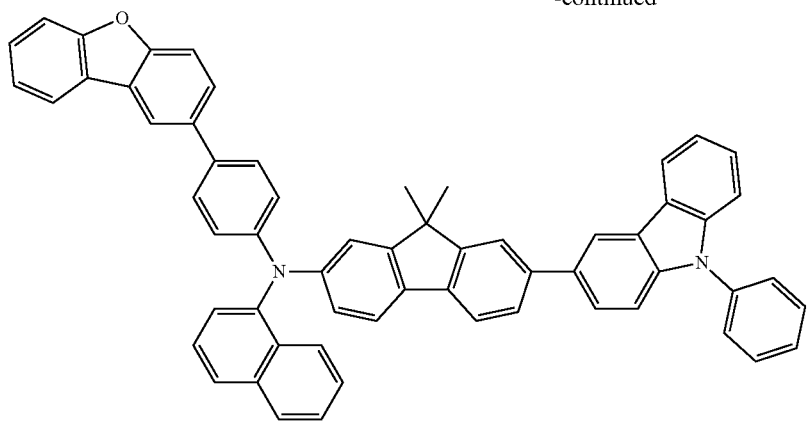
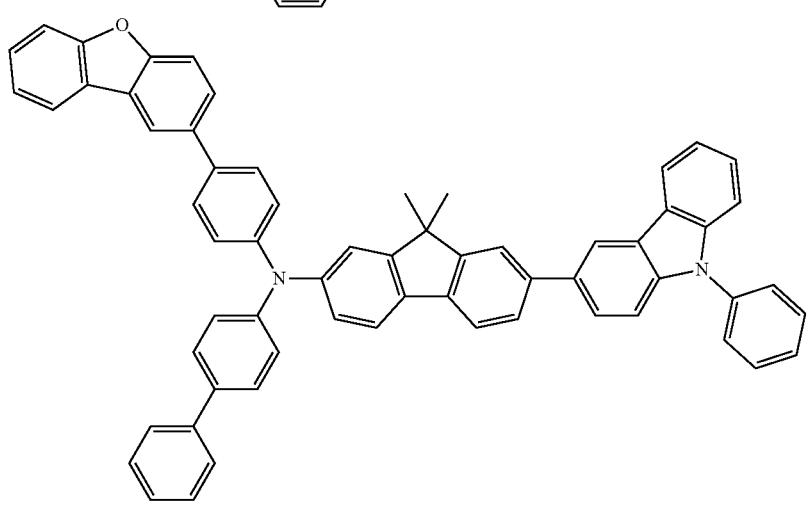
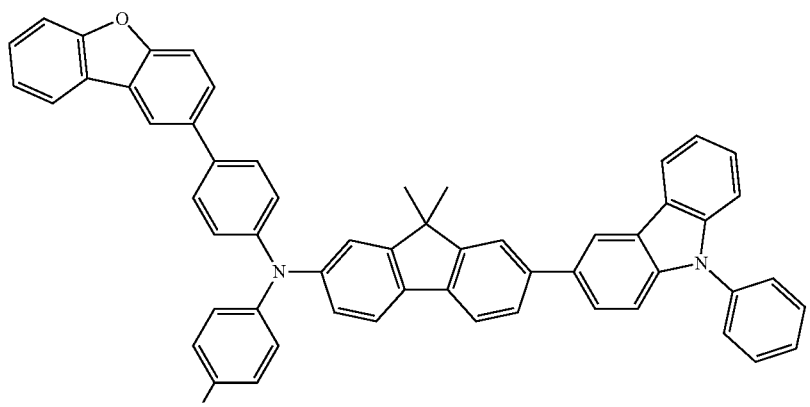
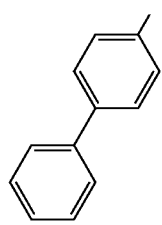

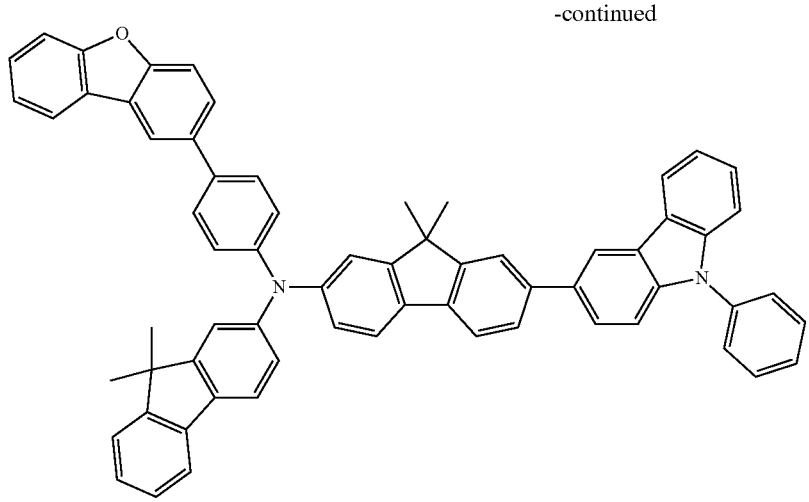
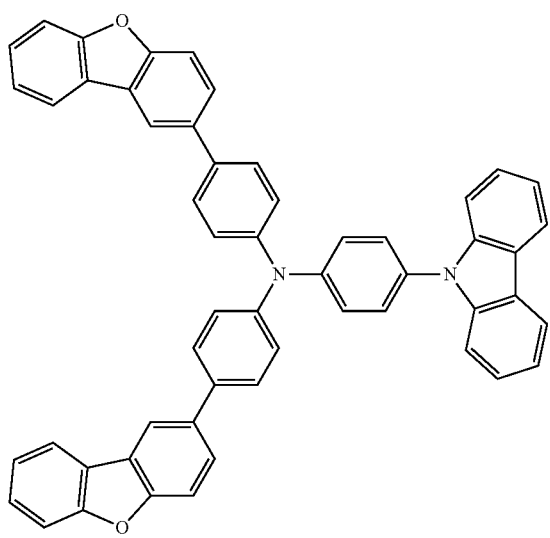
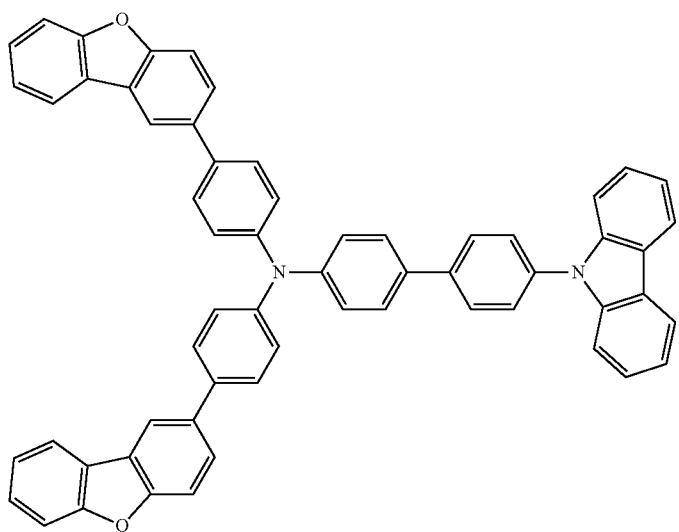

-continued
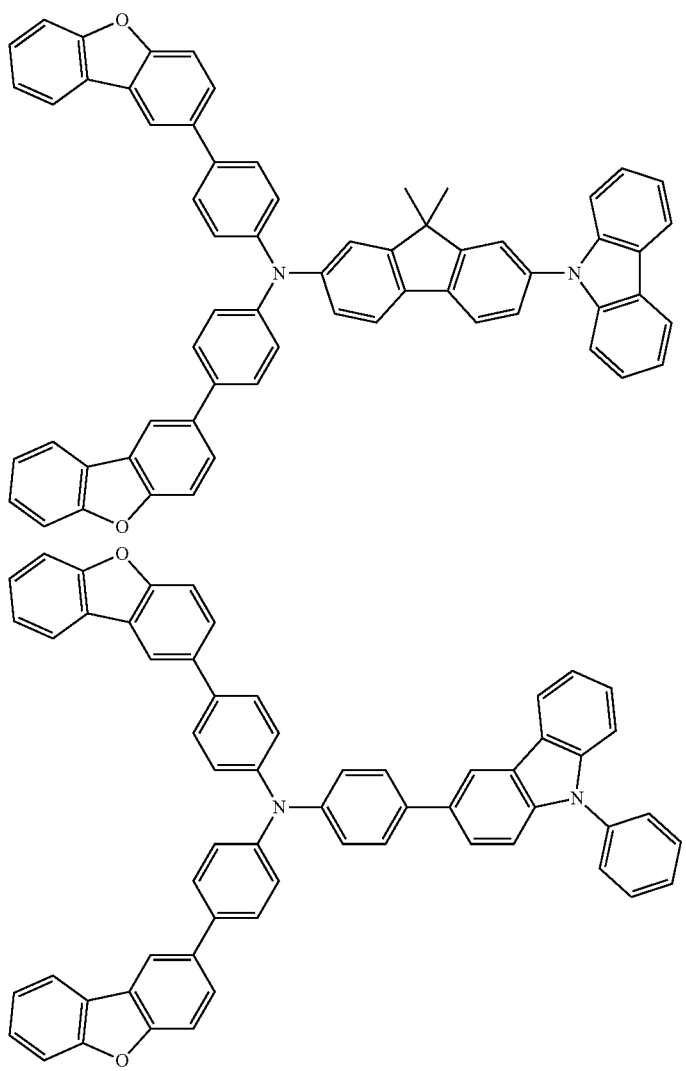
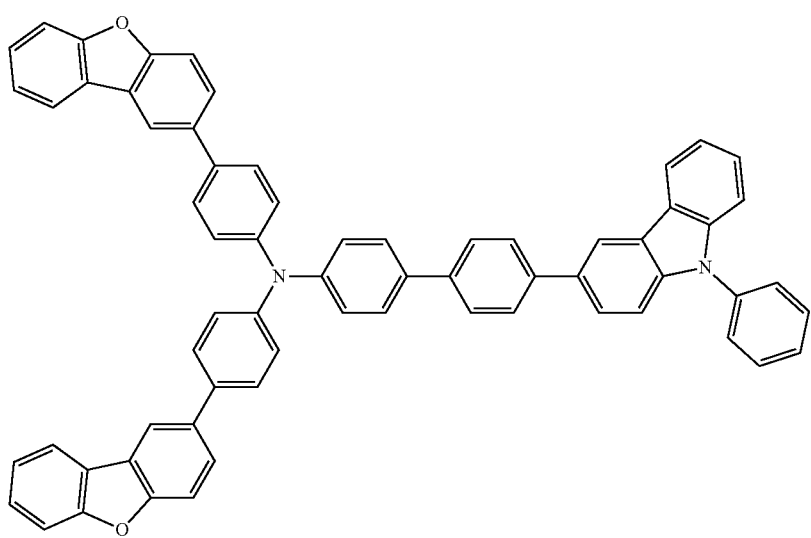

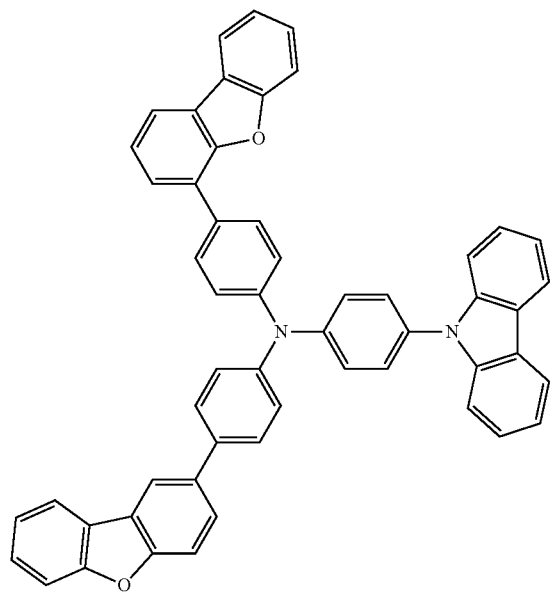
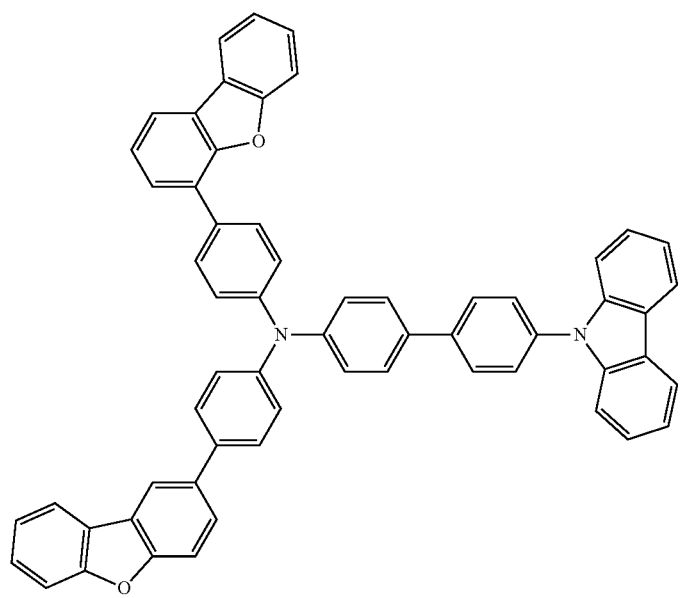

-continued
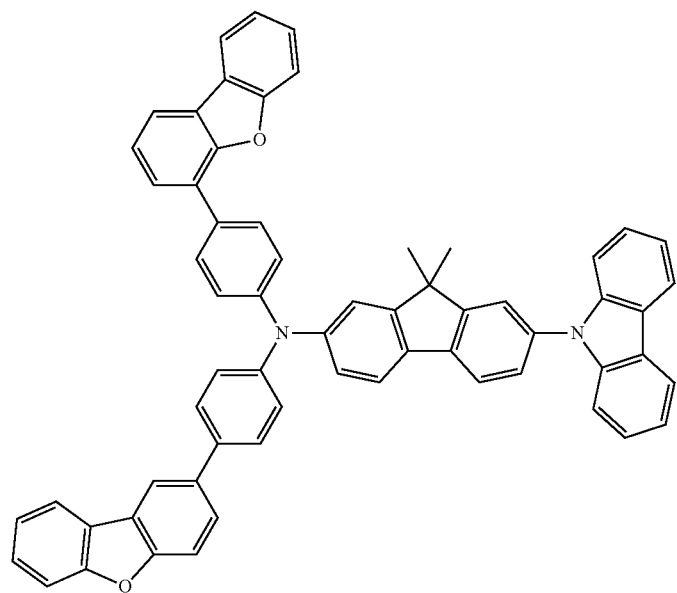
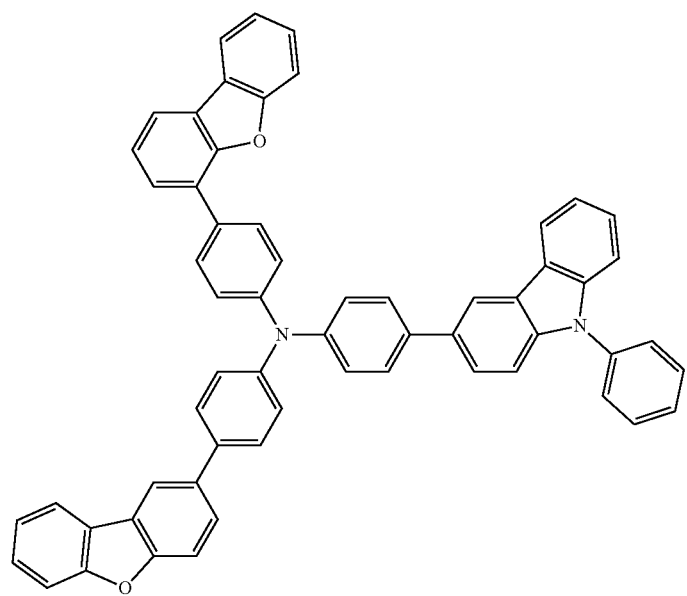

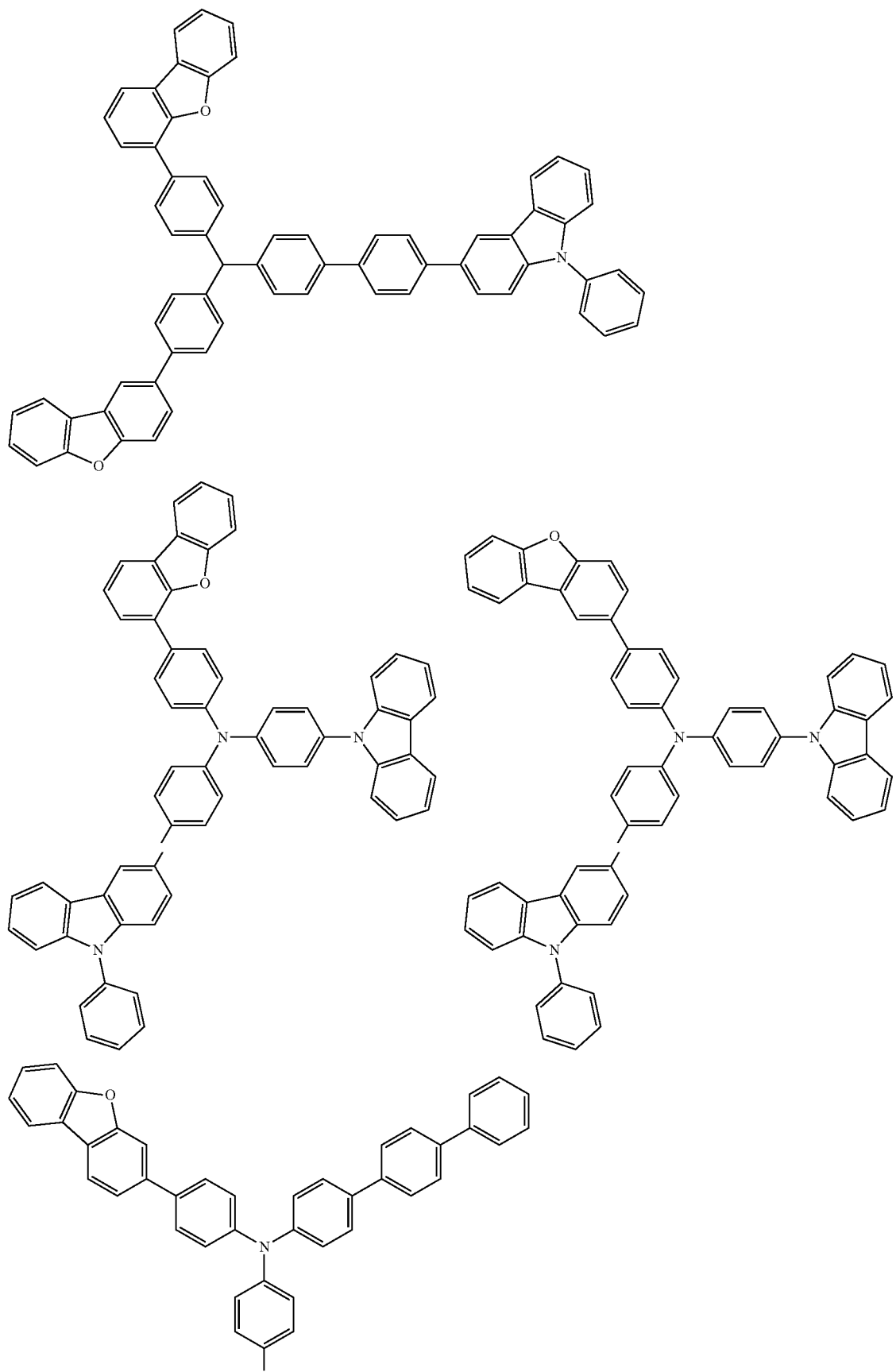

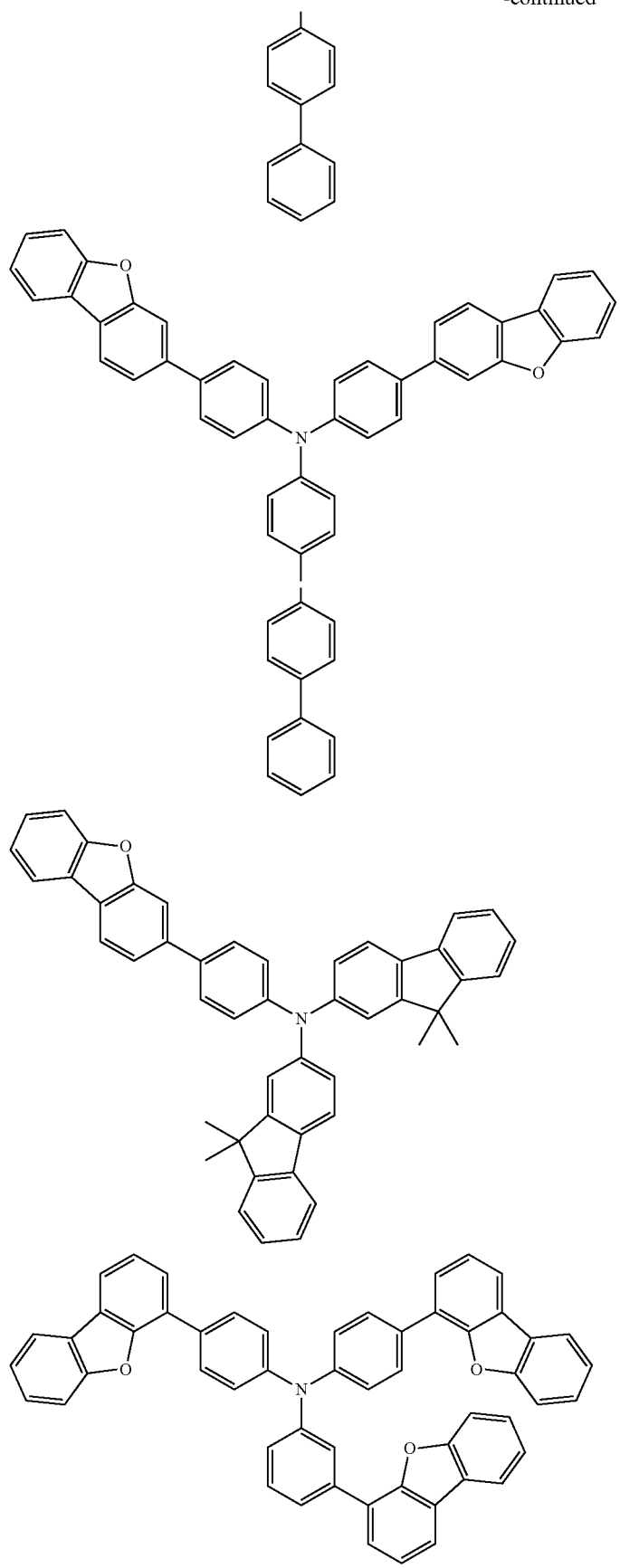

-continued
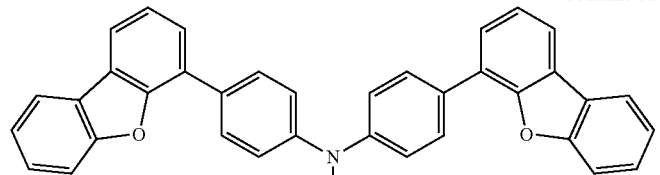
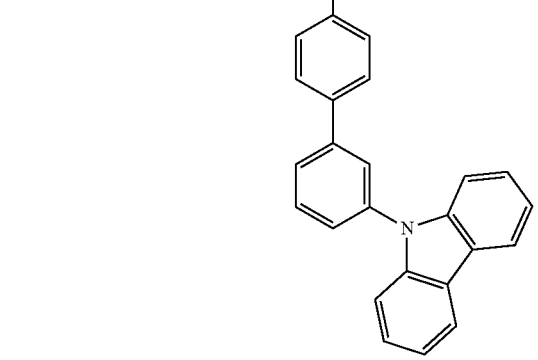
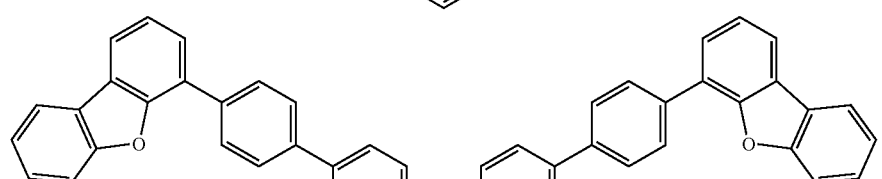
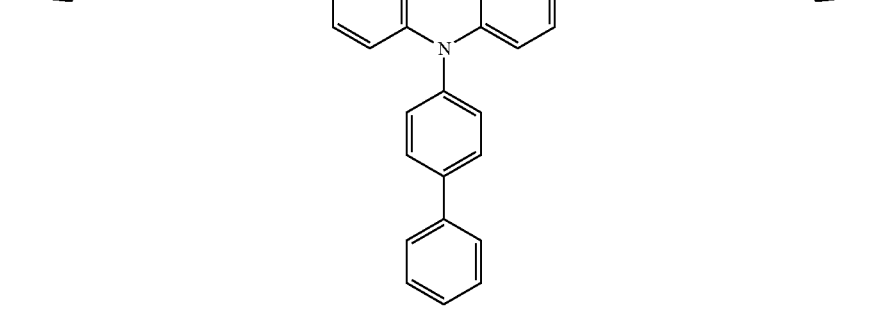

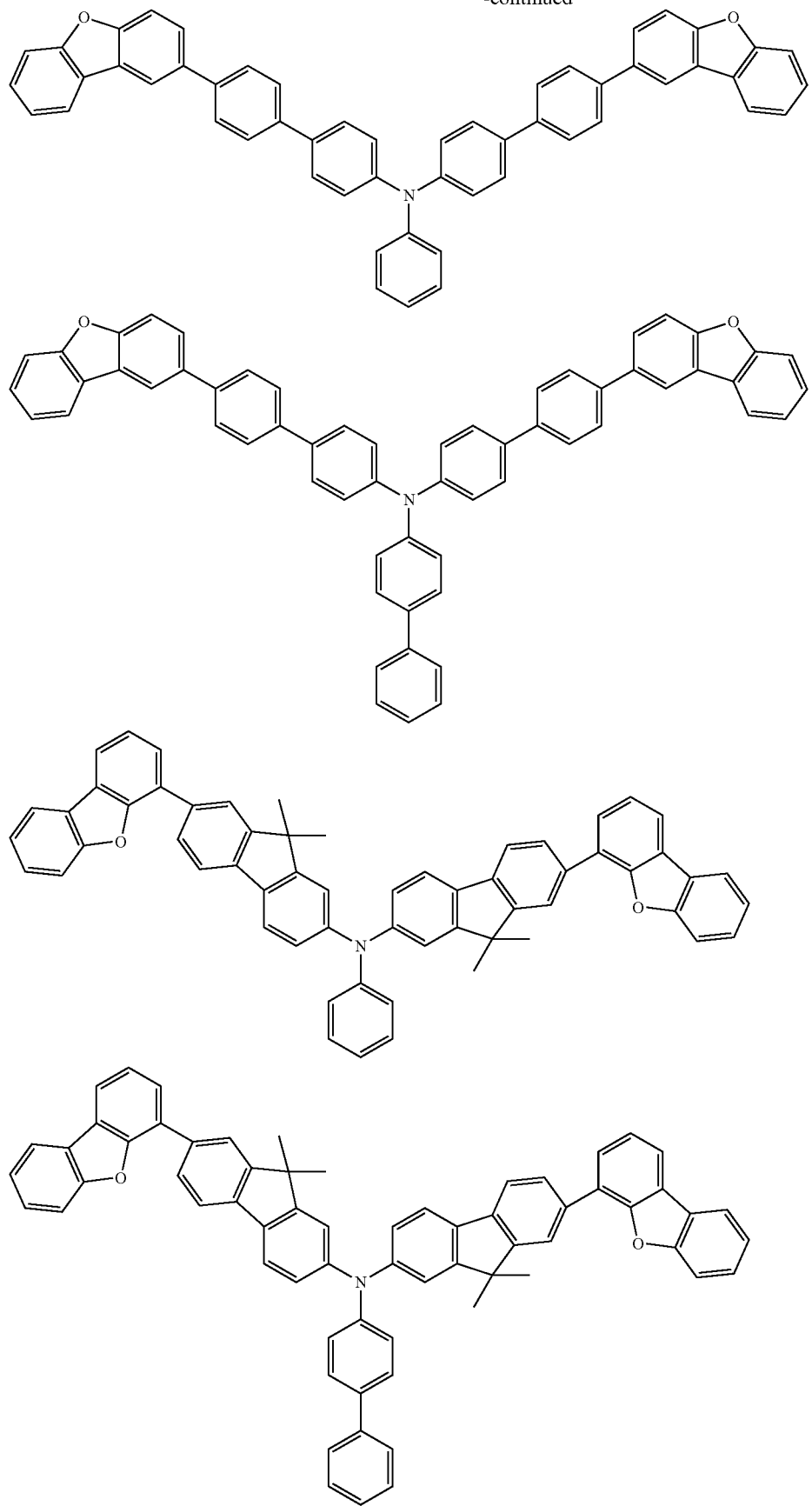

-continued

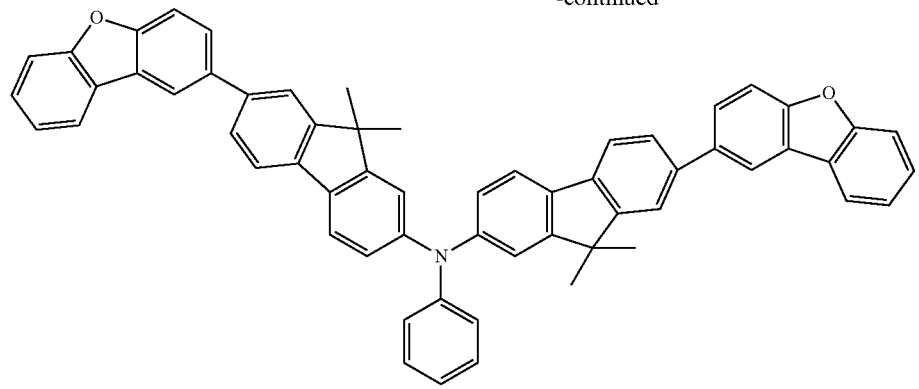

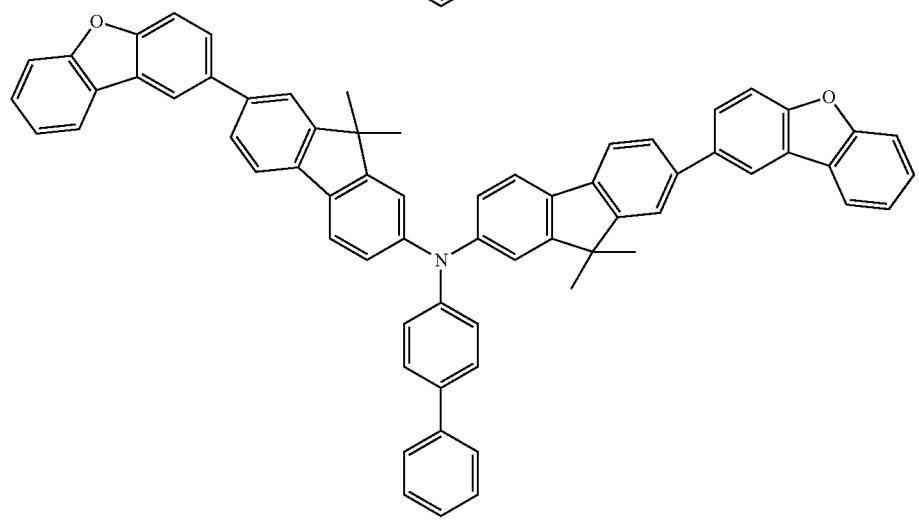

Example of Material for Hole Transporting Layer Adjacent to Light Emitting Layer (Second Hole Transporting Material):

Formulae (5) to (7)

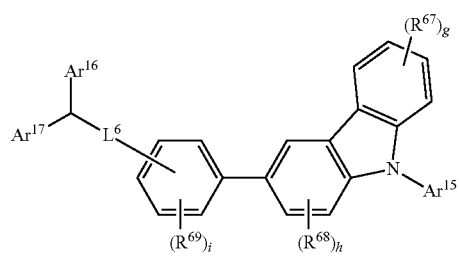 (5)

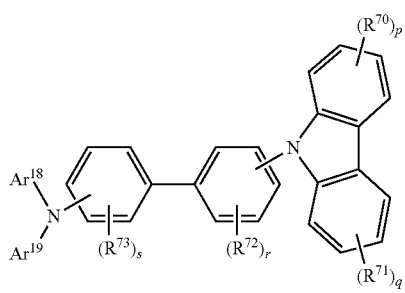 (6)

-continued

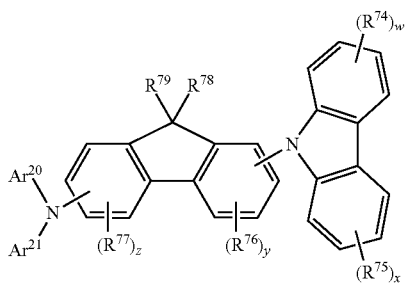 (7)

wherein in the formulae (5) to (7),

Ar$^{15}$ to Ar$^{21}$ each independently represent a substituted or unsubstituted aryl group having from 6 to 50 ring carbon atoms, a substituted or unsubstituted aromatic heterocyclic group having from 5 to 50 ring carbon atoms, a substituted or unsubstituted aryl group having from 8 to 50 carbon atoms having an aromatic amino group bonded thereto, or a substituted or unsubstituted aryl group having from 8 to 50 carbon atoms having an aromatic heterocyclic group bonded thereto, provided that Ar$^{16}$ and Ar$^{17}$, Ar$^{18}$ and Ar$^{19}$, and Ar$^{20}$ and Ar$^{21}$ each may be bonded to each other to form a ring;

L$^6$ represents a single bond or a substituted or unsubstituted arylene group having from 6 to 50 ring carbon atoms, wherein a substituent that may be substituted on L$^6$ is a linear or branched alkyl group having from 1 to 10 carbon atoms, a cycloalkyl group having from 3 to 10 ring carbon atoms, a trialkylsilyl group having from 3 to 10 carbon atoms, a triarylsilyl group having from 18 to 30 ring carbon atoms, an alkylarylsilyl group having from 8 to 15 carbon atoms (in which the aryl moiety has from 6 to 14 ring carbon atoms), an aryl group having from 6 to 50 ring carbon atoms, a halogen atom or a cyano group;

$R^{67}$ to $R^{77}$ each independently represent a halogen atom, a substituted or unsubstituted alkyl group having from 1 to 40 carbon atoms, a substituted or unsubstituted heteroaryl group having from 3 to 20 carbon atoms, a substituted or unsubstituted non-condensed aryl group having from 6 to 40 carbon atoms, a substituted or unsubstituted condensed aryl group having from 6 to 12 carbon atoms, a substituted or unsubstituted aralkyl group having from 7 to 20 carbon atoms, a substituted or unsubstituted alkenyl group having from 2 to 40 carbon atoms, a substituted or unsubstituted alkylamino group having from 1 to 40 carbon atoms, a substituted or unsubstituted aralkylamino group having from 7 to 60 carbon atoms, a substituted or unsubstituted alkylsilyl group having from 3 to 20 carbon atoms, a substituted or unsubstituted arylsilyl group having from 8 to 40 carbon atoms, a substituted or unsubstituted aralkylsilyl group having from 8 to 40 carbon atoms or a substituted or unsubstituted halogenated alkyl group having from 1 to 40 carbon atoms;

$R^{78}$ and $R^{79}$ each independently represent a substituted or unsubstituted alkyl group having from 1 to 40 carbon atoms, a substituted or unsubstituted heteroaryl group having from 3 to 20 carbon atoms, a substituted or unsubstituted non-condensed aryl group having from 6 to 40 carbon atoms, a substituted or unsubstituted condensed aryl group having from 6 to 12 carbon atoms, a substituted or unsubstituted aralkyl group having from 7 to 20 carbon atoms, g, i, p, q, r, s, w and x each independently represent an integer of from 0 to 4; and h, y and z each independently represent an integer of from 0 to 3.

Example of Material for Hole Transporting Layer Adjacent to Light Emitting Layer (Second Hole Transporting Material);

Formula (8)

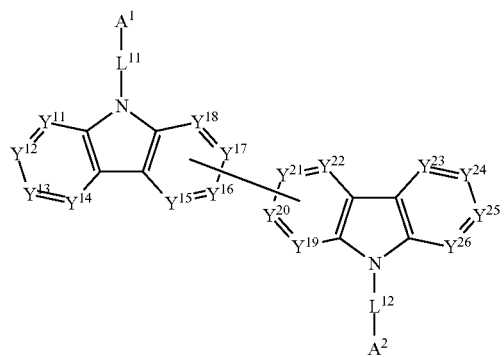

(8)

wherein in the formula (8), $A^1$ and $A^2$ each independently represent a substituted or unsubstituted aryl group having from 6 to 30 ring carbon atoms or a substituted or unsubstituted heteroaryl group having from 2 to 30 ring carbon atoms;

$Y^{11}$ to $Y^{26}$ each independently represent C(R) or a nitrogen atom, wherein R represents a hydrogen atom, a substituent or a bond connected to the carbazole skeleton; and $L^{11}$ and $L^{12}$ each independently represent a single bond or a substituted or unsubstituted arylene group having from 6 to 50 ring carbon atoms, wherein a substituent that may be substituted on the arylene group is a linear or branched alkyl group having from 1 to 10 carbon atoms, a cycloalkyl group having from 3 to 10 ring carbon atoms, a trialkylsilyl group having from 3 to 10 carbon atoms, a triarylsilyl group having from 18 to 30 ring carbon atoms, an alkylarylsilyl group having from 8 to 15 carbon atoms (in which the aryl moiety has from 6 to 14 ring carbon atoms), an aryl group having from 6 to 50 ring carbon atoms, a halogen atom or a cyano group.

(5) Light Emitting Layer

The organic EL device of the present invention may have a light emitting layer containing a fluorescent light emitting material, i.e., a fluorescent light emitting layer. In the fluorescent light emitting layer, a known fluorescent light emitting material may be used. The fluorescent light emitting material is preferably at least one selected from an anthracene derivative, a fluorantene derivative, a styrylamine derivative and an arylamine derivative, and an anthracene derivative and an arylamine derivative are more preferred. In particular, the host material is preferably an anthracene derivative, and the dopant is preferably an arylamine derivative. Specifically, the material may be selected from the preferred materials described in WO 2010/134350 and WO 2010/134352.

The organic EL device of the present invention may have a light emitting layer containing a phosphorescent light emitting material, i.e., a phosphorescent light emitting layer. In the phosphorescent light emitting layer, a known phosphorescent light emitting material may be used. Specifically, reference may be made to WO 2005/079118. In the phosphorescent light emitting material, preferred examples of the dopant include an ortho-metalated complex of metallic iridium (Ir), osmium (Os) or platinum (Pt), and an ortho-metalated complex of iridium is more preferred. In the phosphorescent light emitting material, the host material is preferably a compound having a carbazolyl group, a compound having a carbazolyl group and a triazine skeleton is more preferred, and a compound having two carbazolyl groups and one triazine skeleton is further preferred.

The anthracene derivative as the fluorescent light emitting material preferably has from 26 to 100, more preferably from 26 to 80, and further preferably from 26 to 60, ring carbon atoms. As the anthracene derivative, more specifically, an anthracene derivative represented by the following general formula (10) is preferred.

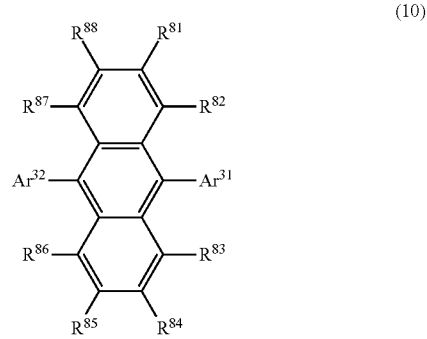

(10)

wherein in the formula (10),

Ar$^{31}$ and Ar$^{32}$ each independently represent a substituted or unsubstituted aryl group having from 6 to 50 ring carbon atoms or a heterocyclic group having from 5 to 50 ring atoms; and R$^{81}$ to R$^{88}$ each independently represent a hydrogen atom, a substituted or unsubstituted aryl group having from 6 to 50 ring carbon atoms, a substituted or unsubstituted heterocyclic group having from 5 to 50 ring atoms, a substituted or unsubstituted alkyl group having from 1 to 50 carbon atoms, a substituted or unsubstituted alkoxy group having from 1 to 50 carbon atoms, a substituted or unsubstituted aralkyl group having from 7 to 50 carbon atoms, a substituted or unsubstituted aryloxy group having from 6 to 50 ring carbon atoms, a substituted or unsubstituted arylthio group having from 6 to 50 ring carbon atoms, a substituted or unsubstituted alkoxycarbonyl group having from 2 to 50 carbon atoms, a substituted or unsubstituted silyl group, a carboxyl group, a halogen atom, a cyano group, a nitro group or a hydroxyl group.

The aryl groups having from 6 to 50 ring carbon atoms are all each preferably an aryl group having from 6 to 40 ring carbon atoms, and more preferably an aryl group having from 6 to 30 ring carbon atoms.

The heterocyclic groups having from 5 to 50 ring atoms are all each preferably a heterocyclic groups having from 5 to 40 ring atoms, and more preferably a heterocyclic groups having from 5 to 30 ring atoms.

The alkyl group having from 1 to 50 carbon atoms is preferably an alkyl group having from 1 to 30 carbon atoms, more preferably an alkyl group having from 1 to 10 carbon atoms, and further preferably an alkyl group having from 1 to 5 carbon atoms.

The alkoxy group having from 1 to 50 carbon atoms is preferably an alkoxy group having from 1 to 30 carbon atoms, more preferably an alkoxy group having from 1 to 10 carbon atoms, and further preferably an alkoxy group having from 1 to 5 carbon atoms.

The aralkyl group having from 7 to 50 carbon atoms is preferably an aralkyl group having from 7 to 30 carbon atoms, and more preferably an aralkyl group having from 7 to 20 carbon atoms.

The aryloxy group having from 6 to 50 ring carbon atoms is preferably an aryloxy group having from 6 to 40 ring carbon atoms, and more preferably an aryloxy group having from 6 to 30 ring carbon atoms.

The arylthio group having from 6 to 50 ring carbon atoms is preferably an arylthio group having from 6 to 40 ring carbon atoms, and more preferably an arylthio group having from 6 to 30 ring carbon atoms.

The alkoxycarbonyl group having from 2 to 50 carbon atoms is preferably an alkoxycarbonyl group having from 2 to 30 carbon atoms, more preferably an alkoxycarbonyl group having from 2 to 10 carbon atoms, and further preferably an alkoxycarbonyl group having from 2 to 5 carbon atoms.

Examples of the halogen atom include a fluorine atom, a chlorine atom and a bromine atom.

In particular, Ar$^{31}$ and Ar$^{32}$ are each preferably a substituted or unsubstituted aryl group having from 6 to 50 ring carbon atoms.

The anthracene derivative represented by the general formula (10) is preferably an anthracene derivative represented by the following general formula (10-1):

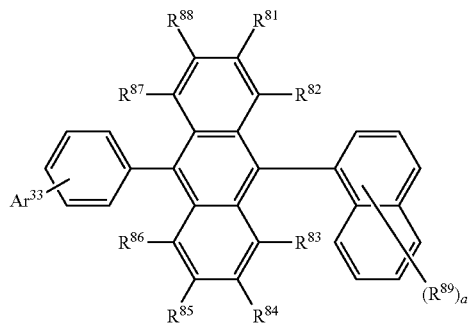

wherein in the formula (10-1), Ar$^{33}$ represents a substituted or unsubstituted aryl group having from 6 to 50 ring carbon atoms or a heterocyclic group having from 5 to 50 ring atoms; R$^{81}$ to R$^{88}$ have the same definition as above; R$^{89}$ has the same definition as R$^{81}$ to R$^{88}$; and a represents an integer of from 1 to 7.

Preferred examples of R$^{81}$ to R$^{88}$ are the same as above. Preferred examples of R$^{89}$ are the same as R$^{81}$ to R$^{88}$. a preferably represents an integer of from 1 to 3, and more preferably 1 or 2.

The aryl group having from 6 to 50 ring carbon atoms represented by A$^{33}$ is preferably an aryl group having from 6 to 40 ring carbon atoms, more preferably an aryl group having from 6 to 30 ring carbon atoms, further preferably an aryl group having from 6 to 20 ring carbon atoms, and particularly preferably an aryl group having from 6 to 12 ring carbon atoms.

The arylamine derivative as the fluorescent light emitting material is preferably an aryldiamine derivative, more preferably an aryldiamine derivative having a pyrene skeleton, and further preferably an aryldiamine derivative having a pyrene skeleton and a dibenzofuran skeleton.

More specifically, the diaryldiamine derivative is preferably an aryldiamine derivative represented by the following general formula (11):

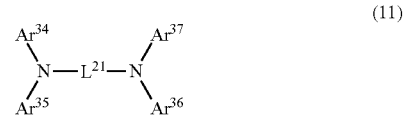

wherein in the formula (11),

Ar$^{34}$ to Ar$^{37}$ each independently represent a substituted or unsubstituted aryl group having from 6 to 50 ring carbon atoms or a substituted or unsubstituted heteroaryl group having from 5 to 50 ring atoms; and L$^{21}$ represents a substituted or unsubstituted arylene group having from 6 to 50 ring carbon atoms or a substituted or unsubstituted heteroarylene group having from 5 to 50 ring atoms.

The aryl group having from 6 to 50 ring carbon atoms is preferably an aryl group having from 6 to 30 ring carbon atoms, more preferably an aryl group having from 6 to 20 ring carbon atoms, further preferably an aryl group having from 6 to 12 ring carbon atoms, and particularly preferably a phenyl group or a naphthyl group.

The heteroaryl group having from 5 to 50 ring atoms is preferably a heteroaryl group having from 5 to 40 ring atoms, more preferably a heteroaryl group having from 5 to 30 ring atoms, and still more preferably a heteroaryl group having from 5 to 20 ring atoms. Examples of the heteroaryl group include a carbazolyl group, a dibenzofuranyl group and a dibenzothiophenyl group, and a dibenzofuranyl group is preferred. Preferred examples of the substituent substituted on the heteroaryl group include an aryl group having from 6 to 30 (preferably from 6 to 20, and more preferably from 6 to 12) ring carbon atoms, and a phenyl group and a naphthyl group are more preferred.

The arylene group having from 6 to 50 ring carbon atoms is preferably an arylene group having from 6 to 40 ring carbon atoms, more preferably an arylene group having from 6 to 30 ring carbon atoms, further preferably an arylene group having from 6 to 20 ring carbon atoms, and particularly preferably a pyrenyl group.

Specific examples of the compound containing a carbazolyl group that is preferred as the host material in the phosphorescent light emitting material include the following compounds.

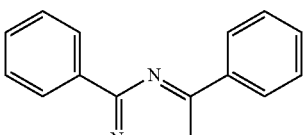
-continued

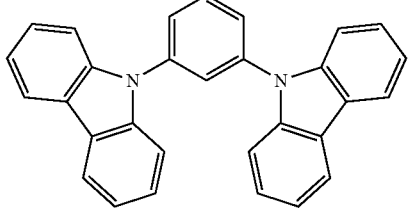

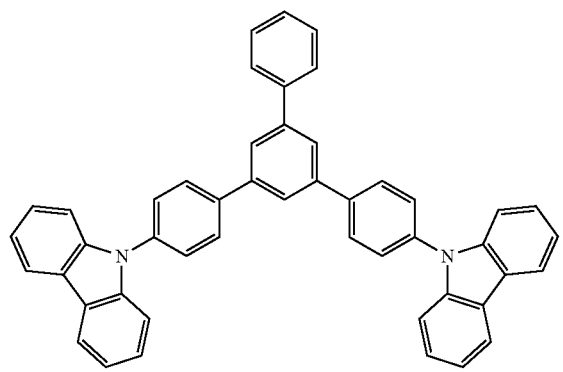

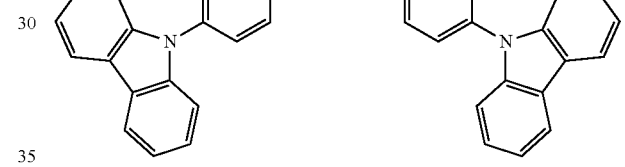

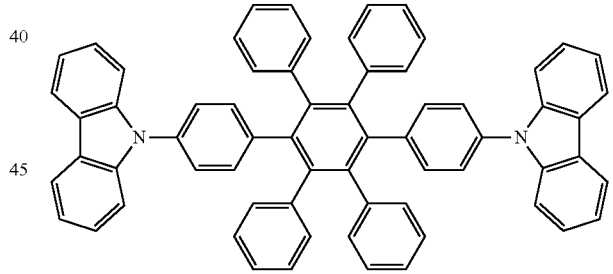

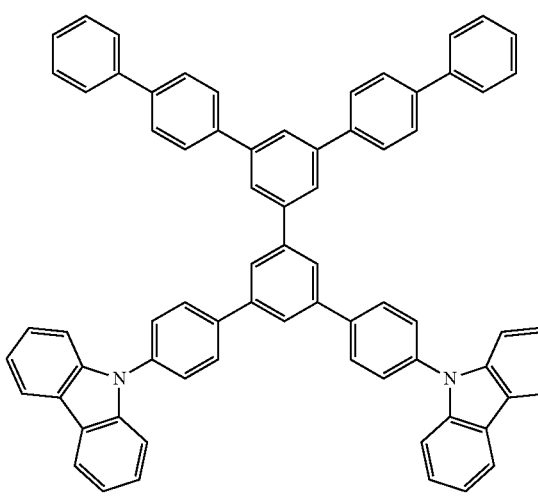

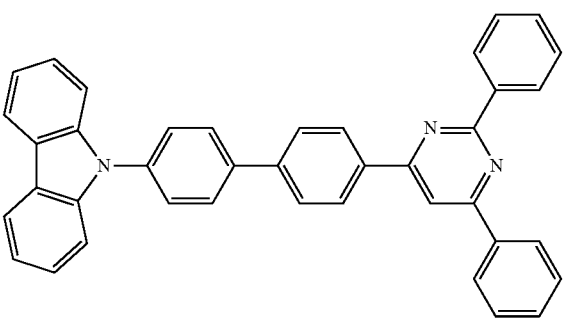

325
-continued
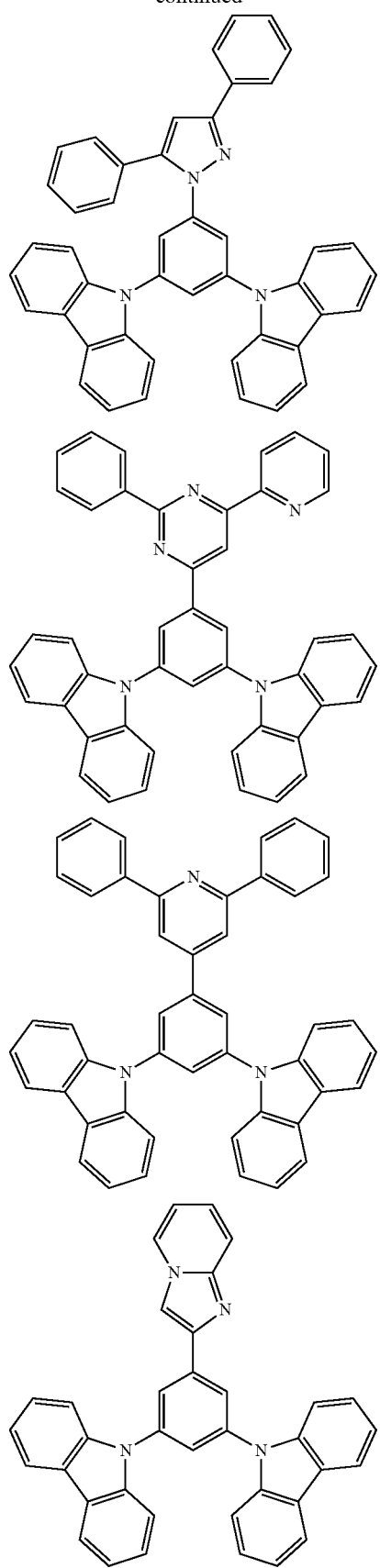
326
-continued
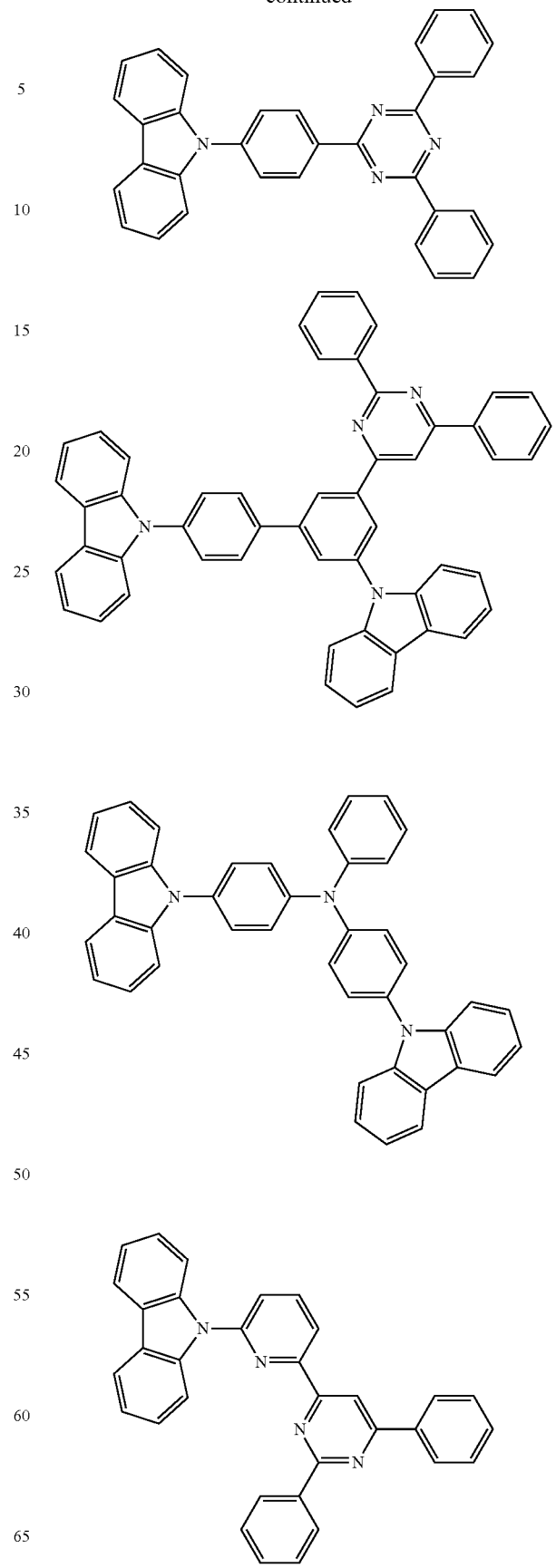

327
-continued
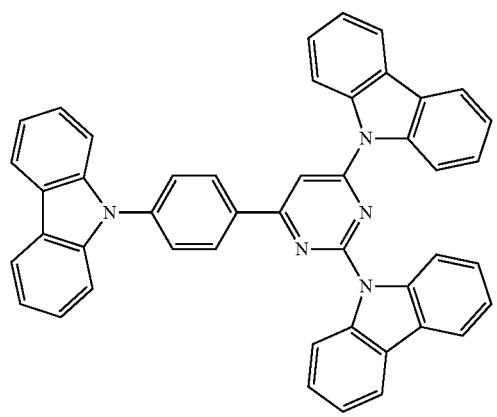
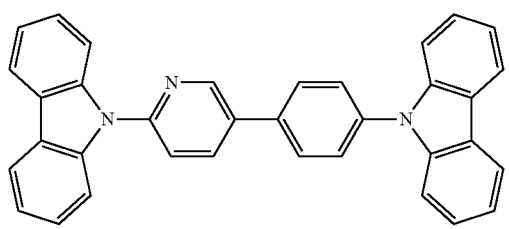
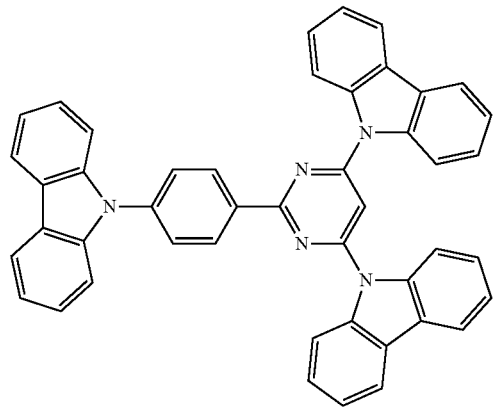
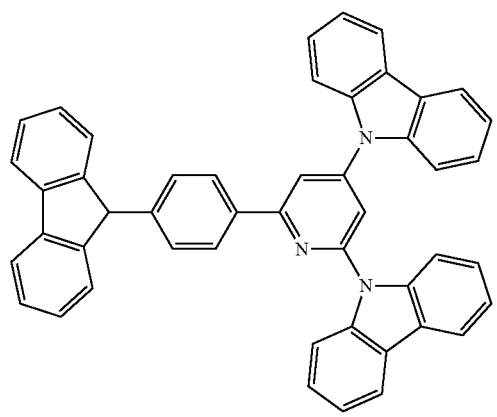
328
-continued
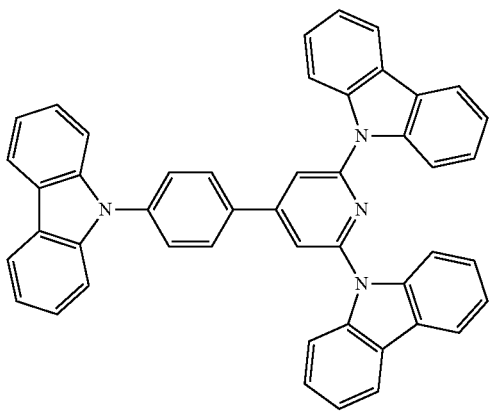
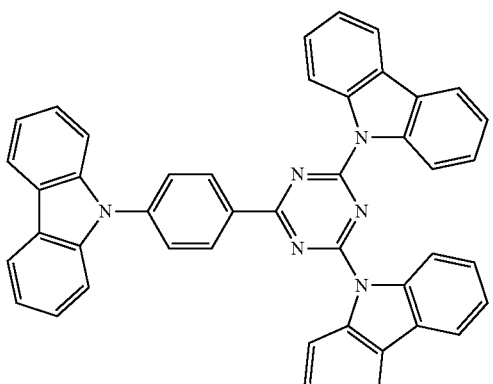
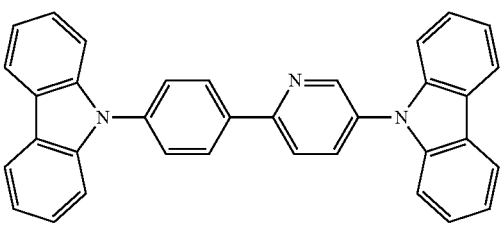
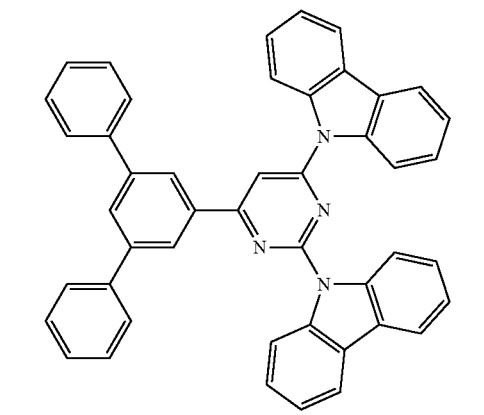

-continued

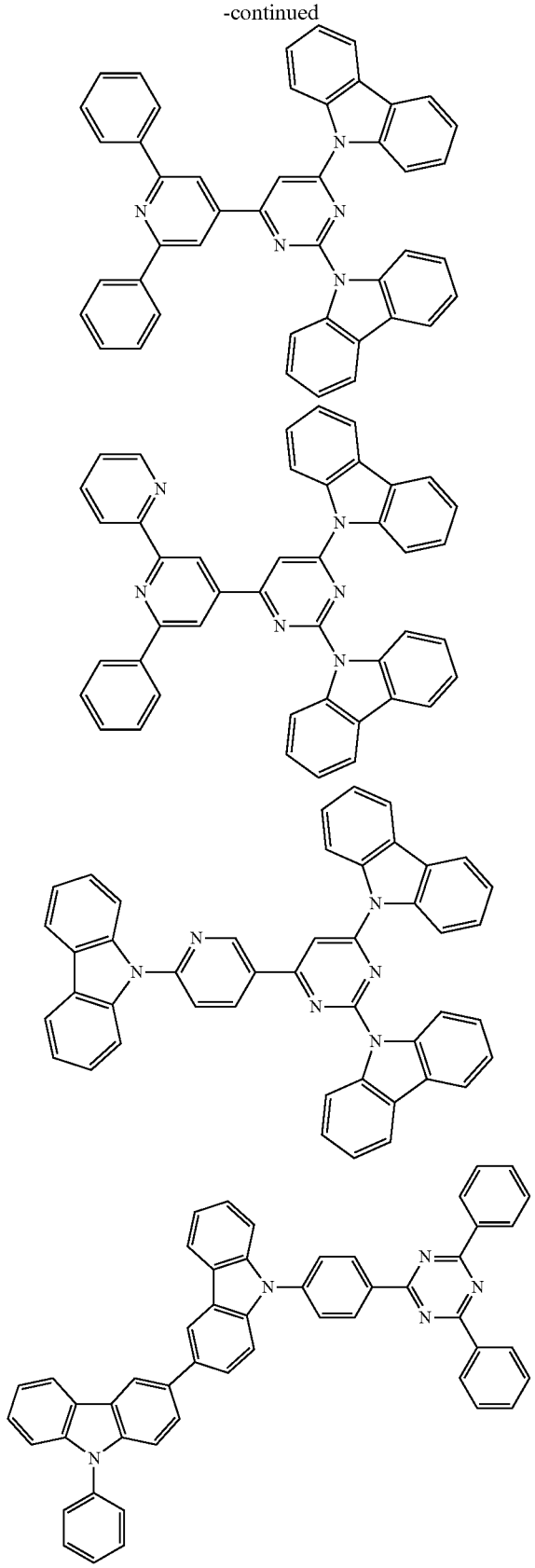

The light emitting layer may be a double host (which may also be referred to as host-cohost) light emitting layer.

Specifically, the carrier balance in the light emitting layer may be controlled by combining an electron transporting host and a hole transporting host in the light emitting layer.

The light emitting layer may be a double dopant light emitting layer. By adding two or more kinds of dopant materials having a large quantum yield to the light emitting layer, the dopants each emit light respectively. For example, the host may be vapor deposited with a red dopant and a green dopant, and thereby a yellow light emitting layer may be realized.

The light emitting layer may contain a hole transporting material, an electron transporting material and a polymer binder depending on necessity.

The thickness of the light emitting layer is preferably 5 to 50 nm, more preferably from 7 to 50 nm, and most preferably from 10 to 50 nm. When the thickness is less than 5 nm the light emitting layer may be difficult to form to make control of the chromaticity difficult, and when the thickness exceeds 50 nm, the driving voltage may be increased.

(6) Electron Injecting-Transporting Layer

The electron injecting-transporting layer is a layer that assists injection of electrons to the light emitting layer and transports electrons to the light emitting region, and the layer has a large electron mobility. The adhesion improving layer is one of the electron injecting-transporting layer that is particularly formed of a material having good adhesion to the cathode.

It is known in the organic EL device that emitted light is reflected by the electrode (i.e., the cathode in this case), and thus light that is taken out directly from the anode and light that is taken out after reflecting by the electrode interfere with each other. For utilizing the interference effectively, the thickness of the electron injecting-transporting layer is appropriately selected from a range of from several nm to several μm, and in the case of the layer having a large thickness in particular, the electron mobility is preferably at least $10^{-5}$ cm$^2$/Vs or more on application of an electric field of from $10^4$ to $10^6$ V/cm in order to avoid increase of the voltage.

The material used in the electron injecting-transporting layer is preferably a metal complex of 8-hydroxyquinoline or a derivative thereof or an oxadiazole derivative. Specific examples of the metal complex of 8-hydroxyquinoline or a derivative thereof include a metal chelated oxinoid compound containing a chelate of oxine (which is generally 8-quinolinol or 8-hydroxyquinoline), such as tris(8-quinolinol)aluminum, which may be used as the electron injecting material.

Examples of the electron injecting material include compounds represented by the following formulae (31) to (36).

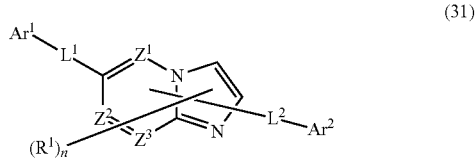

(31)

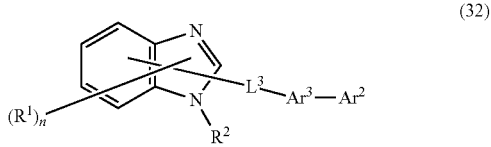

(32)

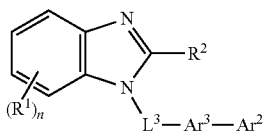
(33)

wherein in the formulae (31) to (33), $Z^1$, $Z^2$ and $Z^3$ each independently represent a nitrogen atom or a carbon atom;

$R^1$ and $R^2$ each independently represent a substituted or unsubstituted aryl group having from 6 to 50 carbon atoms, a substituted or unsubstituted heteroaryl group having from 3 to 50 carbon atoms, an alkyl group having from 1 to 20 carbon atoms, an alkyl group having from 1 to 20 carbon atoms having a halogen atom substituted, or an alkoxy group having from 1 to 20 carbon atoms;

n represents an integer of from 0 to 5, provided that when n is 2 or more, plural groups represented by $R^1$ may be the same as or different from each other, and plural adjacent groups represented by $R^1$ may be bonded to each other to form a substituted or unsubstituted aromatic hydrocarbon ring;

$Ar^1$ represents a substituted or unsubstituted aryl group having from 6 to 50 carbon atoms or a substituted or unsubstituted heteroaryl group having from 3 to 50 carbon atoms;

$Ar^2$ represents a hydrogen atom, an alkyl group having from 1 to 20 carbon atoms, an alkyl group having from 1 to 20 carbon atoms having a halogen atom substituted, an alkoxy group having from 1 to 20 carbon atoms, a substituted or unsubstituted aryl group having from 6 to 50 carbon atoms or a substituted or unsubstituted heteroaryl group having from 3 to 50 carbon atoms;

provided that any one of $Ar^1$ and $Ar^2$ represents a substituted or unsubstituted condensed ring group having from 10 to 50 carbon atoms or a substituted or unsubstituted hetero condensed ring group having from 9 to 50 ring atoms;

$Ar^3$ represents a substituted or unsubstituted arylene group having from 6 to 50 carbon atoms or a substituted or unsubstituted heteroarylene group having from 3 to 50 carbon atoms; and $L^1$, $L^2$ and $L^3$ each independently represent a single bond, a substituted or unsubstituted arylene group having from 6 to carbon atoms, a substituted or unsubstituted hetero condensed ring group having from 9 to 50 ring atoms or a substituted or unsubstituted fluorenylene group.

Specific examples of the aryl group and the alkyl group represented by $R^2$, $Ar^1$ and $Ar^2$ include the same groups as in $R^1$ and $R^2$ in the formula (1), specific examples of the alkoxy group represented thereby include groups formed by bonding an oxygen atom to the alkyl groups, and specific examples of the heteroaryl group represented thereby include the same groups as in $Ar_{31}$ in the formula (h). Specific examples of the arylene group represented by $Ar^3$, $L^1$, $L^2$ and $L^3$ include divalent groups derived from the aryl groups, and specific examples of the hetero condensed ring group represented thereby include condensed ring groups that has a conforming number of carbon atoms among the hetero aryl groups.

$$[X\text{\textemdash}]_q Y \quad (34)$$

wherein X represents a condensed ring containing a nitrogen atom or a sulfur atom; Y represents a group that is formed of a sole member or a combination of a single bond, an alkyl chain, an alkylene chain, a cycloalkyl chain, an aryl chain, a heterocyclic chain, a silyl chain, an ether chain and a thioether chain; and q represents a natural number of 2 or more.

The compound represented by the formula (34) has a molecular weight of 480 or more.

$$[A\text{\textemdash}]_p B \quad (35)$$

wherein A represents a substituent having a phenanthroline skeleton or a benzoquinoline skeleton; B represents a p-valent organic group having a structure represented by the following formula (35A); and p represents a natural number of 2 or more.

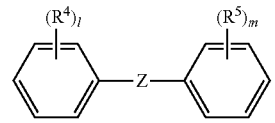
(35A)

wherein $R^4$ and $R^5$ each independently represent an alkyl group or an aryl group (including an aryl group condensed with a phenyl group); l and m each independently represent a natural number of from 0 to 5; and Z represents at least one group selected from the following formula (35B).

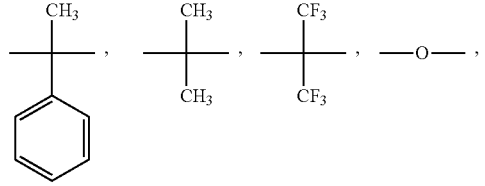
(35B)

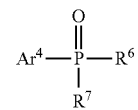
(36)

wherein $R^6$ and $R^7$, which may be the same as or different from each other, each are selected from a hydrogen atom, an alkyl group, a cycloalkyl group, a heterocyclic ring group, an alkenyl group, a cycloalkenyl group, an alkynyl group, an alkoxy group, an alkylthio group, an arylether group, an arylthioether group, an aryl group, a heteroaryl group, a cyano group, a carbonyl group, an ester group, a carbamoyl group, an amino group, a silyl group and a condensed ring formed with the plural adjacent groups; and $Ar^4$ represents an aryl group or a heteroaryl group.

In a preferred embodiment, the organic EL device of the present invention may have at least one of an electron donating dopant and an organic metal complex in the interface region between the cathode and the organic thin film layer.

According to the structure, the organic EL device may be enhanced in the light emission luminance and the service life.

Examples of the electron donating dopant include an alkali metal, an alkali metal compound, an alkaline earth metal, an alkaline earth metal compound, a rare earth metal and a rare earth metal compound, at least one of which may be used.

Examples of the organic metal complex include an organic metal complex containing an alkali metal, an organic metal complex containing an alkaline earth metal and an organic metal complex containing a rare earth metal, at least one of which may be used.

Examples of the alkali metal include lithium (Li) (work function: 2.93 eV), sodium (Na) (work function: 2.36 eV), potassium (K) (work function: 2.28 eV), rubidium (Rb) (work function: 2.16 eV) and cesium (Cs) (work function: 1.95 eV), and ones having a work function of 2.9 eV or less is preferred. Among these, K, Rb and Cs are preferred, Rb and Cs are more preferred, and Cs is the most preferred.

Examples of the alkaline earth metal include calcium (Ca) (work function: 2.9 eV), strontium (Sr) (work function: 2.0 to 2.5 eV) and barium (Ba) (work function: 2.52 eV), ones having a work function of 2.9 eV or less is particularly preferred.

Examples of the rare earth metal include scandium (Sc), yttrium (Y), cerium (Ce), terbium (Tb) and ytterbium (Yb), and ones having a work function of 2.9 eV or less is particularly preferred.

The preferred metals among the aforementioned metals have a particularly high reducing ability, and the addition thereof in a small amount to the electron injection region may enhances the organic EL device in the light emission luminance and the service life.

Examples of the alkali metal compound include an alkali metal oxide, such as lithium oxide ($Li_2O$), cesium oxide ($Cs_2O$) and potassium oxide ($K_2O$), and an alkali metal halogenide, such as lithium fluoride (LiF), sodium fluoride (NaF), cesium fluoride (CsF) and potassium fluoride (KF), and lithium fluoride (LiF), lithium oxide ($Li_2O$) and sodium fluoride (NaF) are preferred.

Examples of the alkaline earth metal compound include barium oxide (BaO), strontium oxide (SrO), calcium oxide (CaO) and mixtures thereof, e.g., barium strontium oxide ($Ba_xSr_{1-x}O$) (wherein 0<x<1) and barium calcium oxide ($Ba_xCa_{1-x}O$) (wherein 0<x<1), and BaO, SrO and CaO are preferred.

Examples of the rare earth metal compound include ytterbium fluoride ($YbF_3$), scandium fluoride ($ScF_3$), scandium oxide ($ScO_3$), yttrium oxide ($Y_2O_3$), cerium oxide ($Ce_2O_3$) gadolinium fluoride ($GdF_3$) and terbium fluoride ($TbF_3$), and $YbF_3$, $ScF_3$ and $TbF_3$ are preferred.

The organic metal complex is not particularly limited as far as at least one of an alkali metal ion, an alkaline earth metal ion and a rare earth metal ion is contained as a metal ion. Preferred examples of the ligand include quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyflavone, bipyridyl, phenanthroline, phthalocyanine, porphyrin, cyclopentadiene, a β-diketone compound, an azomethine compound, and derivatives thereof, but the ligand is not limited thereto.

The electron donating dopant and the organic metal complex may be preferably added to the interface region in the form of a layer or in the form of islands. The method of addition is preferably such a method that while vapor-depositing at least one of the electron donating dopant and the organic metal complex by a resistance heating vapor deposition method, the organic material as the light emitting material or the electron injecting material for forming the interface region is simultaneously vapor-deposited, and thereby at least one of the electron donating dopant and the organic metal complex is dispersed in the organic material. The dispersion concentration in terms of the molar ratio of (organic material)/(electron donating dopant and/or organic metal complex) is generally from 100/1 to 1/100, and preferably 5/1 to 1/5.

In the case where at least one of the electron donating dopant and the organic metal complex is formed in the form of a layer, the light emitting material or the electron injecting material for forming the organic layer of the interface region may be formed into the form of a layer, and then at least one of the electron donating dopant and the organic metal complex may be solely vapor-deposited by a resistance heating vapor deposition method into a layer having a thickness of from 0.1 nm to 15 nm.

In the case where at least one of the electron donating dopant and the organic metal complex is formed in the form of islands, the light emitting material or the electron injecting material for forming the organic layer of the interface region may be formed into the form of islands, and then at least one of the electron donating dopant and the organic metal complex may be solely vapor-deposited by a resistance heating vapor deposition method into islands having a thickness of from 0.05 nm to 1 nm.

In the organic EL device of the present invention, the ratio of the major components to at least one of the electron donating dopant and the organic metal complex in terms of a molar ratio of (major components)/(electron donating dopant and/or organic metal complex) is preferably from 5/1 to 1/5, and more preferably from 2/1 to 1/2.

(7) Cathode

The cathode may contain, as an electrode substance, such as a metal, an alloy, an electroconductive compound, and a mixture thereof, which have a small work function (4 eV or less), for injecting electrons to the electron injecting-transporting layer or the light emitting layer. Specific examples of the electrode substance include sodium, a sodium-potassium alloy, magnesium, lithium, a magnesium-silver alloy, aluminum/aluminum oxide, an aluminum-lithium alloy, indium, and a rare earth metal.

The cathode may be produced by forming the electrode substance into a thin film by such a method as vapor deposition or sputtering.

In the case where light emitted from the light emitting layer is taken out, the cathode preferably has a transmittance to the emitted light of 10% or more.

The cathode preferably has a sheet resistance of several hundred Ω per square or less, and generally has a thickness of from 10 nm to 1 μm, and preferably from 50 to 200 nm.

(8) Dielectric Layer

The organic EL device may often suffer image defects due to leakage or short circuit since an electric field is applied to the ultrathin film. For preventing the defects, a dielectric thin film is preferably inserted between the pair of electrodes.

Examples of the material used in the dielectric layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide and vanadium oxide, and mixtures and laminated products thereof may also be used.

(9) Production Method of Organic EL Device

The organic EL device may be produced by forming the anode, the light emitting layer, the hole transporting layer, and depending on necessity the electron injecting-transporting layer, and then forming the cathode, according to the materials and the formation methods exemplified above. In alternative, the organic EL device may be produced from the cathode to the anode, i.e., in the reverse order to the above.

An example of production of the organic EL device having a structure containing a light transmissive substrate having formed thereon an anode, a hole transporting layer, a light emitting layer, an electron injecting-transporting layer and a cathode in this order is shown below.

On a suitable light transmissive substrate, a thin film formed of an anode material is formed to have a thickness of 1 µm or less, and preferably from 10 to 200 nm, by such a method as vapor deposition or sputtering, thereby producing an anode. On the anode, at least two hole transporting layers are then provided sequentially. The hole transporting layers may be formed by such a method as a vacuum vapor deposition method, a spin coating method, a casting method and an LB method, and is preferably formed by a vacuum vapor deposition method since a uniform film may be obtained, and pinholes may be prevented from being formed. In the case where the hole transporting layers are formed by a vacuum vapor deposition method, the vapor deposition conditions may be preferably selected appropriately from a vapor deposition source temperature of from 50 to 450° C., a vacuum degree of from $10^{-7}$ to $10^{-3}$ Torr, a vapor deposition rate of from 0.01 to 50 nm/sec, a substrate temperature of from −50 to 300° C. and a film thickness of from 5 nm to 5 µm, while the conditions may vary depending on the compounds used (i.e., the materials for the hole transporting layers), and the crystal structure, the recombination structure and the like of the target hole transporting layers.

Subsequently, on forming a light emitting layer on the hole transporting layer, the light transmitting layer may be formed by, using a desired organic light emitting material, forming the organic light emitting material into a thin film by such a method as a vacuum vapor deposition method, a sputtering method, a spin coating method and a casting method, and is preferably formed by a vacuum vapor deposition method since a uniform film may be obtained, and pinholes may be prevented from being formed. In the case where the light emitting layer is formed by a vacuum vapor deposition method, the vapor deposition conditions may be generally selected from the same conditions as in the hole transporting layers, while the conditions may vary depending on the compounds used.

On the light emitting layer, an electron injecting-transporting layer is then formed. As similar to the hole transporting layers and the light emitting layers, the electron injecting-transporting layer is preferably formed by a vacuum vapor deposition method since a uniform film is necessarily provided. The vapor deposition conditions may be preferably selected from the same conditions as in the hole transporting layers and the light emitting layer.

Finally, a cathode is laminated thereon, thereby providing the organic EL device.

The cathode is formed of a metal and may be formed by a vapor deposition method or a sputtering method. A vapor deposition method is preferably used for protecting the organic material layer as the underlayer from being damaged on forming the film.

In the production of the organic EL device, all the layers of from the anode to the cathode are preferably formed in one vacuuming operation.

On application of a direct current voltage to the organic EL device, light emission is observed on application of a voltage of from 5 to 40 V with the anode as a positive pole and the cathode as a negative pole. On application of a voltage thereto with the inverse polarity, no electric current flows, and no light emission occurs. On application of an alternating electric current, uniform light emission is observed at the time with the anode as a positive pole and the cathode as a negative pole. The alternating electric current applied may have an arbitrary waveform.

The organic EL device of the present invention has a tendency of providing blue light emission in the case where the device has a fluorescent light emitting layer. In the case where the device has a phosphorescent light emitting layer, there is a tendency of providing yellow light emission, green light emission or blue light emission, and in many cases, there is a tendency of providing yellow light emission or green light emission.

EXAMPLE

The present invention will be described in more detail with reference to examples below, but the present invention is not limited to the examples unless the substance of the present invention is deviated.

Example 1

Production of Organic EL Device

A glass substrate having a dimension of 25 mm×75 mm×1.1 mm equipped with an ITO transparent electrode line (produced by Geomatec Co., Ltd.) was rinsed with isopropyl alcohol under application of ultrasonic wave for 5 minutes, and the cleaned with UV (ultraviolet ray) and ozone for 30 minutes.

The glass substrate having an ITO transparent electrode line having been rinsed and cleaned was mounted on a substrate holder of a vacuum vapor deposition equipment, and the following acceptor material (A) was vapor-deposited on the surface where the transparent electrode line was formed, to cover the transparent electrode, thereby forming an acceptor layer having a thickness of 5 nm. On the acceptor layer, the following compound (H1) as a first hole transporting material was vapor-deposited, thereby forming a first hole transporting layer having a thickness of 65 nm. Subsequent to the formation of the first hole transporting layer, the following compound (X1) as a second hole transporting material was vapor-deposited, thereby forming a second hole transporting layer having a thickness of 10 nm.

On the second hole transporting layer, the compound (B) as a phosphorescent host material and Ir(ppy)$_3$ as a phosphorescent dopant were co-vapor-deposited to a thickness of 25 nm, thereby providing a phosphorescent light emitting layer. The concentration of Ir(ppy)$_3$ was 10% by mass.

Subsequently, on the phosphorescent light emitting layer, the compound (C) with a thickness of 35 nm, LiF with a thickness of 1 nm and metallic Al with a thickness of 80 nm were laminated sequentially in this order to form a cathode. LiF as the electron injecting electrode was formed at a film forming rate of 1 Å/min.

The resulting organic EL device was driven for light emission with a direct electric current, and the luminance (cd/m$^2$) and the electric current density were measured, from which the light emission efficiency (cd/A) at an electric current density of 10 mA/cm$^2$ and the driving voltage (V) were obtained. The service life of the device until the luminance became 80% of the initial luminance at an electric current density of 50 mA/cm$^2$ was obtained. The results are shown in Table 1.

Acceptor Material (A)

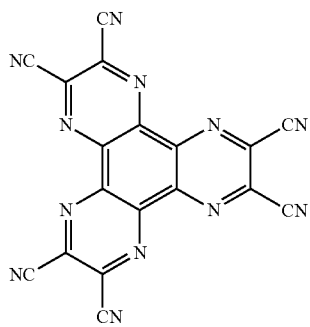 [SMILES: N#Cc1nc2c3nc(C#N)c(C#N)nc3c3nc(C#N)c(C#N)nc3c2nc1C#N]

First Hole Transporting Material (H1)

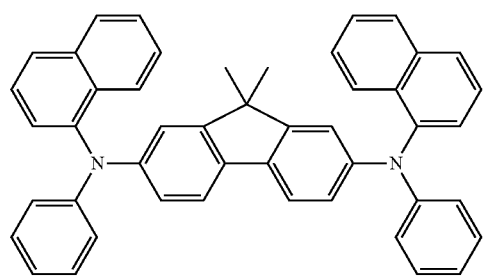 [SMILES: CC1(C)c2cc(N(c3ccccc3)c3cccc4ccccc34)ccc2-c2ccc(N(c3ccccc3)c3cccc4ccccc34)cc21]

Second Hole Transporting Material (X1)

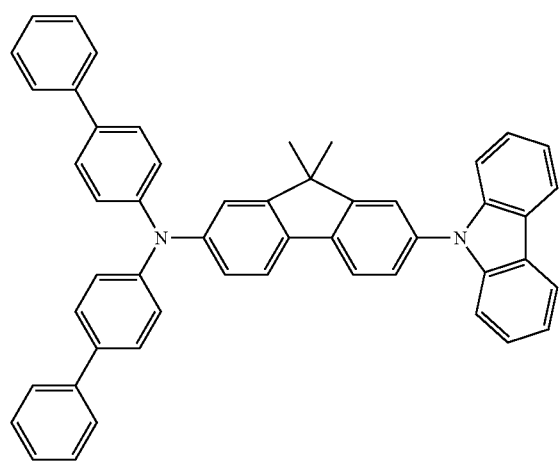 [SMILES: CC1(C)c2cc(N(c3ccc(-c4ccccc4)cc3)c3ccc(-c4ccccc4)cc3)ccc2-c2ccc(-n3c4ccccc4c4ccccc43)cc21]

Host Material (B)

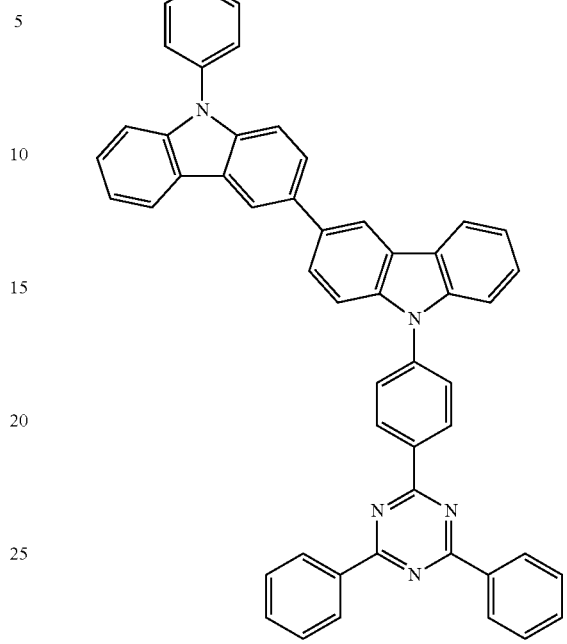

Dopant Ir(ppy)$_3$

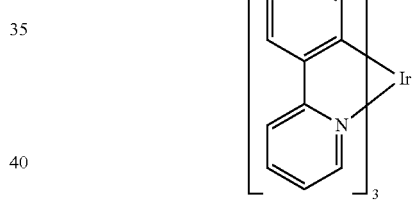

Electron Transporting Material (C)

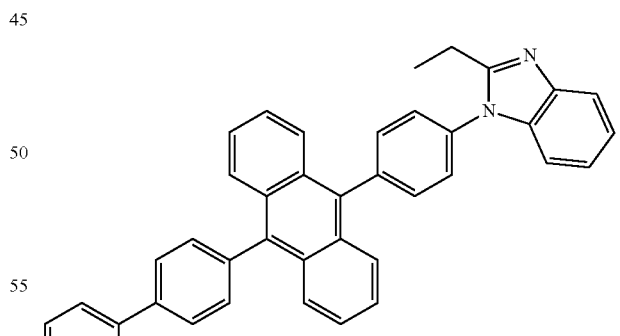

Examples 2 to 8

Organic EL devices were produced in the same manner as in Example 1 except that the following compounds (H2) to (H8) were used as the first hole transporting material instead of the compound (H1).

The resulting organic EL devices were driven for light emission with a direct electric current and evaluated in the same manner as in Example 1. The results are shown in Table 1.

First Hole Transporting Material (H2)

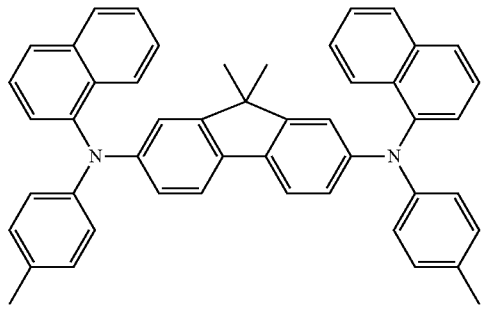 [SMILES: Cc1ccc(N(c2ccc3c(c2)C(C)(C)c2cc(N(c4ccc(C)cc4)c4cccc5ccccc45)ccc2-3)c2cccc3ccccc23)cc1]

First Hole Transporting Material (H3)

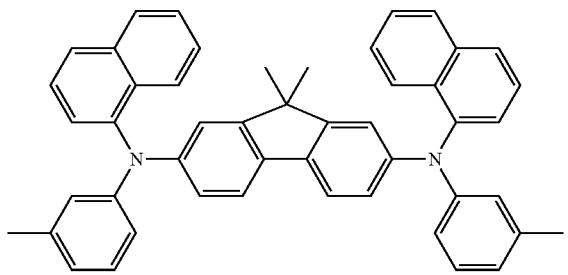

First Hole Transporting Material (H4)

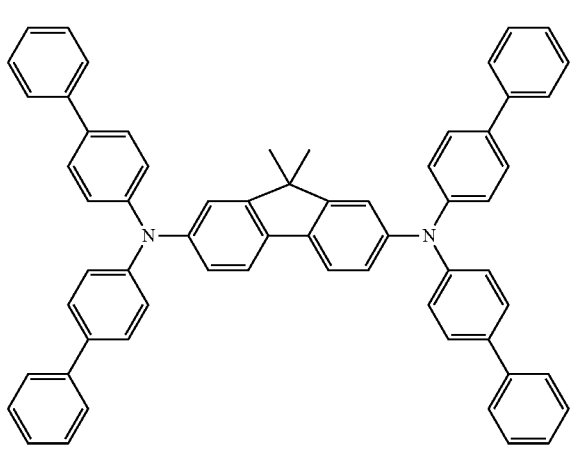 [SMILES: CC1(C)c2cc(N(c3ccc(-c4ccccc4)cc3)c3ccc(-c4ccccc4)cc3)ccc2-c2ccc(N(c3ccc(-c4ccccc4)cc3)c3ccc(-c4ccccc4)cc3)cc21]

First Hole Transporting Material (H5)

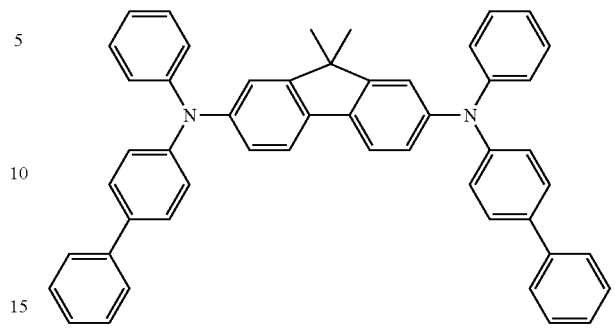

First Hole Transporting Material (H6)

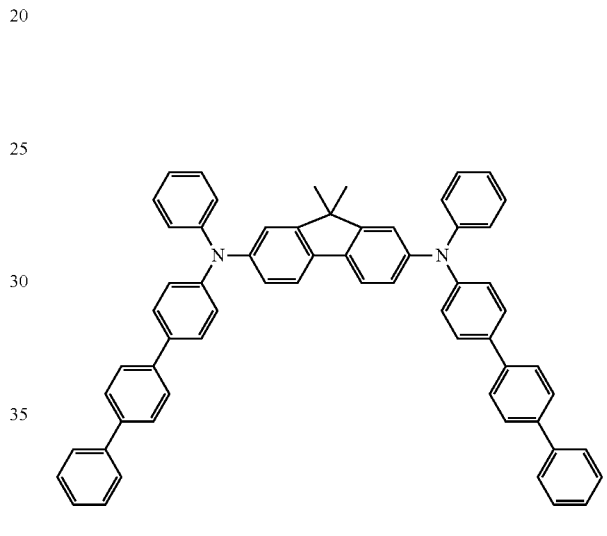

First Hole Transporting Material (H7)

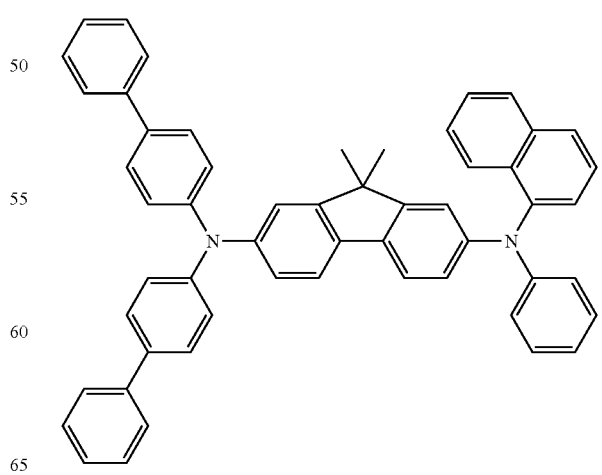

First Hole Transporting Material (H8)

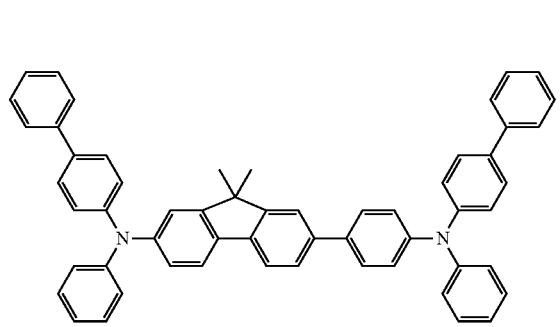 [SMILES: CC1(C)c2cc(-c3ccc(N(c4ccccc4)c4ccc(-c5ccccc5)cc4)cc3)ccc2-c2ccc(N(c3ccccc3)c3ccc(-c4ccccc4)cc3)cc21]

Comparative Compound 1

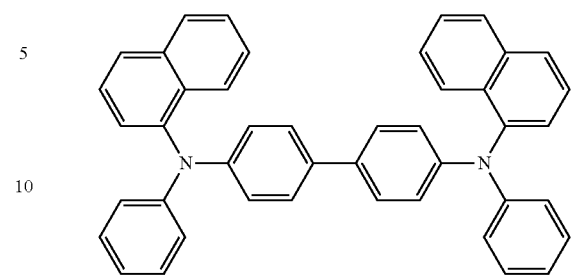

Comparative Compound 2

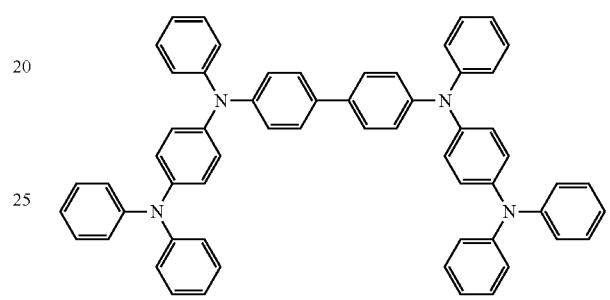

Comparative Compound 3

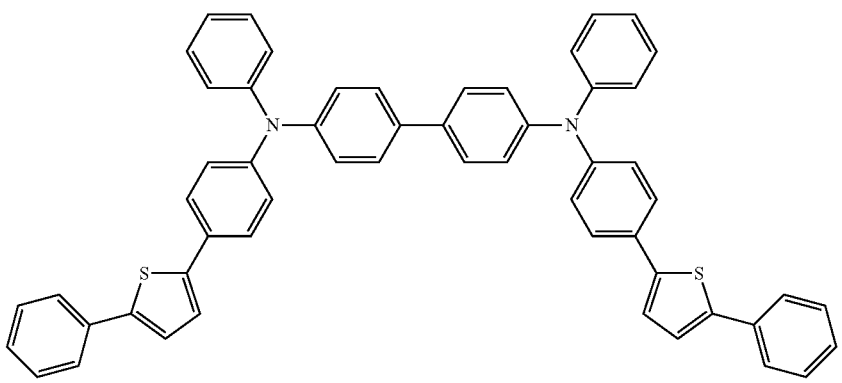 [SMILES: c1ccc(-c2ccc(-c3ccc(N(c4ccccc4)c4ccc(-c5ccc(N(c6ccccc6)c6ccc(-c7ccc(-c8ccccc8)s7)cc6)cc5)cc4)cc3)s2)cc1]

Comparative Compound 4

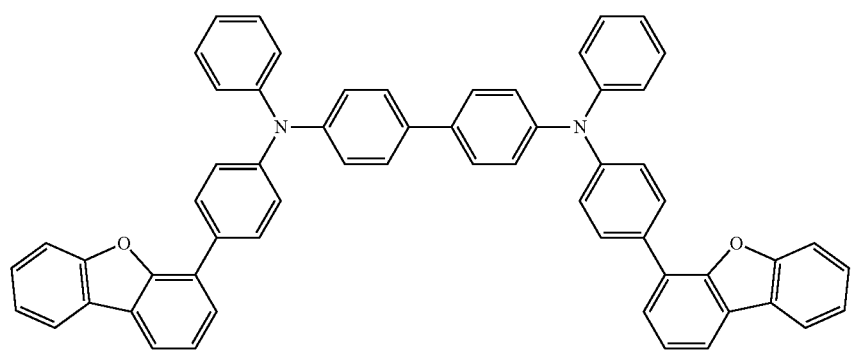 [SMILES: c1ccc(N(c2ccc(-c3ccc(N(c4ccccc4)c4ccc(-c5cccc6c5oc5ccccc56)cc4)cc3)cc2)c2ccc(-c3cccc4c3oc3ccccc34)cc2)cc1]

Comparative Examples 1 to 4

Organic EL devices were produced in the same manner as in Example 1 except that the following comparative compounds 1 to 4 were used as the first hole transporting material instead of the compound (H1).

The resulting organic EL devices were driven for light emission with a direct electric current and evaluated in the same manner as in Example 1. The results are shown in Table 1.

Comparative Example 5

Production of Organic EL Device

A glass substrate having a dimension of 25 mm×75 mm×1.1 mm equipped with an ITO transparent electrode line (produced by Geomatec Co., Ltd.) was rinsed with isopropyl alcohol under application of ultrasonic wave for 5 minutes, and the cleaned with UV (ultraviolet ray) and ozone for 30 minutes.

The glass substrate having an ITO transparent electrode line having been rinsed and cleaned was mounted on a substrate holder of a vacuum vapor deposition equipment, and the following acceptor material (A) was vapor-deposited on the surface where the transparent electrode line was formed, to cover the transparent electrode, thereby forming an acceptor layer having a thickness of 5 nm. On the acceptor layer, the compound (H1) as a hole transporting material was vapor-deposited, thereby forming a hole transporting layer having a thickness of 75 nm.

On the hole transporting layer, the compound (B) as a phosphorescent host material and Ir(ppy)$_3$ as a phosphorescent dopant were co-vapor-deposited to a thickness of 25 nm, thereby providing a phosphorescent light emitting layer. The concentration of Ir(ppy)$_3$ was 10% by mass.

Subsequently, on the phosphorescent light emitting layer, the compound (C) with a thickness of 35 nm, LiF with a thickness of 1 nm and metallic Al with a thickness of 80 nm were laminated sequentially in this order to form a cathode. LiF as the electron injecting electrode was formed at a film forming rate of 1 Å/min.

The resulting organic EL device was driven for light emission with a direct electric current, and the luminance (cd/m$^2$) and the electric current density were measured, from which the light emission efficiency (cd/A) at an electric current density of 10 mA/cm$^2$ and the driving voltage (V) were obtained. The service life of the device until the luminance became 80% of the initial luminance at an electric current density of 50 mA/cm$^2$ was obtained. The results are shown in Table 1.

Examples 9 to 17

Organic EL devices were produced in the same manner as in Example 1 except that the compound (H8) was used as the first hole transporting material instead of the compound (H1), one of the following compounds (Y1) to (Y9) was used as the second hole transporting material instead of the compound (X1), and Ir(bzq)$_3$ was used as the phosphorescent dopant instead of Ir(ppy)$_3$, and evaluated in the same manner as in Example 1. The results are shown in Table 2.

Second Hole Transporting Material (Y1)

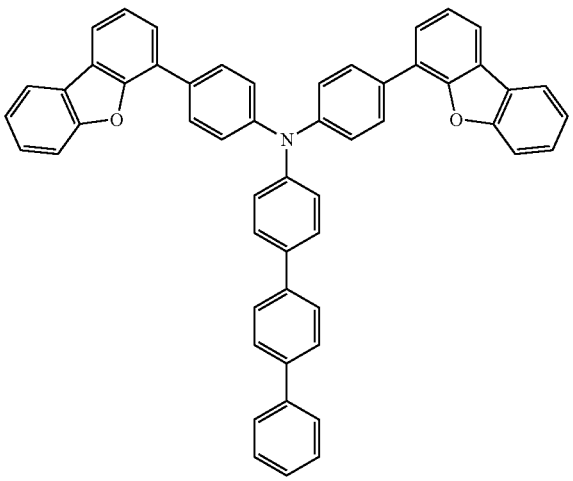 [SMILES: c1ccc(-c2ccc(-c3ccc(N(c4ccc(-c5cccc6c5oc5ccccc56)cc4)c4ccc(-c5cccc6c5oc5ccccc56)cc4)cc3)cc2)cc1]

Second Hole Transporting Material (Y2)

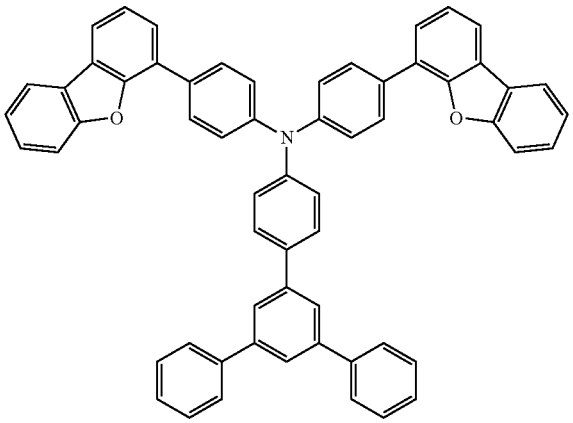 [SMILES: c1ccc(-c2cc(-c3ccccc3)cc(-c3ccc(N(c4ccc(-c5cccc6c5oc5ccccc56)cc4)c4ccc(-c5cccc6c5oc5ccccc56)cc4)cc3)c2)cc1]

Second Hole Transporting Material (Y3)

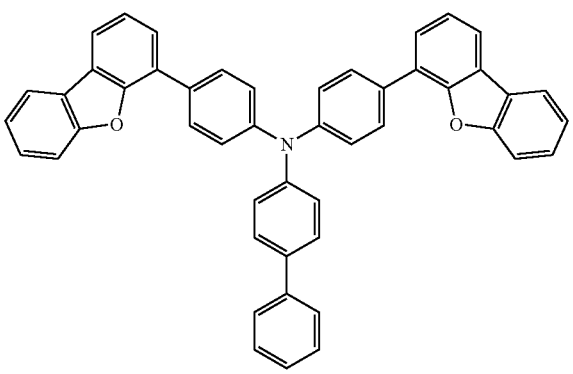 [SMILES: c1ccc(-c2ccc(N(c3ccc(-c4cccc5c4oc4ccccc45)cc3)c3ccc(-c4cccc5c4oc4ccccc45)cc3)cc2)cc1]

345
Second Hole Transporting Material (Y4)
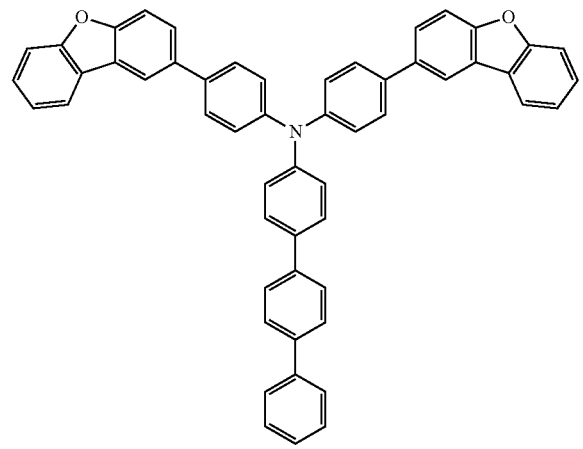 [SMILES: c1ccc(-c2ccc(-c3ccc(N(c4ccc(-c5ccc6oc7ccccc7c6c5)cc4)c4ccc(-c5ccc6oc7ccccc7c6c5)cc4)cc3)cc2)cc1]
Second Hole Transporting Material (Y5)
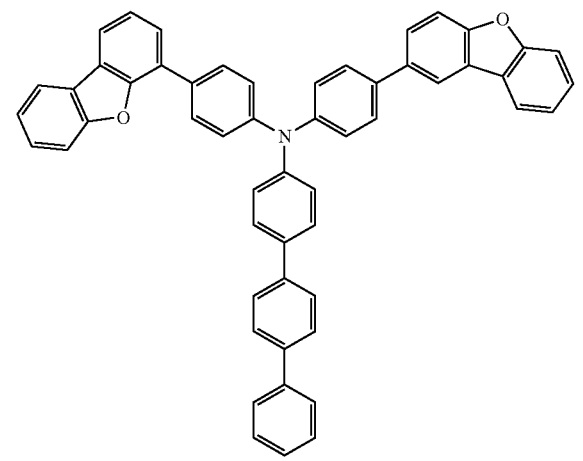 [SMILES: c1ccc(-c2ccc(-c3ccc(N(c4ccc(-c5ccc6oc7ccccc7c6c5)cc4)c4ccc(-c5cccc6c5oc5ccccc56)cc4)cc3)cc2)cc1]
Second Hole Transporting Material (Y6)
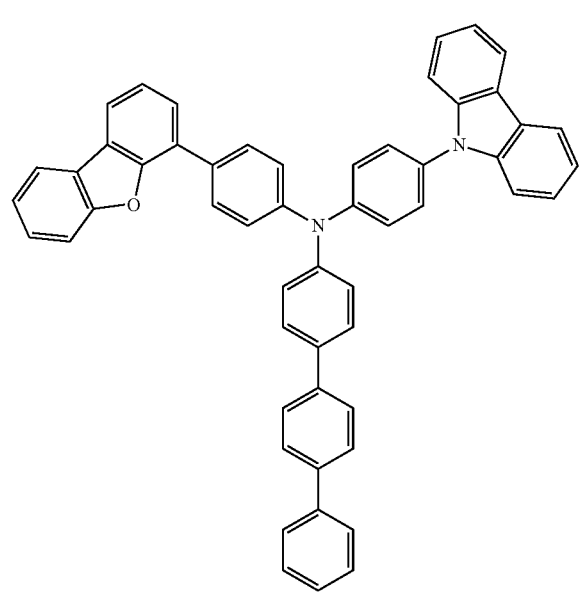 [SMILES: c1ccc(-c2ccc(-c3ccc(N(c4ccc(-c5cccc6c5oc5ccccc56)cc4)c4ccc(-n5c6ccccc6c6ccccc65)cc4)cc3)cc2)cc1]
346
Second Hole Transporting Material (Y7)
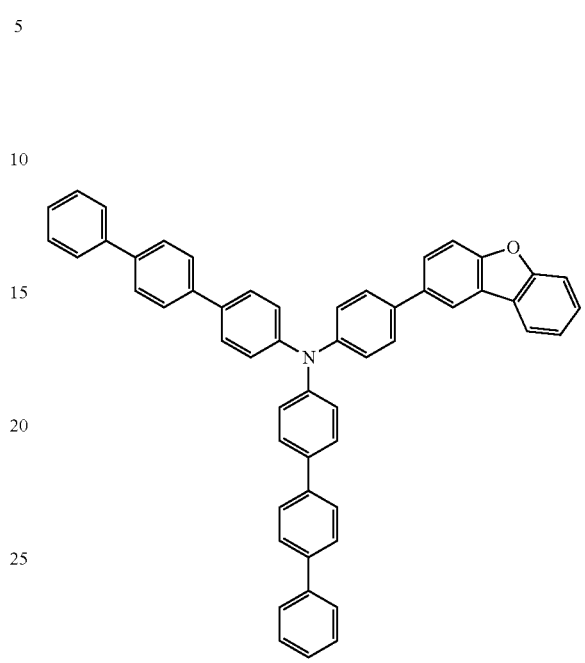
Second Hole Transporting Material (Y8)
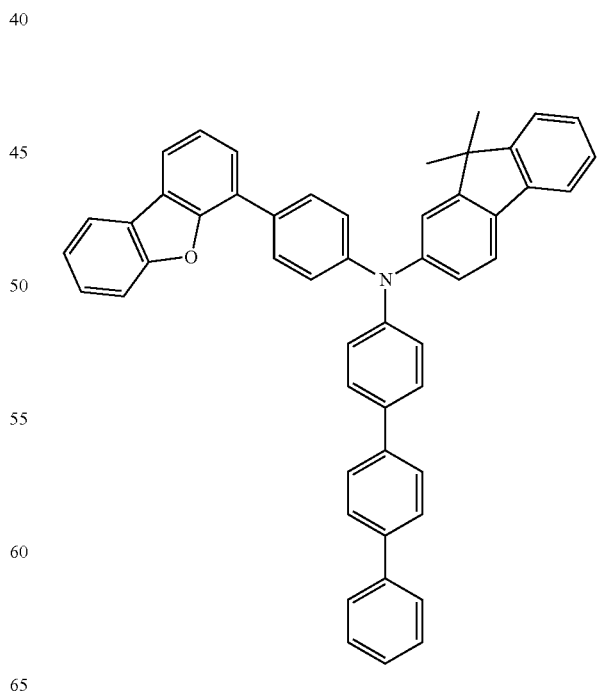

Second Hole Transporting Material (Y9)

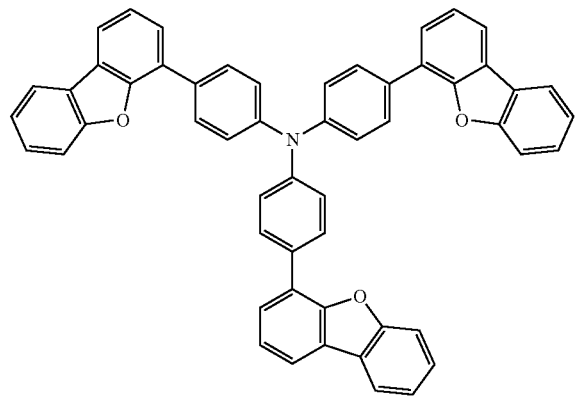 [SMILES: c1ccc2c(c1)oc1c(-c3ccc(N(c4ccc(-c5cccc6c5oc5ccccc56)cc4)c4ccc(-c5cccc6c5oc5ccccc56)cc4)cc3)cccc12]

Dopant Ir(bzq)₃

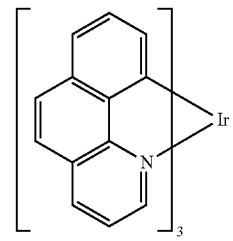

Comparative Examples 6 to 9

Organic EL devices were produced in the same manner as in Example 9 except that the comparative compounds 1 to 4 were used as the first hole transporting material instead of the aromatic amine derivative (H8), and evaluated in the same manner as in Example 1. The results are shown in Table 2.

TABLE 1

| | | Acceptor material | First hole transporting material | Second hole transporting material | Light emitting material (host material/ dopant) | Light emitting efficiency (cd/A) | Driving voltage (V) | 80% life time *1 (hr) | Light emission color |
|---|---|---|---|---|---|---|---|---|---|
| Example | 1 | A | H1 | X1 | B/Ir(ppy)₃ | 66.2 | 3.2 | 200 | green |
| | 2 | A | H2 | X1 | B/Ir(ppy)₃ | 68.2 | 3.3 | 190 | green |
| | 3 | A | H3 | X1 | B/Ir(ppy)₃ | 68.1 | 3.3 | 190 | green |
| | 4 | A | H4 | X1 | B/Ir(ppy)₃ | 60.5 | 3.3 | 210 | green |
| | 5 | A | H5 | X1 | B/Ir(ppy)₃ | 64.1 | 3.1 | 150 | green |
| | 6 | A | H6 | X1 | B/Ir(ppy)₃ | 60.5 | 3.3 | 170 | green |
| | 7 | A | H7 | X1 | B/Ir(ppy)₃ | 63.2 | 3.2 | 150 | green |
| | 8 | A | H8 | X1 | B/Ir(ppy)₃ | 65.3 | 3.3 | 190 | green |
| Comparative Example | 1 | A | Comparative compound 1 | X1 | B/Ir(ppy)₃ | 59.7 | 3.3 | 120 | green |
| | 2 | A | Comparative compound 2 | X1 | B/Ir(ppy)₃ | 60.1 | 3.4 | 40 | green |
| | 3 | A | Comparative compound 3 | X1 | B/Ir(ppy)₃ | 54.8 | 3.2 | 100 | green |
| | 4 | A | Comparative compound 4 | X1 | B/Ir(ppy)₃ | 56.2 | 3.6 | 70 | green |
| | 5 | A | H1 (only one hole transporting layer) | | B/Ir(ppy)₃ | 40.2 | 3.4 | 40 | green |

*1: time of decreasing luminance to 80%

TABLE 2

| | | Acceptor material | First hole transporting material | Second hole transporting material | Light emitting material (host material/ dopant) | Light emitting efficiency (cd/A) | Driving voltage (V) | 80% life time *1 (hr) | Light emission color |
|---|---|---|---|---|---|---|---|---|---|
| Example | 9 | A | H8 | Y1 | B/Ir(bzq)₃ | 57.4 | 3.7 | 580 | yellow |
| | 10 | A | H8 | Y2 | B/Ir(bzq)₃ | 57.1 | 3.7 | 580 | yellow |
| | 11 | A | H8 | Y3 | B/Ir(bzq)₃ | 57.3 | 3.6 | 580 | yellow |
| | 12 | A | H8 | Y4 | B/Ir(bzq)₃ | 62.5 | 3.6 | 610 | yellow |
| | 13 | A | H8 | Y5 | B/Ir(bzq)₃ | 58.2 | 3.7 | 600 | yellow |
| | 14 | A | H8 | Y6 | B/Ir(bzq)₃ | 58.6 | 3.8 | 600 | yellow |
| | 15 | A | H8 | Y7 | B/Ir(bzq)₃ | 56.5 | 3.7 | 600 | yellow |
| | 16 | A | H8 | Y8 | B/Ir(bzq)₃ | 55.4 | 3.7 | 600 | yellow |
| | 17 | A | H8 | Y9 | B/Ir(bzq)₃ | 61.2 | 3.6 | 600 | yellow |
| Comparative Example | 6 | A | Comparative compound 1 | Y1 | B/Ir(bzq)₃ | 51.8 | 3.8 | 350 | yellow |
| | 7 | A | Comparative compound 2 | Y1 | B/Ir(bzq)₃ | 52.1 | 3.9 | 50 | yellow |
| | 8 | A | Comparative compound 3 | Y1 | B/Ir(bzq)₃ | 47.5 | 3.7 | 130 | yellow |

TABLE 2-continued

| | Acceptor material | First hole transporting material | Second hole transporting material | Light emitting material (host material/ dopant) | Light emission capability | | | |
|---|---|---|---|---|---|---|---|---|
| | | | | | Light emitting efficiency (cd/A) | Driving voltage (V) | 80% life time *1 (hr) | Light emission color |
| 9 | A | Comparative compound 4 | Y1 | B/Ir(bzq)$_3$ | 48.7 | 4.1 | 120 | yellow |

*1: time of decreasing luminance to 80%

It is understood from the comparison between Examples 1 to 8 and Comparative Examples 1 to 4 and the comparison between Examples 9 to 17 and Comparative Examples 6 to 9 in Tables 1 and 2 that the organic EL devices containing the compound of the formula (1) in the first hole transporting layer have an increased efficiency and a prolonged service life, as compared to the organic EL devices containing the other compound than the compound of the formula (1) in the first hole transporting layer.

It is also understood from the comparison between Example 1 and Comparative Example 5 that the organic EL device having at least two hole transporting layers and a light emitting layer sequentially according to the present invention has an increased efficiency and a prolonged service life, as compared to the organic EL devices containing only one hole transporting layer.

Example 18

Production of Organic EL Device

A glass substrate having a dimension of 25 mm×75 mm×1.1 mm equipped with an ITO transparent electrode line (produced by Geomatec Co., Ltd.) was rinsed with isopropyl alcohol under application of ultrasonic wave for 5 minutes, and the cleaned with UV (ultraviolet ray) and ozone for 30 minutes.

The glass substrate having an ITO transparent electrode line having been rinsed and cleaned was mounted on a substrate holder of a vacuum vapor deposition equipment, and the following acceptor material (A) was vapor-deposited on the surface where the transparent electrode line was formed, to cover the transparent electrode, thereby forming an acceptor layer having a thickness of 5 nm. On the acceptor layer, the compound (H8) as a first hole transporting material was vapor-deposited, thereby forming a first hole transporting layer having a thickness of 138 nm. Subsequent to the formation of the first hole transporting layer, the following compound (Y1) as a second hole transporting material was vapor-deposited, thereby forming a second hole transporting layer having a thickness of 10 nm.

On the second hole transporting layer, the compound (B2) as a fluorescent host material and a fluorescent dopant (BD) were co-vapor-deposited to a thickness of 25 nm, thereby providing a fluorescent light emitting layer. The concentration of the dopant (BD) in the fluorescent light emitting layer was 5% by mass.

Subsequently, on the fluorescent light emitting layer, the following compound (C2) with a thickness of 20 nm, the following compound (C) with a thickness of 5 nm, LiF with a thickness of 1 nm and metallic Al with a thickness of 80 nm were laminated sequentially in this order to form a cathode. LiF as the electron injecting electrode was formed at a film forming rate of 1 Å/min.

The resulting organic EL device was driven for light emission with a direct electric current, and the luminance (cd/m$^2$) and the electric current density were measured, from which the light emission efficiency (cd/A) at an electric current density of 10 mA/cm$^2$ and the driving voltage (V) were obtained. The service life of the device until the luminance became 80% of the initial luminance at an electric current density of 50 mA/cm$^2$ was obtained. The results are shown in Table 3.

Acceptor Material (A)

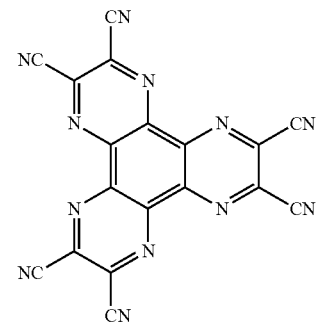 [SMILES: N#Cc1nc2c3nc(C#N)c(C#N)nc3c3nc(C#N)c(C#N)nc3c2nc1C#N]

Second Hole Transporting Material (Y1)

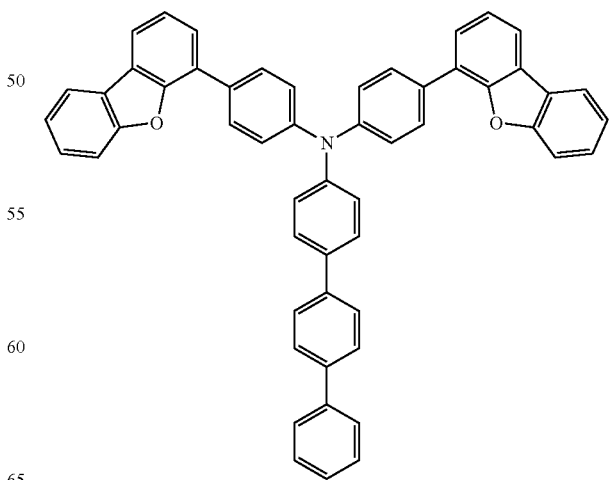

Host Material (B2)

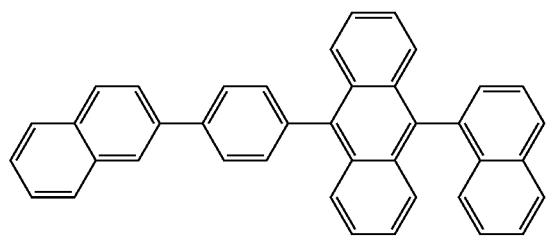 [SMILES: c1ccc2cc(-c3ccc(-c4c5ccccc5c(-c5cccc6ccccc56)c5ccccc45)cc3)ccc2c1]

Dopant (BD)

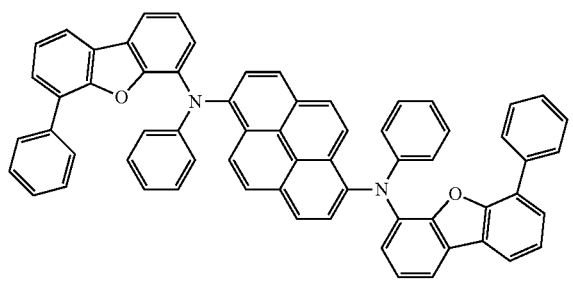 [SMILES: c1ccc(-c2cccc3c2oc2c(N(c4ccccc4)c4ccc5ccc6c(N(c7ccccc7)c7cccc8c7oc7c(-c9ccccc9)cccc78)ccc7ccc4c5c76)cccc23)cc1]

Electron Transporting Material (C2)

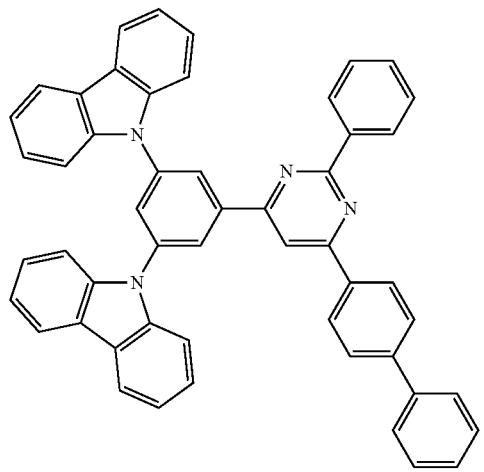 [SMILES: c1ccc(-c2ccc(-c3cc(-c4cc(-n5c6ccccc6c6ccccc65)cc(-n5c6ccccc6c6ccccc65)c4)nc(-c4ccccc4)n3)cc2)cc1]

Electron Transporting Material (C)

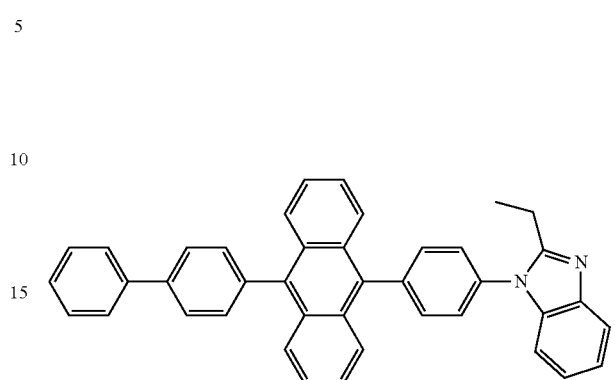

Examples 19 and 20

Organic EL devices were produced in the same manner as in Example 18 except that the following compounds (Y2) or (Y3) were used as the second hole transporting material instead of the compound (Y1).

The resulting organic EL devices were driven for light emission with a direct electric current and evaluated in the same manner as in Example 1. The results are shown in Table 3.

Comparative Examples 10 to 13

Organic EL devices were produced in the same manner as in Example 18 except that the comparative compounds 1 to 4 were used as the first hole transporting material instead of the aromatic amine derivative (H8) and evaluated in the same manner as in Example 1. The results are shown in Table 3.

TABLE 3

|  |  | Acceptor material | First hole transporting material | Second hole transporting material | Light emitting material (host material/ dopant) | Light emission capability | | | |
|---|---|---|---|---|---|---|---|---|---|
|  |  |  |  |  |  | Light emitting efficiency (cd/A) | Driving voltage (V) | 80% life time *1 (hr) | Light emission color |
| Example | 18 | A | H8 | Y1 | B2/BD | 8.5 | 4.3 | 900 | blue |
|  | 19 | A | H8 | Y2 | B2/BD | 8.6 | 4.3 | 700 | blue |
|  | 20 | A | H8 | Y3 | B2/BD | 8.8 | 4.3 | 700 | blue |
| Comparative Example | 10 | A | Comparative compound 1 | Y1 | B2/BD | 7.6 | 4 | 440 | blue |
|  | 11 | A | Comparative compound 2 | Y1 | B2/BD | 6.7 | 4.1 | 50 | blue |
|  | 12 | A | Comparative compound 3 | Y1 | B2/BD | 6.5 | 3.9 | 300 | blue |

TABLE 3-continued

| | Acceptor material | First hole transporting material | Second hole transporting material | Light emitting material (host material/ dopant) | Light emission capability | | | |
| --- | --- | --- | --- | --- | --- | --- | --- | --- |
| | | | | | Light emitting efficiency (cd/A) | Driving voltage (V) | 80% life time *1 (hr) | Light emission color |
| 13 | A | Comparative compound 4 | Y1 | B2/BD | 7.3 | 4.3 | 310 | blue |

*1: time of decreasing luminance to 80%

It is understood from the comparison between Examples 18 to 20 and Comparative Examples 10 to 13 in Table 3 that the organic EL devices containing the compound of the formula (1) in the first hole transporting layer have an increased efficiency and a prolonged service life, as compared to the organic EL devices containing the other compound than the compound of the formula (1) in the first hole transporting layer.

INDUSTRIAL APPLICABILITY

As described in detail above, the organic EL device of the present invention has a hole transporting layer having an increased thickness, is capable of being controlled in the thickness of the optical film of the organic EL device, and is enhanced in the light emitting efficiency and the service life of the device. Accordingly, the organic EL device is useful as a plane light emission device and a backlight of a display device.

What is claim is:

1. An organic electroluminescence device comprising an anode and a cathode facing each other, and intervening therebetween at least two hole transporting layers and a light emitting layer sequentially, wherein:
   the least two hole transporting layers comprises a first hole transporting layer on a side of the anode and a second hole transporting layer on a side of the light emitting layer,
   the second hole transporting layer is an electron barrier layer and adjacent to the light emitting layer,
   the first hole transporting layer comprises a compound represented by the following formula (1) and is not adjacent to the light emitting layer:

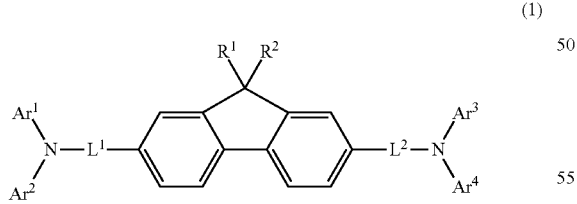

(1)

wherein in the formula (1),
   $R^1$ and $R^2$ each independently represent a hydrogen atom or an alkyl group having from 1 to 10 carbon atoms;
   $L^1$ and $L^2$ each independently represent a single bond or a substituted or unsubstituted arylene group having from 6 to 30 ring carbon atoms; and
   $Ar^1$ to $Ar^4$ each independently represent a substituted or unsubstituted aryl group having from 6 to 30 ring carbon atoms, wherein $Ar^1$ to $Ar^4$ may be substituted with one or more selected from the group consisting of a halogen atom, a cyano group, an alkyl group having from 1 to 20 carbon atoms, a cycloalkyl group having from 3 to 20 carbon atoms, an alkoxy group having from 1 to 20 carbon atoms, a haloalkyl group having from 1 to 20 carbon atoms, an haloalkoxy group having from 1 to 20 carbon atoms, an alkylsilyl group having from 1 to 10 carbon atoms, an aryl group having from 6 to 30 ring carbon atoms, an aryloxy group having from 6 to 30 ring carbon atoms, an arylsilyl group having from 6 to 30 carbon atoms, and an aralkyl group having from 7 to 30 carbon atoms, and
the second hole transporting layer comprises a compound represented by the following formula (4):

(4)

wherein in the formula (4),
   $Ar^{11}$ is a group represented by the following formula (4-2),
   $Ar^{12}$ is a substituted or unsubstituted aryl group having from 6 to 40 carbon atoms, and
   $Ar^{13}$ is a group represented by the following formula (4-2), (4-3) or (4-4) or a substituted or unsubstituted aryl group having from 6 to 40 carbon atoms:

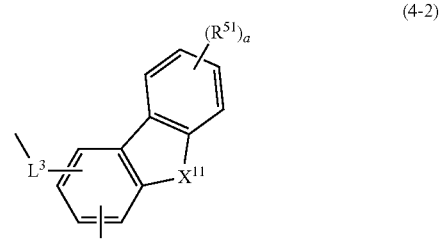

(4-2)

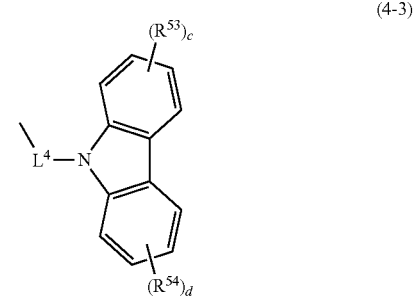

(4-3)

(4-4)

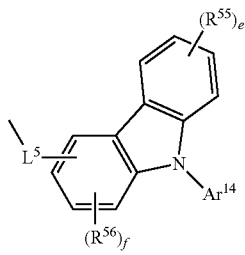

wherein
- $X^{11}$ represents an oxygen atom or a sulfur atom;
- $L^3$ to $L^5$ each independently represents a single bond or a substituted or unsubstituted arylene group having from 6 to 50 ring carbon atoms, wherein a substituent that may be substituted on $L^3$ to $L^5$ is a linear or branched alkyl group having from 1 to 10 carbon atoms, a cycloalkyl group having from 3 to 10 ring carbon atoms, a trialkylsilyl group having from 3 to 10 carbon atoms, a triarylsilyl group having from 18 to 30 ring carbon atoms, an alkylarylsilyl group having from 8 to 15 carbon atoms, an aryl group having from 6 to 50 ring carbon atoms, a halogen atom or a cyano group;
- $Ar^{14}$ represents a substituted or unsubstituted aryl group having from 6 to 50 ring carbon atoms, in which examples of the substituent that may be substituted on $Ar^{14}$ is a linear or branched alkyl group having from 1 to 10 carbon atoms, a cycloalkyl group having from 3 to 10 ring carbon atoms, a trialkylsilyl group having from 3 to 10 carbon atoms, a triarylsilyl group having from 18 to 30 ring carbon atoms, an alkylarylsilyl group having from 8 to 15 carbon atoms, an aryl group having from 6 to 50 ring carbon atoms, a halogen atom or a cyano group;
- $R^{51}$ to $R^{56}$ each independently represents a substituted or unsubstituted linear or branched alkyl group having from 1 to 10 carbon atoms, a substituted or unsubstituted cycloalkyl group having from 3 to 10 ring carbon atoms, a substituted or unsubstituted trialkylsilyl group having from 3 to 10 carbon atoms, a substituted or unsubstituted triarylsilyl group having from 18 to 30 ring carbon atoms, a substituted or unsubstituted alkylarylsilyl group having from 8 to 15 carbon atoms, a substituted or unsubstituted aryl group having from 6 to 50 ring carbon atoms, a halogen atom or a cyano group, provided that the adjacent groups in $R^{51}$ to $R^{56}$ may be bonded to each other to form a saturated or unsaturated divalent group which forms a ring; and
- b and f each independently represent an integer of from 0 to 3, and a, c, d and e each independently represent an integer of from 0 to 4.

2. The organic electroluminescence device according to claim L wherein the compound represented by the formula (1) is a compound represented by the following formula (2):

(2)

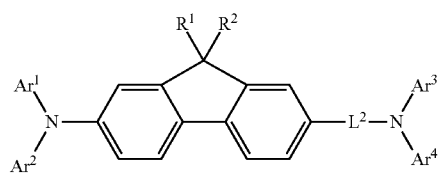

wherein in the formula (2), $R^1$, $R^2$, $L^2$ and $Ar^1$ to $Ar^4$ have the same meanings as in the formula (1).

3. The organic electroluminescence device according to claim 1, wherein the compound represented by the formula (1) is a compound represented by the following formula (3):

(3)

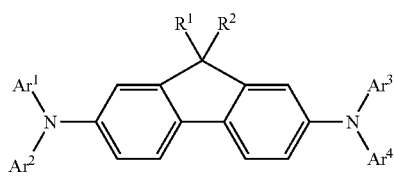

wherein in the formula (3), $R^1$, $R^2$ and $Ar^1$ to $Ar^4$ have the same meanings as in the formula (1).

4. The organic electroluminescence device according to claim 1, wherein $L^3$ in the formula (4-2) represents a substituted or unsubstituted arylene group having from 6 to 50 ring carbon atoms.

5. The organic electroluminescence device according to claim 1, wherein $L^5$ in the formula (4-4) represents a substituted or unsubstituted arylene group having from 6 to 50 ring carbon atoms.

6. The organic electroluminescence device according to claim 1, wherein in $Ar^{12}$ and $Ar^{13}$ in the formula (4), the substituted or unsubstituted aryl group having from 6 to 40 carbon atoms is represented by any one of the following formulae (4-5) to (4-7):

(4-5)

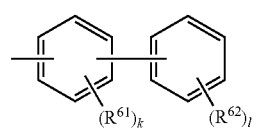

(4-6)

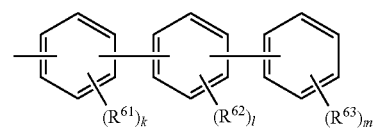

(4-7)

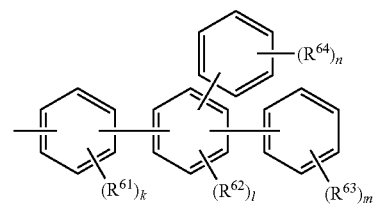

wherein
- $R^{61}$ to $R^{64}$ each independently represent a linear or branched alkyl group having from 1 to 10 carbon atoms, a cycloalkyl group having from 3 to 10 ring carbon atoms, a trialkylsilyl group having from 3 to 10 carbon atoms, a triarylsilyl group having from 18 to 30 ring carbon atoms, an alkylarylsilyl group having from 8 to 15 carbon atoms (in which the aryl moiety has from 6 to 14 ring carbon atoms), an aryl group having from 6 to 50 ring carbon atoms, a halogen atom or a cyano group, provided that the plural adjacent groups in $R^{61}$ to $R^{64}$ may be bonded to each other to form a ring; and
- k, l, m and n each independently represent an integer of from 0 to 4.

7. The organic electroluminescence device according to claim 1, wherein the organic electroluminescence device comprises an acceptor layer comprising an acceptor material between the anode and the at least two hole transporting layers.

8. The organic electroluminescence device according to claim 1, wherein the first hole transporting layer comprises an acceptor material.

9. The organic electroluminescence device according to claim 1, wherein the light emitting layer comprises a phosphorescent light emitting material.

10. The organic electroluminescence device according to claim 1, wherein $Ar^1$ to $Ar^4$ may be substituted with one or more selected from the group consisting of a halogen atom, an alkyl group having from 1 to 20 carbon atoms, a cycloalkyl group having from 3 to 20 carbon atoms, an alkoxy group having from 1 to 20 carbon atoms, a haloalkyl group having from 1 to 20 carbon atoms, an haloalkoxy group having from 1 to 20 carbon atoms, an alkylsilyl group having from 1 to 10 carbon atoms, an aryl group having from 6 to 30 ring carbon atoms, an aryloxy group having from 6 to 30 ring carbon atoms, an arylsilyl group having from 6 to 30 carbon atoms, and an aralkyl group having from 7 to 30 carbon atoms.

11. The organic electroluminescence device according to claim 1, wherein $Ar^1$ to $Ar^4$ may be substituted with one or more selected from the group consisting of a halogen atom, an alkyl group having from 1 to 20 carbon atoms, a cycloalkyl group having from 3 to 20 carbon atoms, an aryl group having from 6 to 30 ring carbon atoms and an aralkyl group having from 7 to 30 carbon atoms.

12. An organic electroluminescence device comprising an anode and a cathode facing each other, and intervening therebetween at least two hole transporting layers and a light emitting layer sequentially,
wherein:
the at least two hole transporting layers comprise a first hole transporting layer on a side of the anode and a second hole transporting layer on a side of the light emitting layer,
the second hole transporting layer is adjacent to the light emitting layer which is a light emitting layer closest to the anode,
the first hole transporting layer comprises a compound represented by the following formula (1) and is not adjacent to the light emitting layer:

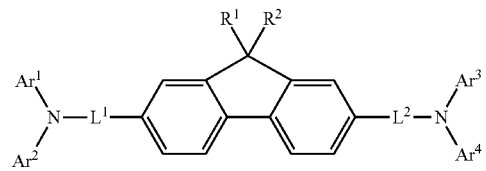

(1)

wherein in the formula (1),
$R^1$ and $R^2$ each independently represent a hydrogen atom or an alkyl group having from 1 to 10 carbon atoms;
$L^1$ and $L^2$ each independently represent a single bond or a substituted or unsubstituted arylene group having from 6 to 30 ring carbon atoms; and
$Ar^1$ to $Ar^4$ each independently represent a substituted or unsubstituted aryl group having from 6 to 30 ring carbon atoms, and the second hole transporting layer comprises a compound represented by the following formula (4):

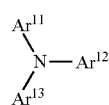

(4)

wherein in the formula (4),
$Ar^{11}$ is a group represented by the following formula (4-2),
$Ar^{12}$ is a substituted or unsubstituted aryl group having from 6 to 40 carbon atoms, and
$Ar^{13}$ is a group represented by the following formula (4-2), (4-3) or (4-4) or a substituted or unsubstituted aryl group having from 6 to 40 carbon atoms:

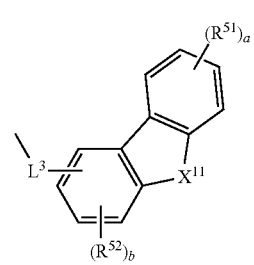

(4-2)

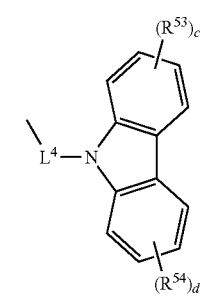

(4-3)

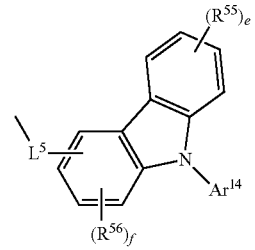

(4-4)

wherein
$X^{11}$ represents an oxygen atom or a sulfur atom;
$L^3$ to $L^5$ each independently represents a single bond or a substituted or unsubstituted arylene group having from 6 to 50 ring carbon atoms, wherein a substituent that may be substituted on $L^3$ to $L^5$ is a linear or branched alkyl group having from 1 to 10 carbon atoms, a cycloalkyl group having from 3 to 10 ring carbon atoms, a trialkylsilyl group having from 3 to 10 carbon atoms, a triarylsilyl group having from 18 to 30 ring carbon atoms, an alkylarylsilyl group having from 8 to 15 carbon atoms, an aryl group having from 6 to 50 ring carbon atoms, a halogen atom or a cyano group;

Ar$^{14}$ represents a substituted or unsubstituted aryl group having from 6 to 50 ring carbon atoms, in which examples of the substituent that may be substituted on Ar$^{14}$ is a linear or branched alkyl group having from 1 to 10 carbon atoms, a cycloalkyl group having from 3 to 10 ring carbon atoms, a trialkylsilyl group having from 3 to 10 carbon atoms, a triarylsilyl group having from 18 to 30 ring carbon atoms, an alkylarylsilyl group having from 8 to 15 carbon atoms, an aryl group having from 6 to 50 ring carbon atoms, a halogen atom or a cyano group;

R$^{51}$ to R$^{56}$ each independently represents a substituted or unsubstituted linear or branched alkyl group having from 1 to 10 carbon atoms, a substituted or unsubstituted cycloalkyl group having from 3 to 10 ring carbon atoms, a substituted or unsubstituted trialkylsilyl group having from 3 to 10 carbon atoms, a substituted or unsubstituted triarylsilyl group having from 18 to 30 ring carbon atoms, a substituted or unsubstituted alkylarylsilyl group having from 8 to 15 carbon atoms, a substituted or unsubstituted aryl group having from 6 to 50 ring carbon atoms, a halogen atom or a cyano group, provided that the adjacent groups in R$^{51}$ to R$^{56}$ may be bonded to each other to form a saturated or unsaturated divalent group which forms a ring; and b and f each independently represent an integer of from 0 to 3, and a, c, d and e each independently represent an integer of from 0 to 4.

13. The organic electroluminescence device according to claim 12, wherein the compound represented by the formula (1) is a compound represented by the following formula (2):

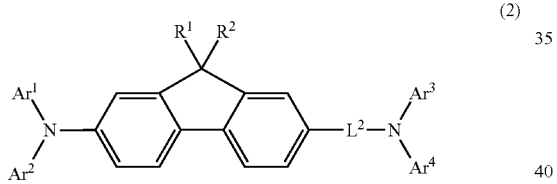

wherein in the formula (2), R$^1$, R$^2$, L$^2$ and Ar$^1$ to Ar$^4$ have the same meanings as in the formula (1).

14. The organic electroluminescence device according to claim 12, wherein the compound represented by the formula (1) is a compound represented by the following formula (3):

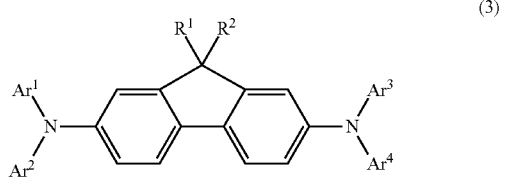

wherein in the formula (3), R$^1$, R$^2$ and Ar$^1$ to Ar$^4$ have the same meanings as in the formula (1).

15. The organic electroluminescence device according to claim 12, wherein L$^3$ in the formula (4-2) represents a substituted or unsubstituted arylene group having from 6 to 50 ring carbon atoms.

16. The organic electroluminescence device according to claim 12, wherein L$^5$ in the formula (4-4) represents a substituted or unsubstituted arylene group having from 6 to 50 ring carbon atoms.

17. The organic electroluminescence device according to claim 12, wherein in Ar$^{12}$ and Ar$^{13}$ in the formula (4), the substituted or unsubstituted aryl group having from 6 to 40 carbon atoms is represented by any one of the following formulae (4-5) to (4-7):

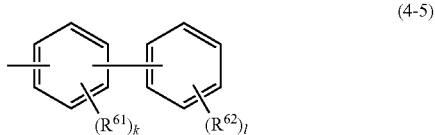

(4-5)

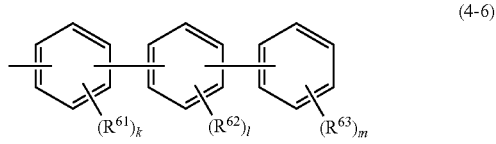

(4-6)

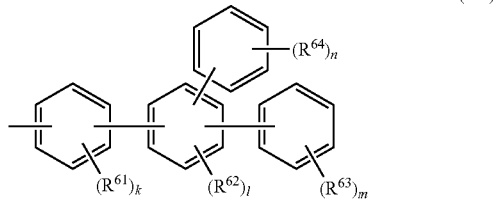

(4-7)

wherein
R$^{61}$ to R$^{64}$ each independently represent a linear or branched alkyl group having from 1 to 10 carbon atoms, a cycloalkyl group having from 3 to 10 ring carbon atoms, a trialkylsilyl group having from 3 to 10 carbon atoms, a triarylsilyl group having from 18 to 30 ring carbon atoms, an alkylarylsilyl group having from 8 to 15 carbon atoms (in which the aryl moiety has from 6 to 14 ring carbon atoms), an aryl group having from 6 to 50 ring carbon atoms, a halogen atom or a cyano group, provided that the plural adjacent groups in R$^{61}$ to R$^{64}$ may be bonded to each other to form a ring; and
k, l, m and n each independently represent an integer of from 0 to 4.

18. The organic electroluminescence device according to claim 12, wherein the organic electroluminescence device comprises an acceptor layer comprising an acceptor material between the anode and the at least two hole transporting layers.

19. The organic electroluminescence device according to claim 12, wherein the first hole transporting layer comprises an acceptor material.

20. The organic electroluminescence device according to claim 12, wherein the light emitting layer comprises a phosphorescent light emitting material.

21. The organic electroluminescence device according to claim 12, wherein Ar$^1$ to Ar$^4$ may be substituted with one or more selected from the group consisting of a halogen atom, an alkyl group having from 1 to 20 carbon atoms, a cycloalkyl group having from 3 to 20 carbon atoms, an alkoxy group having from 1 to 20 carbon atoms, a haloalkyl group having from 1 to 20 carbon atoms, an haloalkoxy group having from 1 to 20 carbon atoms, an alkylsilyl group having from 1 to 10 carbon atoms, an aryl group having from 6 to 30 ring carbon atoms, an aryloxy group having from 6 to 30 ring carbon atoms, an arylsilyl group having from 6 to 30 carbon atoms, and an aralkyl group having from 7 to 30 carbon atoms.

22. The organic electroluminescence device according to claim 12, wherein $Ar^1$ to $Ar^4$ may be substituted with one or more selected from the group consisting of a halogen atom, an alkyl group having from 1 to 20 carbon atoms, a cycloalkyl group having from 3 to 20 carbon atoms, an aryl group having from 6 to 30 ring carbon atoms and an aralkyl group having from 7 to 30 carbon atoms.

23. An organic electroluminescence device comprising an anode and a cathode facing each other, at least two hole transporting layers and a light emitting layer sequentially between the anode and the cathode, and an acceptor layer comprising an acceptor material, wherein:

the at least two hole transporting layers comprise a first hole transporting layer on a side of the anode and a second hole transporting layer on a side of the light emitting layer, the acceptor layer is disposed between the anode and the first hole transporting layer and is adjacent to the first hole transporting layer;

the first hole transporting layer comprises a compound represented by the following formula (1) and is not adjacent to the light emitting layer:

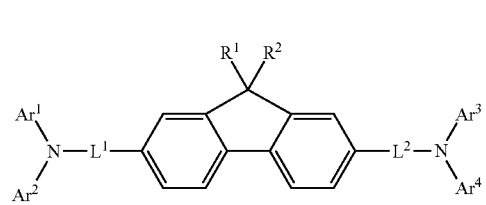

(1)

wherein in the formula (1), $R^1$ and $R^2$ each independently represent a hydrogen atom or an alkyl group having from 1 to 10 carbon atoms;

$L^1$ and $L^2$ each independently represent a single bond or a substituted or unsubstituted arylene group having from 6 to 30 ring carbon atoms; and $Ar^1$ to $Ar^4$ each independently represent a substituted or unsubstituted aryl group having from 6 to 30 ring carbon atoms, and the second hole transporting layer comprises a compound represented by the following formula (4):

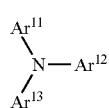

(4)

wherein in the formula (4), $Ar^{11}$ is a group represented by the following formula (4-2), $Ar^{12}$ is a substituted or unsubstituted aryl group having from 6 to 40 carbon atoms, and $Ar^{13}$ is a group represented by the following formula (4-2), (4-3) or (4-4) or a substituted or unsubstituted aryl group having from 6 to 40 carbon atoms:

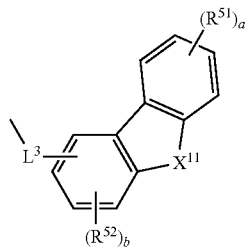

(4-2)

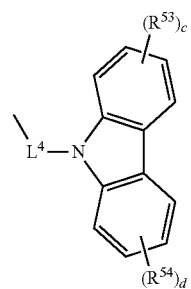

(4-3)

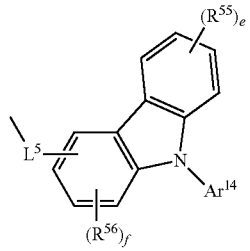

(4-4)

wherein $X^{11}$ represents an oxygen atom or a sulfur atom;

$L^3$ to $L^5$ each independently represents a single bond or a substituted or unsubstituted arylene group having from 6 to 50 ring carbon atoms, wherein a substituent that may be substituted on $L^3$ to $L^5$ is a linear or branched alkyl group having from 1 to 10 carbon atoms, a cycloalkyl group having from 3 to 10 ring carbon atoms, a trialkylsilyl group having from 3 to 10 carbon atoms, a triarylsilyl group having from 18 to 30 ring carbon atoms, an alkylarylsilyl group having from 8 to 15 carbon atoms, an aryl group having from 6 to 50 ring carbon atoms, a halogen atom or a cyano group:

$Ar^{14}$ represents a substituted or unsubstituted aryl group having from 6 to 50 ring carbon atoms, in which examples of the substituent that may be substituted on $Ar^{14}$ is a linear or branched alkyl group having from 1 to 10 carbon atoms, a cycloalkyl group having from 3 to 10 ring carbon atoms, a trialkylsilyl group having from 3 to 10 carbon atoms, a triarylsilyl group having from 18 to 30 ring carbon atoms, an alkylarylsilyl group having from 8 to 15 carbon atoms, an aryl group having from 6 to 50 ring carbon atoms, a halogen atom or a cyano group;

$R^{51}$ to $R^{56}$ each independently represents a substituted or unsubstituted linear or branched alkyl group having from 1 to 10 carbon atoms, a substituted or unsubstituted cycloalkyl group having from 3 to 10 ring carbon atoms, a substituted or unsubstituted trialkylsilyl group having from 3 to 10 carbon atoms, a substituted or unsubstituted triarylsilyl group having from 18 to 30 ring carbon atoms, a substituted or unsubstituted alkylarylsilyl group having from 8 to 15 carbon atoms, a substituted or unsubstituted aryl group having from 6 to 50 ring carbon atoms, a halogen atom or a cyano group, provided that the adjacent groups in $R^{51}$ to $R^{56}$ may be bonded to each other to form a saturated or unsaturated divalent group which forms a ring; and b and f each independently represent an integer of from 0 to 3, and a, c, d and e each independently represent an integer of from 0 to 4.

24. The organic electroluminescence device according to claim 23, wherein the compound represented by the formula (1) is a compound represented by the following formula (2):

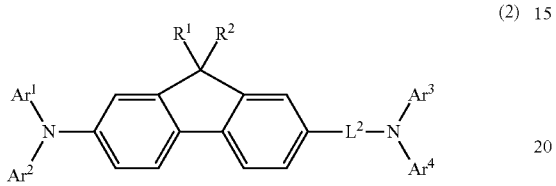

(2)

wherein in the formula (2), $R^1$, $R^2$, $L^2$ and $Ar^1$ to $Ar^4$ have the same meanings as in the formula (1).

25. The organic electroluminescence device according to claim 23, wherein the compound represented by the formula (1) is a compound represented by the following formula (3):

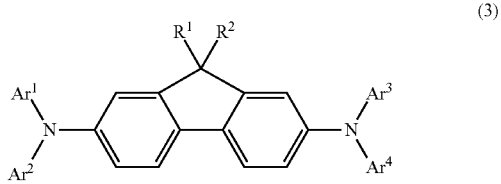

(3)

wherein in the formula (3), $R^1$, $R^2$ and $Ar^1$ to $Ar^4$ have the same meanings as in the formula (1).

26. The organic electroluminescence device according to claim 23, wherein $L^3$ in the formula (4-2) represents a substituted or unsubstituted arylene group having from 6 to 50 ring carbon atoms.

27. The organic electroluminescence device according to claim 23, wherein $L^5$ in the formula (4-4) represents a substituted or unsubstituted arylene group having from 6 to 50 ring carbon atoms.

28. The organic electroluminescence device according to claim 23, wherein in $Ar^{12}$ and $Ar^{13}$ in the formula (4), the substituted or unsubstituted aryl group having from 6 to 40 carbon atoms is represented by any one of the following formulae (4-5) to (4-7):

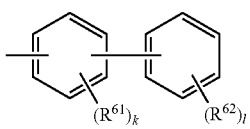

(4-5)

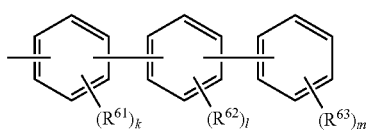

(4-6)

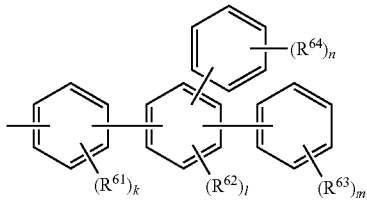

(4-7)

wherein $R^{61}$ to $R^{64}$ each independently represent a linear or branched alkyl group having from 1 to 10 carbon atoms, a cycloalkyl group having from 3 to 10 ring carbon atoms, a trialkylsilyl group having from 3 to 10 carbon atoms, a triarylsilyl group having from 18 to 30 ring carbon atoms, an alkylarylsilyl group having from 8 to 15 carbon atoms (in which the aryl moiety has from 6 to 14 ring carbon atoms), an aryl group having from 6 to 50 ring carbon atoms, a halogen atom or a cyano group, provided that the plural adjacent groups in $R^{61}$ to $R^{64}$ may be bonded to each other to form a ring; and k, l, m and n each independently represent an integer of from 0 to 4.

29. The organic electroluminescence device according to claim 23, wherein the light emitting layer comprises a phosphorescent light emitting material.

30. The organic electroluminescence device according to claim 23, wherein $Ar^1$ to $Ar^4$ may be substituted with one or more selected from the group consisting of a halogen atom, an alkyl group having from 1 to 20 carbon atoms, a cycloalkyl group having from 3 to 20 carbon atoms, an alkoxy group having from 1 to 20 carbon atoms, a haloalkyl group having from 1 to 20 carbon atoms, an haloalkoxy group having from 1 to 20 carbon atoms, an alkylsilyl group having from 1 to 10 carbon atoms, an aryl group having from 6 to 30 ring carbon atoms, an aryloxy group having from 6 to 30 ring carbon atoms, an arylsilyl group having from 6 to 30 carbon atoms, and an aralkyl group having from 7 to 30 carbon atoms.

31. The organic electroluminescence device according to claim 23, wherein $Ar^1$ to $Ar^4$ may be substituted with one or more selected from the group consisting of a halogen atom, an alkyl group having from 1 to 20 carbon atoms, a cycloalkyl group having from 3 to 20 carbon atoms, an aryl group having from 6 to 30 ring carbon atoms and an aralkyl group having from 7 to 30 carbon atoms.

32. The organic electroluminescence device according to claim 1, wherein $R^{51}$ to $R^{56}$ each independently represents a substituted or unsubstituted linear or branched alkyl group having from 1 to 10 carbon atoms, a substituted or unsubstituted cycloalkyl group having from 3 to 10 ring carbon atoms, a substituted or unsubstituted aryl group having from 6 to 50 ring carbon atoms, a halogen atom or a cyano group.

33. The organic electroluminescence device according to claim 12, wherein $R^{51}$ to $R^{56}$ each independently represents a substituted or unsubstituted linear or branched alkyl group having from 1 to 10 carbon atoms, a substituted or unsubstituted cycloalkyl group having from 3 to 10 ring carbon atoms, a substituted or unsubstituted aryl group having from 6 to 50 ring carbon atoms, a halogen atom or a cyano group.

34. The organic electroluminescence device according to claim 23, wherein $R^{51}$ to $R^{56}$ each independently represents a substituted or unsubstituted linear or branched alkyl group having from 1 to 10 carbon atoms, a substituted or unsubstituted cycloalkyl group having from 3 to 10 ring carbon atoms, a substituted or unsubstituted aryl group having from 6 to 50 ring carbon atoms, a halogen atom or a cyano group.

* * * * *

UNITED STATES PATENT AND TRADEMARK OFFICE
CERTIFICATE OF CORRECTION

PATENT NO. : 9,966,539 B2
APPLICATION NO. : 13/767417
DATED : May 8, 2018
INVENTOR(S) : Tomoki Kato et al.

Page 1 of 1

It is certified that error appears in the above-identified patent and that said Letters Patent is hereby corrected as shown below:

In the Claims (1) Claim 2: Column 355 in Line 55, "Claim L" should be "Claim 1,"
(2) Claim 17: Column 360 in Line 41, "k, l, in" should be "k, l, m"

Signed and Sealed this
Fourth Day of June, 2019

Andrei Iancu
*Director of the United States Patent and Trademark Office*